US008664364B2

(12) United States Patent
Schmidt et al.

(10) Patent No.: US 8,664,364 B2
(45) Date of Patent: Mar. 4, 2014

(54) OPTICAL BIOSENSORS

(75) Inventors: Brigitte F. Schmidt, Pittsburgh, PA (US); Christopher S. Szent-Gyorgyi, Pittsburgh, PA (US); Alan S. Waggoner, Pittsburgh, PA (US); Peter B. Berget, Glenshaw, PA (US); Marcel P. Bruchez, Pittsburgh, PA (US); Jonathan W. Jarvik, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 127 days.

(21) Appl. No.: 12/524,328

(22) PCT Filed: Jan. 24, 2008

(86) PCT No.: PCT/US2008/051962
§ 371 (c)(1),
(2), (4) Date: Feb. 3, 2010

(87) PCT Pub. No.: WO2008/092041
PCT Pub. Date: Jul. 31, 2008

(65) Prior Publication Data
US 2011/0159519 A1 Jun. 30, 2011

Related U.S. Application Data

(60) Provisional application No. 61/013,098, filed on Dec. 12, 2007, provisional application No. 60/897,120, filed on Jan. 24, 2007.

(51) Int. Cl.
*G01N 33/50* (2006.01)
*G01N 33/53* (2006.01)
*C07K 16/44* (2006.01)
*C09B 23/00* (2006.01)

(52) U.S. Cl.
USPC ..................... 530/387.3; 530/391.3; 435/7.1

(58) Field of Classification Search
None
See application file for complete search history.

(56) References Cited

U.S. PATENT DOCUMENTS

| | | | |
|---|---|---|---|
| 4,222,744 A | 9/1980 | McConnell | |
| 5,268,486 A | 12/1993 | Waggoner et al. | |
| 5,486,616 A | 1/1996 | Waggoner et al. | |
| 5,569,587 A | 10/1996 | Waggoner | |
| 5,569,766 A | 10/1996 | Waggoner et al. | |
| 5,597,696 A * | 1/1997 | Linn et al. | 435/6.12 |
| 5,616,502 A | 4/1997 | Haugland et al. | |
| 5,627,027 A | 5/1997 | Waggoner | |
| 6,008,373 A | 12/1999 | Waggoner et al. | |
| 6,048,982 A | 4/2000 | Waggoner | |
| 6,225,050 B1 | 5/2001 | Waggoner | |
| 6,437,099 B1 | 8/2002 | Jibu | |
| 6,673,943 B2 | 1/2004 | Waggoner et al. | |
| 6,716,994 B1 | 4/2004 | Menchen et al. | |
| 7,741,128 B2 | 6/2010 | Su | |
| 7,939,313 B2 | 5/2011 | Heyduk et al. | |
| 2004/0058881 A1 | 3/2004 | Humphreys et al. | |
| 2005/0064512 A1 | 3/2005 | Schirner et al. | |
| 2005/0214810 A1* | 9/2005 | Dallwig et al. | 435/6 |
| 2005/0215770 A1* | 9/2005 | Bell et al. | 530/388.22 |
| 2006/0019408 A1 | 1/2006 | Waggoner et al. | |
| 2010/0041087 A1 | 2/2010 | Wang et al. | |

FOREIGN PATENT DOCUMENTS

| | | | |
|---|---|---|---|
| CN | 1766623 A | | 5/2006 |
| EP | 1132397 A1 | | 9/2001 |
| JP | 09-297135 | * | 11/1997 |
| JP | 09-297135 A | | 11/1997 |
| WO | WO 2004-025268 A2 | | 3/2004 |

OTHER PUBLICATIONS

International Preliminary Report on Patentability issued for PCT/US2008/051962 on Jul. 28, 2009.*
Farinas et al., "Receptor-mediated Targeting of Fluorescent Probes in Living Cells," *The Journal of Biological Chemistry*, vol. 274, No. 12, Issue of Mar. 19, pp. 7603-7606, 1999.
Simeonov, et al., "Blue-Fluorescent Antibodies," *Science*, vol. 290, pp. 307-313 (Oct. 13, 2000).
Szent-Gyorgyi, et al.; "Fluorogen-activating single-chain antibodies for imaging cell surface proteins," *Nature Biotechnology*, vol. 26, No. 2, pp. 235-240 (Feb. 2008).
Valyukh I.V. et al., "Spectroscopic study of the fluorescent dyes interaction with DNA," *Functional Materials*, vol. 10, No. 3, pp. 528-533 (2003).
Yoo, et al., "Antibody-ligand interactions studied by fluorescence enhancement methods—I. Properties of the ligands 4-anilinonaphthalene-1-sulfonate and 6-anilinonaphthalene-2-sulfonate." *Immunochemistry*, Pergamon Press 1970, vol. 7, pp. 627-636.
Armentano et al., "Expression of human factor IX in rabbit hepatocytes by retrovirus-mediated gene transfer: Potential for gene therapy of hemophilia B," *Proc. Natl. Acad. Sci. USA*, vol. 87:6141-6145 (1990).
Ben-Bassat et al., "Processing of the Initiation Methionine from Proteins: Properties of the *Escherichia coli* Methionine Aminopeptidase and Its Gene Structure," *J. Bacteriol.* vol. 169:751-757 (1987).
Haj-Ahmad and Graham, "Development of a Helper-Independent Human Adenovirus Vector and Its Use in the Transfer of the Herpes Simplex Virus Thymidine Kinase Gene," *Journal of Virology*, vol. 57:267-274 (1986).
Boder et al., "Directed evolution of antibody fragments with monovalent femtomolar antigen-binding affinity," *Proc. Natl. Acad. Sci USA*, vol. 97:10701-5 (2000).

(Continued)

*Primary Examiner* — Shafiqul Haq
*Assistant Examiner* — Galina Yakovleva
(74) *Attorney, Agent, or Firm* — K&L Gates LLP

(57) ABSTRACT

Provided are biosensors, compositions comprising biosensors, and methods of using biosensors in living cells and organisms. The biosensors are able to be selectively targeted to certain regions or structures within a cell. The biosensors may provide a signal when the biosensor is targeted and/or in response to a property of the cell or organism such as membrane potential, ion concentration or enzyme activity.

26 Claims, 28 Drawing Sheets

(56) References Cited

OTHER PUBLICATIONS

Bujarski, J.J. and P. Kaesberg, "DNA inserted two bases down from the initiation site of a SP6 polymerase transcription vector is transcribed efficiently in vitro," *Nucleic Acids Research*, vol. 15:1337 (1987).
Chao, G. et al., "Isolating and engineering human antibodies using yeast surface display," *Nat. Protocols*, vol. 1, 755-768 (2006).
Cheng, X. et al., "The structure of bacteriophage T7 lysozyme amidase and an inhibitor of T7 RNA polymerase," *Proc. Natl. Acad. Sci. USA*, vol. 91:4034-4038 (1994).
Cristiano et al., "Hepatic gene therapy: Adenovirus enhancement of receptor-mediated gene delivery and expression in primary hepatocytes," *Proc. Natl. Acad. Sci. USA*, vol. 90:2122-2126 (1993).
Colby, D.W. et al., "Development of a Human Light Chain Variable Domain (VL) Intracellular Antibody Specific for the Amino Terminus of Huntingtin via Yeast Surface Display," *J. Mol. Biol.*, vol. 342, 901-912 (Sep. 17, 2004).
Dai et al., "Gene therapy via primary myoblasts: Long-term expression of factor IX protein following transplantation in vitro," *Proc. Natl. Acad. Sci. USA*, vol. 89:10892-10895 (1992).
Danos and Mulligan, "Safe and efficient generation of recombinant retroviruses with amphotropic and ecotropic host ranges," *Proc. Natl. Acad. Sci. USA*, vol. 85:6460-6464 (1988).
De Lorenzo, V. et al., "Operator Sequences of the Aerobactin Operon of Plasmid ColV-K30 Binding the Ferric Uptake Regulation (*fur*) Repressor," *Journal of Bacteriology*, vol. 169:2624-2630 (1987).
Ferry et al., "Retroviral-mediated gene transfer into hepatocytes in vitro," *Proc. Natl. Acad. Sci. USA*, vol. 88:8377-8381 (1991).
Flotte et al., "Expression of the Cystic Fibrosis Transmembrane Conductance Regulator from a Novel Adeno-associated Virus Promoter," *J. Biol. Chem.*, vol.268:3781-3790 (1993).
Giudicelli, V. et al., "IMGT/LIGM-DB, the IMGT® comprehensive database of immunoglobulin and T cell receptor nucleotide sequences," *Nucleic Acids Res.* vol. 34, D781-D784 (Jan. 1, 2006).
Goldberg, M.B. et al., "Transcriptional Regulation by Iron of a *Vibrio cholerae* Virulence Gene and Homology of the Gene to the *Escherichia coli* Fur System," *Journal of Bacteriology*, vol. 172:6863-6870 (1990).
Gregorevic, et al., "Systemic delivery of genes to striated muscles using adeno-associated viral vectors," *Nat Med.* Author Manuscript (16 pages); published in final form as *Nat Med.* (Aug. 2004; vol. 10(8):828-34. Epub Jul. 25, 2004).
Gurley et al., "Upstream Sequences Required for Efficient Expression of a Soybean Heat Shock Gene," *Mol. Cell. Biol.*, vol. 6:559-565 (1986).
Hermonat et al., "Use of adeno-associated virus as a mammalian DNA cloning vector: Transduction of neomycin resistance into mammalian tissue culture cells," *Proc. Natl. Acad. Sci. USA*, vol. 81:6466-6470 (1984).
Herz and Gerard, "Adenovirus-mediated transfer of low density lipoprotein receptor gene actutely accelerates cholesterol clearance in normal mice," *Proc. Natl. Acad. Sci. USA*, vol. 90:2812-2816 (1993).
Huber et al., "Retroviral-mediated gene therapy for the treatment of hepatocellular carcinoma: An innovative approach for cancer therapy," *Proc. Natl. Acad. Sci. USA*, vol. 88:8039-8043 (1991).
Invitrogen Corporation, Chapter 7, "Theory of Binding Data Analysis, Fluorescence Polarization Technical Resource Guide," Fourth Edition, pp. 1-18 (2006).
Jadhav, J.P., S. P. Govindwar, "Biotransformation of malachite green by *Saccharomyces cerevisiae* MTCC 463," *Yeast*, vol. 23, 315-323 (Mar. 2006).
Lemarchand et al., "Adenovirus-mediated transfer of a recombinant human α1-antitrypsin cDNA to human endothelial cells," *Proc. Natl. Acad. Sci. USA*, vol. 89:6482-6486 (1992).
Marks, K.M., M. Rosinov, G. P. Nolan, "In Vivo Targeting of Organic Calcium Sensors via Genetically Selected Peptides," *Chem Biol.*, vol. 11, 347-356 (Mar. 2004).
McLaughlin et al., "Adeno-Asqociated Virus General Transduction Vectors: Analysis of Proviral Structures," *J. Virol.*, vol. 62:1963-1973 (1988).
Miller et al., "N-terminal methionine-specific peptidase in *Salmonella typhimurium*," *Proc. Natl. Acad. Sci. USA*, vol. 84:2718-2722 (1987).
Miller, A.D., "Progress Toward Human Gene Therapy," *Blood, The Journal of the American Society of Hematology*, vol. 76:271-278 (1990).
Motulsky, H., "The GraphPad Guide to Analyzing Radioligand Binding Data," *GraphPad Software, Inc.*, pp. 1-19 (1996).
Mujumdar, R.B., L. A. Ernst, S. R. Mujumdar, C. J. Lewis, A. S. Waggoner, "Cyanine Dye Labeling Reagents: Sulfoindocyanine Succinimidyl Esters," *Bioconjug. Chem.* vol. 4, 105-111 (Mar.-Apr. 1993).
Neda et al., "Chemical Modification of an Ecotropic Murine Leukemia Virus Results in Redirective of Its Target Cell Specificity," *J Biol Chem.*, vol. 266:14143-14146 (1991).
Pack et al., "Tetravalent Miniantibodies with High Avidity Assembling in *Escherichia coli*," *J Mol Biol.*, vol. 246(1): 28-34 (1995).
Quantin et al., "Adenovirus as an expression vector in muscle cells in vivo," *Proc. Natl. Acad. Sci. USA*, vol. 89:2581-2584 (1992).
Roux et al., "A versatile and potentially general approach to the targeting of specific cell types by retroviruses: Application to the infection of human cells by means of major histocompatibility complex class I and class II antigens by mouse ecotropic murine leukemia virus-derived viruses," *Proc. Natl. Acad. Sci. USA*, vol. 86:9079-9083 (1989).
Sagawa, H. et al., "A tightly regulated expression system in *Escherichia coli* with SP6 RNA polymerase," *Gene*, vol. 168:37-41 (1996).
Sakata, et al., "Optical switching of dipolar interactions on proteins," *Proc. Natl. Acad. Sci. USA* vol. 102(13):4759-4764 (2005).
Samulski et al., "Helper-Free Stocks of Recombinant Adeno-Associated Viruses: Normal Integration Does Not Require Viral Gene Expression," *J. Virol.*, vol. 63:3822-3828 (1989).
Simeonov et al., "Blue-Flourescent Antibodies," *Science*, vol. 290, 307-313 (Oct. 13, 2000).
Sims, P.J., A. S. Waggoner, C. H. Wang, J. F. Hoffman, "Studies on the Mechanism by Which Cyanine Dyes Measure Membrane Potential in Red Blood Cells and Phosphatidylcholine Vesicles," *Biochemistry* vol. 13, 3315-3330 (Jul. 30, 1974).
Skerra, "Engineered protein scaffolds for molecular recognition," *J. Mol. Recognition* vol. 13:167-187 (2000).
Smith et al., "Molecular Engineering of the *Autographa californica* Nuclear Polyhedrosis Virus Genome: Deletion Mutations Within the Polyhedrin Gene," *J. Virol.*, vol. 46:584-593 (1983).
Swers et al., "Shuffled antibody libraries created by in vivo homologous recombination and yeast surface display," *Nucl. Acids. Res.* 32(3):e36, 8 pages (2004).
Tacal, O., L. Ozer, "Adduct-Forming Tendencies of Cationic Triarylmethane Dyes with Proteins: Metabolic and Toxicological Implications," *J. Biochem. Mol. Toxicol.* vol. 18, 253-256 (2004).
Takamatsu et al., "Expression of bacterial chloramphenicol acetyltransferase gene in tobacco plants mediated by TMV-RNA," *The EMBO Journal*, vol. 6(2):307-311 (1987).
Tanaka, T., M. N. Lobato, T. H. Rabbitts, "Single Domain Intracellular Antibodies: A Minimal Fragment for Direct In Vivo Selection of Antigen-specific Intrabodies," *J. Mol. Biol.*, vol. 331, 1109-1120 (Aug. 29, 2003).
Tratschin et al., "Genetic Analysis of Adeno-Associated Virus: Properties of Deletion Mutants Constructed In Vitro and Evidence for an Adeno-Associated Virus Replication Function," *J. Virol.*, vol. 51:611-619 (1984).
Tratschin et al., "A Human Parvovirus, Adeno-Associated Virus, as a Eucaryotic Vector: Transient Expression and Encapsidation of the Procaryotic Gene for Chloramphenicol Acetyltransferase," *Mol. Cell. Biol.*, vol. 4:2072-2081 (1984).
Tratschin et al., "Adeno-Associated Virus Vector for High-Frequency Integration, Expression, and Rescue of Genes in Mammalian Cells," *Mol. Cell. Biol.*, vol. 5:3251-3260 (1985).
Tsien, R.Y., "Building and breeding molecules to spy on cells and tumors," *FEBS Lett.* vol. 579, 927-932 (Feb. 7, 2005).

(56) References Cited

OTHER PUBLICATIONS van Beusechem et al., "Long-term expression of human adenosine deaminase in rhesus monkeys transplanted with retrovirus-infected bone-marrow cells," *Proc. Natl. Acad. Sci. USA*, vol. 89:7640-7644 (1992).
Wagner et al., "Influenza virus hemagglutinin HA-2 N-terminal fusogenic peptides augment gene transfer by transferrin-polylysine-DNA complexes: Toward a synthetic virus-like gene-transfer vehicle," *Proc. Natl. Acad. Sci. USA*, vol. 89:7934-7938 (1992).
Wilson et al., "Retrovirus-mediated transduction of adult hepatocytes," *Proc. Natl. Acad. Sci. USA*, vol. 85:3014-3018 (1988).
Yeast Display scFv Antibody Library User's Manual (Pacific Northwest National Laboratory, Richland, WA 99352), pp. 1-44 (2003).
Portmann et al., "Anti-Fluorescein Antibody of High Affinity and Restricted Heterogeneity as Characterized by Fluorescence Polarization and Quenching Equilibrium Techniques", Biochemical and Biophysical Research Communications, received Feb. 24, 1971, vol. 43, No. 1, pp. 207-212.
Iwaki et al., "Antibodies for Fluorescent Molecular Rotors", Biochemistry, 1993, 32, pp. 7589-7592.
Bird et al., "Single-Chain Antigen-Binding Proteins", downloaded from Science Magazine on Jul. 21, 2012, Oct. 21, 1988, vol. 242, pp. 423-426.
Huston et al., "Protein Engineering of Antibody Binding Sites: Recovery of Specific Activity in an Anti-Digoxin Single-Chain Fv Analogue Produced in *Escherichia coli*", Biochemistry, Proc. Natl. Acad. Sci., USA, Aug. 1998, vol. 85, pp. 5879-5883.
Adams, Stephen R., et al., "New Biarsentical Ligands and Tetracysteine Motifs for Protein Labeling in Vitro and in Vivo: Synthesis and Biological Applications," *J. Am. Chem. Soc.*, vol. 124, pp. 6063-6076 (2002).
Babendure, Jeremy R., et al., "Aptamers Switch on Fluorescence of Triphenylmethane Dyes," *J. Am. Chem.*, vol. 125, pp. 14716-14717 (2003).
Balint, Robert F. And James W. Larrick, "Antibody engineering by parsimonious mutagenesis," *Gene*, vol. 137, pp. 109-118 (1993).
Bark, Steven J. and Klaus M. Hahn, "Fluorescent Indicators of Peptide Cleavage in the Trafficking Compartments of Living Cells: Peptides Site-Specifically Labeled with Two Dyes," *Methods*, vol. 20, pp. 429-435 (2000).
Barker, Susan L. R., et al., "Cellular Applications of a Sensitive and Selective Fiber-Optic Nitric Oxide Biosensor Based on a Dye-Labeled Heme Domain of Soluble Guanylate Cyclase," *Anal. Chem.*, vol. 71, No. 9, pp. 2071-2075 (1999).
Barker, Susan L. R., et al., "Ratiometric and Fluorescence-Lifetime-Based Biosensors Incorporating Cytochrome c' and the Detection of Extra- and Intracellular Macrophage Nitric Oxide," *Anal. Chem.*, vol. 71 pp. 1767-1172 (1999).
Benhar, Itai, "Biotechnological applications of phage and cell display," *Biotechnology Advances*, vol. 19, pp. 1-33 (2001).
Berkner, Kathleen L., "Development of Adenovirus Vectors for the Expression of Heterologous Genes," *BioTechniques*, vol. 6, No. 7, pp. 616-629 (1988).
Binz, H. Kaspar, et al., Engineering novel binding proteins from nonimmunoglobulin domains, *Nature Biotechnology*, vol. 23, No. 10, pp. 1257-1268 (2005).
Boder, Eric T. and K. Dane Wittrup, Optimal Screening of Surface-Displayed Polypeptide Libraries, *Biotechnol. Prog.*, vol. 14, pp. 55-62 (1998).
Boder, Eric T. and K. Dane Wittrup, "Yeast Surface Display for Directed Evolution of Protein Expression, Affinity, and Stability," *Methods in Enzymology*, vol. 328, pp. 430-444 (2000).
Bradbury, Andrew, "Selecting by microdialysis," *Nature Biotechnology*, vol. 10, pp. 528-529 (2001).
Brisson, N., et al. "Expression of bacterial gene in plants by using a viral vector," *Nature*, vol. 310 pp. 511-514 (1984).
Broach, James R., et al. "Vectors for High-Level, Inducible Expression of Cloned Genes in Yeast," *Experimental Manipulation of Gene Expression*, pp. 83-117 (1983).
Brown, S.D., et al., The promoter for the procyclic acidic repetitive protein (PARP) genes of *Trypanosoma brucei* shares features with RNA polymerase I promoters, *Mol. Cell. Biol.*, vol. 12, No. 6 (1992).
Carrero, Jenny and Edward W. Voss, Jr., "Temperature and pH Dependence of Fluorescein Binding within the Monoclonal Antibody 9-40 Active Site as Monitored by Hydrostatic Pressure," *The Journal of Biological Chemistry*, vol. 271, No. 10, pp. 5332-5337 (1996).
Cepko, Constance and Warren Pear, "Detection of Helper Virus in Retrovirus Stocks," *Current Protocols in Molecular Biology*, unit 9.13.1-9.13.6 (1996).
Cepko, Constance and Warren Pear, "Retrovirus Infection of Cells In Vitro and In Vivo," *Current Protocols in Molecular Biology*, unit 9.14.1-9.14.6 (1996).
Cepko, Constance and Warren Pear, "Transduction of Genes Using Retrovirus Vectors," *Current Protocols in Molecular Biology*, unit 9.9.1-9.9.16 (2000).
Chamberlain, Chester and Klaus M. Hahn, "Watching Proteins in the Wild: Fluorescence Methods to Study Protein Dynamics in Living Cells," *Traffic*, vol. 1, pp. 755-762 (2000).
Chen, Gang, et al., "Isolation of high-affinity ligand-binding proteins by periplasmic expression with cytometric screening (PECS)," *Nature Biotechnoloy*, vol. 19, pp. 537-542 (2001).
Chowdhury, J. Roy, et al., "Long-Term Improvement of Hypercholesterolemia After ex Vivo Gene Therapy in LDLR-Deficient Rabbits," *Science*, vol. 254, pp. 1802-1805 (1991).
Colby, David W., et al., "Engineering Antibody Affinity by Yeast Surface Display," *Devices, Antibodies, and Vaccines*, vol. 18, pp. 348-358 (2004).
Coloma, M. Josefina and Sherie L. Morrison, "Design and production of novel tetravalent bispecific antibodies," *Nature Biotechnology*, vol. 15, pp. 159-163 (1997).
Coruzzi, Gloria, et al., "Tissue-specific and light-regulated expression of a pea nuclear gene encoding the small subunit of ribulose-1,5-biphosphate carboxylase," *The EMBO Journal*, vol. 3, No. 8, pp. 1671-1679 (1984).
Culp, Sandra J., et al., "Toxicity and metabolism of malachite green and leucomalachite green during short-term feeding to Fischer 344 rats and B6C3F$_1$ mice," *Chemico-Biological Interactions*, vol. 122, pp. 153-170 (1989).
Cunningham, Brian C. and James A. Wells, "High-Resolution Epitope Mapping of hGH-Receptor Interactions by Alanine-Scanning Mutagenesis," *Science*, vol. 244, pp. 1081-1085 (1989).
Cürten, Beate, et al., "Synthesis, Photophysical, Photochemical and Biological Properties of Caged GABA, 4 [[2H-1-Benzopyran-2-one-7amino-4-methoxy) carbonyl] amino] Butanoic Acid," *Photochemistry and Photobiology*, vol. 81, pp. 641-648 (2005).
Cwirla, Steven E., et al., "Peptides on Phage: A vast library of peptides for identifying ligands," *Proc. Natl. Acad. Sci.*, vol. 87, pp. 6378-6382 (1990).
Derossi, Daniele, et al., "Call Internalization of the Third Helix of the Antennapedia Homeodomain Is Receptor-independent," *The Journal of Biological Chemistry*, vol. 271, No. 30, pp. 18188-18193 (1996).
Derossi, Daniele, et al., "The Third Helix of the Antennapedia Homeodomain Translocates through Biological Membranes," *The Journal of Biological Chemistry*, vol. 269, No. 14, pp. 10444-10450 (1994).
Devlin, James J., et al., "Ransom Peptide Libraries: A Source of Specific Protein Binding Molecules," *Science*, vol. 249, pp. 404-406 (1990).
Dooley, Colette T., et al., "Imaging Dynamic Redox Changes in Mammalian Cells with Green Fluorescent Protein Indicators," *The Journal of Biological Chemistry*, vol. 279, No. 21, pp. 22284-22293 (2004).
Dubendorff, John W., and F. William Studier, "Controlling Basal Expression in an Inducible T7 Expression System by Blocking the Target T7 Promoter with *Iac* Repressor," *J. Miol. Biol.*, vol. 219, pp. 45-59 (1991).
Duckert, Peter, et al., "Prediction of preprotein convertase cleavage sites," *Protein Engineering, Design & Selection*, vol. 17, No. 1, pp. 107-112 (2004).

(56) References Cited

OTHER PUBLICATIONS

Duxbury, Debra Faye, "The Photochemistry and Photophysics of Triphenylmethane Dyes in Solid and Liquid Media," *Chem Rev.*, vol. 93, pp. 381-433 (1993).
Feldhaus, Michael J., et al., "Flow-cytometric isolation of human antibodies from a nonimmune *Saccharomyces cerevisae* surface display library," *Nature Biotechnology*, vol. 21, pp. 163-170 (2003).
Flotte, Terence R., et al., "Gene Expression from Adeno-associated Virus Vectors in Airway Epithelial Cells," *Am. J. Respir. Cell. Mol. Biol.*, vol. 7, pp. 349-356 (1992).
Fürstenburg, Alexandra, et al., "Ultrafast Excited-State Dynamics of DNA Fluorescent Intercalators: New Insight into the Fluorescence Enhancement Mechanism," *J. Am. Soc.*, vol. 128, pp. 7661-7669 (2006).
Giepmans, Ben N. G., et al., "The Flourescent Toolbox for Assessing Protein Location and Function," *Science*, vol. 312, pp. 217-224 (2006).
Goud, Bruno, et al., "Antibody-Mediated Binding of a Murine Ecotropic Moloney Retroviral Vector to Human Cells Allows Internalization But Not the Establishment of the Proviral State," *Virology*, vol. 163, pp. 251-254 (1988).
Graham, Frank L. and Ludvik Prevec, "Manipulation of Adenovirus Vectors," *Methods in Molecular Biology*, vol. 7, pp. 109-128 (1991).
Green, Maurice and Paul M. Loewenstein, "Autonomous Functional Domains of Chemically Synthesized Human Immunodeficiency Virus Tat *Trans*-Activator Protein," *Cell*, vol. 55, pp. 1179-1188 (1988).
Greener, Alan, et al., "An Efficient Random Mutagenesis Technique Using an *E.coli* Mutator Strain," *Molecular Biotechnology*, vol, 7, pp. 189-195 (1997).
Grodberg, Jennifer, et al., "Alanine scanning mutagenesis of human erythropoietin identifies four amino acids which are critical for biological activity," *Eur. J. Biochem.*, vol. 218, pp. 597-601 (1993).
Gustin, Kurt, et al., "Characterization of the Role of Individual Protein Binding Motifs within the Hepatitis B Virus Enhancer I on X Promoter Activity Using Linker Scanning Mutagenesis," *Virology*, vol. 193, pp. 653-660 (1993).
Hahn, Klaus M., et al., "A Calcium-sensitive Fluorescent Analog of Calmodulin Based on a Novel Calmodulin-binding Fluorophore," *The Journal of Biological Chemistry*, vol. 265, No. 33, pp. 20335-20345 (1990).
Headley, V., et al., "Expression of aerobactin genes by *Shigella flexneri* during extracellular and intracellular growth," *Infection and Immunity*, vol. 65, No. 2, pp. 818-821 (1997).
Hess, Samuel T., et al., "Fluorescence Photoconversion Kinetics in Novel Green Fluorescent Protein pH Sensors (pHluorins)," *J. Phys. Chem. B*, vol. 108, pp. 10138-10148 (2004).
Hochman, Jacob, et al., "An Active Antibody Fragment (Fv) Composed of the Variable Portions of Heavy and Light Chains," *Biochemistry*, vol. 12, No. 6, pp. 1130-1135 (1973).
Holt, Lucy J., et al. The use of recombinant antibodies in proteomics, *Current Opinion in Biotechnolgy*, vol. 11, pp. 445-449 (2000).
Hu, Wei-Gang, et al., "Humanization and mammalian expression of a murine monoclonal antibody against Venezuelan equine encephalitis virus," *Vaccine*, vol. 25, pp. 3210-3214 (2007).
Hunt, M.D., "Promoter and operator determinants for fur-mediated iron regulation in the bidirectional fepA-fes control region of the *Escherichia coli* enterobactin gene system," vol. 176, No. 13, pp. 3944-3955 (1994).
Hwu, Patrick, et al., Functional and Molecular Characterization of Tumor-Infiltrating Lymphocytes Transduced with Tumor Necrosis Factor-α0 cDNA for the Gene Therapy of Cancer in Humans, vol. 150, No. 9, pp. 4104-4115 (1993).
Ike, Yoshimasa, et al., "Solid phase synthesis of polynucleotides," *Nucleic Acids Research*, vol. 11, No. 2, pp. 477-488 (1983).
Iliades, Peter, et al., "Triabodies: single chain Fv fragments without a linker form trivalent trimers," *FEBS Letters*, vol. 409, pp. 437-441 (1997).

Inouye, Sumiko and Masayori Inouye, "Up-promoter mutations in the *lpp* gene of *Escherichia coli*," *Nucleic Acids Research*, vol. 13, No. 9 (1985).
Itakura, Keiichi, et al., Expression in *Escherichia coli* of a Chemically Synthesized Gene for the Hormone Somatostatin, *Science*, vol. 198, pp. 1056-1063 (1977).
Itakura, Keiichi, et al., "Synthesis and Use of Synthetic Oligonucleotides," *Ann. Rev. Biochem*, vol. 53, pp. 323-356 (1984).
Jones, Laurie J., et al., "Quenched BOPIDY Dye-Labeled Casein Substrates for the Assay of Protease Activity by Direct Fluorescence Measurement," *Analytical Biochemistry*, vol. 251, pp. 144-152 (1997).
Jones, Nicholas and Thomas Shenk, "Isolation of Adenovirus Type 5 Host Range Deletion Mutants Defective for Transformation of Rat Embryo Cells", *Cell*, vol. 17, pp. 683-689 (1979).
Jones, Peter T., et al., "Replacing the complementary-determining regions in a human antibody with those from a mouse," *Nature*, vol. 321, pp. 522-525 (1986).
Julan, Maryse Etienne, et al., The efficiency of cell targeting by recombinant retroviruses depends on the nature of the receptor and the composition of the artificial cell-virus linker, vol. 73, pp. 3251-3255 (1992).
Kay, Mark A., et al., "Hepatic Gene Therapy: Persistent Expression of Human α1-Antitrypsin in Mice after Direct Gene Delivery In Vivo," *Human Gene Therapy*, vol. 3, pp. 641-647 (1992).
Kerppola, Tom K., "Complementary methods for studies of protein interactions in living cells," *Nature Methods*, vol. 3, No. 12, pp. 969-971 (2006).
Kubin, R.F. and A.N. Fletcher, "Fluorescence Quantum Yields of Some Rhodamine Dyes," *Journal of Luminescence*, vol. 27, pp. 455-462 (1982).
Kunkel, Maya T., et al. "Spatio-temporal Dynamics of Protein Kinase B/Akt Signaling Revealed by a Genetically Encoded Fluorescent Reporter," *The Journal of Biological Chemistry*, vol. 280, No. 7, pp. 5581-5587 (2005).
Lowman, Henry B., et al., "Selecting High-Affinity Binding Proteins by Monovalent Phage Display," *Biochemistry*, vol. 30, pp. 10832-10838 (1991).
Magde, Douglas and Maurice W. Windsor, "Ficosecond Internal Conversion in Crystal Violet," *Chemical Physics Letters*, vol. 24, No. 1, pp. 144-148 (1974).
Marks, James D., et al., "By-passing Immunization Human Antibodies from V-gene Libraries Displayed on Phage," *J. Mol. Biol.*, vol. 222, pp. 581-597 (1991).
Martin, Brent R., et al., "Mammalian cell-based optimization of the biarsentical-binding tetracysteine motif for improved fluorescence and affinity," *Nature Biotechnology*, pp. 1-7 (2005).
Maynard, Jennifer, et al., "High-level bacterial secretion of single-chain afl T-cell receptors," *Journal of Immunological Methods*, vol. 306, pp. 51-67 (2005).
Miesenböck, Gero, et al., "Visualizing secretion and synaptic transmission with pH-sensitive green fluorescent proteins," *Nature*, vo. 394, pp. 192-195 (1998).
Miller, Lawrence W. and Virginia W. Cornish, "Selective chemical labeling of proteins in living cells," *Current Opinion in Chemical Biology*, vol. 9, pp. 56-61 (2005).
Mizuno, Masaaki, et al., "Basic Research for Interferon Gene Therapy against Malignant Glioma," *Neurol Surg.*, vol. 20, No. 5, pp. 551-560 (1992). Abstract.
Mizuno, Masaaki, et al., "Growth Inhibition of Glioma Cells by Liposome-mediated Cell Transfection with Tumor Necrosis Faxtor-α Gene," *Neurol Med Chir*, vol. 32, pp. 873-876 (1992).
Mulligan, Richard C., "The Basic Science of Gene Therapy," *Science*, vol. 260, pp. 926-932 (1993).
Mujtaba, S., et al., "Structure and acetyl-lysine recognition of the bromodomain," *Oncogene*, vol. 26, pp. 5521-5527 (2007).
Muzyczka, N., "Use of Adeno-Associated Virus as a General Transduction Vector for Mammalian Cells," *Current Topis in Microbiology and Immunology*, vol. 158, pp. 97-129 (1992).
Myers, Richard M., et al., "Fine Structure Genetic Analysis of a β-Globin Promoter," *Science*, vol. 232, pp. 613-618 (1986).
Nagashima, Mariko, et al., "Alanine-scanning Mutagenesis of the Epidermal Growth Factor-like Domains of Human Thrombomodulin

(56) References Cited

OTHER PUBLICATIONS

Identifies Critical Residues for Its Cofactor Activity," *The Journal of Biological Chemistry*, vol. 268, No. 4, pp. 2888-2892 (1993).

Narang, Saran A., "Tetrahedron Report No. 140 DNA Synthesis," *Tetrahedron*, vol. 39, No. 1, pp. 3-22 (1982).

Nygren, Jan, et al., "The Interactions Between the Fluorescent Dye Thiazole Orange and DNA," *Biopolymers*, vol. 46, pp. 39-51 (1998).

Ochsner, U.A., et al. "Role of the ferric uptake regulator of Pseudomonas aeruginosa in the regulation of siderophores and exotoxin A expression: purification and activity on iron-regulated promoters," *Journal of Bacteriology*, vol. 177, No. 24, pp. 7194-7201 (1995).

Patterson, George H., "Use of the Green Fluorescent Protein and Its Mutants in Quantitative Fluorescence Microscopy," *Biophysical Journal*, vol. 73, pp. 2782-2790 (1997).

Perez, F., et al., "Antennapedia homeobox as a signal for the cellular internalization and nuclear addressing of a small exogenous peptide," *Journal of Cell Science*, vol. 102, pp. 717-722 (1992).

Pertz, Olivier and Klaus M. Hahn, "Designing biosensors for Rho family proteins—deciphering the dynamics of Rho family GTPase activation in living cells," *Journal of Cell Science*, vol. 117, pp. 1313-1318 (2004).

Pertz, Olivier, et al., "Spatiotemporal dynamics of RhoA activity in migrating cells," *Journal of Cell Science*, vol. 440, pp. 1069-1072 (2006).

Prince, R.W., et al., "Regulation of toxA and regA by the *Escherichia coli fur* gene and identification of a Fur homologue in *Pseudomonas aeruginosa* PA103 and PA01," *Molecular Microbiology*, vol. 5, pp. 2823-2831 (1991).

Post, Penny L., et al., "A Genetically Engineered, Protein-based Optical Biosensor of Myosin II Regulatory Light Chain Phosphorylation," *The Journal of Biological Chemistry*, vol. 269, No. 17, pp. 12880-12887 (1994).

Post, Penny L., et al., "A Fluorescent Protein Biosensor of Myosin II Regulatory Light Chain Phosphorylation Reports a Gradient of Phosphorylated Myosin II in Migrating Cells," *Molecular Biology of the Cell*, vol. 6, pp. 1755- 1768 (1995).

Ramjiawan, Bram, et al., "Noninvasive Localization of Tumors by Immunofluorescence Imaging Using a Single Chain Fv Fragment of a Human Monoclonal Antibody with Broad Cancer Specificity," *Cancer*, vol. 89, No. 5, pp. 1134-1344 (2000).

Roberts, Bruce L, et al., "Directed evolution of a protein: Selection of potent neutrophil elastase inhibitors displayed on M13 fusion phage," *Proc. Natl. Acad. Sci.*, vol. 89, pp. 2429-2433 (1992).

Rosenfeld, Melissa A., et al., "Adenovirus-Mediated Transfer of a Recombinant α1-Antitrypsin Gene to the Lung Epithelium in Vivo," *Science*, vol. 252, pp. 431-434 (1991).

Rosenfeld, Melissa A., et al., "In Vivo Transfer of the Human Cystic Fibrosis Transmembrane Conductance Regulator Gene to the Airway Epithelium," *Cell*, vol. 68, pp. 143-155 (1992).

Ruf, Wolfram, et al., "Mutational Mapping of Functional Residues in Tissue Factor: Identification of Factor VII Recognition Determinants in Both Structural Modules of the Predicted Cytokine Receptor Homology Domain," *Biochemistry*, vol. 33, pp. 1565-1572 (1993).

Schmitt, M.P. and S.M. Payne, "Genetic analysis of the enterobactin gene cluster in *Shigella flexneri*,", *Journal of Bacteriology*, vol. 173, No. 2, pp. 816-824 (1991).

Scott, Jamie K. and George P. Smith, "Searching for Peptide Ligands with an Epitope Library," *Science*, vol. 249, pp. 386-390. (1990).

Sharon, Jacqueline and David Givol, "Preparation of Fv Fragment from the Mouse Myeloma XRPC-25 Immunoglobulin Possessing Anti-Dinitrophenyl Activity," *Biochemistry*, vol. 15, No. 7, pp. 1591-1594 (1976).

Siegel, Robert W., et al., "High efficiency recovery and epitope-specific sorting of an scFv yeast display library," *Journal of Immunological Methods*, vol. 286, pp. 141-153 (2004).

Silva, Gloria L., et al., "Experimental and Computational Investigation of Unsymmetrical Cyanine Dyes: Understanding Torsionally Responsive Fluorogenic Dyes," *J. Am. Chem. Soc.*, vol. 129, pp. 5710-5718 (2007).

Studier, F. William, et al., "Use of T7 RNA Polymerase to Direct Expression of Cloned Genes," *Methods in Enzymology*, vol. 185, pp. 60-89, 1990.

Sumner, James P., et al., "A fluorescent PEBBLE nanosensor for intracellular free zinc," *The Analyst*, vol. 127, pp. 11-16 (2002).

Svinarich, David M. and Sunil Palchaudhuri, "Regulation of the SLT-1A Toxin Operon by a Ferric Uptake Regulatory Protein in Toxinogenic Strains of *Shigella dysenteria* type 1," *Journal of Diarrhoeal Disease Research*, vol. 10, pp. 139-145 (1992).

Tempest, Philip R., et al., "Reshaping A Human Monoclonal Antibody to Inhibit human respiratory Syncytial Virus Infection In Vivo," *Biotechnology*, vol. 5, pp. 266-271 (1991).

Tirat, Aline, et al., "Evaluation of two novel tag-based labeling technologies for site-specific modification of proteins," *Int. J. Biol. Macromol.*, vol. 39, pp. 66-76 (2006).

Viac, J., et al., An Immunoelectron Microscopic Localization of Wart Associated Antigens Present in Human Papilloma Virus (HPV) Infected Cells, *The Journal of Investigative Dermatology*, vol. 70, No. 5, pp. 263-266 (1978).

Wang, Su and Steven B. Vik, "Single Amino Acid Insertions Probe the a Subunit of the *Escherichia coli* $F_1F_0$-ATP Synthase," *The Journal of Biological Chemistry*, vol. 269, No. 4, pp. 3095-3099 (1993).

Wagner, Peter, et. al., "Covalent Immobilization of Native Biomolecules onto Au(111) via N-Hydroxysuccinimide Ester Functionalized Self-Assembled Monolayers for Scanning Probe Microscopy," *Biophysical Journal*, vol. 70, pp. 2052-2066 (1996).

Ward, E. Sally, et al., "Binding activities of a repertoire of single immunoglobulin variable domains secreted from *Escherichia coli,*" *Nature*, vol. 341, pp. 544-546 (1989).

Wiseman, Paul W., et al., "Spatial mapping of integrin interactions and dynamics during cell migration by Image Correlation Microscopy," *Journal of Cell Science*, vol. 117, pp. 5521-5534 (2004).

Yao, Jie, et al. "Dynamics of heat shock factor association with native gene loci in living cells," *Nature*, vol. 442, pp. 1050-1053 (2006).

Zhang, Jin, et al., "Genetically encoded reporters of protein kinase A activity reveal impact of substrate tethering," *PNAS*, vol. 98, No. 25, pp. 14997-15002 (2001).

\* cited by examiner

FIGURE 1A

SEQ ID NO: 1

```
   1  CATTT TCAAT TAAGA TGCAG TTACT TCGCT GTTTT TCAAT ATTTT CTGTT
      GTAAA AGTTA ATTCT ACGTC AATGA AGCGA CAAAA AGTTA TAAAA GACAA

51  ATTGC TTCAG TTTTA GCACA GGAAC TGACA ACTAT ATGCG AGCAA ATCCC
      TAACG AAGTC AAAAT CGTGT CCTTG ACTGT TGATA TACGC TCGTT TAGGG

101  CTCAC CAACT TTAGA ATCGA CGCCG TACTC TTTGT CAACG ACTAC TATTT
      GAGTG GTTGA AATCT TAGCT GCGGC ATGAG AAACA GTTGC TGATG ATAAA

151  TGGCC AACGG GAAGG CAATG CAAGG AGTTT TTGAA TATTA CAAAT CAGTA
      ACCGG TTGCC CTTCC GTTAC GTTCC TCAAA AACTT ATAAT GTTTA GTCAT

201  ACGTT TGTCA GTAAT TGCGG TTCTC ACCCC TCAAC AACTA GCAAA GGCAG
      TGCAA ACAGT CATTA ACGCC AAGAG TGGGG AGTTG TTGAT CGTTT CCGTC

251  CCCCA TAAAC ACACA GTATG TTTTT AAGGA CAATA GCTCG ACGAT TGAAG
      GGGGT ATTTG TGTGT CATAC AAAAA TTCCT GTTAT CGAGC TGCTA ACTTC

301  GTAGA TACCC ATACG ACGTT CCAGA CTACG CTCTG CAGGC TAGTC GTGGT
      CATCT ATGGG TATGC TGCAA GGTCT GATGC GAGAC GTCCG ATCAC CACCA

351  GCTGG TTCTG GTGGT GGTGG TTCTG GTGGT GGTGG TTCTG CTAGC CAGGT
      CGACC AAGAC CACCA CCACC AAGAC CACCA CCACC AAGAC GATCG GTCCA

401  GCAGC TGGTG GAATC TGAGG CTGAG GTGAA GAAGC CTGGG TCCTC GGTGA
      CGTCG ACCAC CTTAG ACTCC GACTC CACTT CTTCG GACCC AGGAG CCACT

451  AGGTC TCCTG CAAGG CTTCT GGAGG CACCT TCAGC AGCTA TGCTA TCAGC
      TCCAG AGGAC GTTCC GAAGA CCTCC GTGGA AGTCG TCGAT ACGAT AGTCG

501  TGGGT GCGAC AGGCC CCTGG ACAAG GGCTT GAGTG GATGG GAGGG ATCAT
      ACCCA CGCTG TCCGG GGACC TGTTC CCGAA CTCAC CTACC CTCCC TAGTA

551  CCCTA TCTTT GGTAC AGCAA ACTAC GCACA GAAGT TCCAG GGCAG AGTCA
      GGGAT AGAAA CCATG TCGTT TGATG CGTGT CTTCA AGGTC CCGTC TCAGT

601  CGATT ACCGC GGACG AATCC ACGAG CACAG CCTAC ATGGA GCTGA GCAGC
      GCTAA TGGCG CCTGC TTAGG TGCTC GTGTC GGATG TACCT CGACT CGTCG

651  CTGAG ATCTG AGGAC ACGGC CGTGT ATTAC TGTGT CTTGT TGGAT ACAAC
      GACTC TAGAC TCCTG TGCCG GCACA TAATG ACACA GAACA ACCTA TGTTG

701  TATGG TTACG GGATA CTACT TTGAC TACTG GGGCC AGGGA ACCCT GGTCA
      ATACC AATGC CCTAT GATGA AACTG ATGAC CCCGG TCCCT TGGGA CCAGT

751  CCGTC TCCTC AGGAA TTCTA GGATC CGGTG GCGGT GGCAG CGGCG GTGGT
      GGCAG AGGAG TCCTT AAGAT CCTAG GCCAC CGCCA CCGTC GCCGC CACCA

801  GGTTC CGGAG GCGGC GGTTC TAATT TTATG CTGCA TCAGC CCTCC TCAGC
      CCAAG GCCTC CGCCG CCAAG ATTAA AATAC GACGT AGTCG GGAGG AGTCG

851  GTCTG GGACC CCTGG GCAGA GCGTC ACCAT CTCTT GTTCT GGAAG CGGCT
      CAGAC CCTGG GGACC CGTCT CGCAG TGGTA GAGAA CAAGA CCTTC GCCGA

901  CGAAC ATCGG AAACA ATAAA GTAAA CTGGT ACCAG CAGCT CCCAG GAACG
      GCTTG TAGCC TTTGT TATTT CATTT GACCA TGGTC GTCGA GGGTC CTTGC

951  GCCCC CAAAC TCCTC ATCTA TAGTA ATAAT CAGCG GCCCT CAGGG GTCCC
      CGGGG GTTTG AGGAG TAGAT ATCAT TATTA GTCGC CGGGA GTCCC CAGGG

1001  TGACC GATTC TCTGG CTCCA AGTCT GGCAC CTCAG CCTCC CTGGC CATCA
      ACTGG CTAAG AGACC GAGGT TCAGA CCGTG GAGTC GGAGG GACCG GTAGT

1051  GTGGG CTCCA GTCTG AGGAT GAGGC TGATT ATTAC TGTGC AGCAT GGGAT
      CACCC GAGGT CAGAC TCCTA CTCCG ACTAA TAATG ACACG TCGTA CCCTA

1101  GACAG CCTGA ATGGT TATGT CTTCG GAACT GGGAC CAAGC TCACC GTCCT
      CTGTC GGACT TACCA ATACA GAAGC CTTGA CCCTG GTTCG AGTGG CAGGA

1151  ATCCG GAATT CTAGA ACAAA AGCTT ATTTC TGAAG AAGAC TTGTA ATAGC
      TAGGC CTTAA GATCT TGTTT TCGAA TAAAG ACTTC TTCTG AACAT TATCG

1201  TCGGC GGCCG CATCG AGATC T
      AGCCG CCGGC GTAGC TCTAG A
```

FIGURE 1B

SEQ ID NO: 2

```
  1 MQLLRCFSIF SVIASVLAQE LTTICEQIPS PTLESTFYSL STTTILANGK
 51 AMQGVFEYYK SVTFVSNCGS HPSTTSKGSP INTQYVFKDN SSTIEGRYPY
101 DVPDYALQAS GGGSEGGGS GGGGSASQVQ LVESEAEVKK PGSSVKVSCK
151 ASGGTFSSYA ISWVRQAPGQ GLEWMGIIP LFGTANYAQK FQGRVTITAD
201 ESTSTAYMEL SSLRSEDTAV YYCVLLDTTM VTGYYFDYWG QGTLVTVSSG
251 ILGSGGGGSG GGGSGGGGSN FMLTQPPSAS GTPGQSVTIS CSGSGSNIGN
301 NKVNWYQQLP GTAPKLLIYS NNQRPSGVPD RFSGSKSGTS ASLAISGLQS
351 EDEADYYCAA WDDSLNGYVF GTGTKLTVLS GILEQKLISE EDL
```

FIGURE 1D

```
                                    Aga2p signal peptide
                         ─────────────────────────────────────────
                                    AGA2
                         ─────────────────────────────────────────
  1   CATTT TCAAT TAAGA TGCAG TTACT TCGCT GTTTT TCAAT ATTTT CTGTT
      GTAAA AGTTA ATTCT ACGTC AATGA AGCGA CAAAA AGTTA TAAAA GACAA Aga2p signal peptide
      ───────────────────
                                    AGA2
      ───────────────────────────────────────────────────────────
 51   ATTCC TTCAG TTTTA GCACA GGAAC TGACA ACTAT ATGCG AGCAA ATCCC
      TAACG AAGTC AAAAT CGTGT CCTTG ACTGT TGATA TACGC TCGTT TAGGG AGA2
      ───────────────────────────────────────────────────────────
101   CTCAC CAACT TTAGA ATCGA CGCCG TACTC TTTGT CAACG ACTAC TATTT
      GAGTG GTTGA AATCT TAGCT GCGGC ATGAG AAACA GTTGC TGATG ATAAA AGA2
      ───────────────────────────────────────────────────────────
151   TGGCC AACGG GAAGG CAATG CAAGG AGTTT TTGAA TATTA CAAAT CAGTA
      ACCGG TTGCC CTTCC GTTAC GTTCC TCAAA AACTT ATAAT GTTTA GTCAT AGA2
      ───────────────────────────────────────────────────────────
201   ACGTT TGTCA GTAAT TGCGG TTCTC ACCCC TCAAC AACTA GCAAA GGCAG
      TGCAA ACAGT CATTA ACGCC AAGAG TGGGG AGTTG TTGAT CGTTT CCGTC Linker
                    AGA2                      ──────────────  Xa
      ─────────────────────────────────────   ──────────────────
251   CCCCA TAAAC ACACA GTATG TTTTT AAGGA CAATA GCTCG ACGAT TGAAG
      GGGGT ATTTG TGTGT CATAC AAAAA TTCCT GTTAT CGAGC TGCTA ACTTC Xa                             Linker
      ──────                  ───────────────────
               HA tag
      ─────────────────────
301   GTAGA TACCC ATACG ACGTT CCAGA CTACG CTCTG CAGGC TAGTG GTGGT
      CATCT ATGGG TATGC TGCAA GGTCT GATGC GAGAC GTCCG ATCAC CACCA FR1
             Linker                                 ───────────
      ───────────────────                            IGHV1-69
                                                    ───────────
351   GGTGG TTCTG GTGGT GGTGG TTCTG GTGGT GGTGG TTCTG CTAGC CAGGT
      CCACC AAGAC CACCA CCACC AAGAC CACCA CCACC AAGAC GATCG GTCCA FR1
      ───────────────────────────────────────────────────────────
                                    IGHV1-69
      ───────────────────────────────────────────────────────────
401   GCAGC TGGTG GAATC TGAGG CTGAG GTGAA GAAGC CTGGG TCCTC GGTGA
      CGTCG ACCAC CTTAG ACTCC GACTC CACTT CTTCG GACCC AGGAG CCACT FR1
      ───────────────────────────────────────
                                                         CDR1
                   IGHV1-69                          ───────────
      ───────────────────────────────
451   AGGTC TCCTG CAAGG CTTCT GGAGG CACCT TCAGC AGCTA TGCTA TCAGC
      TCCAG AGGAC GTTCC GAAGA CCTCC GTGGA AGTCG TCGAT ACGAT AGTCG FR2
      ──────────────────────────────────────────────────
                                                         CDR2
                                                       ─────────
                IGHV1-69
      ───────────────────────────────
501   TGGGT GCGAC AGGCC CCTGG ACAAG GGCTT GAGTG GATGG GAGGG ATCAT
      ACCCA CGCTG TCCGG GGACC TGTTC CCGAA CTCAC CTACC CTCCC TAGTA CDR2
      ──────────────────────────────                         FR3
                                                        ────────
                   IGHV1-69
      ───────────────────────────────
551   CCCTA TCTTT GGTAC AGCAA ACTAC GCACA GAAGT TCCAG GGCAG AGTCA
      GGGAT AGAAA CCATG TCGTT TGATG CGTGT CTTCA AGGTC CCGTC TCAGT
```

FIGURE 1D (cont)

```
                                                  FR3
                                  IGHV1-69
    601  CGATT ACCGC GGACG AATCC ACGAG CACAG CCTAC ATGGA GCTGA GCAGC
         GCTAA TGGCG CCTGC TTAGG TGCTC GTGTC GGATG TACCT CGACT CGTCG
                                     FR3
                      IGHV1-69                             D5-18
    651  CTGAG ATCTG AGGAC ACGGC CGTGT ATTAC TGTGT CTTGT TGGAT ACAAC
         GACTC TAGAC TCCTG TGCCG GCACA TAATG ACACA GAACA ACCTA TGTTG
             D5-18                     JH4
    701  TATGG TTACG GGATA CTACT TTGAC TACTG GGGCC AGGGA ACCCT GGTCA
         ATACC AATGC CCTAT GATGA AACTG ATGAC CCCGG TCCCT TGGGA CCAGT
            JH4                        Linker
    751  CCGTC TCCTC AGGAA TTCTA GGATC CGGTG GCGGT GGCAG CGGCG GTGGT
         GGCAG AGGAG TCCTT AAGAT CCTAG GCCAC CGCCA CCGTC GCCGC CACCA
                         Linker                       FR1
                                                IGLV1-44
    801  GGTTC CGGAG GCGGC GGTTC TAATT TTATG CTGAC TCAGC CCCCC TCAGC
         CCAAG GCCTC CGCCG CCAAG ATTAA AATAC GACTG AGTCG GGGGG AGTCG
                            FR1                         CDR1
                                  IGLV1-44
    851  GTCTG GGACC CCTGG GCAGA GCGTC ACCAT CTCTT GTTCT GGAAG CGGCT
         CAGAC CCTGG GGACC CGTCT CGCAG TGGTA GAGAA CAAGA CCTTC GCCGA
                  CDR1                       FR2
                                 IGLV1-44
    901  CCAAC ATCGG AAACA ATAAA GTAAA CTGGT ACCAG CAGCT CCCAG GAACG
         GCTTG TAGCC TTTGT TATTT CATTT GACCA TGGTC GTCGA GGGTC CTTGC
                         FR2                            FR3
                                      CDR2
                               IGLV1-44
    951  GCCCC CAAAC TCCTC ATCTA TAGTA ATAAT CAGCG GCCCT CAGGG GTCCC
         CGGGG GTTTG AGGAG TAGAT ATCAT TATTA GTCGC CGGGA GTCCC CAGGG
                                    FR3
                                   IGLV1-44
   1001  TGACC GATTC TCTGG CTCCA AGTCT GGCAC CTCAG CCTCC CTGGC CATCA
         ACTGG CTAAG AGACC GAGGT TCAGA CCGTG GAGTC GGAGG GACCG GTAGT
                                    FR3
                                                       CDR3
                                 IGLV1-44
   1051  GTGGG CTCCA GTCTG AGGAT GAGGC TGATT ATTAC TGTGC AGCAT GGGAT
         CACCC GAGGT CAGAC TCCTA CTCCG ACTAA TAATG ACACG TCGTA CCCTA
                   CDR3
                                                JL
                         IGLV1-44
   1101  GACAG CCTGA ATGGT TATGT CTTCG GAACT GGGAC CAAGC TCACC GTCCT
         CTGTC GGACT TACCA ATACA GAAGC CTTGA CCCTG GTTCG AGTGG CAGGA
              JL                       c-myc tag
   1151  ATCCG GAATT CTAGA ACAAA AGCTT ATTTC TGAAG AAGAC TTGTA ATAGC
         TAGGC CTTAA GATCT TGTTT TCGAA TAAAG ACTTC TTCTG AACAT TATCG
   1201  TCGGC GGCCG CATCG AGATC T
         AGCCG CCGGC GTAGC TCTAG A
```

FIGURE 2
The ligand-dye complex of wherein the dye has the general structure A-B=A'
wherein A is selected from
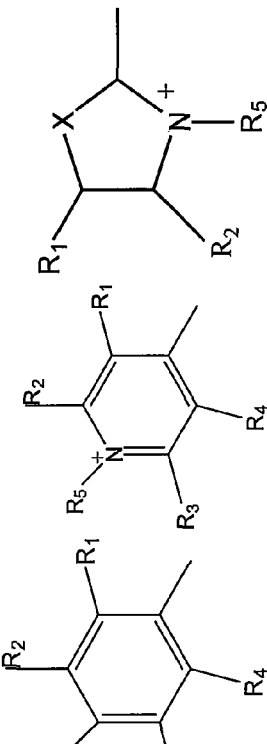
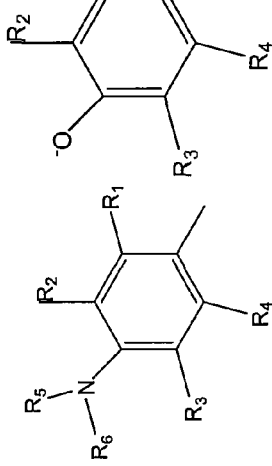
and,
wherein A' is selected from
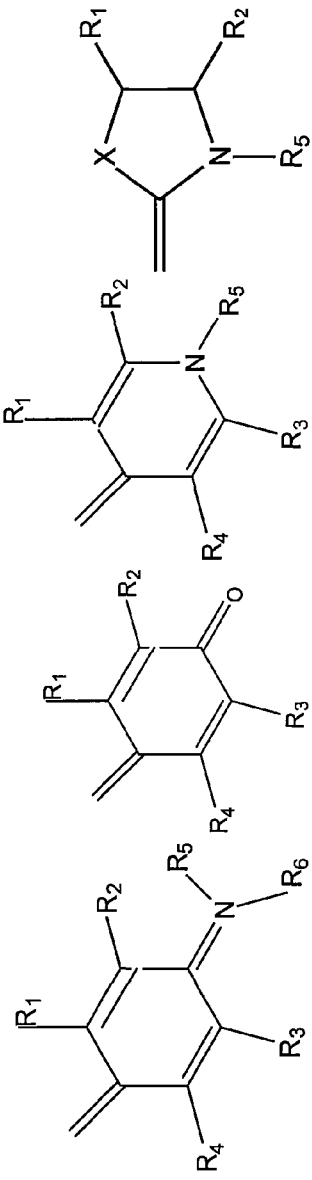
and, wherein B is
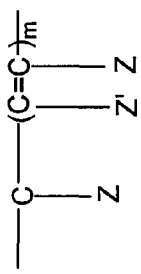

FIGURE 8

```
>HL1-TO1
QVQLVESEAEVKKPGSSVKVSCKASGGTFSSYAISWVRQAPGQGLEWMGGIIPIFGTANYAQKFQGRVTI
TADESTSTAYMELSSLRSEDTAVYYCVLLDTTMVTGYYFDYWGQGTLVTVSSGILGSGGGGSGGGGSGGG
GSNFMLTQPPSASGTPGQSVTISCSGSGSNIGNNKVNWYQQLPGTAPKLLIYSNNQRPSGVPDRFSGSKS
GTSASLAISGLQSEDEADYYCAAWDDSLNGYVFGTGTKLTVL

>HL2-TO1
QVQLQQGGAGLLKPSETLSLTCGVYGGSFSGYYWSWIRQSPGKGLEWIGEINHSGSANYNPSVKSRVTIS
VDTSKNQFSLQLSSVTAADTAVYYCARDRAVLTGEGWYFDLWGRGTLVTVSSGILGSGGGGSGGGGSGGG
GSSYELTQPPSVSVSPGQTASITCSGDKLGDKYTCWYQQKPGQSPVLVLYEDTKRPSGIPERFSGSNSGN
TATLTISRVEAGDEADYYCQLWDSSSDHYVFGSGTKLTVL

>HL1.0.1-TO1
QVQLVESEAEVKKPGSSVKVSCKASGGTFSSYAISWVRQAPGQGLEWMGGTIPIFGTADYAQEFQGRVTI
TTDESTSTAYMELSGLRSEDTAVYYCVLLGTTMVTGHYFDYWGQSTLVTVSSGILGSGGGGSGGGGSGGG
GSNFMLTQPPSASGTPGQSVTISCSGSGSNIGNNKVNWYQQLPGTAPKLLIYSNNQRPSGVPDRFSGSKS
GTSASLAISGLQSEDEADYYCAAWDDGLSGYVFGTGTKLTVL

>HL1.1-TO1
QVQLVESEAEVKKPGSSVKVSCKASGGTPSSYAISWVRQAPGQGLEWMGGTIPIFGTANYAQKFQGRVTI
TADESTSTAYMELSSLRSEDTAVYYCVLLGITMVTGYYFDYWGQGTLVTVSSGILGSGGGGSGGGGSGGG
GSNFTLTQFPSASGTPGQSVTISCSGSGSNIGNNKVNWYQQLPGTAPKLLIYSNNQRPSGVPDRFSGSXS
GTSASLAISGLQSEDEADYYCAAWDDSLNGYVFGTGTKLTVL

>HL4-MG
QVQLVESEGGLVQPGGSLRLSCAASGFTFSSYBMNWVRQAPGKGLEWVSRIDGDGSSTNYADSVKGRFTI
SRDNAKSTLYLQMNSLRAEDTAVYYCTRARYPGSVSPYGMDVWGQGTTVTVSSGILGSGGGGSGGGGSGG
GGSDIRVTQSPSSVSASVGDRVTISCRASQGIATWLGWYQQKPGKPPQLLIYSASTLQTGVPSRFSGSGS
GTDFTLTISSLQPEDVATYYCQEGSTFPLTFGGGTKVDIKSGILEQKLISEEDL

>L5-MG
SASTGSPDSWQQGTLVTVSSGILGSGGGGSGGGGSGGGGSQAVVTQEPSVTVSPGGTVILTCGSSTGAVT
SGHYANWFQQKPGQAPRALIFETDKKYSWTFGRFSGSLLGAKAALTISDAQPEDEAEYYCLLSDVDGYLF
GGGTQLTVLSGILEQKLISEEDL

>H6-MG
QVQLQESGPGLVKPSETLSLTCTVSGASISSSITYYNGWIRQPFGKGPEWIGSMYYSGRTYYNPALKSRVT
ISPDKSKNQFFLKLTSVTAADTAVYYCARSGPTHYYDNSGPIPSDEYFQHWGQGTLVTVSSGILGSGGGG
SGGGGSGGGGLQEF

>HL7-MG
QVQLQQNDAGLVKPSQTLSLTCAISGDSVSSNSAAWNWIRQSPSRGLENPGRTYYRSKWQNNYALSVQGR
ITINPDTSNKQFSLQLDSMTPEDTGVTYCTRGGGSLDYWGGGTLVTVSSGSASAPTGILGSGGGGSGGGG
SGGGGSSYELTQPPSVSVSPGQTATITCSGDENGDKYAYWYQQKPGQAPVLVIYKDSERPSGIPERFSGS
SSGTTVTLTISGVQAEDEADYYCQSADSSGTSVVFGGGTKVTVLSGILEQKLISEEDL

>H8-MG
QVQLQQSGPGLVRPSQTLSLTCAISGDSVPMNGASWNWIRLSPSRGLEWLGRTHYSSRWYHDYAFFVKSR
ITIKVDTSETQVSLQLDSVTPDDTGVYYCARESQRRGWFDLWGQGTLVTVSQEF

>HL9-MG
QVQLQQSGPGRVKPSQTLSLTCDISGDSVSSNSVAWNWIRQSPSRGLEWLGRTYYRSKWINSYGPFVRSR
ITINPDTSKNQFSLQLNSVTPEDTAVYYCATMNNSGYDRSSGHNYGMDVWGQGTTVTVSSGSASAPTGIL
GSGGGGSGGGGSGGGGSSYELTQPPSVSVSPGQTARITCSGDALPKQYTYWYQQKAGQAPVLVIYKDTER
PSGIPERPSGTSSGTTVTLTISGVQAEDEADYYCQSADSSGSYFFGGGTKVTVLSGILEQKLISEEDL
```

FIGURE 9

| Fluorogen[a] | Fluorogen activating protein | scFv format | scFv size (kDa) | Excitation maximum (nm) | Emission maximum (nm) | Cell surface $K_D$ (nM) | Solution $K_D$ (nM) | Extinction coefficient (M$^{-1}$cm$^{-1}$) | Quantum yield ($\Phi$) | Fluorescence enhancement |
|---|---|---|---|---|---|---|---|---|---|---|
| TO1-2p | HL1-TO1 | $V_H$-$V_L$ | 26.1 | 510 | 527 | 360 | | | | |
| $\varepsilon$ = 58,000 M$^{-1}$cm$^{-1}$ | HL2-TO1 | $V_H$-$V_L$ | 26.3 | 516 | 550 | 600 | | | | |
| at 504 nm | HL1.0.1-TO1 | $V_H$-$V_L$ | 25.9 | 509 | 530 | 3.1 | 1.7 | 60,000 | 0.47 | 2,600 |
| MG-2p | HL4-MG | $V_H$-$V_L$ | 26.1 | 629 | 649 | 3.2 | 590 | 133,000 | 0.16 | 15,700 |
| $\varepsilon$ = 74,250 M$^{-1}$cm$^{-1}$ | L5-MG | $V_L$ | 11.5 | 640 | 668 | 1.2 | 320 | 103,000 | 0.048 | 4,100 |
| at 607 nm | H6-MG | $V_H$ | 14.4 | 635 | 656 | 7.5 | 38 | 105,000 | 0.25 | 18,000 |
| | HL7-MG | $V_H$-$V_L$ | 26.5 | 619 | 647 | 0.58 | | | | |
| | H8-MG | $V_H$ | 13.6 | 626 | 646 | 9.4 | | | | |
| | HL9-MG | $V_H$-$V_L$ | 27.9 | 621 | 650 | 0.74 | | | | |

[a]Data for fluorogen at absorbance maximum. Spectral and binding properties determined for fluorogen bound to indicated fluorogen activating protein.

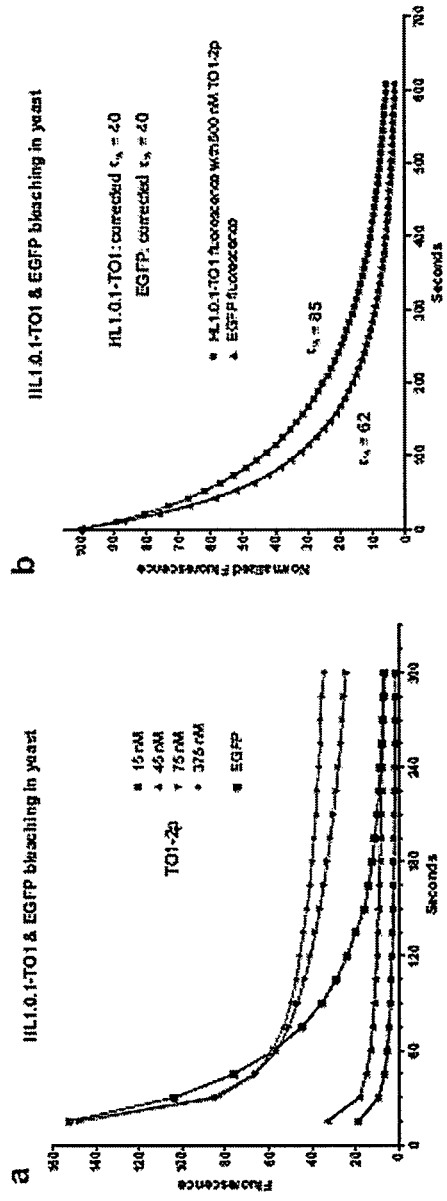
FIGURE 16A
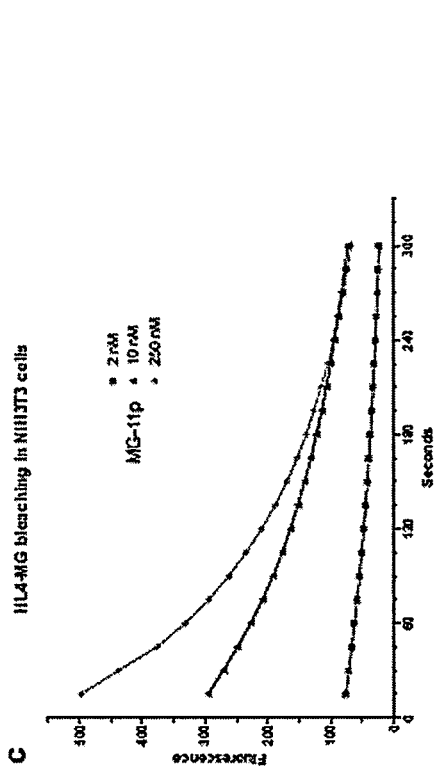
FIGURE 16B
FIGURE 16C

OPTICAL BIOSENSORS

PRIORITY

This application is a U.S. National Stage Application based on International Application Serial No. PCT/US2008/051962 filed 24 Jan. 2008 and claims the benefit of U.S. Provisional Application Ser. No. 60/897,120 filed Jan. 24, 2007 and U.S. Provisional Application Ser. No. 61/013,098 filed Dec. 12, 2007, the contents of each of which are incorporated by reference in their entirety.

GOVERNMENT SUPPORT

The subject invention was made in part with support from the U.S. Government under Grant Number 1-U54-RR022241 awarded by the NIH. Accordingly, the U.S. Government has certain rights in this invention.

REFERENCE TO SEQUENCE LISTING

This Application contains a Sequence Listing in accordance with 37 C.F.R. §§1.821-1.825. The material in the Sequence Listing text file is herein incorporated by reference in its entirety in accordance with 37 C.F.R. §1.52(e)(5). The Sequence Listing, entitled "070683PCTUS Jul. 24, 2012 ST25.txt", contains one 111 Kb text file and was created on Jul. 22, 2009 and amended on Jul. 24, 2012 using an IBM-PC machine format.

BACKGROUND

The identification, analysis and-monitoring of biological analytes (such as polypeptides, polynucleotides, polysaccharides and the like) or environmental analytes (such as pesticides, biowarfare agents, food contaminants and the like) has become increasingly important for research and industrial applications. Conventionally, analyte detection systems are based on analyte-specific binding between an analyte and an analyte-binding receptor. Such systems typically require complex multicomponent detection systems (such as ELISA sandwich assays) or electrochemical detection systems, or require that both the analyte and the receptor are labeled with detection molecules (for example fluorescence resonance energy transfer or FRET systems).

One method for detecting analyte-binding agent interactions involves a solid phase format employing a reporter labeled analyte-binding agent whose binding to or release from a solid surface is dependent on the presence of analyte. In a typical solid-phase sandwich type assay, for example, the analyte to be measured is an analyte with two or more binding sites, allowing analyte binding both to a receptor carried on a solid surface, and to a reporter-labeled second receptor. The presence of analyte is detected based on the presence of the reporter bound to the solid surface.

A variety of devices for detecting analyte/receptor interactions are also known. The most basic of these are purely chemical/enzymatic assays in which the presence or amount of analyte is detected by measuring or quantitating a detectable reaction product, such as gold immunoparticles. Analyte/receptor interactions can also be detected and quantitated by radiolabel assays. Quantitative binding assays of this type involve two separate components: a reaction substrate, e.g., a solid-phase test strip and a separate reader or detector device, such as a scintillation counter or spectrophotometer. The substrate is generally unsuited to multiple assays, or to miniaturization, for handling multiple analyte assays from a small amount of body fluid sample.

Biosensor devices integrate the assay substrate and detector surface into a single device. One general type of biosensor employs an electrode surface in combination with current or impedance measuring elements for detecting a change in current or impedance in response to the presence of a ligand-receptor binding event. This type of biosensor is disclosed, for example, in U.S. Pat. No. 5,567,301. Gravimetric biosensors employ a piezoelectric crystal to generate a surface acoustic wave whose frequency, wavelength and/or resonance state are sensitive to surface mass on the crystal surface. The shift in acoustic wave properties is therefore indicative of a change in surface mass, e.g.; due to a ligand-receptor binding event. U.S. Pat. Nos. 5,478,756 and 4,789,804 describe gravimetric biosensors of this type. Biosensors based on surface plasmon resonance (SPR) effects have also been proposed, for example, in U.S. Pat. Nos. 5,485,277 and 5,492,840. These devices exploit the shift in SPR surface reflection angle that occurs with perturbations, e.g., binding events, at the SPR interface. Finally, a variety of biosensors that utilize changes in optical properties at a biosensor surface are known, e.g., U.S. Pat. No. 5,268,305.

All of the above analyte detection systems are characterized by the requirement for a secondary detection system to monitor interactions between the analyte and the receptor. A need still exists for a direct, homogeneous assay for analyte detection, i.e., one that may be used in living cells, which will be more versatile in terms of the range of applications and devices with which it can be used.

SUMMARY

Provided are biosensors, compositions comprising biosensors, and methods of using biosensors in living cells and organisms. The biosensors are able to be selectively targeted to certain regions or structures within a cell. The biosensors may provide a signal when the biosensor is targeted and/or in response to a property of the cell or organism such as membrane potential, ion concentration or enzyme activity.

In one embodiment, the biosensors comprise at least two components; (1) a selectivity component capable of interacting with a target molecule of interest and a (2) reporter molecule that produces a detectable change in signal upon interaction of the selectivity component with the target molecule. The reporter molecule may be covalently linked to the selectivity component, or it may be able to noncovalently interact with the selectivity component. In certain embodiments, the selectivity component is a ligand of a reporter molecule such as a dye.

The selectivity component, which in certain embodiments is expressed within the cell or organism to be analyzed, may be a polypeptide (including antibodies and non-antibody receptor molecules, and fragments and variants thereof), polynucleotide (including aptamers), template imprinted material, or organic and inorganic binding element. The selectivity component may be biologically selected to favor reporter molecule binding and sensitivity. The selectivity component may bind directly to a target molecule, or be fused to a targeting moiety (such as a protein) that binds to the target molecule.

The reporter molecule may be sensitive to changes in the environment, including, for example, pH sensitive molecules, polarity sensitive molecules, restriction sensitive molecules, or mobility sensitive molecules. The reporter molecule may, in embodiments where in it noncovalently interacts with the selectivity component, comprise an additional moiety that binds to the selectivity component.

The biosensor may optionally comprise a chemical handle suitable to facilitate isolation, immobilization, identification, or detection of the biosensors and/or which increases the solubility of the biosensors.

In one example, the selectivity component is a single chain antibody (scFv) that comprises amino acid sequences that lead to specific binding of certain reporter molecules such as monomethin cyanine dyes (TO1 and its analogs). In yet other embodiments, the selectivity component is a single chain antibody that comprises amino acid sequences that lead to specific binding of a reporter molecule such as Malachite Green (and its analogs). The formation of such protein-dye complexes produces a large increase in fluorescence of the dye (i.e., fluorogen reporter molecule) when it is in the bound state, thereby allowing detection of binding. In other examples, the single chain antibody is coupled (e.g., as a fusion protein or chemical conjugate) to a molecule of interest, such as for example a cell cycle regulatory protein.

In certain other embodiments, a binary biosensor is used to detect a molecule of interest. For example, a $V_H$ chain of a dye-specific antibody can be conjugated to a lipid, sugar, protein or polypeptide of interest, while the corresponding $V_L$ chain can be coupled to another potential ligand or polypeptide of interest. When the target and ligand are in close proximity, the $V_H$ and $V_L$ chains become close enough to form a binding epitope for the dye, a detectable signal is produced.

The biosensors described herein are useful for both in vivo and in vitro applications. In various embodiments, the biosensors may be used for detecting one or more target molecules, detecting environmental pollutants, detecting chemical or biological warfare agents, detecting food contaminants, and detecting hazardous substances. In an exemplary embodiment, the biosensors may be used for intracellular monitoring of one or more target molecules. In such embodiments, at least one component of the biosensor may be expressed within the cell to be analyzed.

BRIEF DESCRIPTION OF THE DRAWINGS

FIG. 1A depicts the DNA sequence of the construct encoding scFv1 (SEQ ID NO:1). FIG. 1B depicts the protein sequence of the construct encoding scFv1 (SEQ ID NO:2). FIG. 1D depicts the DNA sequence (SEQ ID NO:1) of FIG. 1A with regions of the construct encoding scFv1 of FIG. 1C mapped onto the DNA sequence (SEQ ID NO:1).

FIG. 2 shows various fluorescent dye structures.

FIG. 8 contains a table listing the peptide sequences of the scFvs comprising the FBPs of Example 5 (SEQ ID NOS: 3, 5, 7, 9, 11, 13, 15, 17, 19 and 21, corresponding to table entries >HL1-TO1, >HL2-TO1, >HL1.0.1-TO1, >HL1.1-TO1, >HL4-MG, >L5-MG, >H6-MG, >HL7-MG, >H8-MG, and >HL9-MG, respectively).

FIG. 9 contains a table describing the composition and properties of the FBPs of Example 5.

FIG. 10A depicts the fluorescence spectra of FBP/fluorogen complexes. Excitation and emission spectra are determined in the presence of excess purified FBP (2 μM HL 1.0.1-TO 1 and 100 nM TO 1-2p; 2 μM HL4-MG or L5-MG and 200 nM MG-2p). The relative fluorescence of FBP/fluorogen complexes and free fluorogen is determined at fixed excitation and emission on a microplate reader (the 488 nm laser excitation is shown as a dotted line). FIG. 10B depicts fluorescence spectra of FBP/fluorogen complexes using different fluorogen analogs where the depicted R-groups are substituted as the MG-2p R-group. The excitation spectra are determined using 2 μM purified HL4MG or L5-MG and 200 nM of indicated fluorogen analog: (I) malachite green diethylester; (II) crystal violet; (III) malachite green. Fluorescence intensity is normalized; actual fluorescence signal varies, mainly due to differences in binding affinity. Depicted FBP/fluorogen complexes showed 70 to 12,000-fold fluorescence enhancement over free fluorogen.

FIG. 11A depicts the structure of the fluorogenic dyes thiazole orange derivative (TO1-2p) and malachite green derivative (MG-2p) used in various embodiments. FIG. 11B is a graph depicting the isolation of FBPs using FACS. The Sorting screen shows separation of yeast cells bearing malachite green—activating scFvs from a bulk yeast population. The horizontal axis shows distribution of cells by green fluorescence of antibody reagent that labels the c-myc epitope; and the vertical axis depicts distribution of cells by red fluorescence generated by binding of MG fluorogen. Sorting window (I) collects cells enriched for FBPs composed of heavy chain (VH), light chain (VL) and c-myc epitope (M). Sorting window (II) collects cells enriched for FBPs composed only of the heavy chain. FIG. 11C is a graph depicting a homogenous format assay of live yeast cells displaying FBPs. The fluorescence excitation spectrum of displayed HL4-MG is taken on a 96-well microplate reader ($10^7$ yeast cells in 200 ml effective concentration B10 nM scFv are treated with 200 nM MG-2p). The inset illustrates low levels of fluorescence background signal with JAR200 control cells that do not express FBPs.

as identified in the IMGT/V-QUEST database. Amino acid replacements in bold depict residues found in multiple instances within each family of improved descendants (a fragment of HL1.1-TO1, SEQ ID NO: 74 and a fragment of HL1.0.1-TO1, SEQ ID NO: 75). The dominant replacements tend to accumulate in CDRs, wherein replacement CDRs within the fragment of HL1.1-TO1 shown to align with SEQ. ID NOs: 77 and 78 are represented by SEQ ID NOs: 79 and 80 and replacement CDRs within the fragment of HL1.0.1-TO1 shown to align with SEQ. ID NOs: 77 and 78 are represented by SEQ ID NOs: 81 and 82. For HL1-TO1, accumulation of dominant replacements occurs in the heavy chain rather than the light chain. Among 16 unique second generation descendants that are analyzed, 8 positions in the heavy chain accumulate dominant mutations but only 1 position in the light chain accumulates dominant mutations. For the selected clones, it can be seen that the first generation replacements improve both affinity and brightness, whereas second generation replacements improve only affinity.

Figure 13:
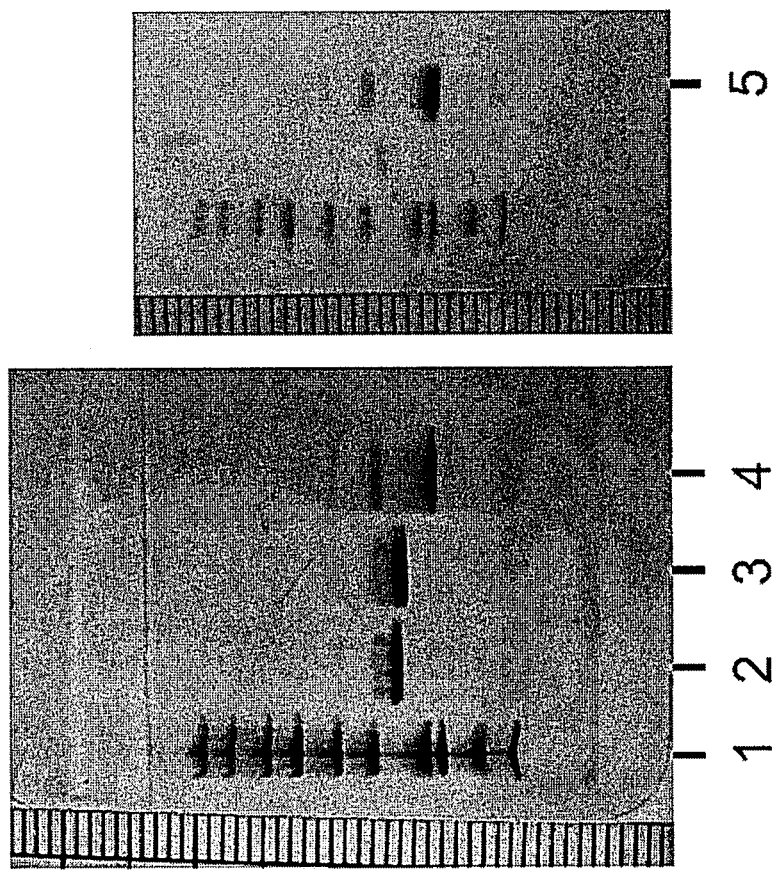

FIG. 13 is an SDS-PAGE gel of purified FBPs with 1 μg of BCA quantitated scFv loaded per lane, where lane-1 is loaded with a MW standard; lane-2 is loaded with HL1.0.1-TO1; lane-3 is loaded with HL4-MG; lane-4 is loaded with L %-MG; and lane-5 is loaded with H6-MG.

Figure 14:
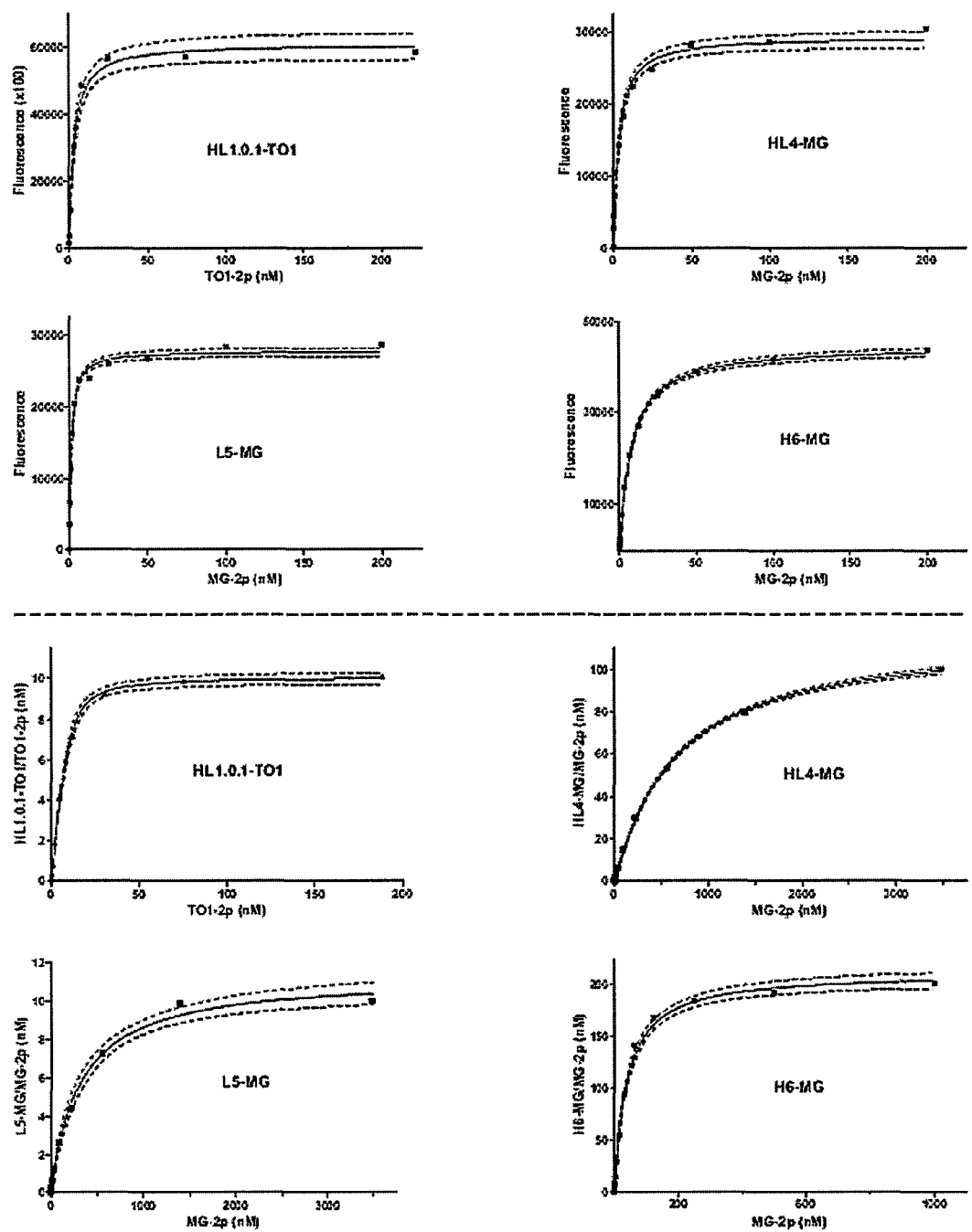

FIG. 14 provides graphs illustrating fluorogen binding to yeast displayed FBPs (above dashed line) and soluble FBPs (below dashed line). Provided are representative binding curves with 95% confidence intervals for each. One-site hyperbolic saturation binding analysis was applied to all displayed FBPs (above dashed line) and soluble H6-MG and a saturation binding with ligand depletion algorithm was applied to other soluble FBPs (below dashed line).

Figure 15:
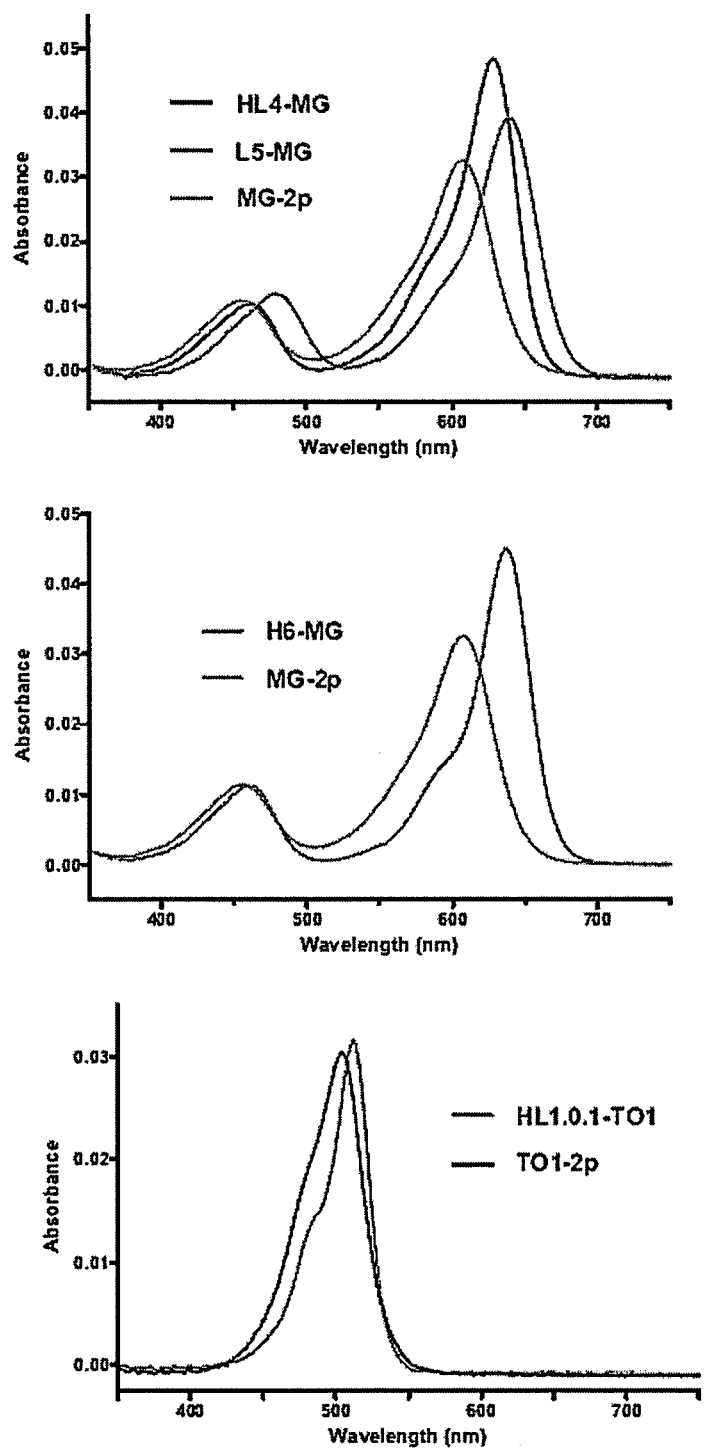

FIG. 15 provides graphs illustrating absorbance of fluorogens and FBP/fluorogen complexes. Shown are samples used in quantum yield determinations. The absorbance of FBP/fluorogen complexes is obtained on a dual beam PerkinElmer Lambda 45 spectrophotometer using an equal concentration of FBP without fluorogen as the reference.

FIGS. 16A, 16B and 16C are graphs depicting photobleaching curves for FBPs. FIG. 16A is a graph of photobleaching curves for TO1-FBP and EGFP displayed on yeast. JAR200 yeast strains displaying HL1.0.1-TO1 and EGFP are immobilized on concanavalin-A treated 35 mm petri dishes with 14 mm optical microwell (MatTek Corp) and bleached in 2 ml modified PBS using an Olympus IX50 inverted microscope equipped with a 100 W Hg lamp, 40×1.3 NA oil objective and a Photometrics CoolSnap HQ camera with HQ470/40 excitation and HQ500 LP emission filters (Chroma set #41018, total irradiance at the specimen plane was measured at 30 mW (13.6 μW/μm2)). Each curve represents an average of scans of 8-12 individual cells. Fluorescence of EGFP is normalized (scaled down ~2.5-fold) to match HL1.0.1-TO1 cells visualized with 375 nM TO1-2p. FIG. 16B is a graph depicting the photobleaching lifetime of yeast displayed TO1-FBP and EGFP. JAR200 yeast cells treated are bleached on a Leica DMI 6000 B confocal microscope using 488 nm laser excitation at 100% power and monitoring emission with a 500-600 nm window. Data from individual cells are averaged and the EGFP signal is normalized (scaled down ~3-fold) to match initial HL1.0.1-TO1 fluorescence. Plotted data points are displayed with a single exponential decay curve (Graphpad Prism 4.0 software). Lifetimes are corrected by comparing excitation intensities of these cells at 488 nm to the intensity at their excitation maxima (EGFP at 502 nm, HL1.0.1-TO1 at 512 nm), determined on a Tecan Safire2 plate reader. FIG. 16C is a graph depicting the photobleaching of MG-FBP displayed on mammalian cells. NIH 3T3 cells stably expressing both HL4-MG and HL1.1-TO1 simultaneously are isolated using FACS, and grown as a layer on the optical window of 35 mm petri dishes. Bleaching experiments are carried out in PBS w/Ca and Mg using HQ620/60 excitation and HQ665 LP emission filters (Chroma set #41024), total specimen plane irradiance is measured at 30 mW.

Figure 17:
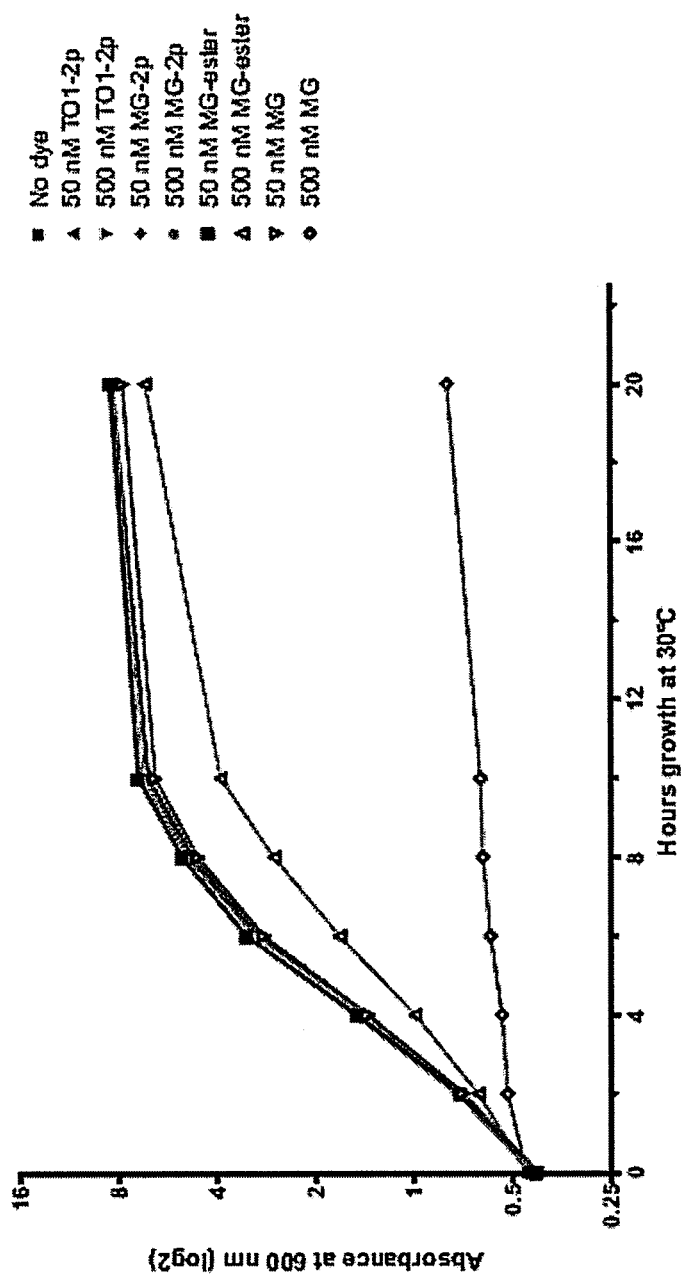

FIG. 17 is a graph depicting the effect of fluorogens on yeast cell growth. JAR200 cells are inoculated at ~$10^6$ cells/ml into 35 ml SD+CAA medium in 125 ml baffled flasks and allowed to grow at 30° C. at 300 RPM for 2 hours prior to addition of fluorogens at the indicated concentrations. One ml samples are removed at indicated time points, and growth halted by addition of 75 μl of 300 mM $NaN_3$ prior to reading absorbance. Doubling time of about 1.9 hrs is unchanged by most fluorogen treatments. For 500 nM MG-ester, the doubling time is about 2.8 hrs; and for 500 nM MG, the doubling time is over 24 hrs.

Figure 18A:
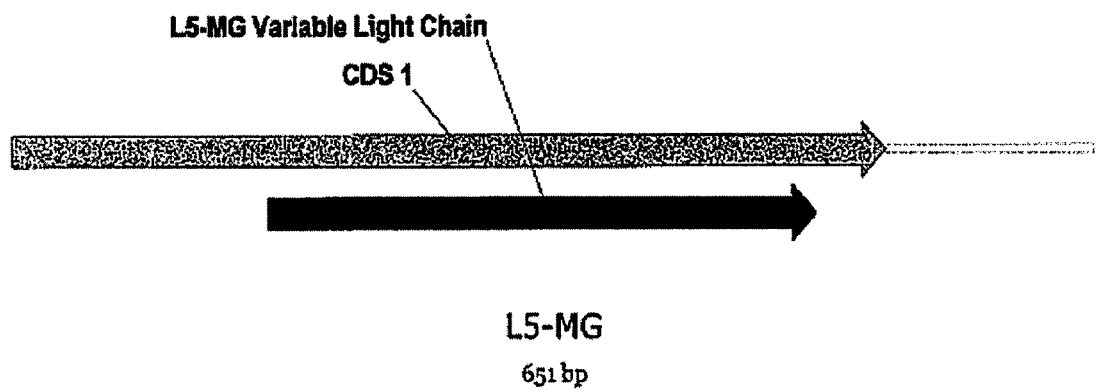
Figure 18B:
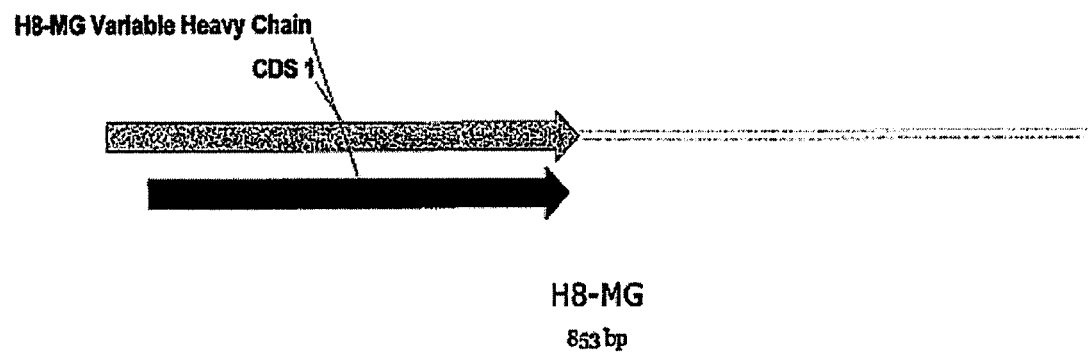

FIG. 18A is a binding schematic for the FBP L5-MG. FIG. 18B is a binding schematic for the FBP H8-MG.

Figure 19A:
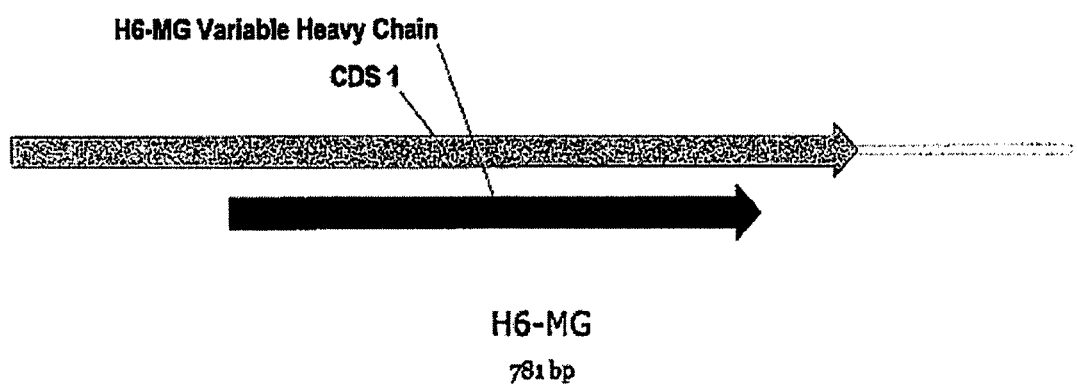
Figure 19B:
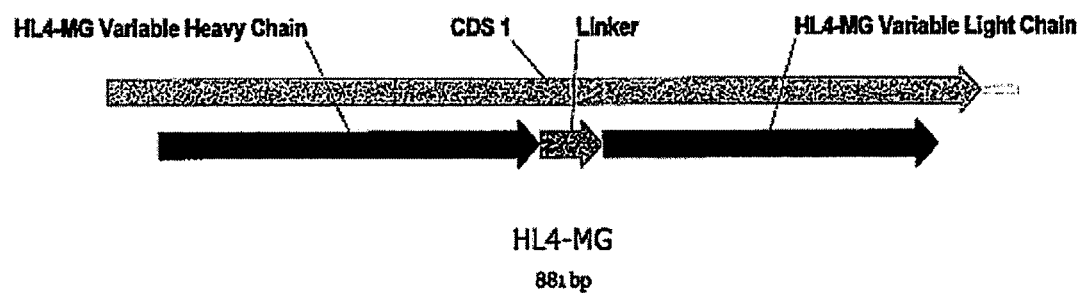

FIG. 19A is a binding schematic for the FBP H6-MG. FIG. 19B is a binding schematic for the FBP HL4-MG.

Figure 20A:
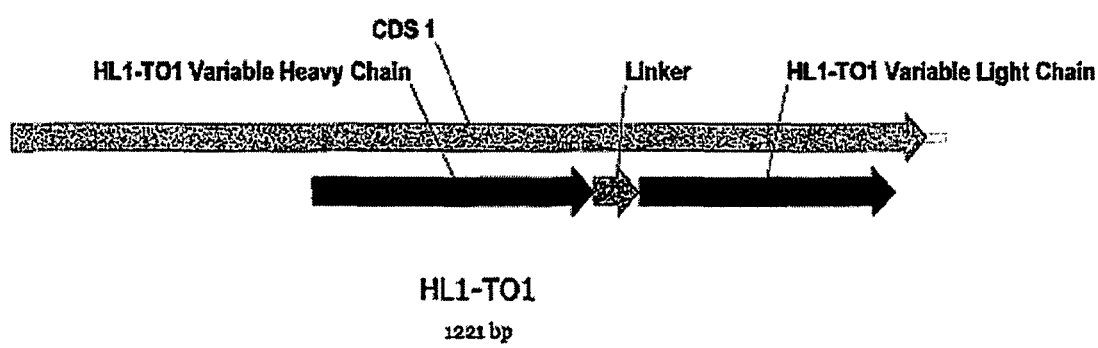
Figure 20B:
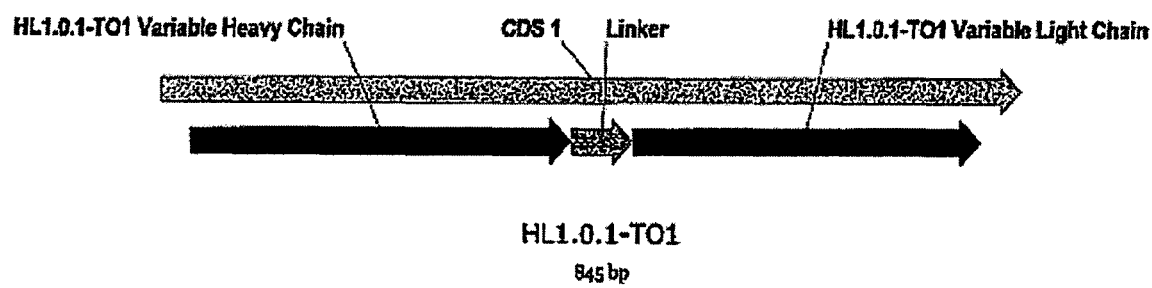

FIG. 20A is a binding schematic for the FBP HL1-TO1. FIG. 20B is a binding schematic for the FBP HL1.0.1-TO1.

Figure 21A:
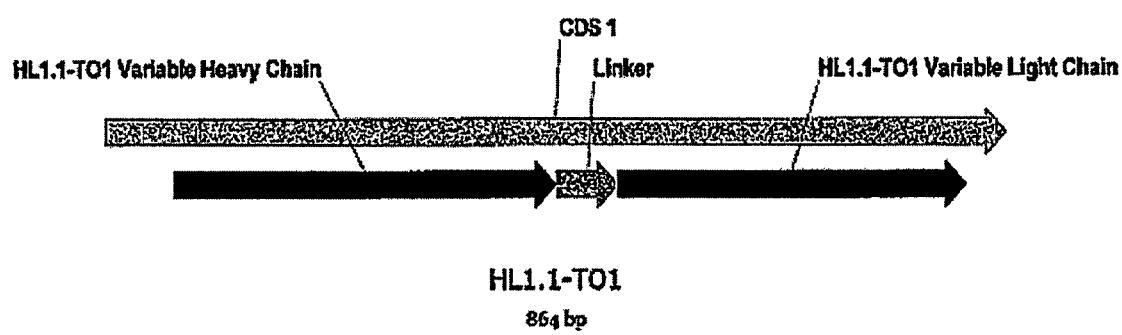
Figure 21B:
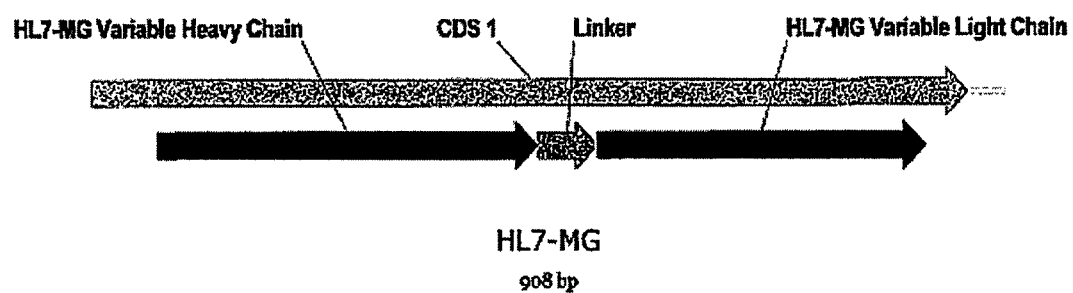

FIG. 21A is a binding schematic for the FBP HL1.1-TO1. FIG. 21B is a binding schematic for the FBP HL7-MG.

Figure 22A:
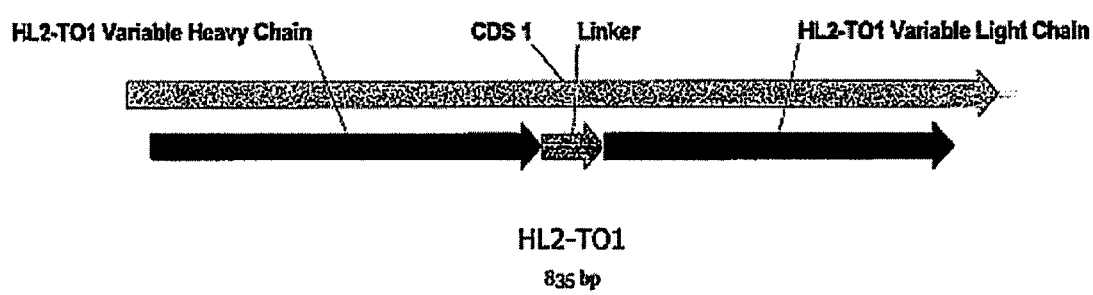
Figure 22B:
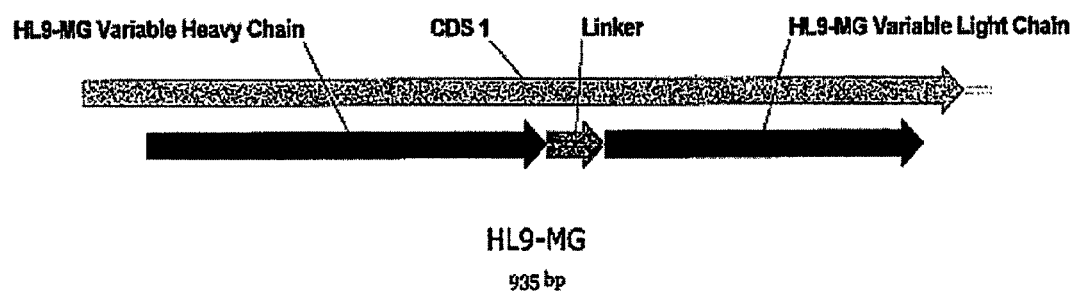

FIG. 22A is a binding schematic for the FBP HL2-TO1. FIG. 22B is a binding schematic for the FBP HL9-MG.

DETAILED DESCRIPTION

To provide an overall understanding, certain illustrative embodiments will now be described; however, it will be understood by one of ordinary skill in the art that the systems and methods described herein can be adapted and modified to provide systems and methods for other suitable applications and that other additions and modifications can be made without departing from the scope of the systems and methods described herein.

Unless otherwise specified, the illustrated embodiments can be understood as providing exemplary features of varying detail of certain embodiments, and therefore unless otherwise specified, features, components, modules, and/or aspects of the illustrations can be combined, separated, interchanged, and/or rearranged without departing from the disclosed systems or methods.

1. Introduction

For convenience, certain terms employed in the specification, examples, and appended claims are collected here. Unless defined otherwise, all technical and scientific terms used herein have the same meaning as commonly understood by one of ordinary skill in the art.

Other than in the examples herein, or unless otherwise expressly specified, all of the numerical ranges, amounts, values and percentages, such as those for amounts of materials, elemental contents, times and temperatures of reaction, ratios of amounts, and others, in the following portion of the specification and attached claims, may be read as if prefaced by the word "about" even though the term "about" may not expressly appear with the value, amount, or range. Accordingly, unless indicated to the contrary, the numerical parameters set forth in the following specification and claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains error necessarily resulting from the standard deviation found in its underlying respective testing measurements. Furthermore, when numerical ranges are set forth herein, these ranges are inclusive of the recited range end points (i.e., end points may be used). When percentages by weight are used herein, the numerical values reported are relative to the total weight.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10. The articles "a" and "an" are used herein to refer to one or to more than one (i.e., to at least one) of the grammatical object of the article. By way of example, "an element" means one element or more than one element.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing.

As used herein, the term "selectivity component" refers to a molecule capable of interacting with a target molecule. Selectivity components having limited cross-reactivity are generally preferred. In certain embodiments, suitable selectivity components include, for example, polypeptides, such as for example, antibodies, monoclonal antibodies, or derivatives or analogs thereof, including without limitation: Fv fragments, single chain Fv (scFv) fragments, Fab' fragments, F(ab')2 fragments, single domain antibodies, camelized antibodies and antibody fragments, humanized antibodies and antibody fragments, and multivalent versions of the foregoing; multivalent binding reagents including without limitation: monospecific or bispecific antibodies, such as disulfide stabilized Fv fragments, scFv tandems ((scFv)$_2$ fragments), diabodies, tribodies or tetrabodies, which typically are covalently linked or otherwise stabilized (i.e., leucine zipper or helix stabilized) scFv fragments; and other binding reagents including, for example, aptamers, template imprinted materials (such as those of U.S. Pat. No. 6,131,580), and organic or inorganic binding elements. In exemplary embodiments, a selectivity component specifically interacts with a single epitope. In other embodiments, a selectivity component may interact with several structurally related epitopes.

The term "ligand" refers to a binding moiety for a specific target molecule. The molecule can be a cognate receptor, a protein, a small molecule, a hapten, or any other relevant molecule.

The term "antibody" refers to an immunoglobulin, derivatives thereof which maintain specific binding ability, and proteins having a binding domain which is homologous or largely homologous to an immunoglobulin binding domain. As such, the antibody operates as a ligand for its cognate antigen, which can be virtually any molecule. Natural antibodies comprise two heavy chains and two light chains and are bi-valent. The interaction between the variable regions of heavy and light chain forms a binding site capable of specifically binding an antigen. The term "$V_H$" refers to a heavy chain variable region of an antibody. The term "$V_L$" refers to a light chain variable region of an antibody. Antibodies may be derived from natural sources, or partly or wholly synthetically produced. An antibody may be monoclonal or polyclonal. The antibody may be a member of any immunoglobulin class, including any of the human classes: IgG, IgM, IgA, IgD, and IgE. In exemplary embodiments, antibodies used with the methods and compositions described herein are derivatives of the IgG class.

The term "antibody fragment" refers to any derivative of an antibody which is less than full-length. In exemplary embodiments, the antibody fragment retains at least a significant portion of the full-length antibody's specific binding ability. Examples of antibody fragments include, but are not limited to, Fab, Fab', F(ab')$_2$, Fv, dsFv, scFv, diabody, and Fd fragments. The antibody fragment may be produced by any means. For instance, the antibody fragment may be enzymatically or chemically produced by fragmentation of an intact antibody, it may be recombinantly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 50 amino acids and more typically will comprise at least about 200 amino acids.

The term "Fab" refers to an antibody fragment that is essentially equivalent to that obtained by digestion of immunoglobulin (typically IgG) with the enzyme papain. The heavy chain segment of the Fab fragment is the Fd piece. Such fragments may be enzymatically or chemically produced by fragmentation of an intact antibody, recombinantly produced from a gene encoding the partial antibody sequence, or it may be wholly or partially synthetically produced. Methods for preparing Fab fragments are known in the art. See, for example, Tijssen, Practice and Theory of Enzyme Immunoassays (Elsevier, Amsterdam, 1985).

The term "Fab'" refers to an antibody fragment that is essentially equivalent to that obtained by reduction of the disulfide bridge or bridges joining the two heavy chain pieces in the F(ab')$_2$ fragment. Such fragments may be enzymatically or chemically produced by fragmentation of an intact antibody, recombinantly produced from a gene encoding the partial antibody sequence, or it may be wholly or partially synthetically produced.

The term "F(ab')$_2$" refers to an antibody fragment that is essentially equivalent to a fragment obtained by digestion of an immunoglobulin (typically IgG) with the enzyme pepsin at pH 4.0-4.5. Such fragments may be enzymatically or chemically produced by fragmentation of an intact antibody, recombinantly produced from a gene encoding the partial antibody sequence, or it may be wholly or partially synthetically produced.

The term "Fv" refers to an antibody fragment that consists of one $V_H$ and one $V_L$ domain held together by noncovalent interactions. The term "dsFv" is used herein to refer to an Fv with an engineered intermolecular disulfide bond to stabilize the $V_H$-$V_L$ pair. Methods for preparing Fv fragments are known in the art. See, for example, Moore et al., U.S. Pat. No. 4,462,334; Hochman et al., *Biochemistry* 12: 1130 (1973); Sharon et al., *Biochemistry* 15: 1591 (1976); and Ehrlich et al., U.S. Pat. No. 4,355,023.

The terms "single-chain Fvs" and "scFvs" refers to recombinant antibody fragments consisting of only the variable light chain ($V_L$) and variable heavy chain ($V_H$) covalently connected to one another by a polypeptide linker. Either $V_L$ or $V_H$ may be the $NH_2$-terminal domain. The polypeptide linker may be of variable length and composition so long as the two variable domains are bridged without serious steric interference. In exemplary embodiments, the linkers are comprised primarily of stretches of glycine and serine residues with some glutamic acid or lysine residues interspersed for solubility. Methods for preparing scFvs are known in the art. See, for example, PCT/US/87/02208 and U.S. Pat. No. 4,704,692.

The term "single domain antibody" or "Fd" refers to an antibody fragment comprising a $V_H$ domain that interacts with a given antigen. An Fd does not contain a $V_L$ domain, but may contain other antigen binding domains known to exist in antibodies, for example, the kappa and lambda domains. In certain embodiments, the Fd comprises only the $F_L$ component. Methods for preparing Fds are known in the art. See, for example, Ward et al., Nature 341:644-646 (1989) and EP 0368684 A1.

The term "single chain antibody" refers to an antibody fragment that comprises variable regions of the light and heavy chains joined by a flexible linker moiety. Methods for preparing single chain antibodies are known in the art. See, for example, U.S. Pat. No. 4,946,778 to Ladner et al.

The term "diabodies" refers to dimeric scFvs. The components of diabodies typically have shorter peptide linkers than most scFvs and they show a preference for associating as dimers. The term diabody is intended to encompass both bivalent (i.e., a dimer of two scFvs having the same specificity) and bispecific (i.e., a dimer of two scFvs having different specificities) molecules. Methods for preparing diabodies are known in the art. See, for example, EP 404097 and WO93/11161.

The term "triabody" refers to trivalent constructs comprising 3 scFv's, and thus comprising 3 variable domains (see, e.g., Iliades et al., *FEBS Lett.* 409(3):43741 (1997)). Triabodies is meant to include molecules that comprise 3 variable domains having the same specificity, or 3 variable domains wherein two or more of the variable domains have different specificities.

The term "tetrabody" refers to engineered antibody constructs comprising 4 variable domains (see, e.g., Pack et al., *J Mol Biol.* 246(1): 28-34 (1995) and Coloma & Morrison, *Nat Biotechnol.* 15(2): 159-63 (1997)). Tetrabodies is meant to include molecules that comprise 4 variable domains having the same specificity, or 4 variable domains wherein two or more of the variable domains have different specificities.

The term "camelized antibody" refers to an antibody or variant thereof that has been modified to increase its solubility and/or reduce aggregation or precipitation. For example; camelids produce heavy-chain antibodies consisting only of a pair of heavy chains wherein the antigen binding site comprises the N-terminal variable region or $V_{HH}$ (variable domain of a heavy chain antibody). The $V_{HH}$ domain comprises an increased number of hydrophilic amino acid residues that enhance the solubility of a $V_{HH}$ domain as compared to a $V_H$ region from non-camelid antibodies. Camelization of an antibody or variant thereof involves replacing one or more amino acid residues of a non-camelid antibody with corresponding amino residues from a camelid antibody.

As used herein, the term "epitope" refers to a physical structure on a molecule that interacts with a selectivity component, such as an antibody. In exemplary embodiments, epitope refers to a desired region on a target molecule that specifically interacts with a selectivity component.

"Interact" is meant to include detectable interactions between molecules, such as may be detected using, for example, a hybridization assay. Interact also includes "binding" interactions between molecules. Interactions may be, for example, protein-protein, protein-nucleic acid, protein-small molecule or small molecule-nucleic acid, and includes for example, antibody-antigen binding, receptor-ligand binding, hybridization, and other forms of binding. In certain embodiments, an interaction between a ligand and a specific target will lead to the formation of a complex, wherein the ligand and the target are unlikely to dissociate. Such affinity for a ligand and its target can be defined by the dissociation constant ($K_d$) as known in the art. A complex may include a ligand for a specific dye and is referred to herein as a "ligand-dye" complex.

The term "immunogen" traditionally refers to compounds that are used to elicit an immune response in an animal, and is used as such herein. However, many techniques used to produce a desired selectivity component, such as the phage display and aptamer methods described below, do not rely wholly, or even in part, on animal immunizations. Nevertheless, these methods use compounds containing an "epitope," as defined above, to select for and clonally expand a population of selectivity components specific to the "epitope." These in vitro methods mimic the selection and clonal expansion of immune cells in vivo, and, therefore, the compounds containing the "epitope" that is used to clonally expand a desired population of phage, aptamers and the like in vitro are embraced within the definition of "immunogens."

Similarly, the terms "hapten" and "carrier" have specific meaning in relation to the immunization of animals, that is, a "hapten" is a small molecule that contains an epitope, but is incapable as serving as an immunogen alone. Therefore, to elicit an immune response to the hapten, the hapten is conjugated with a larger carrier, such as bovine serum albumin or keyhole limpet hemocyanin, to produce an immunogen. A preferred immune response would recognize the epitope on the hapten, but not on the carrier. As used herein in connection with the immunization of animals, the terms "hapten" and "carrier" take on their classical definition. However, in the in vitro methods described herein for preparing the desired binding reagents, traditional "haptens" and "carriers" typically have their counterpart in epitope-containing compounds affixed to suitable substrates or surfaces, such as beads and tissue culture plates.

The term "aptamer" refers to a nucleic acid molecule that may selectively interact with a non-oligonucleotide molecule or group of molecules. In various embodiments, aptamers may include single-stranded, partially single-stranded, partially double-stranded or double-stranded nucleic acid sequences; sequences comprising nucleotides, ribonucleotides, deoxyribonucleotides, nucleotide analogs, modified nucleotides and nucleotides comprising backbone modifications, branchpoints and normucleotide residues, groups or bridges; synthetic RNA, DNA and chimeric nucleotides, hybrids, duplexes, heteroduplexes; and any ribonucleotide, deoxyribonucleotide or chimeric counterpart thereof and/or corresponding complementary sequence. In certain embodiments, aptamers may include promoter or primer annealing sequences that may be used to amplify, transcribe or replicate all or part of the aptamer.

As used herein, the term "reporter molecule" refers to a molecule suitable for detection, such as, for example, spectroscopic detection. Examples of reporter molecules include, but are not limited to, the following: fluorescent labels, enzymatic labels, biotinyl groups, and predetermined polypeptide epitopes recognized by a secondary reporter (e.g., leucine zipper pair sequences, binding sites for secondary antibodies, metal binding domains, epitope tags). Examples and use of such reporter molecules are described in more detail below. In some embodiments, reporter molecules are attached by spacer arms of various lengths to reduce potential steric hindrance. Reporter molecules may be incorporated into or attached (including covalent and non-covalent attachment) to a molecule, such as a selectivity component. Various methods of labeling polypeptides are known in the art and may be used.

As used herein, the term "sensor dye" refers to a reporter molecule that exhibits an increase, decrease or modification of signal in response to a change in the environment. In exemplary embodiments, the sensor dye is a fluorescent molecule that is responsive to changes in polarity and/or mobility of the dye, as well as, the changes microenvironment pH and/or viscosity, or combinations thereof.

A "fusion protein" or "fusion polypeptide" refers to a chimeric protein as that term is known in the art and may be constructed using methods known in the art. In many examples of fusion proteins, there are two different polypeptide sequences, and in certain cases, there may be more. The sequences may be linked in frame. A fusion protein may include a domain which is found (albeit in a different protein) in an organism which also expresses the first protein, or it may be an "interspecies", "intergenic", etc. fusion expressed by different kinds of organisms. In various embodiments, the fusion polypeptide may comprise one or more amino acid sequences linked to a first polypeptide. In the case where more than one amino acid sequence is fused to a first polypeptide, the fusion sequences may be multiple copies of the same sequence, or alternatively, may be different amino acid sequences. The fusion polypeptides may be fused to the N-terminus, the C-terminus, or the N- and C-terminus of the first polypeptide. Exemplary fusion proteins include polypeptides comprising a glutathione S-transferase tag (GST-tag), histidine tag (His-tag), an immunoglobulin domain or an immunoglobulin binding domain.

As used herein, the term "array" refers to a set of selectivity components immobilized onto one or more substrates so that each selectivity component is at a known location. In an exemplary embodiment, a set of selectivity components is immobilized onto a surface in a spatially addressable manner so that each individual selectivity component is located at a different and identifiable location on the substrate.

The term "chemical handle" refers to a component that may be attached to a biosensor as described herein so as to facilitate its isolation, immobilization, identification, or detection and/or which increases its solubility. Suitable chemical handles include, for example, a polypeptide, a polynucleotide, a carbohydrate, a polymer, or a chemical moiety and combinations or variants thereof.

The term "conserved residue" refers to an amino acid that is a member of a group of amino acids having certain common properties. The term "conservative amino acid substitution" refers to the substitution (conceptually or otherwise) of an amino acid from one such group with a different amino acid from the same group. A functional way to define common properties between individual amino acids is to analyze the normalized frequencies of amino acid changes between corresponding proteins of homologous organisms. According to such analyses, groups of amino acids may be defined where amino acids within a group exchange preferentially with each other, and therefore resemble each other most in their impact on the overall protein structure. One example of a set of amino acid groups defined in this manner include: (i) a charged group, consisting of Glu and Asp, Lys, Arg and His, (ii) a positively-charged group, consisting of Lys, Arg and His, (iii) a negatively-charged group, consisting of Glu and Asp, (iv) an aromatic group, consisting of Phe, Tyr and Trp, (v) a nitrogen ring group, consisting of His and Trp, (vi) a large aliphatic nonpolar group, consisting of Val, Leu and Ile, (vii) a slightly-polar group, consisting of Met and Cys, (viii) a small-residue group, consisting of Ser, Thr, Asp, Asn, Gly, Ala, Glu, Gln and Pro, (ix) an aliphatic group consisting of Val, Leu, Ile, Met and Cys, and (x) a small hydroxyl group consisting of Ser and Thr.

"Isolated", with respect to nucleic acids, such as DNA or RNA, refers to molecules separated from other DNAs, or RNAs, respectively, that are present in the natural source of the macromolecule. Isolated also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. "Isolated" also refers to polypeptides which are isolated from other cellular proteins and is meant to encompass both purified and recombinant polypeptides.

The term "mammal" is known in the art, and exemplary mammals include humans, primates, bovines, porcines, canines, felines, and rodents (e.g., mice and rats).

The term "microenvironment" refers to localized conditions within a larger area. For example, association of two molecules within a solution may alter the local conditions surrounding the associating molecules without affecting the overall conditions within the solution.

The term "nucleic acid" refers to a polymeric form of nucleotides, either ribonucleotides or deoxynucleotides or a modified form of either type of nucleotide. The terms should also be understood to include, as equivalents, analogs of either RNA or DNA made from nucleotide analogs, and, as applicable to the embodiment being described, single-stranded (such as sense or antisense) and double-stranded polynucleotides.

The term "polypeptide", and the terms "protein" and "peptide" which are used interchangeably herein, refers to a polymer of amino acids.

The terms "polypeptide fragment" or "fragment", when used in regards to a reference polypeptide, refers to a polypeptide in which amino acid residues are deleted as compared to the reference polypeptide itself, but where the remaining amino acid sequence is usually identical to the corresponding positions in the reference polypeptide. Such deletions may occur at the amino-terminus or carboxy-terminus of the reference polypeptide, or alternatively both. Fragments typically are at least 5, 10, 20, 50, 100, 500 or more amino acids long. A fragment can retain one or more of the biological activities of the reference polypeptide.

The term "sequence homology" refers to the proportion of base matches between two nucleic acid sequences or the proportion of amino acid matches between two amino acid sequences. When sequence homology is expressed as a percentage, e.g., 50%, the percentage denotes the proportion of matches over the length of sequence from a desired sequence (e.g., SEQ. ID NO: 1) that is compared to some other sequence. Gaps (in either of the two sequences) are permitted to maximize matching; gap lengths of 15 bases or less are usually used, 6 bases or less are used more frequently, with 2 bases or less used even more frequently. The term "sequence identity" means that sequences are identical (i.e., on a nucleotide-by-nucleotide basis for nucleic acids or amino acid-by-amino acid basis for polypeptides) over a window of comparison. The term "percentage of sequence identity" is calculated by comparing two optimally aligned sequences over the comparison window, determining the number of positions at which the identical amino acids occurs in both sequences to yield the number of matched positions, dividing the number of matched positions by the total number of positions in the comparison window, and multiplying the result by 100 to yield the percentage of sequence identity. Methods to calculate sequence identity are known to those of skill in the art.

2. Biosensors

Provided are biosensors, compositions comprising biosensors, and methods of using biosensors in living cells and organisms. The biosensors are able to be selectively targeted to certain regions or structures within a cell. The biosensors may provide a signal when the biosensor is targeted and/or in response to a property of the cell or organism such as membrane potential, ion concentration or enzyme activity.

In general, the biosensors comprise at least two components; (1) a selectivity component capable of interacting with a target molecule of interest and a (2) reporter molecule that produces a detectable change in signal upon interaction of the selectivity component with the target molecule. The reporter molecule may be covalently linked to the selectivity component, or it may be able to noncovalently interact with the selectivity component.

In various embodiments, the reporter molecule is responsive to environmental changes, including for example, pH sensitive molecules, restriction sensitive molecules, polarity sensitive molecules, and mobility sensitive molecules. The reporter molecule may be either fluorescent or chemiluminescent. In certain embodiments, the reporter molecule may interact with the selectivity component proximal to a region that binds to the target molecule. In an exemplary embodiment, the reporter molecule is covalently attached to the selectivity component proximal to a region that binds to the target molecule, optionally through an engineered reactive site. The biosensor may respond to changes in the concentration of the target molecule and may be useful for monitoring the concentration of a target molecule over time.

In certain embodiments, the biosensor may comprise two or more reporter molecules, which may be the same or different reporter molecules. The reporter molecule may be detectable by a variety of methods, including, for example, a fluorescent spectrometer, filter fluorometer, microarray reader, optical fiber sensor reader, epifluorescence microscope, confocal laser scanning microscope, two photon excitation microscope, or a flow cytometer.

In certain embodiments, methods for preparing the biosensors include generating selectivity components with an engineered reporter molecule binding site using biological selection methods. The reporter molecule binding site may be engineered to customize any of a number of properties, for example, for optimal binding affinity to the reporter molecule, to enhance or otherwise change or tune the signal from the reporter molecule when it binds the selectivity component, to provide a reactive site in the reporter molecule binding site so that the reporter molecule may covalently associate with the selectivity component upon binding in the binding site, or to modulate or perturb the activity of the selectivity component when the reporter molecule binds to it.

Accordingly, in certain embodiments, methods for generating a biosensor may comprise producing the selectivity component by genetic selection, genetic engineering or a combination of genetic selection and genetic engineering, so as to produce an engineered selectivity component. Methods for producing the engineered selectivity components are described further below.

In other embodiments, particularly where the biosensor is produced from an endogenous source rather than expressed in the cell or tissue to be analyzed, the biosensor may further comprise a chemical handle. The chemical handle may be used to facilitate isolation, immobilization, identification, or detection of the biosensors and/or which increases the solubility of the biosensors.

In certain embodiments, the biosensor may be immobilized onto a substrate surface, including, for example, substrates such as silicon, silica, quartz, glass, controlled pore glass, carbon, alumina, titania, tantalum oxide, germanium, silicon nitride, zeolites, gallium arsenide, gold, platinum, aluminum, copper, titanium, alloys, polystyrene, poly(tetra)fluoroethylene (PTFE), polyvinylidenedifluoride, polycarbonate, polymethylmethacrylate, polyvinylethylene, polyethyleneimine, poly(etherether)ketone, polyoxymethylene (POM), polyvinylphenol, polylactides, polymethacrylimide (PMI), polyalkenesulfone (PAS), polypropylethylene, polyethylene, polyhydroxyethylmethacrylate (HEMA), polydimethylsiloxane, polyacrylamide, polyimide, and block-copolymers. Such substrates may be in the form of beads, chips, plates, slides, strips, sheets, films, blocks, plugs, medical devices, surgical instruments, diagnostic instruments, drug delivery devices, prosthetic implants, and other structures.

In another embodiment, the application provides a composition comprising one or more biosensors. The composition may comprise a pharmaceutically acceptable carrier. The biosensors of the composition may be specific for different target molecules, and may be associated with the same or different reporter molecules.

In another embodiment, two or more biosensors may be immobilized onto a substrate at spatially addressable locations. The biosensors may be specific for different target molecules and may be associated with the same or different reporter molecules.

In another aspect, the application provides a method for detecting at least one target molecule comprising providing at least one biosensor comprising a selectivity component and a reporter molecule and detecting the signal of the reporter molecule, wherein interaction of the biosensor with the target molecule produces a detectable change in the signal of the reporter molecule. In various other aspects, the biosensors of the invention may be used for the detection of environmental pollutants, hazardous substances, food contaminants, and biological and/or chemical warfare agents.

In various embodiments, the biosensors of the invention may be used to detect target molecules, including, for example, cells, microorganisms (bacteria, fungi and viruses), polypeptides, nucleic acids, hormones, cytokines, drug molecules, carbohydrates, pesticides, dyes, amino acids, small organic molecules and small inorganic molecules.

Biosensors may be used for the detection of target molecules both in vivo and in vitro. In certain embodiments, the biosensor may be injected or implanted into a patient and the signal of the reporter molecule is detected externally. In one exemplary embodiment, the biosensors of the application may be used for the detection of intracellular targets. In another exemplary embodiment, the biosensors of the application may be attached to a fiber optic probe to facilitate position of the biosensor within a sample and readout from the biosensor through the optical fiber.

In still other embodiments, the biosensor may be expressed directly into the cell, tissue or subject to be analyzed. Using molecular biology methods, a vector comprising at least a gene encoding a selectivity component is constructed and inserted into the host, resulting in expression of the selectivity component, as described in more detail below.

Various, more detailed embodiments of and methods for producing the selectivity component and reporter molecule components are also further described below.

3. Selectivity Components

The selectivity component may be any molecule which is capable of selectively interacting with a desired target molecule, including, for example, cells, microorganisms (such as bacteria, fungi and viruses), polypeptides, nucleic acids (such as oligonucleotides, cDNA molecules or genomic DNA fragments), hormones, cytokines, drug molecules, carbohydrates, pesticides, dyes, amino acids, or small organic or inorganic molecules.

Exemplary target molecules include, for example, molecules involved in tissue differentiation and/or growth, cellular communication, cell division, cell motility, and other cellular functions that take place within or between cells, including regulatory molecules such as growth factors, cytokines, morphogenetic factors, neurotransmitters, and the like. In certain embodiments, target molecules may be bone morphogenic protein, insulin-like growth factor (IGF), and/or members of the hedgehog and Wnt polypeptide families.

Exemplary selectivity components include, for example, pathway and network proteins (for example, enzymes such as kinases or phosphatases), antibody fragments, non-antibody receptor molecules, aptamers, template imprinted materials, and organic or inorganic binding elements. Selectivity components having limited crossreactivity are generally preferred.

3.A. Exemplary Polypeptide Selectivity Components

In certain embodiments, the selectivity component may be an antibody or an antibody fragment. For example, selectivity components may be monoclonal antibodies, or derivatives or analogs thereof, including without limitation: Fv fragments, single chain Fv (scFv) fragments, Fab' fragments, F(ab')$_2$ fragments, single domain antibodies, camelized antibodies and antibody fragments, humanized antibodies and antibody fragments, and multivalent versions of the foregoing; multivalent selectivity components including without limitation: monospecific or bispecific antibodies, such as disulfide stabilized Fv fragments, scFv tandems ((scFv)$_2$ fragments), diabodies, tribodies or tetrabodies, which typically are covalently linked or otherwise stabilized (i.e., leucine zipper or helix stabilized) scFv fragments; receptor molecules which naturally interact with a desired target molecule.

In one embodiment, the selectivity component may be an antibody. Preparation of antibodies may be accomplished by any number of well-known methods for generating monoclonal antibodies. These methods typically include the step of immunization of animals, typically mice; with a desired immunogen (e.g., a desired target molecule-or fragment thereof). Once the mice have been immunized, and preferably boosted one or more times with the desired immunogen(s), monoclonal antibody-producing hybridomas may be prepared and screened according to well known methods (see, for example, Kuby, Janis, IMMUNOLOGY, Third Edition, pp. 131-139, W.H. Freeman & Co. (1997), for a general overview of monoclonal antibody production, that portion of which is incorporated herein by reference).

Over the past several decades, antibody production has become extremely robust. In vitro methods that combine antibody recognition and phage display techniques allow one to amplify and select antibodies with very specific binding capabilities. See, for example, Holt, L. J. et al., "The Use of Recombinant Antibodies in Proteomics," *Current Opinion in Biotechnology* 2000, 11:445-449, incorporated herein by reference. These methods typically are much less cumbersome than preparation of hybridomas by traditional monoclonal antibody preparation methods. Binding epitopes may range in size from small organic compounds such as bromo uridine and phosphotyrosine to oligopeptides on the order of 7-9 amino acids in length.

In another embodiment, the selectivity component may be an antibody fragment. Preparation of Antibody Fragments May be Accomplished by any Number of Well-Known methods. In one embodiment, phage display technology may be used to generate antibody fragment selectivity components that are specific for a desired target molecule, including, for example, Fab fragments, Fv's with an engineered intermolecular disulfide bond to stabilize the $V_H$-$V_L$ pair, scFvs, or diabody fragments.

Figure 1C:
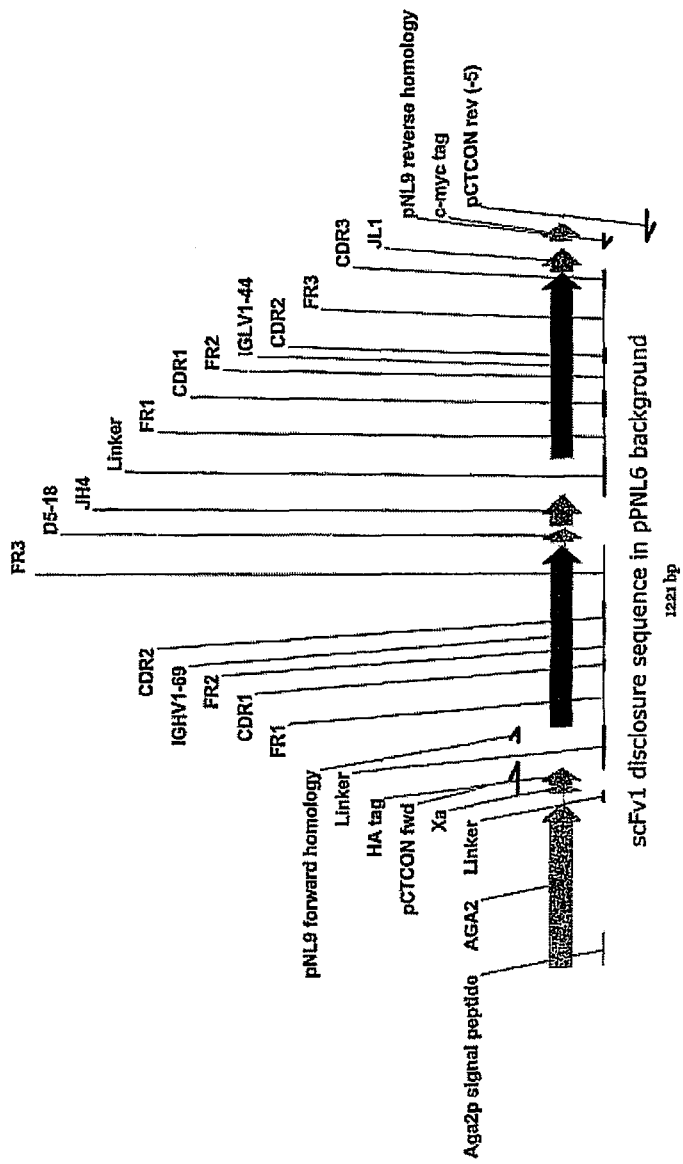
FIG. 1C is a schematic of the construct encoding scFv1.

In certain embodiments, the selectivity component comprises a polypeptide sequence having at least about 85%, at least about 90%, at least about 95%, about 96%, about 97%, about 98%, about 99% or about 100% sequence identity to the polypeptide sequence of SEQ ID NO: 2 (FIG. 1B). Vectors to produce the selectivity component may be prepared as described below with the nucleic acid encoding the polypeptide of SEQ ID NO:2 and its homologs (for example, SEQ ID NO: 1 in FIG. 1A), and used to transfect host cells as described further below.

As an example, production of scFv antibody fragments using phage display is described below. However, scFv antibody fragments for use in the selectivity components may be generated by any method known in the art for doing so, including genetic selection methods from a library of yeast cells (see Boder and Wittrup (2000) *Meth. Enzymol.* 328:430-33; Boder, et al. (2000) *Proc. Natl. Acad. Sci USA* 97:10701-5; and Swers, et al. (2004) *Nucl. Acids. Res.* 32:e36).

For phage display, an immune response to a selected immunogen is elicited in an animal (such as a mouse, rabbit, goat or other animal) and the response is boosted to expand the immunogen-specific B-cell population. Messenger RNA is isolated from those B-cells, or optionally a monoclonal or polyclonal hybridoma population. The mRNA is reverse-transcribed by known methods using either a poly-A primer or murine immunoglobulin-specific primer(s), typically specific to sequences adjacent to the desired $V_H$ and $V_L$ chains, to yield cDNA. The desired $V_H$ and A chains are amplified by polymerase chain reaction (PCR) typically using $V_H$ and A specific primer sets, and are ligated together, separated by a linker. $V_H$ and $V_L$ specific primer sets are commercially available, for instance from Stratagene, Inc. of La Jolla, Calif. Assembled $V_H$-linker-$V_L$ product (encoding an scFv fragment) is selected for and amplified by PCR. Restriction sites are introduced into the ends of the $V_H$-linker-$V_L$ product by PCR with primers including restriction sites and the scFv fragment is inserted into a suitable expression vector (typically a plasmid) for phage display. Other fragments, such as an Fab' fragment, may be cloned into phage display vectors for surface expression on phage particles. The phage may be any phage, such as lambda, but typically is a filamentous phage, such as fd and M 13, typically M13.

In phage display vectors, the $V_H$-linker-$V_L$ sequence is cloned into a phage surface protein (for M 13, the surface proteins g3p (pHI) or g8p, most typically g3p). Phage display systems also include phagemid systems, which are based on a phagemid plasmid vector containing the phage surface protein genes (for example, g3p and g8p of M13) and the phage origin of replication. To produce phage particles, cells containing the phagemid are rescued with helper phage providing the remaining proteins needed for the generation of phage. Only the phagemid vector is packaged in the resulting phage particles because replication of the phagemid is grossly favored over replication of the helper phage DNA. Phagemid packaging systems for production of antibodies are commercially available. One example of a commercially available phagemid packaging system that also permits production of soluble ScFv fragments in bacteria cells is the Recombinant Phage Antibody System (R.PAS), commercially available from Amersham Pharmacia Biotech, Inc. of Piscataway, N.J. and the pSKAN Phagemid Display System, commercially available from MoBiTec, LLC of Marco Island, Fla. Phage display systems, their construction and screening methods are described in detail in, among others, U.S. Pat. Nos. 5,702,892, 5,750,373, 5,821,047 and 6,127,132, each of which are incorporated herein by reference in their entirety.

Typically, once phage are produced that display a desired antibody fragment, epitope specific phage are selected by their affinity for the desired immunogen and, optionally, their lack be used for physically separating immunogen-binding phage from non-binding phage. Typically the immunogen is fixed to a surface and the phage are contacted with the surface. Non-binding phage are washed away while binding phage remain bound. Bound phage are later eluted and are used to re-infect cells to amplify the selected species. A number of rounds of affinity selection typically are used, often increasingly higher stringency washes, to amplify immunogen binding phage of increasing affinity. Negative selection techniques also may be used to select for lack of binding to a desired target. In that case, un-bound (washed) phage are amplified.

Although it is preferred to use spleen cells and/or B-lymphocytes from animals preimmunized with a desired immunogen as a source of cDNA from which the sequences of the $V_H$ and $V_L$ chains are amplified by RT-PCR, naive (un-immunized with the target immunogen) splenocytes and/or B-cells may be used as a source of cDNA to produce a polyclonal set of $V_H$ and $V_L$ chains that are selected in vitro by affinity, typically by the above-described phage display (phagemid) method. When naive B-cells are used, during affinity selection, the washing of the first selection step typically is of very high stringency so as to avoid loss of any single clone that may be present in very low copy number in the polyclonal phage library. By this naive method, B-cells may be obtained from any polyclonal source, B-cell or splenocyte cDNA libraries also are a source of cDNA from which the $V_H$ and $V_L$ chains may be amplified. For example, suitable murine and human B-cell, lymphocyte and splenocyte cDNA libraries are commercially available from Stratagene, Inc. and from Clontech Laboratories, Inc. of Palo Alto, Calif. Phagemid antibody libraries and related screening services are provided commercially by Cambridge Antibody Technology of the U.K. or MorphoSys USA, Inc., of Charlotte, N.C.

The selectivity components do not have to originate from biological sources, such as from naive or immunized immune cells of animals or humans. The selectivity components may be screened from a combinatorial library of synthetic peptides. One such method is described in U.S. Pat. No. 5,948,635, incorporated herein by reference, which described the production of phagemid libraries having random amino acid insertions in the pIII gene of M13. These phage may be clonally amplified by affinity selection as described above.

Panning in a culture dish or flask is one way to physically separate binding phage from non-binding phage. Panning may be carried out in 96 well plates in which desired immunogen structures have been immobilized. Functionalized 96 well plates, typically used as ELISA plates, may be purchased from Pierce of Rockwell, Ill. Polypeptides immunogens may be synthesized directly on $NH_2$ or COOH functionalized plates in an N-terminal to C-terminal direction. Other affinity methods for isolating phage having a desired specificity include affixing the immunogen to beads. The beads may be placed in a column and phage may be bound to the column, washed and eluted according to standard procedures. Alternatively, the beads may be magnetic so as to permit magnetic separation of the binding particles from the non-binding particles. The immunogen also may be affixed to a porous membrane or matrix, permitting easy washing and elution of the binding phage.

In certain embodiments, it may be desirable to increase the specificity of the selectivity component for a given target molecule or reporter molecule using a negative selection step in the affinity selection process. For example, selectivity component displaying phage may be contacted with a surface functionalized with immunogens distinct from the target molecule or reporter molecule. Phage are washed from the surface and non-binding phage are grown to clonally expand the population of non-binding phage thereby de-selecting phage that are not specific for the desired target molecule. In certain embodiments, random synthetic peptides may be used in the negative selection step. In other embodiments, one or more immunogens having structural similarity to the target molecule or reporter molecule may be used in the negative selection step. For example, for a target molecule comprising a polypeptide, structurally similar immunogens may be polypeptides having conservative amino acid substitutions, including but not limited to the conservative substitution groups such as: (i) a charged group, consisting of Glu and Asp, Lys, Arg and His, (ii) a positively-charged group, consisting of Lys, Arg and His, (iii) a negatively-charged group, consisting of Glu and Asp, (iv) an aromatic group, consisting of Phe, Tyr and Trp, (v) a nitrogen ring group, consisting of His and Trp, (vi) a large aliphatic nonpolar group, consisting of Val, Leu and Ile, (vii) a slightly polar group, consisting of Met and Cys, (viii) a small-residue group, consisting of Ser, Thr, Asp, Asn, Gly, Ala, Glu, Gln and Pro, (ix) an aliphatic group consisting of Val, Leu, Ile, Met and Cys, and (x) a small hydroxyl group consisting of Ser and Thr. Conservative substitutions also may be determined by one or more methods, such as those used by the BLAST (Basic Local Alignment Search Tool) algorithm, such as a BLOSUM Substitution Scoring Matrix; such as the BLOSUM 62 matrix, and the like. A functional way to define common properties between individual amino acids is to analyze the normalized frequencies of amino acid changes between corresponding proteins of homologous Screening of selectivity components will best be accomplished by high throughput parallel selection, as described in Holt et al. Alternatively, high throughput parallel selection may be conducted by commercial entities, such as by Cambridge Antibody Technologies or MorphoSys USA, Inc.

Alternatively, selection of a desired selectivity component-displaying phage may be carried out using the following method:

Step 1: Affinity purify phage under low stringency conditions for their ability to bind to an immunogen fixed to a solid support (for instance, beads in a column).

Step 2: Elute the bound phage and grow the eluted phage. Steps 1 and 2 may be repeated with more stringent washes in Step 1.

Step 3: Absorb the phage under moderate stringency with a given protein mixture digested with a proteolytic agent of interest. Wash away the unbound phage with a moderately stringent wash and grow the washed phage. Step 3 may be repeated with less stringent washes.

Step 4: Affinity purify phage under high stringency for their ability to bind to the immunogen fixed to a solid support. Elute the bound phage and grow the eluted phage.

Step 5: Plate the phage to select single plaques. Independently grow phage selected from each plaque and confirm the specificity to the desired immunogen.

This is a general-guideline for the clonal expansion of immunogen-specific selectivity components. Additional steps of varying stringency may be added at any stage to optimize the selection process, or steps may be omitted or re-ordered. One or more steps may be added where the phage population is selected for its inability to bind to other immunogens by absorption of the phage population with those other immunogens and amplification of the unbound phage population. That step may be performed at any stage, but typically would be performed after step 4.

In certain embodiments, it may be desirable to mutate the binding region of the selectivity component and select for selectivity components with superior binding characteristics as compared to the un-mutated selectivity component. This may be accomplished by any standard mutagenesis technique, such as by PCR with Taq polymerase under conditions that cause errors. In such a case, the PCR:primers could be used to amplify scFv-encoding sequences of phagemid plasmids under conditions that would cause mutations. The PCR product may then be cloned into a phagemid vector and screened for the desired specificity, as described above.

In other embodiments, the selectivity components may be modified to make them more resistant to cleavage by proteases. For example, the stability of the selectivity components of the present invention that comprise polypeptides may be increased by substituting one or more of the naturally occurring amino acids in the (L) configuration with D-amino acids. In various embodiments, at least 1%, 5%, 10%, 20%, 50%, 80%, 90% or 100% of the amino acid residues of the selectivity components may be of the D configuration. The switch from L to D amino acids neutralizes the digestion capabilities of many of the ubiquitous peptidases found in the digestive tract. Alternatively, enhanced stability of the selectivity components of the invention may be achieved by the introduction of modifications of the traditional peptide linkages. For example, the-introduction of a cyclic ring within the polypeptide backbone may confer enhanced stability in order to circumvent the effect of many proteolytic enzymes known to digest polypeptides in the stomach or other digestive organs and in serum. In still other embodiments, enhanced stability of the selectivity components may be achieved by intercalating one or more dextrorotatory amino acids (such as, dextrorotatory phenylalanine or dextrorotatory tryptophan) between the amino acids of the selectivity component. In exemplary embodiments, such modifications increase the protease resistance of the selectivity components without affecting their activity or specificity of interaction with a desired target molecule or reporter molecule.

In certain embodiments, the antibodies or variants thereof, may be modified to make them less immunogenic when administered to a subject. For example, if the subject is human, the antibody may be "humanized"; where the complimentarily determining region(s) of the hybridoma-derived antibody has been transplanted into a human monoclonal antibody, for example as described in Jones, P. et al. (1986), *Nature* 321, 522-525, Tempest et al. (1991) *Biotechnology* 9, 266-273, and U.S. Pat. No. 6,407,213. Also, transgenic mice, or other mammals, may be used to express humanized antibodies. Such humanization may be partial or complete.

In another embodiment, the selectivity component is a Fab fragment. Fab antibody fragments may be obtained by proteolysis of an immunoglobulin molecule using the protease papain. Papain digestion yields two identical antigen-binding fragments, termed "Fab fragments", each with a single antigen-binding site, and a residual "Fc fragment". In an exemplary embodiment, papain is first activated by reducing the sulfhydryl group in the active site with cysteine, mercaptoethanol or dithiothreitol. Heavy metals in the stock enzyme may be removed by chelation with EDTA (2 mM) to ensure maximum enzyme activity. Enzyme and substrate' are normally mixed together in the ratio of 1:100 by weight. After incubation, the reaction can be stopped by irreversible alkylation of the thiol group with iodoacetamide or simply by dialysis. The completeness of the digestion should be monitored by SDS-PAGE and the various fractions separated by protein A-Sepharose or ion exchange chromatography.

In still another embodiment, the selectivity component is a $F(ab')_2$ fragment. $F(ab')_2$ antibody fragments may be prepared from IgG molecules using limited proteolysis with the enzyme pepsin. Exemplary conditions for pepsin proteolysis are 100 times antibody excess w/w in acetate buffer at pH 4.5 and 37° C. Pepsin treatment of intact immunoglobulin molecules yields an $F(ab')_2$ fragment that has two antigen-combining sites and is still capable of crosslinking antigen. Fab' antibody fragments may be obtained by reducing $F(ab')_2$ fragments using 2-mercaptoethylamine. The Fab' fragments may be separated from unsplit $F(ab')_2$ fragments and concentrated by application to a Sephadex G-25 column (MT=46,000-58,000). In other embodiments, the selectivity component may be a non-antibody receptor molecule, including, for example, receptors which naturally recognize a desired target molecule, receptors which have been modified to increase their specificity of interaction with a target molecule, receptor molecules which have been modified to interact with a desired target molecule not naturally recognized by the receptor, and fragments of such receptor molecules (see, e.g., Skerra, *J. Molecular Recognition* 13: 167-187 (2000)).

In other embodiments, the selectivity component may be a network or pathway protein such as an enzyme, for example, a phosphatase or kinase. Such proteins may be mutated to create a binding site for a reporter and/or target molecule. For example, a method of creating a biosensor from network and pathway proteins in cells and tissues may comprise mutating a specific region on the selected protein to create a binding site for a reporter or target molecule. The region selected for mutation may be randomly or partially randomly mutated by creating mutations in selected regions of the gene that codes for the protein that is to be converted into a selectivity component. The gene with the mutated region(s) may be incorporated by transfection into a system capable of expressing the protein in a way that allows reporter molecule (or target molecule) binding and fluorescence sensitivity to the activity (if a reporter molecule) to be assayed. For example, the DNA with the mutated region may be transfected into yeast cells that are able to express many copies of the mutated protein molecules on the cell surface (see Boder and Wittrup (2000) *Meth. Enzymol.* 328:430-33; Boder, et al. (2000) *Proc. Natl. Acad. Sci USA* 97:10701-5; and Swers, et al. (2004) *Nucl. Acids. Res.* 32:e36). By isolating and identifying by selection methods the genetic sequence of the particular protein within the mutated population that functions optimally as a selectivity component. For example, reporter molecule binding mutants may be detected and selected using magnetic bead separation and by flow cytometry or image cytometry. Mutants that show a particular fluorescence signal change from bound reporter molecule in response to protein activity changes may be detected and isolated. In the case of engineering a reporter molecule binding site that is reactive, a reactive group may be engineered into the site (such as a thiol) and ability to covalently bind the reporter molecule may be assayed. A biosensor can then be produced by combining the reporter molecule with the optimized selectivity component containing the engineered site.

In other embodiments, a library of mutants is generated from a degenerate oligonucleotide sequence. There are many ways by which the library may be generated from a degenerate oligonucleotide sequence. Chemical synthesis of a degenerate gene sequence may be carried out in an automatic DNA synthesizer, and the synthetic genes may then be ligated into an appropriate vector for expression. One purpose of a degenerate set of genes is to provide, in one mixture, all of the sequences encoding the desired set of potential protein sequences. The synthesis of degenerate oligonucleotides is well known in the art (see for example, Narang, S A (1983) *Tetrahedron* 39:3; Itakura et al., (1981) *Recombinant DNA, Proc.* 3rd Cleveland Sympos. Macromolecules, ed. AG Walton, Amsterdam: Elsevier pp. 273-289; Itakura et al., (1984) *Annu. Rev. Biochem.* 53:323; Itakura et al., (1984) *Science* 198:1056; Ike et al., (1983) *Nucleic Acid Res.* 11:477). Such techniques have been employed in the directed evolution of other proteins (see, for example, Scott et al., (1990) *Science* 249:386-390; Roberts et al., (1992) *Proc. Natl. Acad. Sci. USA* 89:2429-2433; Devlin et al., (1990) *Science* 249: 404-406; Cwirla et al., (1990) *Proc. Natl. Acad. Sci. USA* 87: 6378-6382; as well as U.S. Pat. Nos. 5,223,409, 5,198,346, and 5,096,815).

Alternatively, other forms of mutagenesis may be utilized to generate a combinatorial library. For example, mutants may be generated and isolated from a library by screening using, for example, alanine scanning mutagenesis and the like (Ruf et al., (1994) *Biochemistry* 33:1565-1572; Wang et al., (1994) *J. Biol. Chem.* 269:3095-3099; Balint et al., (1993) *Gene* 137:109-118; Grodberg et al., (1993) *Eur. J. Biochem.* 218:597-601; Nagashima et al., (1993) *J. Biol. Chem.* 268: 2888-2892; Lowman et al., (1991) *Biochemistry* 30:10832-10838; and Cunningham et al., (1989) *Science* 244:1081-1085), by linker scanning mutagenesis (Gustin et al., (1993) *Virology* 193:653-660; Brown et al., (1992) *Mol. Cell. Biol.* 12:2644-2652; McKnight et al., (1982) *Science* 232:316); by saturation mutagenesis (Meyers et al., (1986) *Science* 232: 613); by PCR mutagenesis (Leung et al., (1989) *Method Cell Mol Biol* 1:11-19); or by random mutagenesis (Miller et al., (1992) A Short Course in Bacterial Genetics, CSHL Press, Cold Spring Harbor, N.Y.; and Greener et al., (1994) *Strategies in Mol Biol* 7:32-34). Linker scanning mutagenesis, particularly in a combinatorial setting, is an attractive method for identifying selectivity components.

3.B. Exemplary Polynucleotide Selectivity Components

In still other embodiments, the selectivity component may be an aptamer. Aptamers are oligonucleotides that are selected to bind specifically to a desired molecular structure. Aptamers typically are the products of an affinity selection process similar to the affinity selection of phage display (also known as in vitro molecular evolution). The process involves performing several tandem iterations of affinity separation, e.g., using a solid support to which the desired immunogen is bound, followed by polymerase chain reaction (PCR) to amplify nucleic acids that bound to the immunogens. Each round of affinity separation thus enriches the nucleic acid population for molecules that successfully bind the desired immunogen. In this manner, a random pool of nucleic acids may be "educated" to yield aptamers that specifically bind target molecules. Aptamers typically are RNA, but may be DNA or analogs or derivatives thereof, such as, without limitation, peptide nucleic acids and phosphorothioate nucleic acids.

In exemplary embodiments, nucleic acid ligands, or aptamers, may be prepared using the "SELEX" methodology which involves selection of nucleic acid ligands which interact with a target in a desirable manner combined with amplification of those selected nucleic acids. The SELEX process, is described in U.S. Pat. Nos. 5,475,096 and 5,270,163 and PCT Application No. WO 91/19813. These references, each specifically incorporated herein by reference, are collectively called the SELEX Patents.

The SELEX process provides a class of products which are nucleic acid molecules, each having a unique sequence, and each of which has the property of binding specifically to a desired target compound or molecule. In various embodiments, target molecules may be, for example, proteins, carbohydrates, peptidoglycans or small molecules. SELEX methodology can also be used to target biological structures, such as cell surfaces or viruses, through specific interaction with a molecule that is an integral part of that biological structure.

In its most basic form, the SELEX process may be defined by the following series of steps:

1) A candidate mixture of nucleic acids of differing sequence, is prepared. The candidate mixture generally includes regions of fixed sequences (i.e., each of the members of the candidate mixture contains the same sequences in the same location) and regions of randomized sequences. The fixed sequence regions are selected either, (a) to assist in the amplification steps described below, (b) to mimic a sequence known to bind to the target, or (c) to enhance the concentration of a given structural arrangement of the nucleic acids in the candidate mixture. The randomized sequences can be totally randomized (i.e., the probability of finding a base at any position being one. in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5-50%) are retained during partitioning.

4) Those nucleic acids selected during partitioning as having the relatively higher affinity for the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic-acids to the target will generally increase. The SELEX-process ultimately may yield a candidate mixture containing one or a small number of unique nucleic acids representing those nucleic acids from the original candidate mixture having the highest affinity to the target molecule.

The basic SELEX method has been modified to achieve a number of specific objectives. For example, U.S. Pat. No. 5,707,796 describes the use of the SELEX process in conjunction with gel electrophoresis to select nucleic acid molecules with specific structural characteristics, such as bent DNA. U.S. Pat. No. 5,580,737 describes a method for identifying highly specific nucleic acid ligands able to discriminate between closely related molecules, termed CounterSELEX. U.S. Pat. No. 5,567,588 describes a SELEX-based method which achieves highly efficient partitioning between oligonucleotides having high and low affinity for a target molecule. U.S. Pat. Nos. 5,496,938 and 5,683,867 describe methods for obtaining improved nucleic acid ligands after SELEX has been performed.

In certain-embodiments, nucleic acid ligands as described herein may comprise modifications that increase their stability, including, for example, modifications that provide increased resistance to degradation by enzymes such as endonucleases and exonucleases, and/or modifications that enhance or mediate the delivery of the nucleic acid ligand (see, e.g., U.S. Pat. Nos. 5,660,985 and 5,637,459). Examples of such modifications include chemical substitutions at the ribose and/or phosphate and/or base positions. In various embodiments, modifications of the nucleic acid ligands may include, but are not limited to, those which provide other chemical groups that incorporate additional charge, polarizability, hydrophobicity, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, unusual base-pairing combinations such as the isobases isocytidine and isoguanidine and the like. Modifications may also include 3' and 5' modifications such as capping. In exemplary embodiments, the nucleic acid ligands are RNA molecules that are 2'-fluoro (2'-F) modified on the sugar moiety of pyrimidine residues.

3.C. Other Exemplary Selectivity Components

In other embodiments, the selectivity components may be template imprinted material. Template imprinted materials are structures which have an outer sugar layer and an underlying plasma-deposited layer. The outer sugar layer contains indentations or imprints which are complementary in shape to a desired target molecule or template so as to allow specific interaction between the template imprinted structure and the target molecule to which it is complementary. Template imprinting can be utilized on the surface of a variety of structures, including, for example, medical prostheses (such as artificial heart valves, artificial limb joints, contact lenses and stents), microchips (preferably silicon-based microchips) and components of diagnostic equipment designed to detect specific microorganisms, such as viruses or bacteria. Template-imprinted materials are discussed in U.S. Pat. No. 6,131,580, which is hereby incorporated by reference in its entirety.

3.D. Modification of Selectivity Components for Incorporation into Biosensors and Exemplary Embodiments Wherein the Selectivity Component is Produced Independently of the Cell or Tissue to be Analyzed In certain embodiments, a selectivity component of the invention may contain a chemical handle which facilitates its isolation, immobilization, identification, or detection and/or which increases its solubility. In various embodiments, chemical handles may be a polypeptide, a polynucleotide, a carbohydrate, a polymer, or a chemical moiety and combinations or variants thereof. In certain embodiments, exemplary chemical handles, include, for example, glutathione S-transferase (GST); protein A, protein G, calmodulin-binding peptide, thioredoxin, maltose binding protein, HA, myc, poly arginine, poly H is, poly His-Asp or FLAG tags. Additional exemplary chemical handles include polypeptides that alter protein localization in vivo, such as signal peptides, type III secretion system-targeting peptides, transcytosis domains, nuclear localization signals, etc.

In various embodiments, a selectivity component of the invention may comprise one or more chemical handles, including multiple copies of the same chemical handle or two or more different chemical handles. It is also within the scope of the invention to include a linker (such as a polypeptide sequence or a chemical moiety) between a selectivity component of the invention and the chemical handle in order to facilitate construction of the molecule or to optimize its structural constraints.

In another embodiment, a selectivity component of the invention may be modified so that its rate of traversing the cellular membrane is increased. For example, the selectivity component may be attached to a peptide which promotes "transcytosis," e.g., uptake of a polypeptide by cells. The peptide may be a portion of the HIV transactivator (TAT) protein, such as the fragment corresponding to residues 37-62 or 48-60 of TAT, portions which have been observed to be rapidly taken up by a cell in vitro (Green and Loewenstein, (1989) Cell 55:1179-1188). Alternatively, the internalizing peptide may be derived from the Drosophila antennapedia protein, or homologs thereof. The 60 amino acid long homeodomain of the homeo-protein antennapedia has been demonstrated to translocate through biological membranes and can facilitate the translocation of heterologous polypeptides to which it-is coupled. Thus, selectivity components may be fused to a peptide consisting of about amino acids 42-58 of Drosophila antennapedia or shorter fragments for transcytosis (Derossi et al. (1996) J Biol Chem 271:18188-18193; Derossi et al. (1994) J Biol Chem 269:10444-10450; and Perez et al. (1992) J Cell Sci 1.02:717-722). The transcytosis polypeptide may also be a non-naturally-occurring membrane-translocating sequence (MTS), such as the peptide sequences disclosed in U.S. Pat. No. 6,248,558.

In still other embodiments, the selectivity component may comprise a fusion protein of any of the above-described polypeptide selectivity components containing at least one domain which increases its solubility and/or facilitates its purification, identification, detection, targeting and/or delivery. Exemplary domains, include, for example, glutathione S-transferase (GST), protein A, protein G, calmodulin-binding peptide, thioredoxin, maltose binding protein, HA, myc, poly arginine, poly His, poly His-Asp or FLAG fusion proteins and tags. Additional exemplary domains include domains that alter protein localization in vivo, such as signal peptides, type III secretion system-targeting peptides, transcytosis domains, nuclear localization signals, and targeting moieties, i.e. proteins specific for a target molecule, etc. In various embodiments, a polypeptide of the invention may comprise one or more heterologous fusions. Polypeptides may contain multiple copies of the same fusion domain or may contain fusions to two or more different domains. The fusions may occur at the N-terminus of the polypeptide, at the C-terminus of the polypeptide, or at both the N- and C-terminus of the polypeptide. Linker sequences between a polypeptide of the invention and the fusion domain may be included in order to facilitate construction of the fusion protein or to optimize protein expression or structural constraints of the fusion protein.

In exemplary embodiments, the dissociation constant of the selectivity component for a target molecule is optimized to allow real time monitoring of the presence and/or concentration of the analyte in a given patient, sample, or environment.

The selectivity components (for example, phage, antibodies, antibody fragments, aptamers, etc.) may be affixed to a suitable substrate by a number of known methods. Typically the surface of the substrate is functionalized in some manner, so that a crosslinking compound or compounds may covalently link the selectivity component to the substrate. For example, a substrate functionalized with carboxyl groups may be linked to free amines in the selectivity components using EDC or by other common chemistries, such as by linking with N-hydroxysuccinimide. A variety of crosslinking chemistries are commercially available, for instance, from Pierce of Rockford, Ill.

For attachment of the sensor units to surfaces there are a number of traditional attachment technologies. For example, activated carboxyl groups on the substrate will link the sensor units to the substrate via —$NH_2$ groups on the selectivity component of the biosensor. The substrate of the array may be either organic or inorganic, biological or non-biological, or any combination of these materials. Numerous materials are suitable for use as a substrate for the sensor units of the invention. For instance, the substrate of the invention sensors can comprise a material selected from a group consisting of silicon, silica, quartz, glass, controlled pore glass, carbon, alumina, titania, tantalum oxide, germanium, silicon nitride, zeolites, and gallium arsenide. Many metals such as gold, platinum, aluminum, copper, titanium, and their alloys are also options for substrates of the array. In addition, many ceramics and polymers may also be used as substrates. Polymers which may be used as substrates include, but are not limited to, the following: polystyrene; poly(tetra)fluoroethylene (PTFE); polyvinylidenedifluoride; polycarbonate; polymethylmethacrylate; polyvinylethylene; polyethyleneimine; poly(etherether)ketone; polyoxymethylene (POM); polyvinylphenol; polylactides; polymethacrylimide (PMI); polyalkenesulfone (PAS); polypropylethylene, polyethylene; polyhydroxyethylmethacrylate (HEMA); polydimethylsiloxane; polyacrylamide; polyimide; and block copolymers. Preferred substrates for the array include silicon, silica, glass, and polymers. The substrate on which the sensors reside may also be a combination of any of the aforementioned substrate materials.

A biosensor of the present invention may optionally further comprise a coating between the substrate and the bound biosensor molecule. This coating may either be formed on the substrate or applied to the substrate. The substrate can be modified with a coating by using thin-film technology based, for instance, on physical vapor deposition (PVD), plasma-enhanced chemical vapor deposition (PECVD), or thermal processing. Alternatively, plasma exposure can be used to directly activate or alter the substrate and create a coating. For instance, plasma etch procedures can be used to oxidize a polymeric surface (for example, polystyrene or polyethylene to expose polar functionalities such as hydroxyls, carboxylic acids, aldehydes and the like) which then acts as a coating.

The coating may also comprise a composition selected from the group consisting of silicon, silicon oxide, titania, tantalum oxide, silicon nitride, silicon hydride, indium tin oxide, magnesium oxide, alumina, glass, hydroxylated surfaces, and polymers.

The substrate surface shall comprise molecules of formula X(a)-R(b)-Y(c), wherein R is a spacer, X is a functional group that binds R to the surface, Y is a functional group for binding to the biosensor, (a) is an integer from 0 to about 4, (b) is either 0 or 1, and (c) is an integer not equal to 0. Note that when both (a) and (b) are zero, the substrate surface comprises functional groups Y as would be seen, for example, with polymeric substrates or coatings. When (a) and (b) are not equal to 0, then X(a)-R(b)-Y(c) describes, for example, monolayers such as a self assembled monolayers that form on a metal surface. X(a)-R(b)-Y(c) may also describe such compounds as 3-aminopropyltrimethoxysilane, wherein X is —$Si(OMe)_3$, R is —$CH_2CH_2CH_2$—, and Y is —$NH_2$. This compound is known to coat porous glass surfaces to form an aminopropyl derivative of the glass. *Biochem. Biophys. Act.*, 1970, 212, 1; *J. Chromatography*, 1974, 97, 39.

Other definitions for F, X, and Y include the following. R optionally comprises a linear or branched hydrocarbon chain from about 1 to about 400 carbons long. The hydrocarbon chain may comprise an alkyl, aryl, alkenyl, alkynyl, cycloalkyl, alkaryl, aralkyl group, or any combination thereof. If (a) and (c) are both equal to one, then R is typically an alkyl chain from about 3 to about 30 carbons long. In a preferred embodiment, if (a) and (b) are both equal to one, then R is an alkyl, chain from about 8 to about 22 carbons long and is, optionally, a straight alkane. However, it is also contemplated that in an alternative embodiment, R may readily comprise a linear or branched hydrocarbon chain from about 2 to about 400 carbons long and be interrupted by at least one hetero atom. The interrupting hetero groups can include —O—, —$CONH_2$, —CONHCO—, —NH—, —CSNH—, —CO—, —CS—, —S—, —SO—, —($OCH_2CH_2$)n- (where n=1-20), —($CF_2$)n (where n=1-22), and the like. Alternatively, one or more of the hydrogen moieties of R can be substituted with deuterium. In alternative embodiments, R may be more than about 400 carbons long.

X may be chosen as any group which affords chemisorption or physisorption of the monolayer onto the surface of the substrate (or the coating, if present). When the substrate or coating is a-metal or metal alloy, X, at least prior to incorporation into the monolayer, can in one embodiment be chosen to be an asymmetrical or symmetrical disulfide, sulfide, diselenide, selenide, thiol, isonitrile, selenol, a trivalent phosphorus compound, isothiocyanate, isocyanate, xanthanate, thiocarbamate, a phosphine, an amine, thio acid or a dithio acid. This embodiment is especially preferred when a coating or substrate is used that is a noble metal such as gold, silver, or platinum.

If the substrate is a material such as silicon, silicon oxide, indium tin oxide, magnesium oxide, alumina, quartz, glass, or silica, then, in one embodiment, the biosensor may comprise an X that, prior to incorporation into said monolayer, is a monohalosilane, dihalosilane, tihalosilane, trialkoxysilane, dialkoxysilane, or a monoalkoxysilane. Among these silanes, trichlorosilane and trialkoxysilane are exemplary.

In certain embodiments, the substrate is selected from the group consisting of silicon, silicon dioxide, indium tin oxide, alumina, glass, and titania; and X is selected from the group consisting of a monohalosilane, dihalosilane, tihalosilane, trichlorosilane, trialkoxysilane, dialkoxysilane, monoalkoxysilane, carboxylic acids, and phosphates.

In another embodiment, the substrate of the sensor is silicon and X is an olefin.

In still another embodiment, the coating (or the substrate if no coating is present) is titania or tantalum oxide and X is a phosphate.

In other embodiments, the surface of the substrate (or coating thereon) is composed of a material such as titanium oxide; tantalum oxide, indium tin oxide, magnesium oxide, or alumina where X is a carboxylic acid or alkylphosphoric acid. Alternatively, if the surface of the substrate (or coating thereon) of the sensor is copper, then X may optionally. be a hydroxamic acid.

If the substrate used in the invention is a polymer, then in many cases a coating on the substrate such as a copper coating will be included in the sensor. An appropriate functional group X for the coating would then be chosen for use in the sensor. In an alternative embodiment comprising a polymer substrate, the surface of the polymer may be plasma modified to expose desirable surface functionalities for monolayer formation. For instance, EP 780423 describes the use of a monolayer molecule that has an alkene X functionality on a plasma exposed surface. Still another possibility for the invention sensor comprised of a polymer is that the surface of the polymer on which the monolayer is formed is functionalized by copolymerization of appropriately functionalized precursor molecules.

Another possibility is that prior to incorporation into the monolayer, X can be a free radical-producing moiety. This functional group is especially appropriate when the surface on which the monolayer is formed is a hydrogenated silicon surface. Possible free-radical producing moieties include, but are not limited to, diacylperoxides, peroxides, and azo compounds. Alternatively, unsaturated moieties such as unsubstituted alkenes, alkynes, cyanocompounds and isonitrile compounds can be used for —X, if the reaction with X is accompanied by ultraviolet, infrared, visible, or microwave radiation.

In alternative embodiments, X may be a hydroxyl, carboxyl, vinyl, sulfonyl, phosphoryl, silicon hydride, or an amino group.

The component Y is a functional group responsible for binding a dye containing sensor onto the substrate. In one embodiment, the Y group is either highly reactive (activated) towards the dye containing sensor or is easily converted into such an activated form. In certain embodiments, the coupling of Y with the selectivity component of the biosensor occurs readily under normal physiological conditions. The functional group Y may either form a covalent linkage or a non-covalent linkage with the selectivity component of the biosensor. In other embodiments, the functional group Y forms a covalent linkage with the selectivity component of the biosensor. It is understood that following the attachment of the selectivity component of the biosensor to Y, the chemical nature of Y may have changed. Upon attachment of the biosensor, Y may even have been removed from the organic linker.

In one embodiment of the sensor of the present invention, Y is a functional group that is activated in situ. Possibilities for this type of functional group include, but are not limited to, such simple moieties such as a hydroxyl, carboxyl, amino, aldehyde, carbonyl, methyl, methylene, alkene, allyne, carbonate, aryliodide, or a vinyl group. Appropriate modes of activation would be obvious to one skilled in the art. Alternatively, Y can comprise a functional group that requires photoactivation prior to becoming activated enough to trap the protein capture agent.

In another embodiment, Y is a complex and highly reactive functional moiety that needs no in situ activation prior to reaction with the selectivity component of the biosensor. Such possibilities for Y include, but are not limited to, maleimide, N-hydroxysuccinimide (Wagner et al., *Biophysical Journal*, 1996, 70:2052-2066), nitrilotriacetic acid (U.S. Pat. No. 5,620,850), activated hydroxyl, haloacetyl, bromoacetyl, iodoacetyl, activated carboxyl, hydrazide, epoxy, aziridine, sulfonylchloride, trifluoromethyldiaziridine, pyridyldisulfide, N-acyl-imidazole, imidazolcearbatnate, vinylsulfone, succinimidylcarbonate, arylazide, anhydride, diazoacetate, benzophenone, isothiocyanate, isocyanate, imidoester, fluorobenzene, and biotin.

In an alternative embodiment, the functional group Y is selected from the group of simple functional moieties. Possible Y functional groups include, but are not limited to —OH, —NH$_2$, —COOH, —COOR, —RSR, —PO$_4^{-3}$, —OSO$_3^{-2}$, —COONR$_2$, SOO$^-$, —CN, —NR$_2$, and the like.

In another embodiment, one or more biosensor species may be bound to discrete beads or microspheres. The microspheres typically are either carboxylated or avidin-modified so that proteins, such as antibodies, non-antibody receptors and variants and fragments thereof, may be readily attached to the beads by standard chemistries. In an exemplary embodiment, the selectivity components are scFv fragments. The scFv fragments may be bound to carboxylated beads by one of many linking chemistries, such as, for example, EDC chemistry, or bound to avidin-coated beads by first biotinylating the scFv fragment by one of many common biotinylation chemistries, such as, for example, by conjugation with sulfo-NHS-LC-biotin.

In another embodiment, two or more biosensors are affixed to one or more supports at discrete locations (that is, biosensors having a first specificity are affixed at a first spatial location, biosensors having a second specificity are affixed at a second spatial location, etc.). In one embodiment, the biosensors are affixed to a substrate in a tiled array, with each biosensor represented in one or more positions in the tiled array. The spatial configuration of the substrate or substrates may be varied so long as each biosensor species is bound at detectably discrete locations. The substrate and tiled biosensor pattern typically is planar, but may be any geometric configuration desired. For instance, the substrate may be a strip or cylindrical, as illustrated in U.S. Pat. No. 6,057,100. In exemplary embodiments, the substrate may be glass-or other silicic compositions; such as those used in the semiconductor industry.

Fabrication of the substrate may be by one of many well-known processes. In various embodiments, the biosensors of the array may be associated with the same reporter molecule or may be associated with different reporter molecules. Identification of a biosensor that interacts with a target molecule may be based on the signal from the reporter molecule, the location of the biosensor on the array, or a combination thereof. Arrays may be used in association with both the in vitro and in vivo applications of the invention.

In various embodiments, the arrays may comprise any of the biosensors described herein, including, for example, arrays of biosensors wherein the selectivity components are polypeptides (including, antibodies and variants or fragments thereof), polynucleotides (i.e., aptamers), template imprinted materials, organic binding elements, and inorganic binding elements. The arrays may comprise one type of biosensor or a mixture of different types of biosensors (e.g., a mixture of biosensors having polypeptide and polynucleotide selectivity components). Protein microarrays are described, for example, in PCT Publication WO 00/04389, incorporated herein by reference. Examples of commercially available protein microarrays are those of Zyomyx of Hayward, Calif., Ciphergen Biosystems, Inc. of Fremont, Calif. and Nanogen, Inc. of San Diego, Calif. Nucleic acid microarrays are described, for example, in U.S. Pat. Nos. 6,261,776 and 5,837,832. Examples of commercially available nucleic acid microarrays are those of Affymetrix, Inc. of Santa Clara, Calif., BD Biosciences Clontech of Palo Alto, Calif. and Sigma-Aldrich Corp. of St. Louis, Mo.

3.E. Exemplary Embodiments Wherein the Selectivity Component is Expressed in the Cell or Tissue to be Analyzed In other embodiments, the selectivity component is expressed within the cell or organism or subject to be analyzed. The expression methods described below may also be used to express a selectivity component in a host cell that is then isolated and purified for use in the methods, wherein the biosensor is generated from a source external to the cell or tissue to be analyzed.

Generally, a nucleic acid encoding a selectivity component is introduced into a host cell, such as by transfection or infection, and the host cell is cultured under conditions allowing expression of the selectivity component. Methods of introducing nucleic acids into prokaryotic and eukaryotic cells are well known in the art. Suitable media for mammalian and prokaryotic host cell culture are well known in the art. In some instances, the nucleic acid encoding the subject polypeptide is under the control of an inducible promoter, which is induced once the host cells comprising the nucleic acid have divided a certain number of times. For example, where a nucleic acid is under the control of a beta-galactose operator and repressor, isopropyl beta-D-thiogalactopyranoside (IPTG) is added to the culture when the bacterial host cells have attained a density of about $OD_{600}$ 0.45-0.60. The culture is then grown for some more time to give the host cell the time to synthesize the polypeptide. Cultures are then typically frozen and may be stored frozen for some time, prior to isolation and purification of the polypeptide.

Thus, a nucleotide sequence encoding all or part of a selectivity component may be used to produce a recombinant form of a selectivity component via microbial or eukaryotic cellular processes. Ligating the sequence into a polynucleotide construct, such as an expression vector, and transforming, infecting, or transfecting into hosts, either eukaryotic (yeast, avian, insect or mammalian) or prokaryotic (bacterial cells), are standard procedures. Similar procedures, or modifications thereof, may be employed to prepare recombinant polypeptides by microbial means or tissue-culture technology in accord with the subject invention.

Other embodiments of nucleic acid sequences encoding the selectivity components, as well as vectors, host cells, and cultures thereof are further described below.

In another embodiment, the nucleic acid encoding a selectivity component is operably linked to a bacterial promoter, e.g., the anaerobic *E. coli*, NirB promoter or the *E. coli* lipoprotein 11p promoter, described, e.g., in Inouye et al. (1985) *Nucl. Acids Res.* 13:3101; *Salmonella* pagC promoter (Miller et al., supra), *Shigella* ent promoter (Schmitt and Payne, *J. Bacteriol.* 173:816 (1991)), the tet promoter on Tn10 (Miller et al., supra), or the ctx promoter of *Vibrio cholera*. Any other promoter can be used in the invention. The bacterial promoter can be a constitutive promoter or an inducible promoter. An exemplary inducible promoter is a promoter which is inducible by iron or in iron-limiting conditions. In fact, some bacteria, e.g., intracellular organisms, are believed to encounter iron-limiting conditions in the host cytoplasm. Examples of iron-regulated promoters of FepA and TonB are known in the art and are described, e.g., in the following references: Headley, V. et al. (1997) *Infection & Immunity* 65:818; Ochsner, U. A. et al. (1995) *Journal of Bacteriology* 177:7194; Hunt, M. D. et al. (1994) *Journal of Bacteriology* 176:3944; Svinarich, D. M. and S. Palchaudhuri. (1992) *Journal of Diarrhoeal Diseases Research* 10:139; Prince, R. W. et al. (1991) *Molecular Microbiology* 5:2823; Goldberg, M. B. et al. (1990) *Journal of Bacteriology* 172:6863; de Lorenzo, V. et al. (1987) *Journal of Bacteriology* 169:2624; and Hantke, K. (1981) *Molecular & General Genetics* 182:288.

In another embodiment, a signal peptide sequence is added to the construct, such that the selectivity component is secreted from cells. Such signal peptides are well known in the art.

In one embodiment, the powerful phage T5 promoter, that is recognized by *E. coli* RNA polymerase is used together with a lac operator repression module to provide tightly regulated, high level expression or recombinant proteins in *E. coli*. In this system, protein expression is blocked in the presence of high levels of lac repressor.

In one embodiment, the DNA is operably linked to a first promoter and the bacterium further comprises a second DNA encoding a first polymerase which is capable of mediating transcription from the first promoter, wherein the DNA encoding the first polymerase is operably linked to a second promoter. In a preferred embodiment, the second promoter is a bacterial promoter, such as those delineated above. In an even more preferred embodiment, the polymerase is a bacteriophage polymerase, e.g., SP6, T3, or T7 polymerase and the first promoter is a bacteriophage promoter, e.g., an SP6, T3, or T7 promoter, respectively. Plasmids comprising bacteriophage promoters and plasmids encoding bacteriophage polymerases can be obtained commercially, e.g., from Promega Corp. (Madison, Wis.) and InVitrogen (San Diego, Calif.), or can be obtained directly from the bacteriophage using standard recombinant DNA techniques (J. Sambrook, E. Fritsch, T. Maniatis, Molecular Cloning: A Laboratory Manual, Cold Spring Laboratory Press, 1989). Bacteriophage polymerases and promoters are further described, e.g., in the following references: Sagawa, H. et al. (1996) *Gene* 168:37; Cheng, X. et al. (1994) *Proc. Natl. Acad. Sci. USA* 91:4034; Dubendorff, J. W. and F. W. Studier (1991) *Journal of Molecular Biology* 219:45; Bujarski, J. J. and P. Kaesberg (1987) *Nucleic Acids Research* 15:1337; and Studier, F. W. et al. (1990) *Methods in Enzymology* 185:60). Such plasmids can further be modified according to the specific embodiment of the invention.

In another embodiment, the bacterium further comprises a DNA encoding a second polymerase which is capable of mediating transcription from the second promoter, wherein the DNA encoding the second polymerase is operably linked to a third promoter. In a preferred embodiment, the third promoter is a bacterial promoter. However, more than two different polymerases and promoters could be introduced in a bacterium to obtain high levels of transcription. The use of one or more polymerase for mediating transcription in the bacterium can provide a significant increase in the amount of polypeptide in the bacterium relative to a bacterium in which the DNA is directly under the control of a bacterial promoter. The selection of the system to adopt will vary depending on the specific use of the invention, e.g., on the amount of protein that one desires to produce.

When using a prokaryotic host cell, the host cell may include a plasmid which expresses an internal T7 lysozyme, e.g., expressed from plasmid. Lysis of such host cells liberates the lysozyme which then degrades the bacterial membrane.

Other sequences that may be included in a vector for expression in bacterial or other prokaryotic cells include a synthetic ribosomal binding site; strong transcriptional terminators, e.g., t0 from phage lambda and t4 from the rrnB operon in *E. coli*, to prevent read through transcription and ensure stability of the expressed polypeptide; an origin of replication, e.g., ColE1; and beta-lactamase gene, conferring ampicillin resistance.

Other host cells include prokaryotic host cells. Even more preferred host cells are bacteria, e.g., *E. coli*. Other bacteria that can be used include *Shigella* spp., *Salmonella* spp., *Listeria* spp., *Rickettsia* spp., *Yersinia* spp., *Escherichia* spp., *Klebsiella* spp., *Bordetella* spp., *Neisseria* spp., *Aeromonas* spp., *Franciesella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Vibrio* spp., *Bacillus* spp., and *Erysipelothrix* spp. Most of these bacteria can be obtained from the American Type Culture Collection (ATCC; 10801 University Blvd., Manassas, Va. 20110-2209).

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al., (1983) in Experimental Manipulation of Gene Expression, ed. M. Inouye Academic Press, p. 83). These vectors may replicate in *E. coli* due the presence of the pBR322 ori, and in *S. cerevisiae* due to the replication determinant of the yeast 2 micron plasmid. In addition, drug resistance markers such as ampicillin may be used.

In certain embodiments, mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see Molecular Cloning A Laboratory Manual, 2nd Ed., ed. by Sambrook, Fritsch and Maniatis (Cold Spring Harbor Laboratory Press, 1989) Chapters 16 and 17. In some instances, it may be desirable to express the recombinant protein by the use of a baculovirus expression system. Examples of such baculovirus expression systems include pVL-derived vectors (such as pVL1392, pVL1393 and pVL941), pAcUW-derived vectors (such as pAcUW1), and pFastBac-derived vectors.

In another variation, protein production may be achieved using in vitro translation systems. In vitro translation systems are, generally, a translation system which is a cell-free extract comprising at least the minimum elements necessary for translation of an RNA molecule into a protein. An in vitro translation system typically comprises at least ribosomes, tRNAs, initiator methionyl-tRNAMet, proteins or complexes involved in translation, e.g., eIF2, eIF3, the cap-binding (CB) complex, comprising the cap-binding protein (CBP) and eukaryotic initiation factor 4F (eIF4F). A variety of in vitro translation systems are well known in the art and include commercially available kits. Examples of in vitro translation systems include eukaryotic lysates, such as rabbit reticulocyte lysates, rabbit oocyte lysates, human cell lysates, insect cell lysates and wheat germ extracts. Lysates are commercially available from manufacturers such as Promega Corp., Madison, Wis.; Stratagene, La Jolla, Calif.; Amersham, Arlington Heights, Ill.; and GIBCO/BRL, Grand Island, N.Y. In vitro translation systems typically comprise macromolecules, such as enzymes, translation, initiation and elongation factors, chemical reagents, and ribosomes. In addition, an in vitro transcription system may be used. Such systems typically comprise at least an RNA polymerase holoenzyme, ribonucleotides and any necessary transcription initiation, elongation and termination factors. An RNA nucleotide for in vitro translation may be produced using methods known in the art. In vitro transcription and translation may be coupled in a one-pot reaction to produce proteins from one or more isolated DNAs.

When expression of a carboxy terminal fragment of a polypeptide is desired, i.e. a truncation mutant, it may be necessary to add a start codon (ATG) to the oligonucleotide fragment comprising the desired sequence to be expressed. It is well known in the art that a methionine at the N-terminal position may be enzymatically cleaved by the use of the enzyme methionine aminopeptidase (MAP). MAP has been cloned from *E. coli* (Ben-Bassat et al., (1987) *J. Bacteriol.* 169:751-757) and *Salmonella typhimurium* and its in vitro activity has been demonstrated on recombinant proteins (Miller et al., (1987) *Proc. Natl. Acad. Sci. USA* 84:2718-1722). Therefore, removal of an N-terminal methionine, if desired, may be achieved either in vivo by expressing such recombinant polypeptides in a host which produces MAP (e.g., *E. coli* or CM89 or *S. cerevisiae*), or in vitro by use of purified MAP (e.g., procedure of Miller et al.).

In cases where plant expression vectors are used, the expression of a polypeptide may be driven by any of a number of promoters. For example, viral promoters such as the 35S RNA and 19S RNA promoters of CaMV (Brisson et al., 1984, *Nature,* 310:511-514), or the coat protein promoter of TMV (Takamatsu et al., 1987, *EMBO J.,* 6:307-311) may be used; alternatively, plant promoters such as the small subunit of RUBISCO (Coruzzi et al., 1994, *EMBO J.,* 3:1671-1680; Broglie et al., 1984, *Science,* 224:838-843); or heat shock promoters, e.g., soybean hsp 17.5-E or hsp 17.3-B (Gurley et al., 1986, *Mol. Cell. Biol.,* 6:559-565) may be used. These constructs can be introduced into plant cells using Ti plasmids, Ri plasmids, plant virus vectors; direct DNA transformation; microinjection, electroporation, etc. For reviews of such techniques see, for example, Weissbach & Weissbach, 1988, *Methods for Plant Molecular Biology*, Academic Press, New York, Section VIII, pp. 421-463; and Grierson & Corey, 1988, *Plant Molecular Biology,* 2d Ed., Blackie, London, Ch. 7-9.

An alternative expression system which can be used to express a polypeptide is an insect system. In one such system, *Autographa californica* nuclear polyhedrosis virus (AcNPV) is used as a vector to express foreign genes. The virus grows in *Spodoptera frugiperda* cells. The PGHS-2 sequence may be cloned into non-essential regions (for example the polyhedrin gene) of the virus and placed under control of an AcNPV promoter (for example the polyhedrin promoter). Successful insertion of the coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (e.g., see Smith et al., 1983, *J. Virol.,* 46:584, Smith, U.S. Pat. No. 4,215,051).

In a specific embodiment of an insect system, the DNA encoding the subject polypeptide is cloned into the pBlue-BacIII recombinant transfer vector (Invitrogen, San Diego, Calif.) downstream of the polyhedrin promoter and transfected into Sf9 insect cells (derived from *Spodoptera fru-* giperda ovarian cells, available from Invitrogen, San Diego, Calif.) to generate recombinant virus. After plaque purification of the recombinant virus high-titer viral stocks are prepared that in turn would be used to infect Sf9 or High Five™ (BTI-TN-5B1-4 cells derived from *Trichoplusia ni* egg cell homogenates; available from Invitrogen, San Diego, Calif.) insect cells, to produce large quantities of appropriately post-translationally modified subject polypeptide. Although it is possible that these cells themselves could be directly useful for drug assay, the subject polypeptides prepared by this method can be used for in vitro assays.

In another embodiment, the subject polypeptides are prepared in transgenic animals, such that in certain embodiments, the polypeptide is secreted, e.g., in the milk of a female animal.

Viral vectors may also be used for efficient in vitro introduction of a nucleic acid into a cell. Infection of cells with a viral vector has the advantage that a large proportion of the targeted cells can receive the nucleic acid. Additionally, polypeptides encoded by genetic material in the viral vector, e.g., by a nucleic acid contained in the viral vector, are expressed efficiently in cells that have taken up viral vector nucleic acid.

Retrovirus vectors and adeno-associated virus vectors are generally understood to be the recombinant gene delivery system of choice for the transfer of exogenous genes in vivo, particularly into mammals. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (see Miller, A. D. (1990) *Blood* 76:271). Thus, recombinant retrovirus can be constructed in which part of the retroviral coding sequence (gag, pol, env) has been replaced by nucleic acid encoding one of the antisense E6AP constructs, rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10-9.14, and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include Crip, Cre and Am. Retroviruses have been used to introduce a variety of genes into many different cell types, including neural cells, epithelial cells, endothelial cells, lymphocytes, myoblasts, hepatocytes, bone marrow cells, in vitro and/or in vivo (see for example Eglitis, et al. (1985) *Science* 230:1395-1398; Danos and Mulligan (1988) *Proc. Natl. Acad. Sci. USA* 85:6460-6464; Wilson et al. (1988) *Proc. Natl. Acad. Sci. USA* 85:3014-3018; Armentano et al. (1990) *Proc. Natl. Acad. Sci. USA* 87:6141-6145; Huber et al. (1991) *Proc. Natl. Acad. Sci. USA* 88:8039-8043; Ferry et al. (1991) *Proc. Natl. Acad. Sci. USA* 88:8377-8381; Chowdhury et al. (1991) *Science* 254:1802-1805; van Beusechem et al. (1992) *Proc. Natl. Acad. Sci. USA* 89:7640-7644; Kay et al. (1992) *Human Gene Therapy* 3:641-647; Dai et al. (1992) *Proc. Natl. Acad. Sci. USA* 89:10892-10895; Hwu et al. (1993) *J. Immunol.* 150: 4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

In choosing retroviral vectors as a gene delivery system for nucleic acids encoding the subject polypeptides, it is important to note that a prerequisite for the successful infection of target cells by most retroviruses, and therefore of stable introduction of the genetic material, is that the target cells must be dividing. In general, this requirement will not be a hindrance to use of retroviral vectors. In fact, such limitation on infection can be beneficial in circumstances wherein the tissue (e.g., nontransformed cells) surrounding the target cells does not undergo extensive cell division and is therefore refractory to infection with retroviral vectors.

Furthermore, it has been shown that it is possible to limit the infection spectrum of retroviruses and consequently of retroviral-based vectors, by modifying the viral packaging proteins on the surface of the viral particle (see, for example, PCT publications WO93/25234, WO94/06920, and WO94/11524). For instance, strategies for the modification of the infection spectrum of retroviral vectors include: coupling antibodies specific for cell surface antigens to the viral env protein (Roux et al. (1989) *Proc. Natl. Acad. Sci. USA* 86:9079-9083; Julan et al. (1992) *J. Gen Virol* 73:3251-3255; and Goud et al. (1983) *Virology* 163:251-254); or coupling cell surface ligands to the viral env proteins (Neda et al. (1991) *J Biol Chem* 266:14143-14146). Coupling can be in the form of the chemical cross-linking with a protein or other variety (e.g., lactose to convert the env protein to an asialoglycoprotein), as well as by generating chimeric proteins (e.g., single-chain antibody/env chimeric proteins). This technique, while useful to limit or otherwise direct the infection to certain tissue types, and can also be used to convert an ecotropic vector in to an amphotropic vector.

Moreover, use of retroviral gene delivery can be further enhanced by the use of tissue- or cell-specific transcriptional regulatory sequences which control expression of the genetic material of the retroviral vector.

Another viral gene delivery system utilizes adenovirus-derived vectors. The genome of an adenovirus can be manipulated such that it encodes a gene product of interest, but is inactive in terms of its ability to replicate in a normal lytic viral life cycle (see, for example, Berkner et al. (1988) *Bio-Techniques* 6:616; Rosenfeld et al. (1991) *Science* 252:431-434; and Rosenfeld et al. (1992) *Cell* 68:143-155). Suitable adenoviral vectors derived from the adenovirus strain Ad type 5 dl324 or other strains of adenovirus (e.g., Ad2, Ad3, Ad7, etc.) are well known to those skilled in the art. Recombinant adenoviruses can be advantageous in certain circumstances in that they are capable of infecting non-dividing cells and can be used to infect a wide variety of cell types, including airway epithelium (Rosenfeld et al. (1992) cited supra), endothelial cells (Lemarchand et al. (1992) *Proc. Natl. Acad. Sci. USA* 89:6482-6486), hepatocytes (Herz and Gerard (1993) *Proc. Natl. Acad. Sci. USA* 90:2812-2816) and muscle cells (Quantin et al. (1992) *Proc. Natl. Acad. Sci. USA* 89:2581-2584). Furthermore, the virus particle is relatively stable and amenable to purification and concentration, and, as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham (1986) *J. Virol.* 57:267). Most replication-defective adenoviral vectors currently in use and therefore favored by the present invention have deleted for all or parts of the viral E1 and E3 genes but retain as much as 80% of the adenoviral genetic material (see, for example, Jones et al. (1979) *Cell* 16:683; Berkner et al., supra; and Graham et al. in *Methods in Molecular Biology*, E. J. Murray, Ed. (Humana, Clifton, N.J., 1991) vol. 7. pp. 109-127). Expression of the inserted genetic material can be under control of, for example, the E1A promoter, the major late promoter (MLP) and associated leader sequences, the E3 promoter, or exogenously added promoter sequences.

Yet another viral vector system useful for delivery of genetic material encoding the subject polypeptides is the adeno-associated virus (AAV). Adeno-associated virus is a naturally occurring defective virus that requires another virus, such as an adenovirus or a herpes virus, as a helper virus for efficient replication and a productive life cycle. (see Muzyczka et al. *Curr. Topics in Micro. and Immunol.* (1992) 158:97-129). It is also one of the few viruses that may integrate its DNA into non-dividing cells, and exhibits a high frequency of stable integration (see for example Flotte et al. (1992) *Am. J. Respir. Cell. Mol. Biol.* 7:349-356; Samulski et al. (1989) *J. Virol.* 63:3822-3828; and McLaughlin et al. (1989) *J. Virol.* 62:1963-1973). Vectors comprising as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251-3260 can be used to introduce DNA into cells. A variety of nucleic acids have been introduced into different cell types using AAV vectors (see for example Hermonat et al. (1984) *Proc. Natl. Acad. Sci. USA* 81:6466-6470; Tratschin et al. (1985) *Mol. Cell. Biol.* 4:2072-2081; Wondisford et al. (1988) *Mol. Endocrinol.* 2:32-39; Tratschin et al. (1984) *J. Virol.* 51:611-619; and Flotte et al. (1993) *J. Biol. Chem.* 268:3781-3790).

In particular, a AAV delivery system suitable for targeting muscle tissue has been developed by Gregorevic, et al., *Nat Med.* 2004 August; 10(8):828-34. Epub 2004 July 25, which is able to 'home-in' on muscle cells and does not trigger an immune system response. The delivery system also includes use of a growth factor, VEGF, which appears to increase penetration into muscles of the gene therapy agent.

Other viral vector systems may be derived from herpes virus, vaccinia virus, and several RNA viruses.

In addition to viral transfer methods, such as those illustrated above, non-viral methods can also be employed to cause expression of nucleic acids encoding the subject polypeptides, e.g. in a cell in vitro or in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of genetic material by the targeted cell. Exemplary gene delivery systems of this type include liposomal derived systems, polylysine conjugates, and artificial viral envelopes.

In a representative embodiment, genetic material can be entrapped in liposomes bearing positive charges on their surface (e.g., lipofectins) and, optionally, which are tagged with antibodies against cell surface antigens of the target tissue (Mizuno et al. (1992) *No Shinkei Geka* 20:547-551; PCT publication WO91/06309; Japanese patent application 1047381; and European patent publication EP-A-43075). For example, lipofection of papilloma-infected cells can be carried out using liposomes tagged with monoclonal antibodies against PV-associated antigen (see Viac et al. (1978) *J Invest Dermatol* 70:263-266; see also Mizuno et al. (1992) *Neurol. Med. Chir.* 32:873-876).

In yet another illustrative embodiment, the gene delivery system comprises an antibody or cell surface ligand which is cross-linked with a gene binding agent such as polylysine (see, for example, PCT publications WO93/04701, WO92/22635, WO92/20316, WO92/19749, and WO92/06180). For example, genetic material encoding the subject chimeric polypeptides can be used to transfect hepatocytic cells in vivo using a soluble polynucleotide carrier comprising an asialoglycoprotein conjugated to a polycation, e.g., polylysine (see U.S. Pat. No. 5,166,320). It will also be appreciated that effective delivery of the subject nucleic acid constructs via mediated endocytosis can be improved using agents which enhance escape of the gene from the endosomal structures. For instance, whole adenovirus or fusogenic peptides of the influenza HA gene product can be used as part of the delivery system to induce efficient disruption of DNA-comprising endosomes (Mulligan et al. (1993) *Science* 260-926; Wagner et al. (1992) *Proc. Natl. Acad. Sci. USA* 89:7934; and Christiano et al. (1993) *Proc. Natl. Acad. Sci. USA* 90:2122).

Tissue-specific expression of a selectivity component may be achieved by use of a construct comprising a tissue-specific promoter.

4. Reporters

The reporter may be any molecule which produces a detectable signal change in response to an alteration in the environment. For example; the signal change may be an increase or decrease in signal intensity, or a change in the type of signal produced. In exemplary embodiments, suitable reporters include molecules which produce optically detectable signals; including, for example, fluorescent and chemiluminescent molecules. In certain embodiments, the reporter molecule is a long wavelength fluorescent molecule which permits detection of the reporter signal through a tissue sample, especially non-invasive detection of the reporter in conjunction with in vivo applications.

Without being bound by theory, in certain embodiments, the reporter molecule is a pH sensitive fluorescent dye (pH sensor dye) which shows a spectral change upon interaction of a selectivity component with a target molecule. Interaction of the selectivity component with a target molecule may lead to a shift in the pH of the microenvironment surrounding the selectivity component due to the composition of acidic and basic residues on the selectivity and/or target molecules. In turn, the shift in the pH microenvironment leads to a detectable spectral change in the signal of the pH sensitive fluorescent dye molecule associated with the selectivity component. In exemplary embodiments, a pH sensitive dye is selected with an appropriate pKa to lead to an optimal spectral change upon binding of the particular selectivity component/target molecule combination. A variety of pH sensitive dyes suitable for use in accordance with the invention are commercially available. In exemplary embodiments, pH sensitive dyes include, for example, fluorescein, umbelliferones (coumarin compounds), pyrenes, resorufin, hydroxy esters, aromatic acids, styryl dyes, tetramethyl rhodamine dyes, and cyanine dyes, and pH sensitive derivatives thereof.

Without being bound by theory, in other embodiments, the reporter molecule is a polarity sensitive fluorescent dye (polarity sensor dye) which shows a spectral change upon interaction-of-a-selectivity component with a target molecule. Interaction of the selectivity component with a target molecule may lead to a shift in the polarity of the microenvironment surrounding the selectivity component due to the composition of polar and/or non-polar residues on the selectivity and/or target molecules. In turn, the change in the polarity of the microenvironment leads to a detectable spectral change in the signal of the polarity sensitive fluorescent dye molecule associated with the selectivity component. A variety of polarity sensitive dyes suitable for use in accordance with the invention are commercially available. In exemplary embodiments, polarity sensitive dyes include, for example, merocyanine dyes, 5-((((2-iodoacetyl)amino)ethyl)amino)naphthalene-1-sulfonic acid (1,5-IAEDANS), and CPM, and polarity sensitive derivatives of merocyanine dyes, IAEDANS, and CPM.

Without being bound by theory, in certain embodiments, the reporter molecule is a fluorescent dye that is sensitive to changes in the microviscosity of the local environment (restriction sensor dye). Interaction of the selectivity component with a target molecule may lead to a change in the microviscosity in the local environment surrounding the selectivity component. In turn, the change in microviscosity may lead to a detectable spectral change in the signal of the mobility sensor dye molecule associated with the selectivity component. For example, an increase of microviscosity upon target binding will restrict the dye and increase the quantum yield of the emitted fluorescence signal. A variety of restriction sensor dyes suitable for use in accordance with the invention are commercially available. In exemplary embodiments, restriction sensor dyes include, for example, monomethine and trimethine cyanine dyes, and microviscosity sensitive derivatives of monomethine and trimethine cyanine dyes.

Without being bound by theory, in certain embodiments, the reporter molecule is a fluorescent dye that exhibits a spectral change due to a modification in the tumbling rate of the dye as measured on a nanosecond time scale (mobility sensor dye). Mobility sensor dye molecules may be linked to the selectivity component using a linker molecule that permits free rotation of the dye molecule. Upon interaction of the selectivity component with a target molecule, the rotation of the dye molecule around the linker may become restricted leading to a change in the ratio of parallel to perpendicular polarization of the dye molecule. A change in polarization of the mobility sensor dye may be detected as a change in the spectral emission of the dye and can be measured using light polarization optics for both excitation and emission to determine the tumbling rate of the dye. Abbott's fluorescence polarization technology is an exemplary method for determining the polarization of the dye. In exemplary embodiments, the mobility sensor dye is attached to the selectivity component using a triple-bond containing linker that extends the dye away from the surface of the selectivity component. A variety of mobility sensor dyes suitable for use in accordance with the invention are commercially available. In exemplary embodiments, mobility sensor dyes include, for example, cyanine dyes and derivatives thereof.

Figure 6:
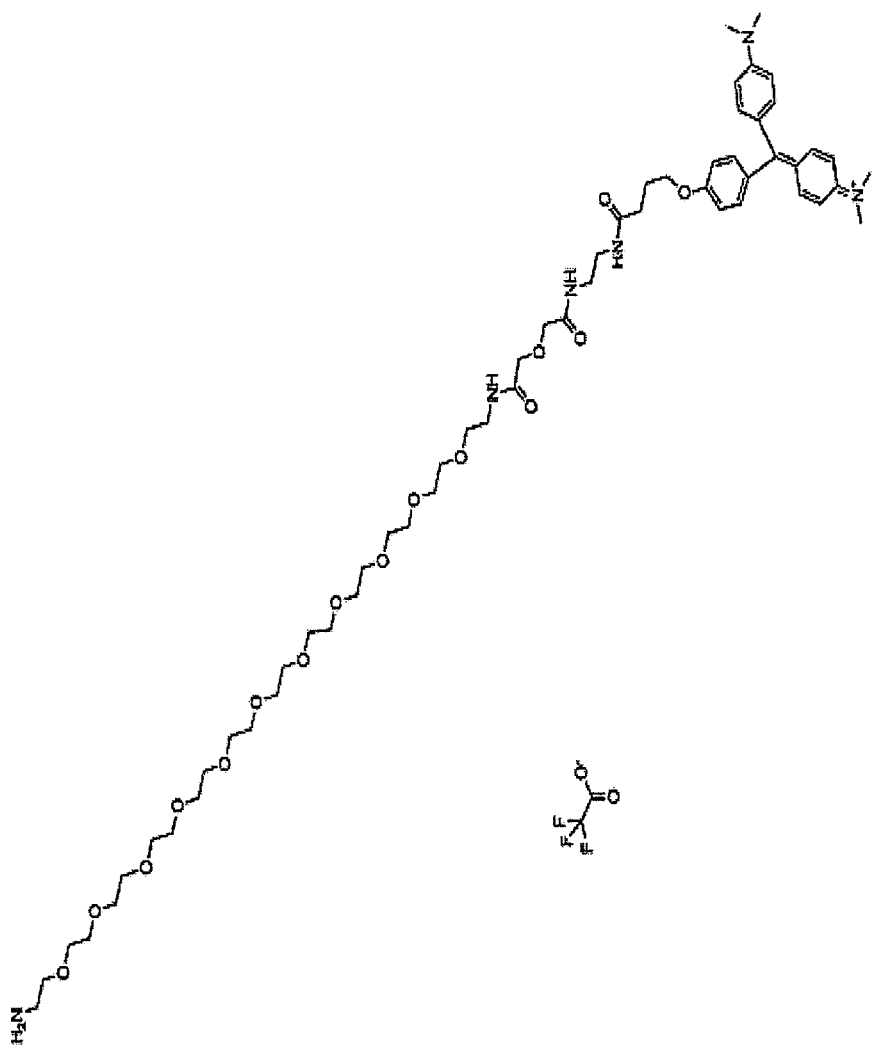
FIG. 6 depicts the structure of Malachite Green derivatized with a PEG amine. In some embodiments, the amino group may be covalently modified with a biotin group for streptavidin coated magnetic bead enrichment of yeast bearing scFv proteins that bind to the Malachite Green on the opposite end of the PEG linker.

In certain embodiments, the reporter molecule is a dye that exhibits a change in its spectral properties when specifically bound to a selectivity component. A nucleic acid, e.g. an aptamer, may be designed to specifically bind such a dye, for example Malachite Green (see R. Babendure, et al. (2003) *J. Am. Chem. Soc.* 125:14716). Such dyes, when in complex with the nucleic acid or protein that is specific for them, change their spectral properties. For example, Malachite Green and its analogs, which is not normally fluorescent, becomes strongly fluorescent when bound to an aptamer specific for it or an scFv. FIG. 6 depicts the structure of Malachite Green derivatized with a PEG amine.

In certain embodiments, the reporter molecule is represented by structure I, II, or III:

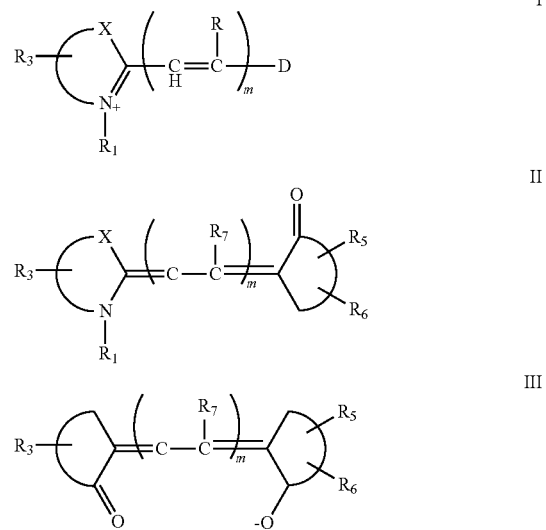

wherein:
the curved lines represent the atoms necessary to complete a structure selected from one ring, two fused rings, and three fused rings, each said ring having five or six atoms, and each said ring comprising carbon atoms and, optionally, no more than two atoms selected from oxygen, nitrogen and sulfur;
D, if present, is

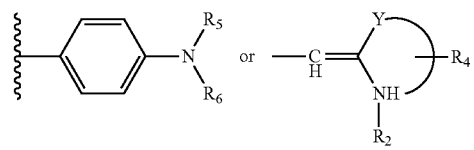

m is 1, 2, 3 or 4, and for cyanine, oxynol and thiazole orange, m can be 0;
X and Y are independently selected from the group consisting of O, S, and —C(CH$_3$)$_2$—;
at least one R1, R2, R3, R4, R5, R6, or R7 is selected from the group consisting of: a moiety that controls water solubility and non-specific binding, a moiety that prevents the reporter molecule from entering the cell through the membrane, a group that comprises, optionally with a linker, biotin a hapten, a His-tag, or other moiety to facilitate the process of isolating the selection entity, a fluorescent label optionally comprising a linker, a photoreactive group, or a reactive group such as a group containing isothiocyanate, isocyanate, monochlorotriazine, dichlorotriazine, mono- or di-halogen substituted pyridine, mono- or di-halogen substituted diazine, phosphoramidite, maleimide, aziridine, sulfonyl halide, acid halide, hydroxysuccinimide ester, hydroxysulfosuccinimide ester, imido ester, hydrazine, axidonitrophenyl, azide, 3-(2-pyridyl dithio)-proprionamide, glyoxal, haloacetamido, or aldehyde;
further-providing that R1 and R2 may be joined by a —CHR$_8$—CHR$_8$— or —BF$_2$— biradical;
wherein;
R$_8$ independently for each occurrence is selected from the group consisting of hydrogen, amino, quaternary amino, aldehyde, aryl, hydroxyl, phosphoryl, sulfhydryl, water solubilizing groups, alkyl groups of twenty-six carbons or less, lipid solubilizing groups, hydrocarbon solubilizing groups, groups promoting solubility in polar solvents, groups promoting solubility in nonpolar solvents, and -E-F; and further providing that any of R1, R2, R3, R4, R5, R6, or R7 may be substituted with halo, nitro, cyan, —CO$_2$alkyl, —CO$_2$H, —CO$_2$aryl, NO$_2$, or alkoxy, wherein:

F is selected from the group consisting of hydroxy, protected hydroxy, alkoxy, sulfonate, sulfate, carboxylate, and lower alkyl substituted amino or quarternary amino;

E is spacer group of formula —(CH$_2$)n- wherein n is an integer from 0-5 inclusively;

In other embodiments, wherein m=0 in structures I, II, and III, the following general structures IV, V and VI are afforded:

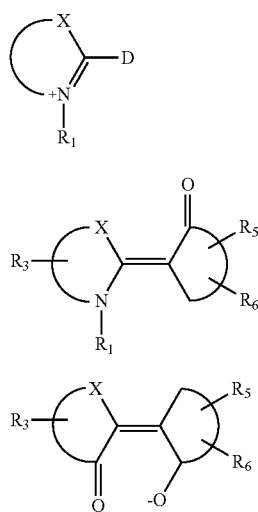

wherein:

the curved lines represent the atoms necessary to complete a structure selected from one ring, two fused rings, and three fused rings, each said ring having five or six atoms, and each said ring comprising carbon atoms and, optionally, no more than two atoms selected from oxygen, nitrogen and sulfur;

D, if present, is

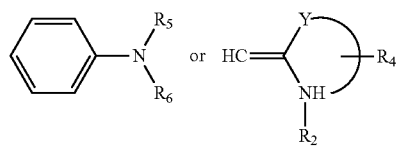

X and Y are independently selected from the group consisting of O, S, and —C(CH$_3$)$_2$—;

at least one R1, R2, R3, R4, R5, R6, or R7 is selected from the group consisting of: a moiety that controls water solubility and non-specific binding, a moiety that prevents the reporter molecule from entering the cell through the membrane, a group that comprises, optionally with a linker, biotin a hapten, a His-tag, or other moiety to facilitate the process of isolating the selection entity, a fluorescent label optionally comprising a linker, a photoreactive group, or a reactive group such as a group containing isothiocyanate, isocyanate, monochlorotriazine, dichlorotriazine, mono- or di-halogen substituted pyridine, mono- or di-halogen substituted diazine, phosphoramidite, maleimide, aziridine, sulfonyl halide, acid halide, hydroxysuccinimide ester, hydroxysulfosuccinimide ester, imido ester, hydrazine, axidonitrophenyl, azide, 3-(2-pyridyl dithio)-propri-onamide, glyoxal, haloacetamido, or aldehyde;

further-providing that R1 and R2 may be joined by a —CHR$_8$—CHR$_8$— or —BF$_2$— biradical;

wherein;

R$_8$ independently for each occurrence is selected from the group consisting of hydrogen, amino, quaternary amino, aldehyde, aryl, hydroxyl, phosphoryl, sulfhydryl, water solubilizing groups, alkyl groups of twenty-six carbons or less, lipid solubilizing groups, hydrocarbon solubilizing groups, groups promoting solubility in polar solvents, groups promoting solubility in nonpolar solvents, and -E-F; and further providing that any of R1, R2, R3, R4, R5, R6, or R7 may be substituted with halo, nitro, cyan, —CO$_2$alkyl, —CO$_2$H, —CO$_2$aryl, NO$_2$, or alkoxy wherein:

F is selected from the group consisting of hydroxy, protected hydroxy, alkoxy, sulfonate, sulfate, carboxylate, and lower alkyl substituted amino or quarternary amino;

E is spacer group of formula —(CH$_2$)n- wherein n is an integer from 0-5 inclusively;

The following are more specific examples of reporter molecules according to structure I, II, or III:

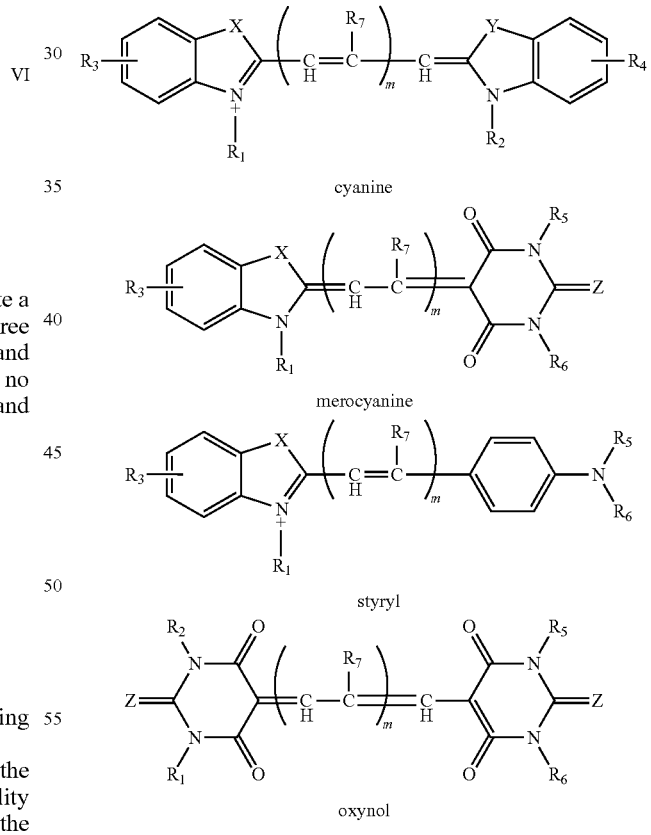

In these structures X and Y are selected from the group consisting of O, S and —CH(CH$_3$)$_2$—;

Z is selected from the group consisting of O and S;

m is an integer selected from the group consisting of 0, 1, 2, 3 and 4 and, preferably an integer from 1-3.

In the above formulas, the number of methine groups determines in part the excitation color. The cyclic azine structures can also determine in part the excitation color. Often, higher values of m contribute to increased luminescence and absorbance. At values of m above 4, the compound becomes unstable. Thereupon, further luminescence can be imparted by modifications at the ring structures. When m=2, the excitation wavelength is about 650 nm and the compound is very fluorescent. Maximum emission wavelengths are generally 15-100 nm greater than maximum excitation wavelengths.

The polymethine chain of the luminescent dyes of this invention may also contain one or more cyclic chemical groups that form bridges between two or more of the carbon atoms of the polymethine chain. These bridges might serve to increase the chemical or photostability of the dye and might be used to alter the absorption and emission wavelength of the dye or change its extinction coefficient or quantum yield. Improved solubility properties may be obtained by this modification.

In certain embodiments, the reporter molecule is represented by structure VII:

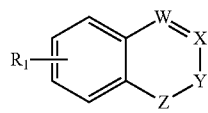

wherein:
W is N or C(R1);
X is C(R2)$_2$;
Y is C(R3)$_2$;
Z is NR$_1$, O, or S;
at least one R1, R2, or R3 is selected from the group consisting of: a moiety that controls water solubility and non-specific binding, a moiety that prevents the reporter molecule from entering the cell through the membrane, a group that comprises, optionally with a linker, biotin, a hapten, a His-tag, or other moiety to facilitate the process of isolating the selection entity, a fluorescent label optionally comprising a linker, a photoreactive group, or a reactive group such as a group containing isothiocyanate, isocyanate, monochlorotriazine, dichlorotriazine, mono- or di-halogen substituted pyridine, mono- or di-halogen substituted diazine, phosphoramidite, maleimide, aziridine, sulfonyl halide, acid halide, hydroxysuccinimide ester, hydroxysulfosuccinimide ester, imido ester, hydrazine, axidonitrophenyl, azide, 3-(2-pyridyl dithio)-proprionamide, glyoxal, haloacetamido, or aldehyde;
further providing that two R3 taken together may form O, S, NR1, or N+(R1)$_2$; or two R3 along with R2 may form

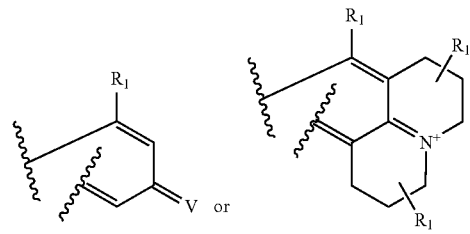

wherein V is O, S, NR1, or N+(R1)$_2$; and
further providing that any of R1, R2, or R3 may be substituted with halo, nitro, cyano, —CO$_2$alkyl, —CO$_2$H, —CO$_2$aryl, NO$_2$, or alkoxy.

The following are more specific examples of reporter molecules according to structure VII:

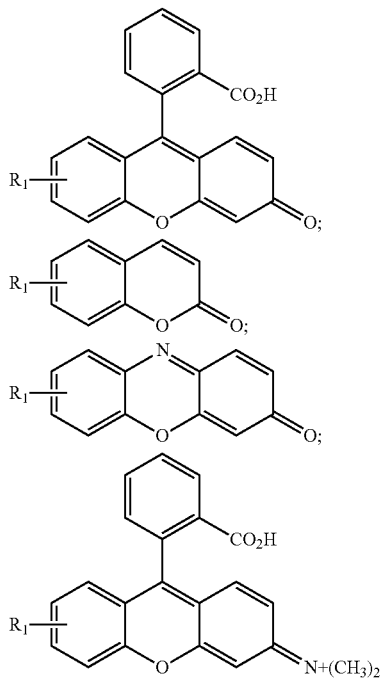

In certain embodiments, the reporter molecule is represented by structure VIII:

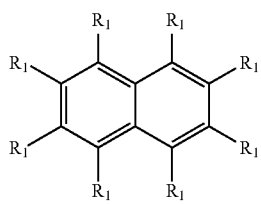

wherein:
at least one R1 is selected from the group consisting of: a moiety that controls water solubility and non-specific binding, a moiety that prevents the reporter molecule from entering the cell through the membrane, a group that comprises, optionally with a linker, biotin, a hapten, a His-tag, or other moiety to facilitate the process of isolating the selection entity, a fluorescent label optionally comprising a linker, a photoreactive group, or a reactive group such as a group containing isothiocyanate, isocyanate, monochlorotriazine, dichlorotriazine, mono- or di-halogen substituted pyridine, mono- or di-halogen substituted diazine, phosphoramidite, maleimide, aziridine, sulfonyl halide, acid halide, hydroxysuccinimide ester, hydroxysulfosuccinimide ester, imido ester, hydrazine, axidonitrophenyl, azide, 3-(2-pyridyl dithio)-proprionamide, glyoxal, haloacetamido, or aldehyde;
further providing that any two adjacent R1, in certain embodiments, may be joined to form a fused aromatic ring; and
further providing that R1, in certain embodiments, may be substituted with halo, nitro, cyan, —CO$_2$alkyl, —CO$_2$H, —CO$_2$aryl, NO$_2$, or alkoxy.

In certain embodiments, at least one, preferably only one, and possibly two or more of either R1, R2, R3, R4, R5, R6 and R7 groups in each of the foregoing moleculesis or contains a reactive group covalently reactive with amine, protected or unprotected hydroxy or sulfhydryl nucleophiles for attaching the dye to the labeled component. For certain reagents, at least one of said R1, R2, R3, R4, R5, R6 and R7 groups on each molecule may also be a group that increases the solubility of the chromophore, or affects the selectivity of labeling of the labeled component or affects the position of labeling of the labeled component by the dye. Reactive groups that may be attached directly or indirectly to the chromophore to form R1, R2, R3, R4, R5, R6 and R7 groups may include reactive moieties such as groups containing isothiocyanate, isocyanate, monochlorotriazine, dichlorotriazine, -mono- or di-halogen substituted pyridine, mono- or di-halogen substituted diazine, phosphoramidite, maleimide, aziridine, sulfonyl halide, acid halide, hydroxysuccinimide ester, hydroxysulfosuccinimide ester, imido ester, hydrazine, axidonitrophenyl, azide, 3-(2-pyridyl dithio)-proprionamide, glyoxal, haloacetamido, and aldehyde.

Specific examples of R1, R2, R3, R4, R5, R6 and R7 groups that are especially useful as reactive groups (e.g., for attaching dye to a substrate, linkers, biotin, beads, microarrays, et alia) for labeling components with available amino-, hydroxy-, and sulfhydryl groups include:

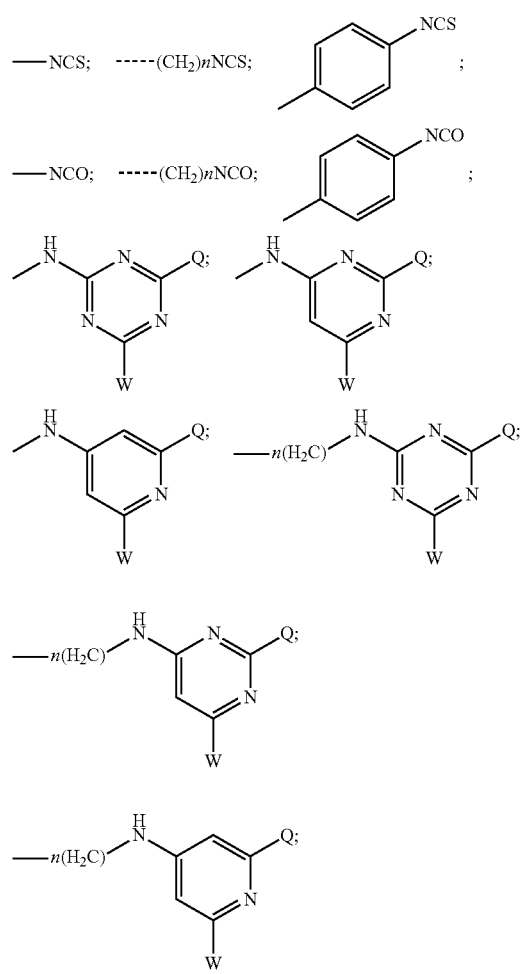

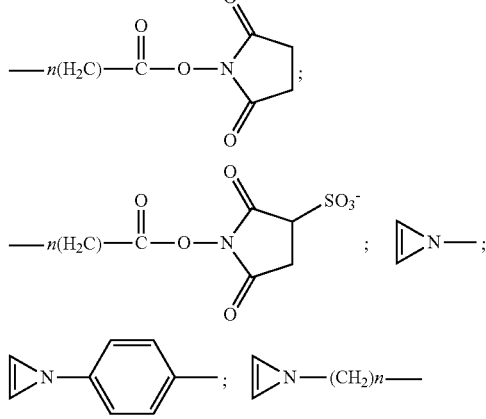

wherein at least one of Q or W is a leaving group such as I, Br or Cl and n is an integer from 0 to 4.

Specific examples of R1, R2, R3, R4, R5, R6 and R7 groups that are especially useful for labeling components with available sulfhydryls which can be used for labeling selectivity components in a two-step process are the following:

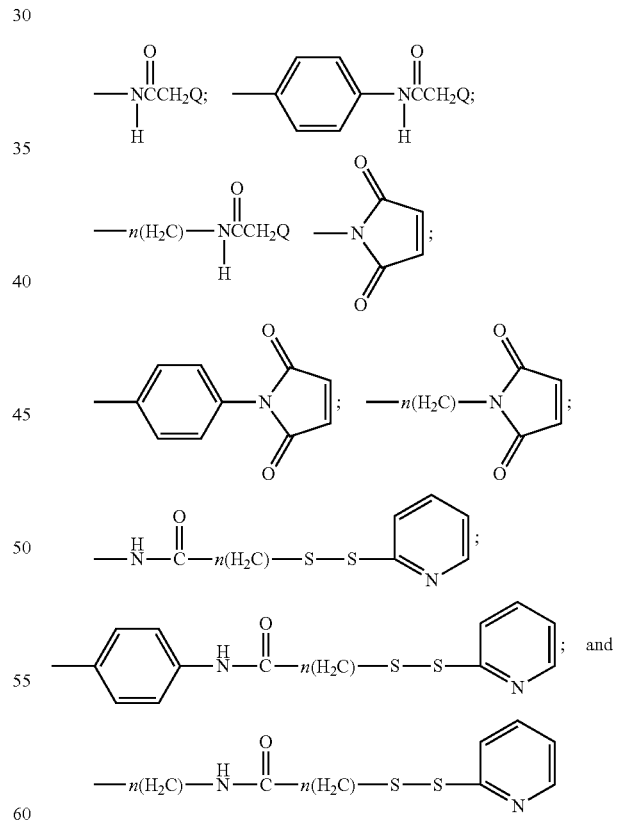

wherein Q is a leaving group such as I or Br, and wherein n is an integer from 0 to 4.

Specific examples of R1, R2, R3, R4, R5, R6 and R7 groups that are especially useful for labeling components by light-activated cross linking include:

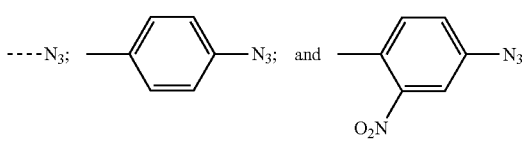

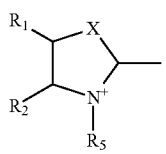

-continued wherein A' is selected from

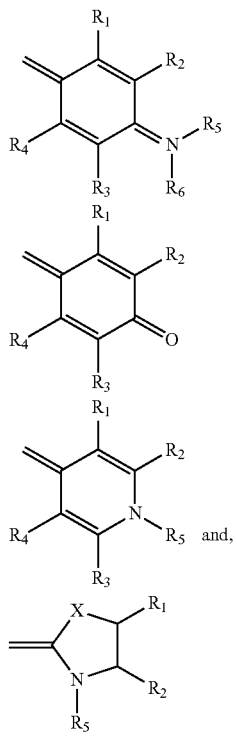

For the purpose of increasing water solubility or reducing unwanted nonspecific binding of the labeled component to inappropriate components in the sample or to reduce the interactions between two or more reactive chromophores on the labeled component which might lead to quenching of fluorescence, the R1, R2; R3, R4, R5, R6 and R7 groups can be selected from the well known polar and electrically charged chemical groups.

In certain embodiments of the invention, the reporter molecule is represented by structure I, II, III, IV, V, VI, VII or VIII and the accompanying definitions, and is a pH sensitive reporter molecule.

In certain embodiments of the invention, the reporter molecule is represented by structure I, II, III, IV, V, VI, VII or VIII and the accompanying definitions, and is a polarity sensitive reporter molecule.

In certain embodiments of the invention, the reporter molecule is represented by structure I, II, III, IV, V, VI, VII or VIII and the accompanying definitions, and is a microviscosity reporter molecule.

In certain embodiments of the invention, the reporter molecule is represented by structure I, II, III, IV, V, VI, VII or VIII and the accompanying definitions, and is a mobility sensor reporter molecule.

In various other embodiments, the reporter is a of the type class IV: wherein the dye has the general structure $$A-B=A'$$

wherein A is selected from

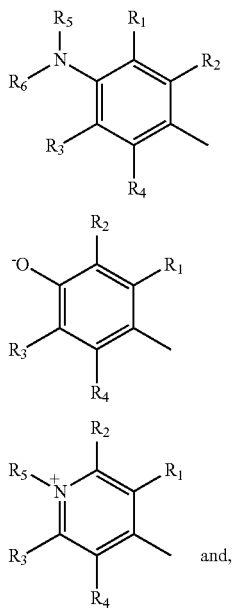

wherein R1, R2, R3, R4, R5 and R6 are selected from the group consisting of: a moiety that controls water solubility and non-specific binding, a moiety that prevents the dye from entering a cell through a membrane, a group that comprises, optionally with a linker, biotin, a hapten, a His-tag, or a moiety to facilitate isolation of the ligand, a fluorescent label optionally comprising a linker, a photoreactive group, a reactive containing isothiocyanate, isocyanate, monochlorotriazine, dichlorotriazine, mono- or di-halogen substituted pyridine, mono- or di-halogen substituted diazine, phosphoramidite, maleimide, aziridine, sulfonyl halide, acid halide, hydroxysuccinimide ester, hydroxysulfosuccinimide ester, imido ester, hydrazine, axidonitrophenyl, azide, 3-(2-pyridyl dithio)-proprionamide, glyoxal, haloacetamido, or aldehyde, and, R1 and R2 may be joined by a —$CHR_8$—$CHR_8$— or —$BF_2$— biradical, wherein $R_8$ independently for each occurrence is selected from the group consisting of hydrogen, amino, quaternary amino, aldehyde, aryl, hydroxyl, phosphoryl, sulfhydryl, water solubilizing groups, alkyl groups of twenty-six carbons or less, lipid solubilizing groups, hydrocarbon solubilizing groups, groups promoting solubility in polar solvents, groups promoting solubility in nonpolar solvents, and -E-F, wherein F is selected from the group consisting of hydroxy, protected hydroxy, alkoxy, sulfonate, sulfate, carboxylate, and alkyl substituted amino or quartenary amino and E is spacer group of formula —$(CH_2)n$- wherein n is an integer from 0-5 inclusively; and, any of R1, R2, R3, R4, R5, R6, or R7 may be substituted with halo, nitro, cyan, —$CO_2$alkyl, —$CO_2H$, —$CO_2$aryl, $NO_2$, or alkoxy;

wherein B is

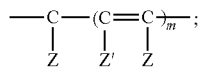

m is an integer from 0 to 4;

Z is selected from is H, $C_1$-$C_{18}$ alkyl, $C_1$-$C_{18}$ substituted alkyl, cyclic and heterocyclic having from one ring, two fused rings, and three fused rings, each said ring having three to six atoms, and each said ring comprising carbon atoms and from zero to two atoms selected from oxygen, nitrogen and sulfur and containing zero to 1 oxygen, nitrogen or sulfur substituents attached; and, Z' is selected from H, $C_1$-$C_{18}$ alkyl, $C_1$-$C_{18}$ substituted alkyl, cyclic and heterocyclic having from one ring, two fused rings, and three fused rings, each said ring having three to six atoms, and each said ring comprising carbon atoms and from zero to two atoms selected from oxygen, nitrogen and sulfur, A, and A'. (See FIG. 2.)

In various embodiments, the spectral change of the sensor dye upon interaction of the selectivity component and a target molecule may include, for example, a shift in absorption wavelength, a shift in emission wavelength, a change in quantum yield, a change in polarization of the dye molecule, and/or a change in fluorescence intensity. The change can be two-fold, ten-fold, one hundred-fold, one thousand-fold or even higher. Any method suitable for detecting the spectral change associated with a given sensor dye may be used in accordance with the inventions. In exemplary embodiments, suitable instruments for detection of a sensor dye spectral change, include, for example, fluorescent spectrometers, filter fluorometers, microarray readers, optical fiber sensor readers, epifluorescence microscopes, confocal laser scanning microscopes, two photon excitation microscopes, and flow cytometers.

In variant embodiments, the reporter molecule may be associated with the selectivity component or the target molecule. In exemplary embodiments, the reporter molecule is covalently attached to the selectivity component. The reporter molecule may be covalently attached to the selectivity component using standard techniques. In certain embodiments the reporter molecule may be directly attached to the selectivity component by forming a chemical bond between one or more reactive groups on the two molecules. In an exemplary embodiment, a thiol reactive reporter molecule is attached to a cysteine residue (or other thiol containing molecule) on the selectivity component. Alternatively, the reporter molecule may be attached to the selectivity component via an amino group on the selectivity component molecule. In other embodiments, the reporter molecule may be attached to the selectivity component via a linker group. Suitable linkers that may be used in accordance with the inventions include, for example, chemical groups, an amino acid or chain of two or more amino acids, a nucleotide or chain of two or more polynucleotides, polymer chains, and polysaccharides. In exemplary embodiments, the reporter molecule is attached to the selectivity component using a linker having a maleimide moiety. Linkers may be homofunctional (containing reactive groups of the same type), heterofunctional (containing different reactive groups), or photoreactive (containing groups that become reactive on illumination). A variety of photoreactive groups are known, for example, groups in the nitrene family.

In various embodiments, one or more reporter molecules may be attached at one or more locations on the selectivity component. For example, two or more molecules of the same reporter may be attached at different locations on a single selectivity component molecule. Alternatively, two or more different reporter molecules may be attached at different locations on a single selectivity component molecule. In exemplary embodiments, 2, 3, 4, 5, 6, 7, 8, 9, 10 or more reporter molecules are attached at different sites on the selectivity component. The one or more reporter molecules may be attached to the selectivity component so as to maintain the activity of the reporter molecule and the selectivity component.

In certain embodiments, the location of the reporter molecule is optimized to permit exposure of the reporter molecule to changes in the microenvironment upon interaction of the selectivity component with a target molecule while maintaining the ability of the selectivity component to interact with the target molecule. In exemplary embodiments, the reporter molecule is attached to the selectivity component in spatial proximity to the target binding site without affecting the ability of the selectivity component to interact with the target molecule.

In certain embodiments, the reporter molecule further comprises a moiety that is specific for the selectivity component. For example, the reporter molecule may be linked to a substrate, a hapten, etc. that is specific for the selectivity component if it is an enzyme, hapten-binding protein, etc. The reporter molecule may be covalently attached to the moiety using standard techniques. In certain embodiments the reporter molecule may be directly attached to the moiety by forming a chemical bond between one or more reactive groups on the two molecules. In other embodiments, the reporter molecule may be attached to the moiety via a linker group. Suitable linkers that may be used in accordance with the inventions include, for example, chemical groups, an amino acid or chain of two or more amino acids, a nucleotide or chain of two or more polynucleotides, polymer chains, and polysaccharides. Linkers may be homofunctional (containing reactive groups of the same type), heterofunctional (containing different reactive groups), or photoreactive (containing groups that become reactive on illumination).

5. Exemplary Uses

The biosensors of the invention may be used to detect and/or quantitate analytes in any solid, liquid or gas sample, as well as in any cell or tissue or organism of interest.

In various exemplary embodiments, the biosensors of the invention may be used for a variety of diagnostic and/or research applications, including, for example, monitoring the development of engineered tissues, in vivo monitoring of analytes of interest (including polynucleotides, polypeptides, hormones, lipids, carbohydrates, and small inorganic and organic compounds and drugs) using injectable free biosensors or implants functionalized with one or more biosensors, biological research (including developmental biology, cell biology, neurobiology, immunology, and physiology); detection of microbial, viral and botanical polynucleotides or polypeptides, drug discovery, medical diagnostic testing, environmental detection (including detection of hazardous substances/hazardous wastes, environmental pollutants, chemical and biological warfare agents, detection of agricultural diseases, pests and pesticides and space exploration), monitoring of food freshness and/or contamination, food additives, and food production and processing streams, monitoring chemical and biological products and contaminants, and monitoring industrial and chemical production and processing streams.

In one embodiment, the biosensors described herein may be used for detecting environmental pollutants, including, air, water and soil pollutants. Examples of air pollutants, include, for example, combustion contaminants such as carbon monoxide, carbon dioxide, nitrogen dioxide, sulfur dioxide, and tobacco smoke; biological contaminants such as animal dander, molds, mildew, viruses, pollen, dust mites, and bacteria; volatile organic compounds such as formaldehyde, fragrance products, pesticides, solvents, and cleaning agents; heavy metals such as lead or mercury; and asbestos, aerosols, ozone, radon, lead, nitrogen oxides, particulate matter, refrigerants, sulfur oxides, and volatile organic compounds. Examples of soil pollutants, include, for example, acetone, arsenic, barium, benzene, cadmium, chloroform, cyanide, lead, mercury, polychlorinated biphenyls (PCBs), tetrachloroethylene, toluene, and trichloroethylene (TCE). Examples—of water pollutants, include, for example, arsenic, contaminated sediment, disinfection byproducts, dredged material, and microbial pathogens (e.g., *Aeromonas, Coliphage, Cryptosporidium, E. coli, Enterococci, Giardia*, total coliforms, viruses).

In other embodiments, the biosensors described herein may be used for detecting hazardous substances, including, for example, arsenic, lead, mercury, vinyl chloride, polychlorinated biphenyls (PCBs), benzene, cadmium, benzopyrene, polycyclic aromatic hydrocarbons, benzofluoranthene, chloroform, DDT, aroclors, trichloroethylene, dibenz[a,h]anthracene, dieldrin, hexavalent chromium, chlordane, hexachlorobutadiene, etc.

In another embodiment, the biosensors described herein may be used for detecting chemical and biological warfare agents. Examples of biological warfare agents, include, for example, bacteria such as anthrax (*Bacillus anthracis*), botulism (*Clostridium botulinum* toxin), plague (*Yersinia pestis*), tularemia (*Francisella tullarensis*), brucellosis (*Brucella* species), epsilon toxin from *Clostridium peringens*, food safety threats (e.g., *Salmonella* species, *Escherichia coli* 0157:H7, *Shigella*); water safety threats (e.g., *Vibrio cholerae* and *Cryptosporidium parvum*), glanders (*Burkholderia mallei*), Melioidosis (*Burkholderia pseudomallei*), Psittacosis (*Chlamydia psittaci*), Q fever (*Coxiella burnetii*), Ricin toxin from *Ricinus communis, Staphylococcal* enterotoxin B, Typhus fever (*Rickettsia prowaaekii*) and viruses, such as filoviruses (e.g., ebola or Marburg), arenaviruses (e.g., Lassa and Machupo), hantavirus, smallpox (variola major), hemorrhagic fever virus, Nipah virus, and alphaviruses (e.g., Venezuelan equine encephalitis, eastern equine encephalitis, western equine encephalitis). Examples of chemical warfare agents, include for example, blister agents (e.g., distilled mustard, lewisite, mustard gas, nitrogen mustard, phosgene oxime, ethyldichloroarsine, methyldichloroarsine, phenodichloroarsine, sesqui mustard), blood poisoning agents (arsine, cyanogen chloride, hydrogen chloride, hydrogen cyanide), lung damaging agents (chlorine, diphosgene, cyanide, nitrogen oxide, perfluorisobutylene, phosgene, red phosphorous, sulfur trioxide-chlorosulfonic acid, teflon, titanium tetrachloride, zinc oxide), incapacitating agents (agent 15, BZ, canniboids, fentanyls, LSD, phenothiazines), nerve agents (cyclohexyl sarin, GE, Soman, Sarin, Tabun, VE, VG, V-Gas, VM, VX), riot control/tear gas agents (bromobenzylcyanide, chloroacetophenone, chloropicrin, CNB, CNC, CNS, CR, CS), and vomit inducing agents (adamsite, diphenylchloroarsine, diphenylcyanoarsine).

In another embodiment, the biosensors described herein may be used for monitoring food freshness and/or contamination, food additives, and food production and processing streams: Examples of bacterial contaminants that may lead to foodborne illnesses include, for example, *Bacillus anthracis, Bacillus cereus, Brucella abortus, Brucella melitensis, Brucella suis, Campylobacter jejuni, Clostridium botulinum, Clostridium perfringens*, enterohemorrhagic *E. coli* (including *E. coli* 0157:H7-and-other Shiga toxin-producing; *E. coli*), enterotoxigenic *E. coli, Listeria monocytogenes, Salmonella, Shigella, Staphylococcus aureus, Vibrio cholerae, Vibrio parahaemolyticus, Vibrio vulnificus, Yersinia enterocolytica* and *Yersinia pseudotuberculosis*. Examples of viral contaminants that may lead to foodborne illnesses include, for example, hepatitis A, norwalk-like viruses, rotavirus, astroviruses, caliciviruses, adenoviruses, and parvoviruses. Examples of parasitic contaminants that may lead to foodborne illnesses include, for example, *Cryptosporidium parvum, Cyclospora cayetanensis, Entamoeba histolytica, Giardia lamblia, Toxoplasma gondii*, and *Trichinella spiralis*. Examples of noninfectious toxins or contaminants that may lead to foodborne illnesses include, for example, antimony, arsenic, cadmium, ciguatera toxin, copper, mercury, museinol, muscarine, psilocybin, coprius artemetaris, ibotenic acid, amanita, nitrites, pesticides (organophosphates or carbamates), tetrodotoxin, scombroid, shellfish toxins, sodium floride, thallium, tin, vomitoxin, and zinc.

In one embodiment, the biosensors described herein may be used for in vitro and/or in vivo monitoring of analytes of interest. The biosensors may be injected or otherwise administered to a patient as free molecules or may be immobilized onto a surface before introduction into a patient. When administered. as free molecules, the biosensors may be used to detect analytes of interest in both interstitial spaces and inside cells. For detection of analytes inside of cells, the selectivity component may be modified, as described above, with a tag that facilitates translocation across cellular membranes. Alternatively, the selectivity components may be introduced into cells using liposome delivery methods or mechanical techniques such as direct injection or ballistic-based particle delivery systems (see for example, U.S. Pat. No. 6,110,490). In other embodiments, the biosensors may be immobilized onto a surface (including, for example, a bead, chip, plate, slide, strip, sheet, film, block, plug, medical device, surgical instrument, diagnostic instrument, drug delivery device, prosthetic implant or other-structure) and then introduced into a patient, for example, by surgical implantation. In exemplary embodiments, the biosensors are immobilized onto the surface of an implant, such as an artificial or replacement organ, joint, bone, or other implant. The biosensors of the invention may also be immobilized onto particles, optical fibers, and polymer scaffolds used for tissue engineering. For example, one or more biosensors may be immobilized onto a fiber optic probe for precise positioning in a tissue. The fiber optic then provides the pathway for excitation light to the sensor tip and the fluorescence signal back to the photodetection system. In still other embodiments, at least the selectivity component of the biosensor is transfected in cell or other host organism of interest and expressed within the cell or other host organism of interest.

In each of the various embodiments of the invention, a single biosensor may be used for detection of a single target molecule or two or more biosensors may be used simultaneously for detection of two or more target molecules. For example, 2, 5, 10, 20, 50, 100, 1000, or more different selectivity components may be used simultaneously for detection of multiple targets.

When using multiple selectivity components simultaneously, each selectivity component may be attached to a different reporter molecule to permit individual detection of target binding to each selectivity component. Alternatively, a dual detection system may be used where two or more selectivity components may be attached to the same reporter molecule (for example, the same sensor dye) and be identified based on a second detectable signal. For example, selectivity components having different target specificities but containing the same sensor dye may be distinguished based on the signal from a color coded particle to which it is attached. The readout for each selectivity component involves detection of the signal from the sensor dye, indicating association with the target molecule, and detection of the signal from the color coded particle, permitting identification of the selectivity component. In an exemplary embodiment, a panel of biosensors may be attached to a variety of color coded particles to form a suspension array (Luminex Corporation, Austin, Tex.). The mixture of coded particles associated with the biosensors of the invention may be mixed with a biological sample or administered to a patient. Flow cytometry or microdialysis may then be used to measure the signal from the sensor dye and to detect the color code for each particle. In various embodiments, the identification signal may be from a color coded particle or a second reporter molecule, including, for example, chemiluminescent, fluorescent, or other optical molecules, affinity tags, and radioactive molecules.

In other embodiments, one or more biosensors of the invention may be immobilized onto a three dimensional surface suitable for implantation into a patient. The implant allows monitoring of one or more analytes of interest in a three dimensional space, such as, for example, the spaces between tissues in a patient.

In other embodiments, the biosensors of the invention may be exposed to a test sample. Any test sample suspected of containing the target may be used, including, but not limited to, tissue samples such as biopsy samples and biological fluids such as blood, sputum, urine and semen samples, bacterial cultures, soil samples, food samples, cell cultures, etc. The target may be of any origin, including animal, plant or microbiological (e.g., viral, prokaryotic, and eukaryotic organisms, including bacterial, protozoal, and fungal, etc.) depending on the particular purpose of the test. Examples include surgical specimens, specimens used for medical diagnostics, specimens used for genetic testing, environmental specimens, cell culture specimens, food specimens, dental specimens and veterinary specimens. The sample may be processed or purified prior to exposure to the biosensor(s) in accordance with techniques known or apparent to those skilled in the art.

In other embodiments, the biosensors of the invention may be used to detect bacteria and eucarya in food, beverages, water, pharmaceutical products, personal care products, dairy products or environmental samples. The biosensors of the invention are also useful for the analysis of raw materials, equipment, products or processes used to manufacture or store food, beverages, water, pharmaceutical products, personal care products, dairy products or environmental samples.

Alternatively, the biosensors of the invention may be used to diagnose a condition of medical interest. For example the methods, kits and compositions of this invention will be particularly useful for the analysis of clinical specimens or equipment, fixtures or products used to treat humans or animals. In one preferred embodiment, the assay may be used to detect a target sequence which is specific for a genetically based disease or is specific for a predisposition to a genetically based disease. Non-limiting examples of diseases include, beta-thalassemia, sickle cell anemia, Factor-V Leiden, cystic fibrosis and cancer related targets such as p53, p 10, BRC-1 and BRC-2. In still another embodiment, the target sequence may be related to a chromosomal DNA, wherein the detection, identification or quantitation of the target sequence can be used in relation to forensic techniques such as prenatal screening, paternity testing, identity confirmation or crime investigation.

In still other embodiments, the methods of the invention include the analysis or manipulation of plants and genetic materials derived therefrom as well as bio-warfare reagents. Biosensors of the invention will also be useful in diagnostic applications, in screening compounds for leads which might exhibit therapeutic utility (e.g. drug development) or in screening samples for factors useful in monitoring patients for susceptibility to adverse drug interactions (e.g. pharmacogenomics).

In certain embodiments, the biosensors of the invention, or nucleic acids encoding them, may be formulated into a pharmaceutical composition comprising one or more biosensors and a pharmaceutically acceptable carrier, adjuvant, or vehicle. The term "pharmaceutically acceptable carrier" refers to a carrier(s) that is "acceptable" in the sense of being compatible with the other ingredients of a composition and not deleterious to the recipient thereof. Methods of making and using such pharmaceutical compositions are also included in the invention. The pharmaceutical compositions of the invention can be administered orally, parenterally, by inhalation spray, topically, rectally, nasally, buccally, vaginally, or via an implanted reservoir. The term "parenteral" as used herein includes subcutaneous, intracutaneous, intravenous, intramuscular, intraarticular, intrasynovial, intrasternal, intrathecal, intralesional, and intracranial injection or infusion techniques.

In other embodiments, the invention contemplates kits including one or more biosensors of the invention, and other subject materials, and optionally instructions for their use. Uses for such kits include, for example, environmental and/or biological monitoring or diagnostic applications.

A biosensor, or an isolated, purified biosensor, comprising the selectivity component may have at least about 85% sequence identity with SEQ ID NO:1 through 72. The selectivity component may reversibly bind either a monomethin cyanine dye, or Malachite Green, or an analog thereof A host cell may express the biosensor. Further, a vector may be comprised of a nucleic acid sequence having at least about 85%, and preferably 95%, sequence identity to a polynucleotide encoding a protein with SEQ ID NO:1 through 72. A host cell may comprise the vector.

EXAMPLES

Figure 7:
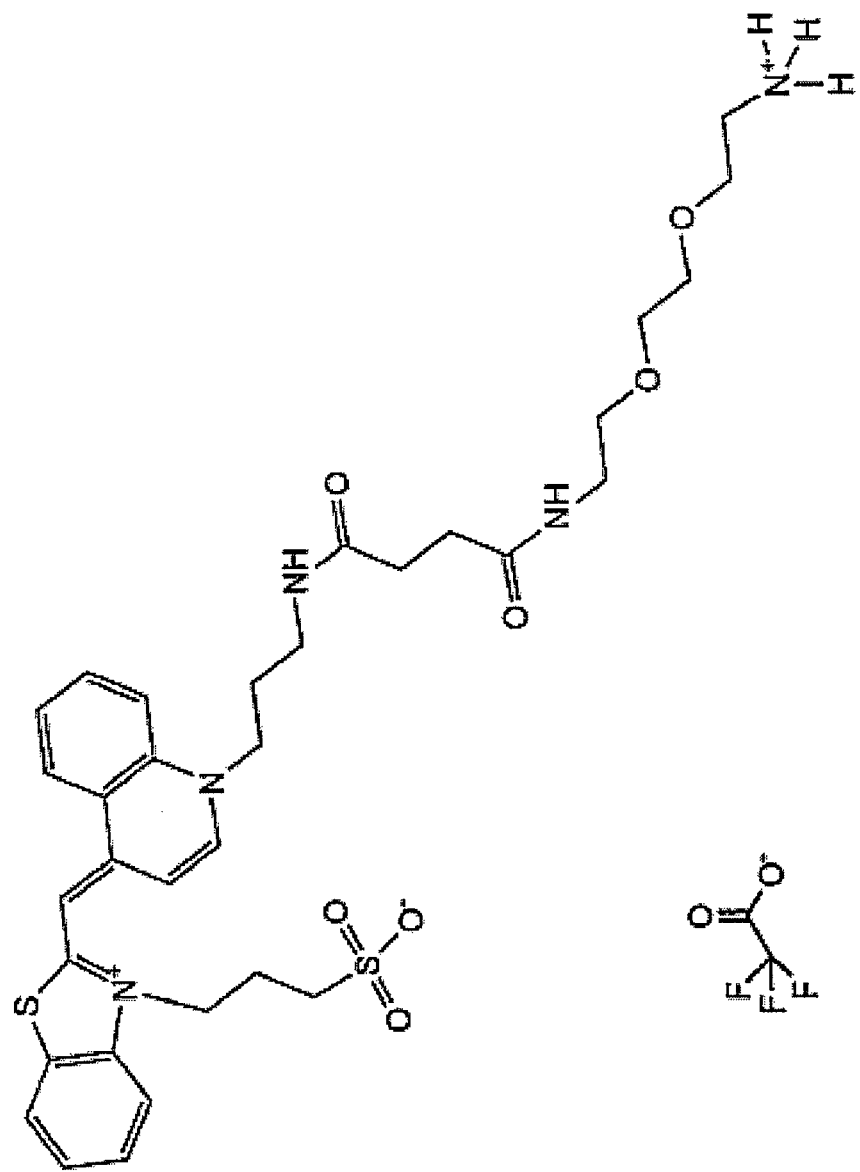
FIG. 7 depicts the structure of Thiazole Orange 1 (TO1) derivatized with a PEG amine. In some embodiments, the amino group may be covalently modified with a biotin group for streptavidin coated magnetic bead enrichment of yeast bearing scFv proteins that bind to the TO1 on the opposite end of the PEG linker.

The invention now being generally described, it will be more readily understood by reference to the following examples, which are included merely for purposes of illustration of certain aspects and embodiments of the present invention, and are not intended to limit the invention. Provided are several single chain antibody (scFv) based sensors that comprise amino acid sequences that lead to specific binding of certain monomethin cyanine dyes (TO1 and its analogs (the structure of TO1 derivatized with PEG amine is shown in FIG. 7) and Malachite Green (and its analogs) in a way that produces a large increase in fluorescence of the dye (a "fluorogen") when it is in the bound state.

Example 1 scFv-Based Sensors that Reversibly Bind Fluorescent Dyes

Figure 10A:
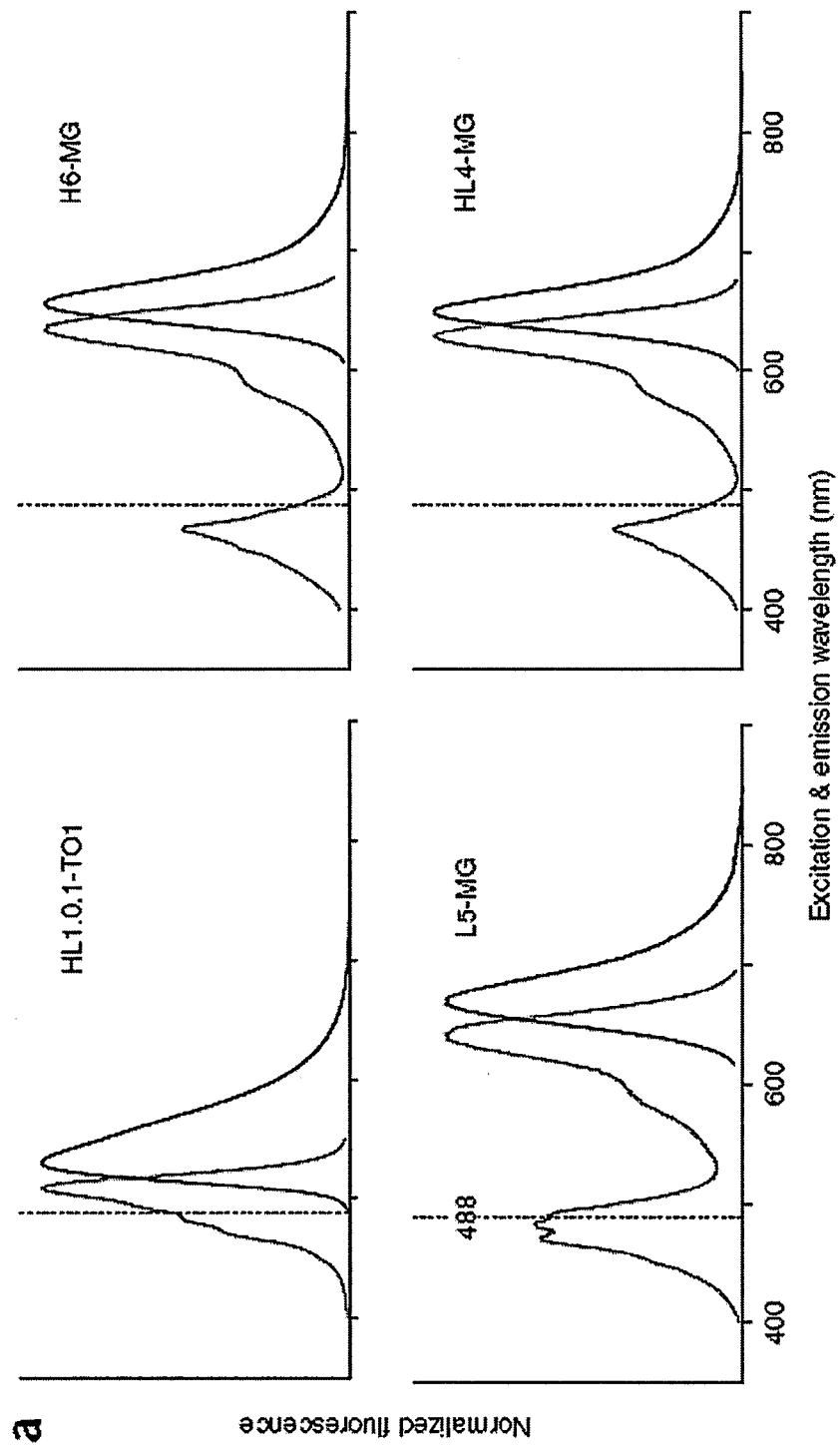
FIGS. 10A and 10B are graphs depicting the fluorescence characterization of purified FBPs.

In one experiment, an scFv that reversibly binds noncovalently the dye TO1 ("scFv1") was produced. See, for example, SEQ ID NO:1. A 2700-fold increase in fluorescence was detected (by methods described below) when the TO1 binds to the scFv. This sequence was used in subsequent work to produce additional scFvs that bind to TO1 with a stronger binding affinity and have enhanced fluorescence. In other experiments, scFvs were developed that bind certain derivatives of malachite green where the noncovalent binding is strong and again a large increase in fluorescence is produced upon binding of the dye to the scFv. See, FIGS. 9, 10A and 10B.

1A

The genetic sequence of this scFv may be inserted into genes for other proteins so that the expressed fusion protein will contain the dye-binding scFv. For example, a cell surface membrane protein was labeled with scFv1 by genetic methods and expressed on the cell surface of cultured mammalian cells. When the relatively non-fluorescent (in water or buffer) dye TO1 was added to cell suspensions containing the protein-scFv, a fraction of the dye binds to the scFv with a large (more than 2500x) fluorescence increase upon binding and thereby produced a fluorescent label on the protein of interest on the membrane surface. Thus, the appearance of fluorescence when the scFv and the dye are both present is very rapid. Thus, TO1 and the corresponding TO1 scFv may be used to detect protein expression of the scFv-fusion protein on the surface of the cell where the scFv will have access to the membrane impermeant dye that has been added to the culture medium. Other proteins may be labeled with the scFv and if the labeled protein is present inside the cell, a membrane permeant fluorogen may be used to detect the presence of that particular scFv fusion protein.

The presence of the scFv can be used to ascertain the amount, expression, degradation, or location of the fusion protein.

In one experiment, yeast FAPs were fused via AGA2 to the AGA1-AGA2 complex, which is directed to the outer leaflet of the plasma membrane by a C-terminal glycosylphosphatidylinositol (GPI) anchor before insertion into the cell wall. Live cell imaging using fluorescent proteins fused to GPIs or GPI-anchored proteins is useful for studying organization and function of membrane proteins, including signaling receptors and cell adhesion molecules, but these constructs may also label cell structures involved in biosynthesis, secretion and degradation. Dynamic imaging of lipid rafts and other surface features would benefit by confining fluorescence to proteins anchored to the outer leaflet. Whereas methods such as total internal reflection fluorescence microscopy have evolved to allow selective observation, there are no methods for selective labeling and homogenous detection. To illustrate such labeling and detection, an MG FAP and an identically anchored AGA2-GFP fusion protein was imaged. The MG FAP and the GFP were visualized on the extracellular surface, but intracellular structures, many with the morphology expected of vacuoles and nuclear membranes (endoplasmic reticulum), were visualized only by the GFP. To explore fluorogenic labeling of mammalian cell surface proteins, selected TO1 and MG FAPs were fused to the N terminus of platelet-derived growth factor receptor (PDGFR) transmembrane domain. The TO1 and MG FAPs were than expressed stably in NIH3T3 mouse fibroblasts and in M21 human renal carcinoma cells. In each case the transfected cells exhibited strong surface fluorescence when exposed to low concentrations of TO1-2p or MG-11p fluorogen. No significant intracellular fluorescence was observed under these experimental conditions; TO1-2p and MG-11p controls did not enter living NIH3T3 cells. It is noteworthy that little or no photobleaching of cell surface fluorescence was observed. Separate experiments showed that TO1-2p FAPs resisted bleaching about as well as EGFP and that MG FAPs were even more bleach resistant (FIG. 16). Fluorescence signal of TO1-2p FAPs decayed to a TO1-2p concentration dependent steady state, which suggests without being bound by theory, that rapid exchange of fluorogen (and/or fluorogen photoproducts) between the solution and the FAP itself was effectively buffering the system against photobleaching. For MG FAPs, other mechanisms may contribute, such as loose sequestration of dark fluorogen on the plasma membrane outer surface. In aqueous solution mobile fluorogens such as MG or TO1 show almost no photoreactivity, but under illumination MG conjugated to an antibody generates reactive oxygen species at a rate similar to GFP, sufficient to be phototoxic under continuous or intense excitation. Phototoxicity correlates with photobleaching, suggesting that MG and TO1 FAPs generated reactive oxygen species at GFP-like rates. MG has also been used as an antifungal agent; at experimental concentrations the MG derivatives studied here had little or no effect on yeast growth (FIG. 17). Cell surface-exposed FAPs visualized with a membrane-impermeant fluorogen were seen at the plasma membrane only. When exposed to a membrane-permeant fluorogen, however, these same cells showed additional fluorescence within elements of the secretory apparatus, including the nuclear endoplasmic reticulum and the Golgi. This result suggests that permeant fluorogens can be used to visualize FAPs shortly after cotranslational insertion into the lumen, and thus potentially report protein folding in near real time. Permeant fluorogens can be added and withdrawn at will, facilitating development of pulse-chase and other approaches to studying secretory and endocytic pathways. When incorporated into fusion proteins, FAP domains provided a reporter of protein location and abundance in time and space. Fluorescence signal was generated only upon addition of a second component (the fluorogen); in this respect FAPs resemble the site-specific chemical labeling systems. However, all chemical labeling systems require additional manipulation such as enzymatic conjugation steps or washes to reduce background signal, whereas FAPs can be visualized directly after fluorogen addition on a time scale of seconds (on the cell surface) to minutes (within the secretory apparatus). Fluorescence visualization can also be spatially controlled by the appropriate choice of fluorogen, enabling one to selectively observe fusion proteins at particular cellular locations. Multicolor imaging of spectrally and antigenically distinct FAPs co-expressed within a cell will greatly enhance the usefulness of different fluorogens to dynamically monitor complex cellular functions. ScFv-based FAPs contain internal disulfide linkages and are currently adapted for use only in nonreducing environments, mainly the cell surface and secretory apparatus. FAP/fluorogens thus complement the biarsenical system, which is generally limited to intracellular reducing environments, primarily the cytoplasmic and nuclear compartments. However, it has been shown that functional scFvs can be expressed cytoplasmically in a disulfide-free format in yeast and mammalian cells, and future developments of scFv and other FAP platforms will address these intracellular compartments.

1B

Additionally, the genetic sequence of an scFv may be used to create molecular biosensors. In one example, the initial sequence of an scFv is modified to make the binding of a reporter molecule by the scFv sensitive to the presence of other molecular interactions with the scFv. Such interactions include contact with another protein or peptide. Such interactions can involve contact with a kinase or phosphatase or other covalent modification that alters an amino acid of the scFv to produce a change in fluorogen fluorescence. The interaction can produce a steric change or allosteric change near the reporter group on the sensor that produces the fluorescence signal. The interaction can alter a charged amino acid side chain or an ionizable group on a side chain or hydrogen bonding group or a non-polar group near the reporter that produces a fluorescence signal.

1C

The TO1 scFv was created using a large PNNL Yeast Display library comprised of cells that each express on its surface on of an estimated $10^9$ different sequence variations in the heavy and light variable regions that constitute the displayed scFv proteins. The TO1-binding scFv was isolated in two steps. First, a TO1 dye linked via a PEG polymer to a biotin was used in a magnetic bead separation procedure to isolate a population of cells that was enriched for cells that bind in variable degrees to the TO1 dye. In a second step, flow cytometry experiments were carried out to select for cells that bind the dye and make it highly fluorescent. One of the highly fluorescent cells was sorted and cloned. This yeast cell was the source of the scFv. Yeast plasmid DNA encoding this scFv clone was amplified by PCR methods, and then sequenced. Flow cytometry data has demonstrated the successful cloning of this highly fluorescent TO1-binding scFv. Similarly for malachite green.

1D

It is possible to engineer and select other proteins that are capable of binding to the fluorescent reporters of this invention such that they also would function as biosensors in a way similar to the scFv1 of this example. Such engineered proteins that can be used as biosensors we call Fluorescent Binding Protein (FBP) sensors. Examples of such non-immunological binding proteins engineered to bind small-to-medium molecular weight molecules are described by Bintz et al. (2005) *Nature Biotech.* 23:1257-1268.

Example 2

Reporter Molecule-Localizing System Based on SAb scFv Technology

In this example, a combination of reagents with which the location of the reporter molecule can be controlled within a cell by genetic methods In biological research and pharmaceutical drug discovery it is useful to be able to target specific reporter molecules to certain regions or structures within a cell. Examples of such specific reporter molecules include regulatory metabolites such as small peptides, growth factors, and inhibitory RNAs. Also such reporter molecules s may include synthetic and natural molecules that modify cellular behavior such as those often used and developed by the pharmaceutical industry. Further, such reporter molecules might also include fluorescent or light absorbing molecules that provide a signal for targeting of a protein within a cell or that are sensitive to a physiological property of the cell such as membrane potential, ion concentration or enzyme activity. In other words, the reporter molecules are used to modulate or perturb the activity of specific proteins, pathways and networks within cells or to measure biochemical, structural and physiological properties of cells. The reporter molecules allow control of targeting of the region of a cell or tissue where the perturbation or measurement occurs.

Figure 3:
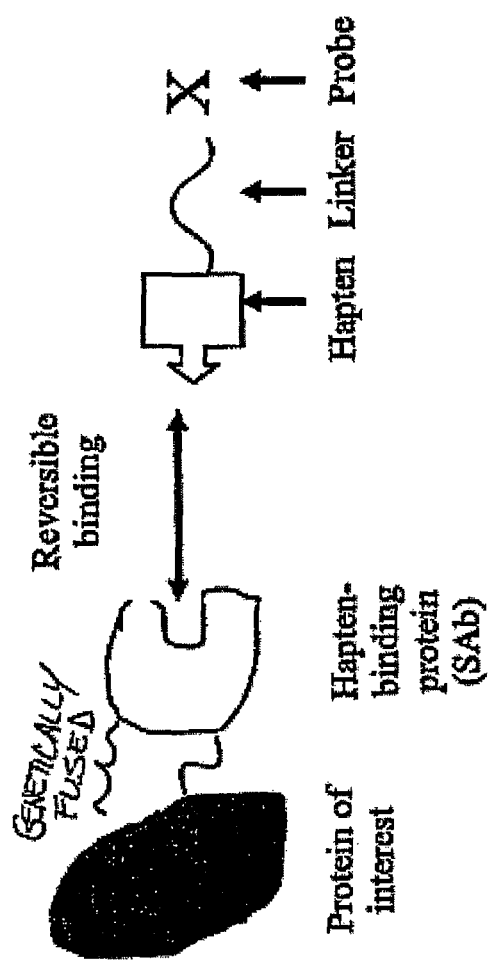
FIG. 3 depicts a reporter-molecule localizing system based on sAb technology.

Many types of reporter molecules diffuse into cells and perturb or report from many regions of a cell where the probe non-specifically associates. The targeting in the reporter molecules may be controlled by bringing together two molecular entities within a cell or on its surface or in a tissue. One such entity may comprise the reporter molecule, a hapten and a water soluble linker that separates the probe and the hapten. The hapten is a molecule with which antibodies that bind the molecule can be generated by known procedures. This three part structure is shown on the right hand side of FIG. 3. Such a reporter might be a voltage sensitive dye, a calcium indicator, a pH indicator, ion indicator, polarity indicator, mechanical stress indicator or an indicator of some other physiological or molecular process occurring in the cell.

The second entity required for targeting the probe in a cell consists of a selectivity component, e.g., a hapten-binding antibody, specifically a scFv that may be genetically fused to a "protein of interest" within the cell. The protein of interest serves the purpose of localizing the reporter molecule-binding scFv, and thus the reporter molecule after it has been incorporated in the cell or tissue, to a specific region of interest within or on a cell. The protein of interest and the scFv are illustrated on the left hand side of FIG. 3.

The process of targeting the reporter molecule within the cell takes place in several steps: (1) first, a hapten-linker-reporter molecule must be synthesized, then (2) a hapten-binding scFv must be created. This may be done, for example, by yeast selection procedures developed by Wittrup, et al. (*Methods Enzymol.* (2000) 328:430-33; *Proc. Natl. Acad. Sci. USA* (2000) 97:10701-5; *Nucleic Acids Res* (2004) 32:e36). (3) The cell of interest must be transfected with a gene that codes for the protein of interest fused to the hapten-binding protein. (4) The hapten-linker-reporter molecule must be incorporated into the cell by diffusion through the membrane or microinjection or by another means.

The result of this process will be noncovalent placement of the reporter molecule into the protein of interest that may be in the nucleus, or an organelle, in the cytoplasm, on the internal surface of the membrane, or in a specific location of a tissue. By using a photoreactive group or a reactive functional group the reporter moiety may be covalently attached to the protein of interest.

Several variations are possible:

Variation 1: Non-Covalent Binding of the Hapten-Linker-Reporter Molecule to the scFv.

The affinity of this binding depends on the structure of the scFv and the hapten. In some cases, it is desirable to have relatively weak binding so that the reporter molecule can experience the targeted protein of interest but also other regions of the cell. In other cases, it is desirable to have strong binding so that the probe is predominantly at the scFv. In this case, there would be less non-specific binding of the hapten-linker-reporter molecule to other regions of the tissue and the modulating or measuring capabilities of the reporter molecule would be targeted mainly to the scFv-protein of interest region. There would therefore be a better signal-to-noise in the experiment. The binding constant of the hapten to the antibody (often expressed as a dissociation constant, Kd) can be adjusted by the procedures used to create the hapten-binding scFv. By yeast selection procedures and by a process called affinity maturation (where the scFv is genetically mutated and further selection is carried out) it is possible to considerably decrease Kd (increase the binding affinity).

Variation 2: Covalent Linkage of the Hapten-Linker-Reporter Molecule to the scFv Using Light.

Figure 4:
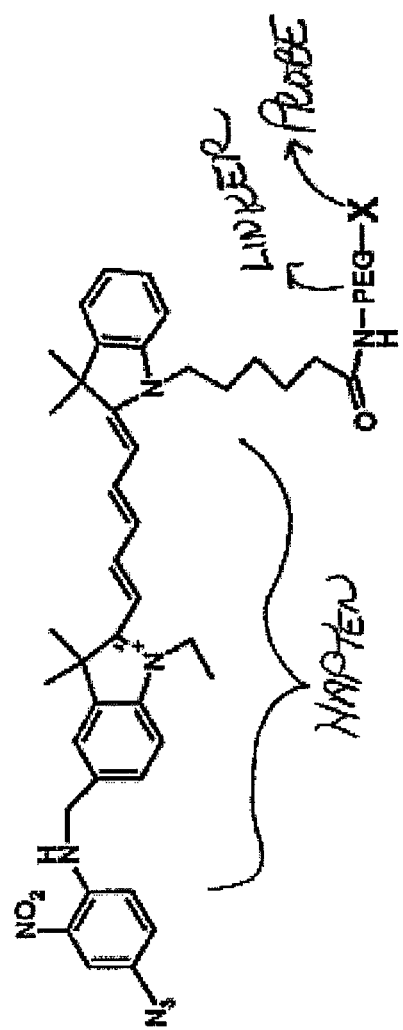
FIG. 4 depicts a photoreactive hapten with PEG linker and reporter molecule X.

In this case, the hapten is modified to contain a specific reactive group or a photo-reactive group that will cause the scFv binding group to permanently and covalently associate with the targeting scFv. The photoreactive group could be placed adjacent to the hapten or could be structurally part of the hapten. A scFv that binds the hapten or the modified hapten may be created. The photoreactive hapten is called a "photohapten." Illumination of the cell or tissue containing the photohapten-linker-probe and the scFv-protein of interest would cause covalent linkage of the photohapten groups that are within the scFv binding site to a region of the scFv. A potential advantage of this approach is that excess non-scFv associating hapten-linker-reporter molecule could be washed out, so long as it does not photochemically react with other cellular structures. Any of a variety of known photoreactive groups may be used, such as those of the nitrene family. Several examples of reporter molecules are shown in FIG. 4. The compounds have sites for attachment to a linker and thus to a reporter molecule.

Variation 3: Photo-Controlled Reversible Binding of the Reporter Molecule to the scFv.

The binding of the reporter molecule may be reversibly controlled with light by a photoreaction upon illumination of the scFv binding group chromophores that alters its molecular conformation and thereby its affinity for the binding site of the targeting scFv. There are known organic chromophores that undergo conformational changes upon illumination. Stilbenes and azo-compounds undergo cis-trans isomerization. Spiranes undergo ring opening as shown in FIG. 5.

Figure 5:
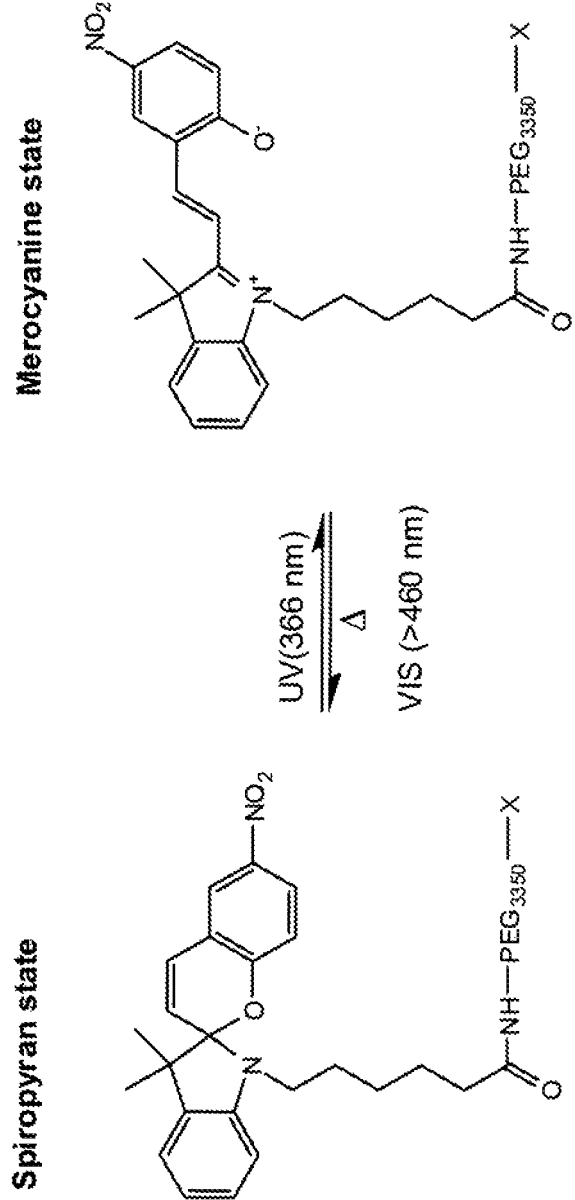
FIG. 5 depicts a photoreversible hapten with PEG linker and reporter molecule X.

In producing such a reversible system, the scFv may be generated using the predominant species of the equilibrium at room temperature, which for example is the spiro form of the compound in FIG. 5 that is >99% in the absence of UV light. When the reagent system is in the cell or tissue, the reporter molecule would then be released from the scFv-protein of interest by illuminating the sample with UV light. For recapture of the reporter molecule by the scFv a longer wavelength of illumination that excites the mero form may be used, or the reaction may be incubated to achieve thermal re-equilibrium of the reaction to favor the spiro form. Such a reagent system may be used to transient release of metabolic factors or drugs that modify regulatory pathways in cells and tissues. A variety of photoreversible chromophores are known in the art and have been recently described in Sakata, et al., *Proc. Natl. Acad. Sci. USA* (2005) 102(13):4759-4764.

Variation 4: Photo-Release of Targeted Reporter Molecule

Photo-uncaging of cell and tissue modulating agents have been widely used by biologists and biophysicists. Generally, an inactive form of a modulating agent or reporter molecule is illuminated to release an active form into the illuminated region. In this case, the modulating agent may be active, but targeted to the scFv-containing region of the cell or tissue. Illumination would release the material, allowing it to diffuse and produce effects elsewhere in the cell or tissue. Photo-uncaging chemistries are known (Curtin, et al. *Photochemistry and Photobiology* (2005) 81:641-648) and may be inserted at a convenient site between the hapten and the reporter molecule.

Currently, there is no way to target such reagents to specific types of cells in a heterogeneous mixture of cells. Through genetic targeting, the reporter molecule could be sequestered and remain caged in a defined region of the cell through the genetic targeting of the scFv to the cell of interest. Also, addition of the "caged reporter molecule" to the cells would allow the targeted scFv containing cell to specifically and strongly bind the caged reporter molecule. Washing the cells would remove the caged reporter molecule from cells that are not of interest and illumination would produce release of the reporter molecule only in the cells of interest.

In this invention scFv-based binding proteins offer one type of fluorescent binding protein that can be used to create biosensors as in Example 3. As mentioned earlier there are other FBPs that could also be engineered to create sensors.

Example 3

A Biosensor for Protein-Protein Interaction Based on scFv Technology

Protein-protein interactions are widely used by living cells to regulate important pathways controlling cell growth and behavior. There are examples in the literature of the study of protein-protein interactions by protein complementation (T K Kerppola (2006) *Nature Methods* 3:969). The protein-protein interaction event is detected by attaching the two cleaved parts of a sensor protein to the two proteins whose interaction is to be detected. When the interaction takes place the cleaved parts of the sensor protein complement (interact with) one another to form a functional protein. The known examples in the literature do not include the use of fluorescent reporter binding scFvs described above.

This example involves the use of the heavy (H) and light (L) fragments of single chain antibodies (scFvs) that have been selected to bind fluorescent reporter molecules. Once a ScFv with appropriate fluorogen has been obtained and the genetic sequence of the ScFv determined, molecular biology methods are available to modify genetic sequences into the ScFv gene at certain locations. The modified genetic sequences can be inserted into yeast expression systems to produce secreted protein or to produce surface displayed ScFv that correspond to the genetic modifications. It is further possible to eliminate the genetic sequence corresponding to the short polypeptide linker that holds the H and L chains of the selected ScFv together. Thus it is possible to obtain independently the H and L halves of the original ScFv. It is further possible to attach the genetic sequence of the H chain to a protein, for example, P1, and the L chain to a second protein, P2 to obtain two DNA sequences that will give fusion proteins upon protein expression. The goal is to investigate whether P1 and P2 interact within or outside cells. The genetic sequences for the P1-H and P2-L fusion proteins can then be transfected into living cells where the cells will produce the two fusion protein products. In this example when the P1-H and P2-L are diffusing independently in the interior of a cell, neither the H nor the L fragments alone will bind the fluorogen (that bound with a fluorescence increase to the original ScFv from which the H and L halves were obtained) to produce a significant fluorescence signal. However, when P1 and P2 interact, the H and L components will be brought into close proximity and will interact as well to form the original combining site that will bind to the fluorogen. If this is the case, a fluorescence signal will occur on interaction of P1 and P2.

The protein-protein biosensor of this example has advantages of quick fluorescence response, good sensitivity and relative reversibility. It is possible to use fragments of other FBPs to create protein-protein interaction sensors similar to the one described above.

Example 4

Eight Unique FBPs That Elicit Intense Fluorescence From Otherwise Dark Dyes

In this experiment, it was demonstrated that fluorescent proteins for live cell applications could be created. Eight unique FBPs that elicit intense fluorescence from otherwise dark dyes were isolated by screening a yeast display library of human single chain antibodies (scFvs) using derivatives of thiazole orange (TO) and malachite green (MG). When displayed on yeast or mammalian cell surfaces, these FBPs bind their fluorogens with nanomolar affinity, increasing their respective green or red fluorescence by several thousand-fold to brightness levels similar to that of enhanced green fluorescent protein. Significant spectral variation is generated within the family of malachite green FBPs by use of different proteins and chemically modified fluorogens. These diverse FBPs and fluorogens provide opportunities to create new classes of biosensors and new homogeneous cell-based assays. These studies were aimed at creating a new class of protein/dye reporters whose spectral properties are determined by the interplay of a protein moiety (a Fluorescent Binding Protein or FBP) and a noncovalently bound fluorogen. In the ideal case: (1) neither the FBP nor the fluorogen exhibits fluorescence in the absence of the other, (2) the increase in fluorescence upon binding is dramatic, (3) the fluorogenic interaction between FBP and fluorogen is highly specific, eliminating the need for washes or blocking agents, (4) neither the FBP nor the fluorogen is toxic or have intrinsic biological activity, 5) variation of the FBP and/or the fluorogen elicits useful variation in fluorescence color, binding affinity and other properties, and 6) the FBP can fold or readjust its conformation rapidly with an associated fluorescence change.

For example, such a system may allow the experimenter to modulate fluorescence as needed by adding or removing fluorogens. Or, fluorogens could be tailored to address specific requirements, such as cell membrane permeability and exclusion, or binding to a given FBP with different affinities and colors to facilitate pulse-chase techniques. Unrelated fluorogen-FBP pairs that do not cross-react could be developed to support FRET applications. As proof-of-principle, it was demonstrated that cells expressing single chain antibodies (scFvs) display intense fluorescence enhancement after exposure to two unrelated dyes, TO1 and MG. ScFvs were chosen because these small (<30 kDa) molecules retain the full range of antigen recognition capabilities of the humoral antibodies and are amenable to use as recombinant tags in fusion proteins. A complex human scFv library composed of ~$10^9$ synthetically recombined heavy and light chain variable regions was available in a yeast surface-display format, enabling us to use Fluorescence Activated Cell Sorting (FACS) to directly screen for fluorogenic binding to the dyes.

TO1 and MG are known fluorogens; strong fluorescence activation is observed when TO1 intercalates into DNA or when MG binds to a specific RNA aptamer. Without being bound by theory, enhanced fluorescence is thought to occur because rapid rotation around a single bond within the chromophore is constrained upon binding. Enhanced fluorescence of such 'molecular rotors' has also been reported for an antibody-dye complex, although with comparatively modest increase.

TO1 and MG were coupled to 3350 or 5000 MW polyethylene glycol (PEG)-biotin, and the dye-PEG-biotin conjugates were used with streptavidin and anti-biotin magnetic beads to affinity enrich the yeast surface display library for dye-binding scFvs. The TO1- and MG-affinity enriched scFv libraries were further enriched and then screened for fluorescence-generating scFvs by 2-4 rounds of FACS using the dye-PEG conjugates. For subsequent binding studies, TO1 and MG were coupled to diethylene glycol diamine (TO1-2p and MG-2p) to maintain antigenic structure and aqueous dye solubility.

Sixteen clones that enhanced MG-2p fluorescence and two clones that enhanced TO1-2p fluorescence were isolated from the library (FIG. 8). Sequence analysis revealed that the TO1-2p scFvs were encoded by different heavy and light chain germline genes. The fluorogenic MG-2p scFvs represented six germline configurations, three composed of the usual heavy and light chain segments, and three composed of only a single heavy or light chain segment (FIG. 9). The 11.5-14.4 kD single chain species are about half the size of GFP (26.7 kD). When expressed on the yeast cell surface, spectra of the fluorescent scFvs could be determined in a 96 well homogenous assay format in the presence of free dye. We took advantage of the robust surface expression to spectrally characterize and determine the affinity of all of our FBPs when bound to these two fluorogens (FIG. 9). The dissociation constants for HL1-TO1 and HL2-TO1 were high nanomolar range. To obtain stronger binders, one of the clones (HL1-TO1) was affinity matured by directed evolution using two rounds of error prone PCR mutagenesis and FACS selection for increased fluorescence at low fluorogen concentration, generating several FBPs with improved properties (FIG. 8). The most improved FBP, HL 1.0.1-TO1, bound TO 1-2p with a cell surface $K_D$ of about 3 nM. HL 1.0.1-T01 and HL2-TO1 each exhibited modest red excitation shifts (509 and 515 nm, respectively) relative to free dye absorbance (504 nm) but differed significantly from one another in emission maxima (530 and 550 nm.)

Each of the anti-MG FBPs bound MG-2p tightly when assayed on the cell surface, with an apparent $K_D$ in the low nanomolar range. Cell surface spectra showed significant variation among MG-2p binding FBPs. Excitation maxima of the FBP/MG-2p complexes ranged from 620-640 nm, markedly to the red of free dye absorbance (607 nm), whereas emission maxima ranged from 645-670 nm.

To more rigorously investigate the properties of FBP/fluorogens, secreted forms of HL1.0.1-TO1, HL4-MG and L5-MG were produced and affinity-purified (FIG. 8). In solution HL1.0.1-TO1 bound TO1-2p with a $K_D$ very similar to that observed on the cell surface. Direct measurement showed that the fluorescence of TO1-2p increased about 2.600-fold upon binding to the HL 1.0.1-TO1. The extinction coefficient and quantum yield of the HL1.0.1-TO1/TO1-2p complex ($\Sigma$=60,000 M$^{-1}$ cm$^{-1}$ and Ø=0.47) are comparable to the values for Aequorea EGFP (53,000 and 0.60), and predict that this FBP/fluorogen has EGFP-like brightness.

Figure 10B:
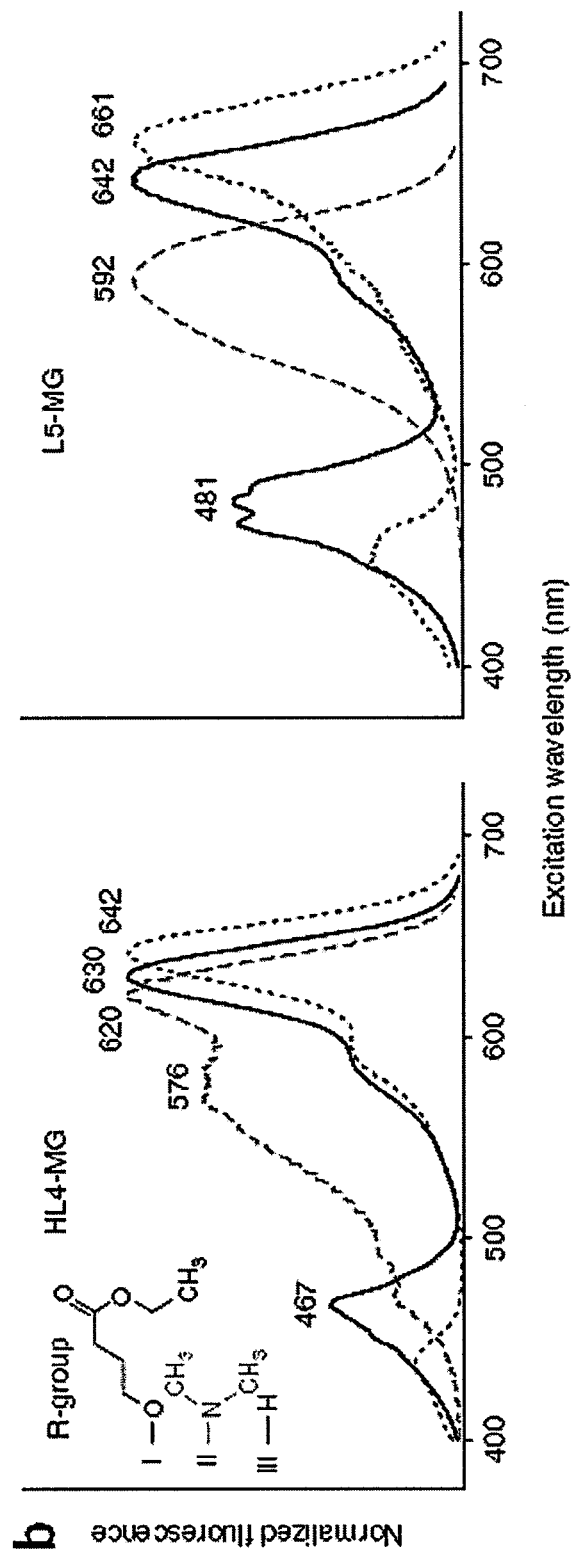
Figure 11A:
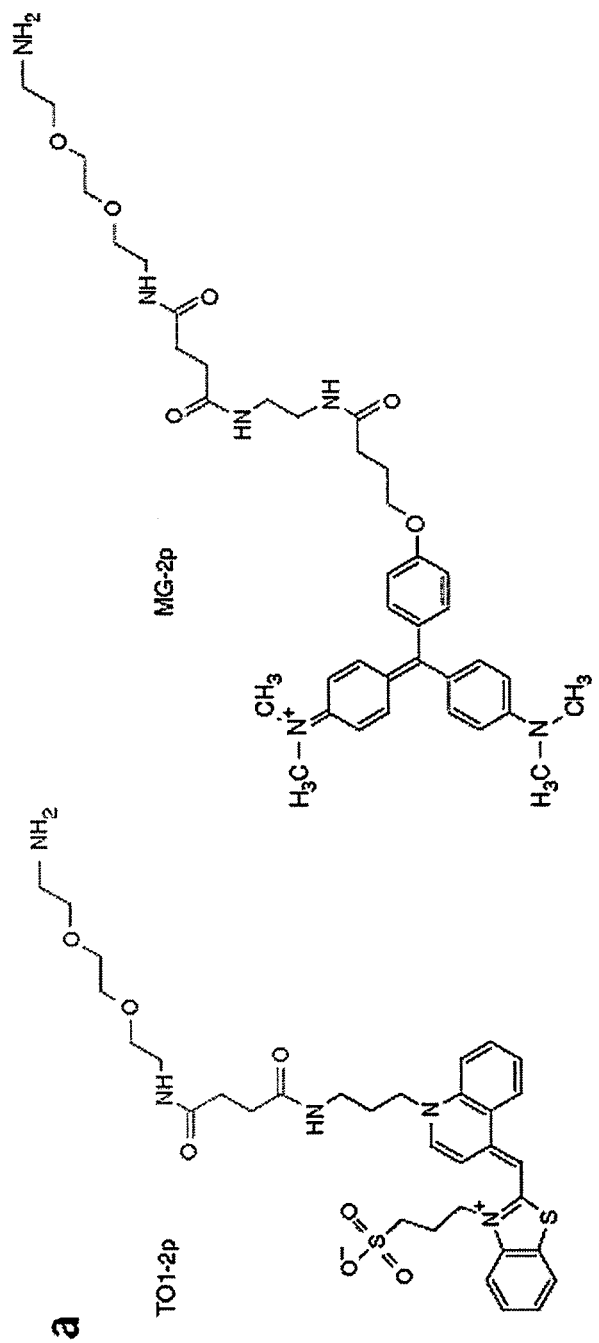
FIGS. 11A, 11B and 11C illustrate fluorogen embodiments and their use with yeast displayed scFvs.
Figure 11B:
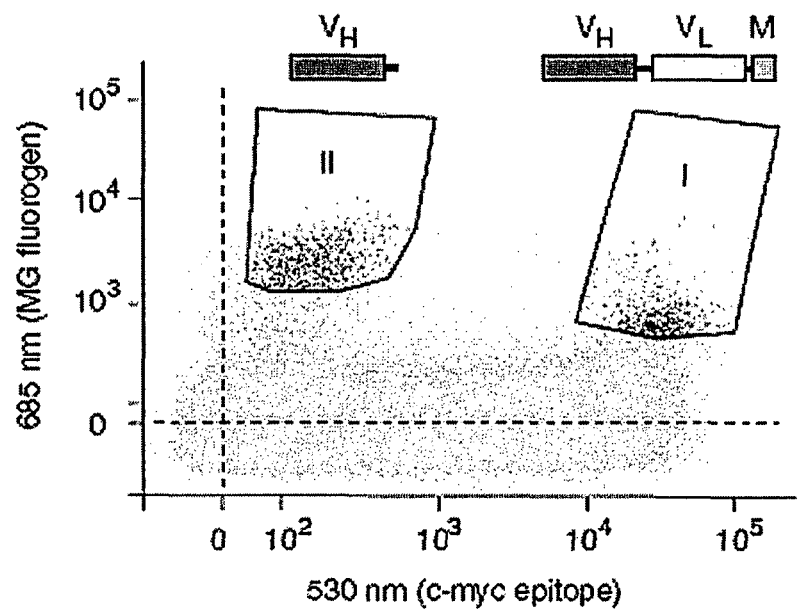
Figure 11C:
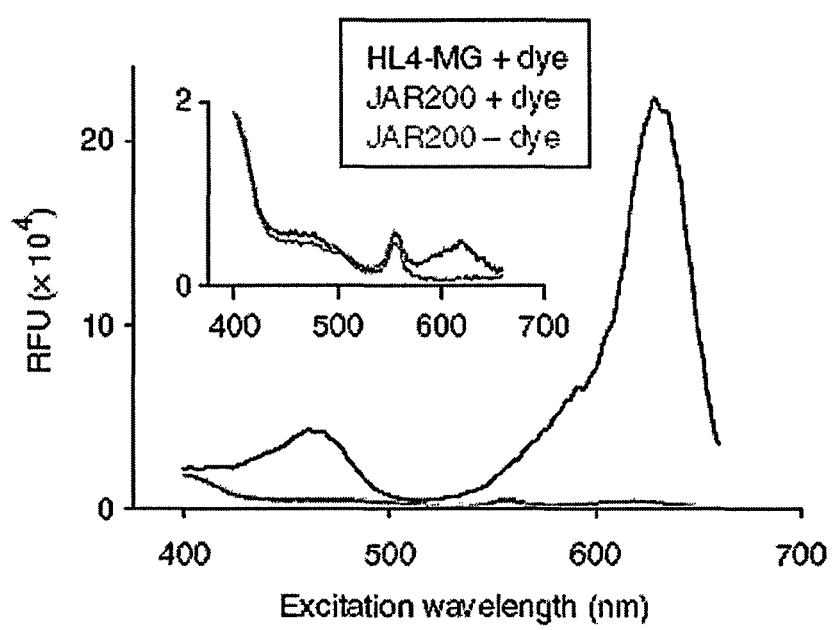
Figure 12:
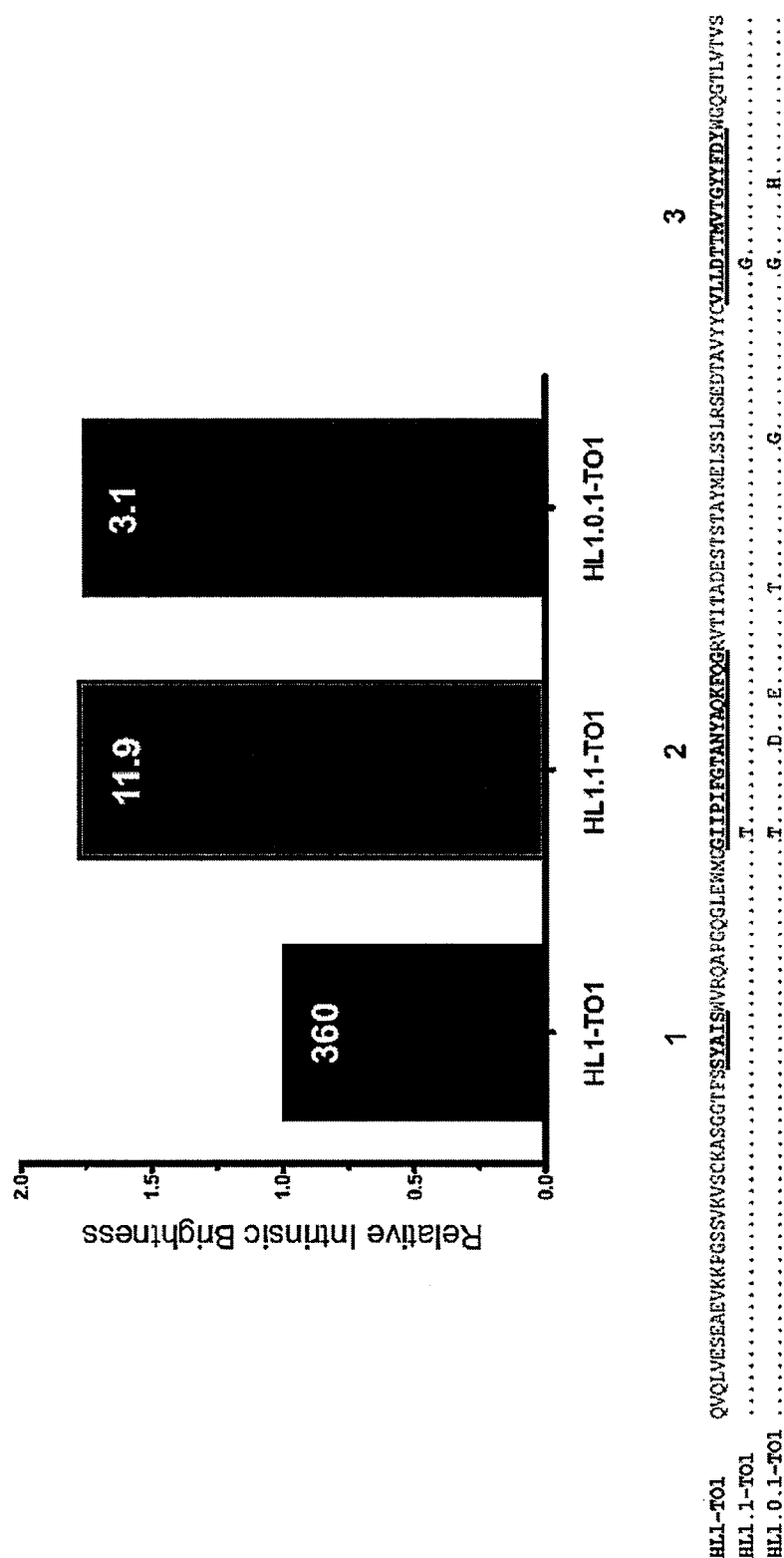
FIG. 12 depicts the improvement of binding affinity and intrinsic brightness of HL1-TO1 by directed evolution. Affinity and total cellular brightness are measured using yeast cell surface displayed scFvs. Total cellular brightness is measured at saturating fluorogen concentration on a Tecan Safire 2 plate reader, and intrinsic brightness calculated by normalizing total signal to the relative number of scFvs, determined separately by FACS analysis of immunolabeled c-myc epitope. The bar graph depicts relative intrinsic brightness for selected scFvs employed after one or two generations of directed evolution. Numbers on the bars represent cell surface binding $K_D$ (nM). The sequence alignments show the distribution of acquired mutations within the heavy chain variable region of HL1-TO1 (SEQ ID NO: 73, a fragment corresponding to residues 1-121 of SEQ ID NO: 3). Complementarity Determining Regions ("CDRs") within HL1-TO1 implicated in antigen recognition are underlined and numbered 1, 2 and 3, (corresponding to SEQ ID NOs 76, 77 and 78, respectively)

HL4-MG and L5-MG respectively showed 185- and 265-fold reduced affinity for MG-2p in solution as compared to surface display but affinity of H6-ME was reduced only five-fold (FIG. 9). This behavior differs markedly from that of HL1.0.1-TOL. The quantum yield of the HL4-MG/MG-2p complex (0.17) is similar to the quantum yield (0.187) of the malachite green RNA aptamer. Our result reflects a fluorescence enhancement of about 18,000-fold as compared to free fluorogen, which is much greater than the 40 to 100-fold enhancement for other antibody/fluorogen complexes but less than the 50.000-fold increase observed when a quenched FlAsH-EDT2 reagent binds its cognate tetracysteine peptide. Absorbance of the FBP/fluorogen is more than 1.4-fold greater than free MG-2p, corresponding to an extinction coefficient of about 105,000M$^{-1}$ cm$^{-1}$. The combined absorbance and quantum yield predict a red fluorescent probe with high brightness. We have synthesized and obtained several derivatives of the MG fluorogen to explore whether fluorogenic properties can be usefully modulated by altered chemistry, and have observed among our six MG FBPS many changes in binding affinity, fluorescence intensity and excitation/emission spectra. FIG. 10B illustrates striking spectral changes produced by 3 MG fluorogen derivatives. It can be seen that a given fluorogen derivative tends to shift the spectrum to the blue or the red within a spectral context established by the FBP. However, in some cases for some fluorogens, specific features of the FBP can greatly alter the extent of this shift or generate new spectral bands. Malachite green and most derivatives have a secondary absorbance peak at near ultraviolet to blue wavelengths that is sensitive to fluorogenic modulation by the FBP. We have taken advantage of this behavior to demonstrate fluorescent reporting in two colors excited by a single laser (non-overlapping green and red colors singly excited by the 488 nm argon laser.) It was found that color is a property of the combined FBP/fluorogen. Protein context thus changes the fluorescent behavior of these fluorogens, as has also been shown for stilbenes.

It has been long established that certain dyes exhibit enhanced fluorescence upon binding to proteins, and there are other reports of fluorogenic binding of dye to an antibody. Several features of what we report are new and provide promise for development of a new generation of biosensor systems and live-cell assays. Unlike fluorogen-activating monoclonal antibodies previously described, the fluorogen-activating scFvs described here are relatively small and compact monomeric proteins that can be recombinantly manipulated and expressed, making scFvs suited for use as genetically expressed tags or as injectable sensors. Unlike GFP and related fluorescent proteins, the reversibly bound fluorogen chromophore is directly accessible to experiment and its chemistry can be modified to alter reporting and sensing capabilities. In particular, control of access to the dye can afford a new level of selectivity. Unlike the biarsenical target peptide and the enzymatic peptide tags, scFvs provide a rich well-understood source of binding variation, which can be exploited to clone new FBPs that bind new fluorogens, or to enhance the functionality of existing FBPs and fluorogen variants using directed evolution technology.

These studies demonstrated that FBP/fluorogen reporters are well suited for expression at the extracellular side of the cell membrane. Although scFvs are derived from extracellular antibodies and contain internal disulfide linkages, it has been shown that functional scFvs can be expressed intracellularly in a disulfide-free format. In addition, the FBP concept can be extended to protein scaffolds beyond scFvs, as has been done for dye binding motifs such as the rhodamine binding fluorettes and other structures.

Example 5

Materials and Methods for Example 5

Yeast Display Library

A yeast cell surface display library, composed of ~$10^9$ recombinant human scFv's derived from cDNA representing a naive germline repertoire, is obtained from Pacific Northwest National Laboratory (PNNL). The original version of the library was obtained from PNNL and was the source of our first isolated FBP, HL1TO1. However, this library was subsequently found to be contaminated by a low level of another yeast strain (Candida parapsilosis) that overwhelmed yeast cultures after repeated outgrowth steps. We obtained another library that represents a subset of the original PNNL library. The estimated complexity of this library is ~$8×10^8$ independent scFvs. This library shows no evidence of contamination, and was the source of all other FBPS isolated for this study. This uncontaminated library version is currently available from PNNL.

Yeast Strains

EBY100 was host to the yeast display library and YVH10 was used to secrete scFvs, as described. For studies of individual FBPs, pPNL6 plasmids were transferred to JAR200, a G418 resistant derivative of EBY100. JAR200 expressed higher levels of displayed scFvs and gave higher transformation transformation rates with pPNL6 plasmids than EBY100.

YVH10: Mat α ura3-52, trp1, leu2δ200, his3δ200, pep4: HIS3, prbd1.6R, can1, GAL, GAPDH promoter-PDI1

EBY100: Mat α ura3-52, trp1, leu2δ200, his3δ200, pep4: HIS3, prbd1.6R, can1, GAL, GAL promoter-AGAI:URA3

AR200: Mat α ura3-52, trp1, leu2δ200, his3δ200, pep4: HIS3, prbd1.6R, can1, GAL, GAL promoter-AGAI:: URA3:G418r Yeast Buffer System We employed a modified PBS buffer (PBS pH 7.4, 2 mM EDTA, 0.1% w/v Pluronic F-127 (Molecular Probes, Invitrogen)) for magnetic bead enrichment, FACS experiments, and all assays of yeast surface displayed or purified scFvs. Inclusion of Pluronic F-127 was found to greatly reduce absorption of low concentrations of TOI and MG dyes to plastic and glass surfaces; microplate samples of 500 nM free dye gave stable readings for at least 18 hours.

Standard Procedure for Cloning of Single Chain Antibodies

All FBPs other than HL1-TOI (see below) were cloned essentially as described except that a 2-color FACS enrichment screen based on enhanced fluorescence of the fluorogen was employed instead of a 2-color screen based on antigen labeled with independent fluorophore. FACS enrichment was carried out on a Becton Dickinson FACSVantage SE with FACSDiva option; candidate FBPS were autocloned onto agar plates prior to characterization. 1 µM TO1-PEG5000-biotin or 500 nM MG-PEG5000 biotin were used to magnetically enrich and sort for respective FBPS, except that 50 nM MG-PEG5000-biotin was used to autoclone highest affinity MG-FBP candidates.

Cloning of HL1-TOI

A large population of induced cells was directly enriched for FBPS by 3 successive rounds of FACS. Briefly, cells were enriched for affinity by two rounds of magnetic bead treatment, and the output cells grown and induced. $10^8$ of these cells were sorted on a MoFlo high speed FACS, and the output $9×10^6$ cells were immediately resorted under the same conditions to give $7×10^4$ cells. These cells were again sorted to give ~1500 cells as final output. After growth and induction, these cells were sorted on an Epics Elite FACS, and the small population of cells (~0.5%) with significantly improved fluorogen signal was collected, regrown and resorted. These cells exclusively displayed HL1-TO1. Subsequent attempts at cloning other FBPs using this direct approach failed.

Identification of FBPs

Autocloned yeast cells displaying candidate FBP isolates were grown in small cultures, and yeast plasmid DNA isolated using a Zymoprep kit (Zymo Research). The scFv insert was PCR amplified, and the amplified DNA product purified on an agarose gel and then DNA sequenced. scFv variable region sequences were classified as to human germline composition by analysis on the IMGTN-QUEST website.

Spectral Characterization of FBPs

Yeast surface displayed scFvs were spectrally characterized using fluorescence bottom reading in 96 well microplates on a Tecan Safire2 plate reader. $10^6$ cells in 200 µl yeast buffer were assayed with 100-1000 nM MG-2p or TO1-2p. Spectra were corrected by subtraction of fluorescence of control cells not expressing scFvs.

Affinity Maturation of HL1-TO1

Affinity maturation of HL1-TO1 followed described methods for random mutagenesis and selection of improved clones, except that the 2-color FACS screen used in our standard cloning procedure was employed using TO1-2p as the fluorogen.

Secretion and Purification of Soluble FBPs

Induction and secretion of scFvs were at 20° or 25° C. as described, except that YEPD was replaced by a tryptone-based secretion medium:

5 g/L casamino acids (-ade, -ura, -trp) 50 g/L Bacto-Tryptone (BD #211705)
1.7 g/L Yeast Nitrogen Base w/out ammonium sulfate amino acids (BD #233520)
5.3 g/L ammonium sulfate
10.19 g/L $Na_2HPO_4.7H_2O$
8.56 g/L $NaH_2PO_4.H_2O$ FBP secretion in 1 liter cultures was monitored during the 2-5 day course of induction by assaying the fluorescence of culture supernatants on a 96-well Tecan Safire2 plate reader. 100 µl of 2× assay buffer (100 mM $Na_xH_xPO_4$, pH 7.4, 4 mM EDTA, 0.2% Pluronic F-127) containing either 1 µM TO1-2p or 200 nM MG-2p was added to 100 µl of culture supernatant for reading; readings were corrected for background by subtracting the fluorescence of identically treated virgin secretion medium. Tryptone secretion medium gave 2 to 10-fold increased yields of secreted scFvs as compared to YEPD.

Culture supernatants were dialysed and concentrated 3 times against 6 liters PBS on an Amicon Model 2000 high performance ultrafiltration cell using a 10,000 mw cut-off cellulose membrane. To purify the 6-his tagged FBPS, the concentrated dialysate (~50 ml) was subjected to nickel-nitrilotriacetic acid chromatography (Ni-NTA) according to manufacturer's instructions. Appropriate dilutions of eluted fractions were assayed for fluorogenic activity using essentially the same assay as for secretion. Fluorescent fractions were pooled, assayed for protein content using a BCA protein assay kit, and analyzed by SDS gel electrophoresis.

Determination of Fluorogen Binding Affinity to Yeast Surface Displayed FBPs

A homogenous assay under equilibrium binding conditions was devised to determine the binding affinity of fluorogen to yeast displayed scFvs. A flow cytometric method for titrating yeast displayed scFvs with fluorescently labeled antigen was adapted to the use of fluorogens. $10^6$ induced yeast in 200 µl modified PBS (~1 nM displayed scFvs) containing fluorogen over a concentration range of 0.1-1000 nM were assayed in duplicate for fluorescence in 96 well microplates on a Tecan Safire2 reader. As controls, mock induced JAR200 cells that do not express scFvs were treated with equal concentrations of fluorogen; fluorescence was corrected by subtraction of the fluorescence of control cells. Cell surface $K_D$ values were determined on Prism Graphpad Prism 4.0 software by non-linear regression analysis using a one-site binding algorithm for saturation binding:

$$Y=B_{max}*X=(KD+X)$$

where X is the concentration of fluorogen.

Determination of Fluorogen Binding Affinity to Soluble FBPs

Binding affinity to soluble scFvs was determined by monitoring fluorogenic signal under conditions of ligand depletion using a homogenous 96 well microplate assay similar to above. 1 nM HL1.0.1-TO1, 10 nM L5-MG and 100 nM HL4-MG were each assayed with a 0.1 to 1000 nM range of fluorogen. Fluorescence of each FBP+dye sample was corrected by subtracting the fluorescence of a dye only sample. $K_D$ values were determined by non-linear regression using Graphpad Prism 4.0 and a ligand depletion algorithm.

$$Y=(X+K_D+R-\sqrt{(-X-K_D-R)^2-4*X*R})\div 2$$

where X is the concentration of fluorogen, and R is the concentration of FBP/fluorogencomplex at the observed or extrapolated plateau at maximum fluorescence.

Determination of Quantum Yields

Quantum yields were determined by comparing integrated spectra of FBP/fluorogen complexes with those of reference dyes. Corrected emission spectra were taken at concentrations of FBP/fluorogen complex and reference dyes giving similar absorbances at the excitation wavelength, and the intensity integral computed. Provisional quantum yields were calculated by the relation:

$$\Phi = \Phi_R * \frac{I*A_R*\eta^2}{I_R*A*\eta_R^2}$$

where (phi is the quantum yield, I is the integrated intensity, A is the absorbance, η is the refractive index, and R designates the reference dye. Provisional quantum yields were adjusted to 1:1 complexation by using the solution $K_D$ of the complex to quantify the proportional occupancy at these concentrations (using Graphpad Prism 4.0 and the above ligand depletion algorithm).

A cyanic dye, Cy5.18 in PBS and Di-S—C2-(5) in MeOH were used as reference fluorophores for the determination of HL4-MG/MG-2p and L5-MG/MG-2p quantum yields. 2 µM scFv and 440 nM MG-2p were employed; emission spectra of respective complexes were taken in duplicate. Absorbances of the respective complexes were significantly higher than free MG-2p. These differences in absorbance magnitude underrepresent actual differences because of incomplete complexation at these concentrations. HL4MG/MG-2p and L5-MG/MG-2p quantum yields were respectively multiplied by 1.35 and 1.20 to correct for incomplete complexation.

Fluorescein in 0.1 N NaOH and Rhodamine-6-G in MeOH were used as reference fluorophores for the determination of the quantum yield of HL1.0.1-TO1/T012p. At the employed concentrations of 2 µM scFv and 520 nM TO1-2p, virtually complete complexation is expected, and no correction was used. Only slight changes in absorbance magnitude were noted.

Determination of Fluorogenic Enhancement

Fluorogenic enhancement of HL4-MG, L5-MG and HL1.0.1-TO1 was measured in 96 well microplates on a Tecan Safire2 reader by comparison of the fluorescence of 500 nM free fluorogen with the fluorescence of a mixture of 500 nM fluorogen and 2 µM respective FBP. After a 1 hour incubation to allow complex formation, fluorescence was measured at the excitation and emission maxima of the fluorogen/FBP complexes. Fluorescence of yeast PBS buffer was subtracted from all samples. Fluorescence readings were stable for at least 16 hours.

Extended gain settings were used to increase numerical accuracy. For HL4-MG and L5MG, the differences in fluorescence between complexes and free dye exceeded the extended gain range of the instrument, so intermediate concentrations of Cy5 were also measured to allow interpolation between the extreme values. Two independent experiments, each with triplicate measurements, were carried out for each of the 3 FBPS; standard deviations for averaged values of FBPS, free fluorogen or PBS were less than 5%. The fold-enhancement values for HL4-MG and L5-MG were respectively multiplied by 1.35 and 1.20 to correct for partial complexation.

Mammalian cell-surface expression of FBP molecules

Plasmids expressing surface-displayed scFv's were generated as follows. A 375 by PCRamplicon was amplified from E. coli C600 DNA using as primers:

```
SEQ ID NO: 23:
GGGGCTACCAGTTTGAGGGGACGACGA

SEQ ID NO: 24:
GGCCCCTGCGGCCGTTAGCTCACTCATTAGGCA
```

This molecule, which contains the lac promoter and 271 nucleotides of beta-galactosidase coding sequence flanked by SfiI sites, was cut with XmaI and ligated into pDisplay (Invitrogen) between the SmaI and XmaI sites to produce vector pDisplayBlue. Individual scFv sequences were prepared for insertion between the SfiI sites in pDisplayBlue by PCR-amplifying the scFv sequences from pPNL6 clones using as primers:

```
SEQ ID NO: 25:
TATATAGGCCCAGCCGGCCTACCCATACGACGTTCCAGAC

SEQ ID NO: 26:
TATATAGGCCCCTGCGGCCAATTCCGGATAGGACGGTGAG
```

These amplicons were cut with SfiI, ligated into SfiI-cut vector, transformed into DH5cc E. coli to ampicillin resistance, and Lac+ colonies picked for DNA sequencing. DNA was prepared from selected transformants using Qiagen Mini-Prep kits and transfected into NIH3T3 cells or M21 mouse melanoma cells (~1 μg DNA per $10^5$ cells) in 24-well-plates using Lipofectamine 2000 (Invitrogen) following the protocols supplied by the manufacturer. Stable transfectants were isolated by successive rounds of FACS sorting of cells exposed to the appropriate fluorogens.

Example 6

Fusion of scFv Sequences to a Transmembrane Domain Derived from Human Fibroblast Growth Factor Receptor 2, and Expression of the Fusion Constructs in Mammalian Cells Mammalian Cell-Surface Expression of Fluorogen-Activating Polypeptide Molecules.

NIH3T3 cells stably expressing HL4-MG fused to PDGFR were imaged by confocal microscope at 633 nm excitation after treatment for 5 min in PBS with 200 nM MG-11p or 200 nM MG-ester. On longer incubation, MG-ester illuminated intracellular features such as the nuclear periphery (endoplasmic reticulum) and Golgi become more difficult to visualize. Fluorescence images were excited at 633 nm using a 650 nm long pass filter. Fluorescence images were unprocessed; interference lines on DIC images were removed using a fourier transform filter in Photoshop. Images in were acquired on a Zeiss LSM510 META laser scanning microscope using a 63× objective. Fluorescence images were excited at 633 nm using a 650 nm long pass filter.

In addition, surface labeling of human tumor cells with a MG fluorogen-activating polypeptide was shown. Stably transformed M21 melanoma cells expressing HL4-MG fused to PDGFR were imaged as a confocal stack at 488-nm excitation using 10 nM MG-11p. Images were acquired on a Zeiss LSM510 META laser scanning microscope using a 63× objective. Images were acquired on a Zeiss Axioplan 2 with Apotome microscope. Green false color (TO1-2p) was imaged using 540/25 and 605/55 nm excitation and emission filters; red false color was imaged using 560/55 and 710/75 nm excitation and emission filters. Images were reconstructed from 72 1 μm sections, displayed as 15 projections in NIH Image software, and false colored in Adobe Photoshop.

Also, surface labeling of fibroblasts with a TO1 fluorogen-activating polypeptide was detected. Stably transformed NIH3T3 cells expressing HL1.1-TO1 fused to PDGFR and imaged using 40 nM TO1-2p. Images were acquired on a Zeiss Axioplan 2 with Apotome microscope. Green false color (TO1-2p) was imaged using 540/25 and 605/55 nm excitation and emission filters; red false color was imaged using 560/55 and 710/75 nm excitation and emission filters. Images were reconstructed from 72 1 μm sections, displayed as 15 projections in NIH Image software, and false colored in Adobe Photoshop. The HL1.1-TO1 expressing cells were excited at 488 nm and visualized with a 500 nm long pass filter.

In another experiment, it was shown that simultaneous surface labeling of fibroblasts with MG and TO1 FAPs occurred. NIH3T3 cells respectively expressing the FAPs 1:1 and imaged using 10 nM MG-2p and 40 nM TO1-2p. The transparency of surface-labeled cells allows fine discrimination of contact surfaces between cells of different colors. Images were acquired on a Zeiss Axioplan 2 with Apotome microscope. Green false color (TO1-2p) was imaged using 540/25 and 605/55 nm excitation and emission filters; red false color was imaged using 560/55 and 710/75 nm excitation and emission filters. Images were reconstructed from 72 1 μm sections, displayed as 15 projections in NIH Image software, and false colored in Adobe Photoshop. a 700/75 nm bandpass filter was used to visualize the 488 nm excitation of HL4-MG Example 7

Fusion of scFv Sequences to the Human Glucose Transporter GLUT4, and Expression of the Fusion Constructs in Mammalian Cells An open reading frame comprising the coding sequence of human GLUT4 was cloned 5' to the PDGFR sequence in the modified pDisplay vector described in Example 5 that was further modified to accept the insert between PflMI restriction sites. Fluorogen-activating scFv sequence HL1.1-TO1 was cloned between the SfiI sites of these constructs as described in Example 5. NIH3T3-L1 cells were transfected with the constructs, and stable transfectants were isolated by multiple rounds of FACS sorting for fluorogen-activating cells.

Imaging by fluorescence microscopy after incubation in the presence of fluorogen showed distinct surface labeling when cells were treated with a membrane impermeant fluorogen, and internal as well as surface labeling when cells were transfected with a control plasmid with EGFP cloned between the SfiI sites.

Images were taken with Apotome microscope with 63× water immersion lens. Excitation occurred at 488 nm with emission collected in GFP channel. Cells are undifferentiated 3T3-L1 fibroblasts. These results indicate that a fusion protein between GLUT4 and a fluorogen-activating scFv is correctly localized at the cell surface, as well as in the expected subcellular compartments of the endomembrane system.

Example 8

Fusion of scFv Sequences to the Human G-Protein Coupled Receptor ADRB2, and Expression of the Fusion Constructs in Mammalian Cells The coding sequence of human ADRB2 was PCR amplified from an ADRB2 fosmid and cloned into the BsmI site in the modified pDisplay vector described in example N, with an in frame stop codon at the 3' end of the ADRB2 sequence. Fluorogen-activating scFv sequences HL1.1-TO1 and HL4MG were cloned into the SfiI sites of these constructs as described in example N. NIH3T3 cells were transfected with the constructs, and stable transfectants were isolated by multiple rounds of FACS sorting for fluorogen-activating cells.

Imaging by fluorescence microscopy after incubation in the presence of fluorogen showed distinct surface labeling when cells were treated with membrane impermeant fluorogens, and internal as well as surface labeling when cells were treated with membrane permeant fluorogens. Further, when cells were treated with the ADRB2 agonist isoproterenol at physiological concentrations, internalization of the ADRB fusion protein was observed, indicating that the fusion protein was physiologically active with respect to recognition and internalization of the agonist.

Example 9

Cell Surface Complementation

This experiment demonstrated that the light chain and heavy chains of a selected scFv can be separately fused to two different proteins, and that when these two proteins are in close proximity, the heavy and light chains associate to produce a binding site for the same dye that binds to the original scFv leading to a fluorescence increase. In the following experiments three classes of yeast cells were generated by molecular biology methods known in the art. One class of yeast expressed only the heavy chain of the scFv on the surface. A second class expressed only the light chain of the scFv on its surface. The third class expressed both the heavy and light chains on the surface. When the fluorescent reporter TO1 was added independently to solutions containing the three classes of yeast cells, only the third class that expressed both heavy and light chains at a high surface density produced a fluorescence increase, as shown below. Specifically, two vectors, pPNL6 and pPNL6URA3 were prepared, where the TRP1 gene of pPNL6 was replaced with the URA3 gene of S. cerevisiae. This approach allowed selection for both plasmids in a single cell. Fragments carrying scFv1, scFv1 HO (heavy only chain), or scFv1 LO (light only chain) were cloned into each of the two vectors.

JAR200 yeast cells were transformed with each single plasmid as well as both scFv1 HO (PNL6)+scFv1 LO (PNL6URA3) or both scFv1 HO (PNL6URA3)+scFv1 LO (PNL6). Analysis by FACS and TECAN followed induction of the cells. In both cases, 1 µM TO1-2P was used.

In the first approach, flow cytometry was used to assay cellular fluorescence of the three classes of yeast in the presence and absence of TO1. The population of induced cells was analyzed by measuring fluorescence emitted at 685 from a signal caused by protein labeled by anti-C-myc Alexa 647. This allowed confirmation that the three classes of yeast cells were expressing full length heavy, light, or heavy and light chains on the cell surface. For cells that expressed full length fragments the TO1-2p fluorescence was observed as emission at 530.

TABLE 1

| PLASMID | MEAN 530 SIGNAL | |
|---|---|---|
| scFv1 PNL6 | 840 | Intact origininal scFv |
| scFv1 PNL6URA3 | 760 | Intact origininal scFv |
| HO PNL6 | 88 | Heavy chain only |
| HO PNL6URA3 | 82 | Heavy chain only |
| LO PNL6 | 102 | Light chain only |
| LO PNL6URA3 | 100 | Light chain only |
| HO PNL6 + LO PNL6URA3 | 317 | Heavy and light same cell |
| HO PNL6URA3 + LO PNL6 | 261 | Heavy and light same cell |

The cells expressing both heavy and light were 2.5-3 times more fluorescent than cells expressing heavy or light only. The signal increase is likely to be larger in assays where the two proteins containing the heavy and light chains are associating in a pair-wise manner rather that a statistical association. With pair-wise protein-protein interactions the fluorescence of the complex may approach that of the original scFv PNL6 or PNL6URA3 in which the heavy and light chains are directly linked through a short-serine-glycine-polymeric linker.

In the second approach, a fluorescence spectrometer was used to quantify the fluorescence from suspensions of cells. The fluorescence excitation wavelength was 506 nm and the emission wavelength was 610 nm. Values presented below are corrected from raw data by subtracting out the values for (buffer+dye) and induced (no dye) samples. They were then corrected for the percent of the population that was induced, as determined by the flow cytometry analysis analysis.

TABLE 2

| PLASMID | Fluorescence | % Pop. Ind | F/(% Pop IND) |
|---|---|---|---|
| scFv1 PNL6 | 23934 | 60.3 | 39691 |
| scFv1 PNL6URA3 | 28686 | 48.4 | 59268 |
| HO PNL6 | 135 | 84.2 | 160 |
| HO PNL6URA3 | −605 | 70.6 | / |
| LO PNL6 | −16 | 73.7 | / |
| LO PIML6URA3 | 882 | 64.4 | 1369 |
| HO PNL6 + LO PIML6URA3 | 6553 | 84.2 | 7782 |
| HO PNL6URA3 + LO PNL6 | 4571 | 73.1 | 6253 |

The fluorescence spectroscopy measurements demonstrated that cells expressing both heavy and light were significantly more fluorescent than cells expressing heavy or light only.

Example 10
Syntheses of Dyes
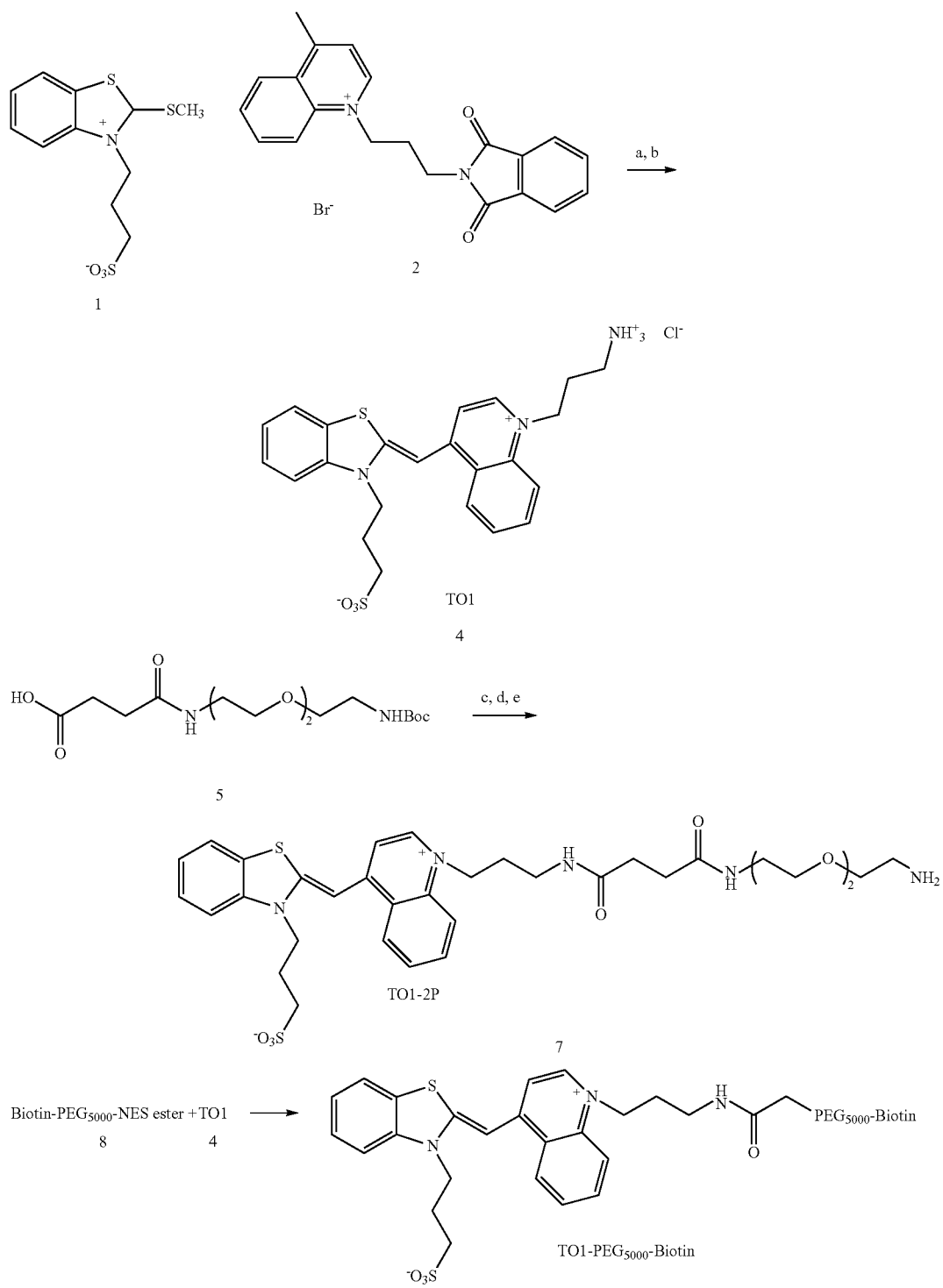
a) Boiling EtOH:NEt₃ 3:
b) HCl_conc:EtOH
c) DCC:NHS:AN TO1 6:
d) 1N HCl:MeOH;
e) NaHCO₃
f) NaHCO₃

2-[(1-[3-[3[(1,3-Dihydro-1,3-dioxo-2H-isoindol-2-yl)propyl]-4(1H)quinolinylidene)methyl]-3-(3-sulfopropyl)benzothiazolinium inner salt 3

1-(3-N-Phthalimidopropyl)-4-methyl-quinolinium bromide 2 (822 mg, 2 mmol) and 3-(3-Sulfopropyl)-2-methylthio-benzothiazole 1 (1.2 g, 4 mmol) were dissolved in 150 mL boiling anhydrous ethanol. Triethylamine (0.28 ml, 4 mmol) was gradually added over a 15 minutes time period. The reaction mixture was refluxed for one hour. The precipitated solid was filtered off from the hot reaction mixture to give 822 mg of a red powder. Yield: 820 mg (70%); $C_{31}H^{27}N_3O_5S_2$ MW=585.7 g/mol Theory: C 63.57% H 4.65%; N 7.17% Found: C 63.62% H 4.61% N 7.05%

$^1$H-NMR (CDCl$_3$/MeOD): 8.85 (1H, d); 8.33 (1H, d); 7.68-7.87 (8H, m); 7.52-7.62 (2H, m); 7.31 (2H, m); 7.06 (1H, s); 4.75 (2H, t); 4.51 (2H, t); 3.84 (2H, t); 3.11 (2H, t); 2.34 (4H, m).

-[(1-(3-Aminopropyl)-4(1H)-quinolinylidene)methyl]-3-(3-sulfopropyl)benzothiazolinium hydrochloride "TO1" 4

2-[(1-[3-[3[(1,3-dihydro-1,3-dioxo-2H-isoindol-2-yl)propyl]-4(1H) quinolinylidene)methyl]-3-(3-sulfopropyl)benzothiazolinium inner salt 3 (585.7 mg; 1 mmol) was suspended in 20 mL concentrated hydrochloric acid and 5 mL ethanol. The reaction mixture was refluxed for 48 hrs. The solvent was removed under vacuum. The residue was dissolved in 10 ml of methanol and the dye was precipitated with 50 mL methylene chloride. The dye was filtered off; dissolved in water and filtered. The filtrate was concentrated under vacuum to give 400 mg of a red powder. Yield: 394 mg (80%) $C_{23}H_{26}ClN_3O_3S_2$ MW: 492.06 g/mol; Theory: C 54.16% H 5.53% N 8.23%; Found: C 54.39% H 5.70% N 7.82%

$^1$H-NMR (D$_2$O): 7.64 (1H, d); 7.63 (1H); 7.53 (1H); 7.43 (1H); 7.23 (1H); 7.1 (1H); 6.92 (1H); 6.9 (1H); 6.54 (1H); 6.29 (1H); 5.9 (1H); 3.7 (4H); 2.95 (2H); 2.82 (2H); 1.81 (4H). $C_{23}H_{26}ClN_3O_3S_2$ x H$_2$O; MW 510.07 g/mol; LTV/VIS λmax=488 nm; εmol, =58000

[2-[(1-(Boc-18-amino-4,9-diaza-12,15-dioxa-5,8-dioxo-octadecanyl)-4(1H)quinolinylidene)methyl]-3-(3-sulfopropyl)benzothiazolinium] inner salt "TO1-2P—NHBOC" 6

Boc-14-amino-5-aza-8,11-dioxa-4-oxo-tetradecanoic acid 5 (700 mg, 2 mmol) was dissolved in dry CH$_3$CN (10 mL). N-Hydroxysuccinimide (2.1 mmol, 300 mg) and dicyclohexylcarbodiimide (500 mg, 2.1 mmol) were added. The reaction mixture was stirred at room temperature overnight. The precipitated urea was filtered off and the filtrate was used in the next reaction step. TO1-amine (500 mg, 1 mmol) was dissolved in a mixture of water (10 mL) and acetonitrile (10 mL). The active ester solution was added in portions of 0.5 mL. After 30 min of stirring a precipitate formed. TLC control (silica gel) showed the product in the solution phase (9:1 CHC13/McOH/1 TFA). The solid was filtered off and the filtrate concentrated under vacuum. The residue was purified by column chromatography on silica gel. Yield: 1.1 g (75%); $C_{33}H_{44}ClN_5O_7S_2$ MW: 725.48 g/mol 1H-NMR (MeOD): 8.64 (1H, d); 8.31 (1H, d); 7.75 (2H, m); 5.59 (2H, m); 7.44 (2H, m); 7.12 (1H, t); 7.07 (1H, d); 6.79 (1H, s); 4.65 (2H, bt); 4.39 (2H, t); 3.60 (4H, s); 3.5 (4H, m); 3.38 (2H, t); 3.21 (2H, t); 3.13 (2H, t); 2.58 (4H, m); 2.33 (2H, m); 2.06 (2H, m); 1.42 (9H, m). UV/VIS,% m, =508 nm

[2-[(1-(18-amino-4,9-diaza-12,15-dioxa-5,8-dioxo-octadecanyl)-4(1H)-quinolinylidene)methyl]-3-(3-sulfopropyl)benzothiazolinium]trifluoroacetate "TO1-2P"7

TO1-2P-BOC 6 (368 mg, 0.5 mmol) was dissolved in methanol (50 mL) and 1N hydrochloric acid 5 mL was added. The reaction mixture was stirred overnight at room temperature. The solvent was removed under vacuum to give an orange resin. The product was purified by HPLC; Waters μ-Bondapak C18; gradient 10-40% water/acetonitrile/0.1% TFA $^1$H-NMR (MeOD): 8.53 (1H, d); 8.27 (1H, d); 7.75 (1H, t); 7.68 (1H, d); 7.55 (1H, t); 7.49 (1H, d); 7.43 (1H, d); 7.37 (1H, t); 7.05 (1H, t); 7.01 (1H, d); 6.68 (1H, d-exchanges); 4.57 (2H, t); 4.35 (2H, t); 3.72 (2H, t); 3.65 (4H, m); 3.57 (2H, t); 3.39 (2H, t); 3.31 (2H, t); 3.14 (2H, m); 3.12 (2H, m); 2.26 (2H, m); 2.04 (2H, m); $C_{35}H_{44}F_3N_5O_9S_2$ MW: 799.9 g/mol εmol (λ504 in H2O) 34000; εmol (λ504 in MeOH) 49500

Biotin-PEG5000-TO1 9

2-[(1-(3-Aminopropyl)-4(1H)-quinolinylidene)methyl]-3-(3-sulfopropyl)benzothiazolinium hydrochloride TO1 4 (5.8 mg; 0.01 mmol) was dissolved in 0.1 mL of water. Biotin-PEG5000-NHS ester 8 (Nektar Therapeutics) (50 mg; 0.01 mmol) dissolved in 0.1 mL of DMF was added to the TO1 solution followed by 0.1 mL of saturated sodium bicarbonate solution. The reaction mixture was stirred for 1 hr. The solvents were removed under vacuum and the residue was taken up in a minimum of water and passed through a P4 sized exclusion column to remove free TO1. The PEG fraction was concentrated and purified on Q-Sepharose (Amerscham Biosciences) to separate unlabeled Biotin-PEG from Biotin-PEG5000-TO1. MS: $M_n$ 5743.56;

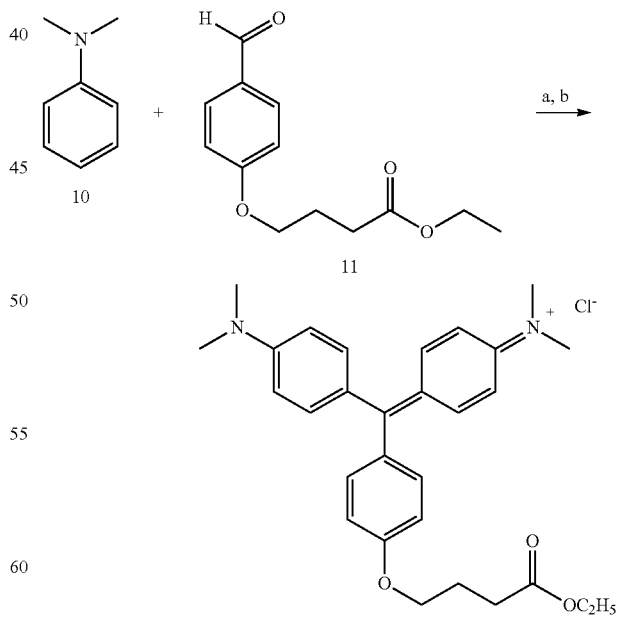

a) ZnCl$_2$:EtOH:12
b) TCB:ethyl acetate

[4-(1-Oxa-3-carboethoxypropyl)phenyl]bis[4-(dimethylamino)phenyl-methane 12

Dimethylaniline 10 (7.27 g; 60 mmol) and ethyl 4(4-formylphenoxy)butanoate 11 (7.08 g; 30 mmol) were dissolved in anhydrous ethanol (300 mL). Anhydrous zinc chloride (8.2 g) was added and the reaction mixture was refluxed for 2 days, distilling off the ethanol 4-5 times and replacing it with anhydrous ethanol. After cooling to room temperature, the reaction mixture was concentrated. The residue was taken up in ethyl acetate and water. The organic phase was separated, washed with water, dried, concentrated and purified on silica gel. Eluent: Ethyl acetate. MW $C_{29}H_{36}N_2O_4$ 476.62 g/mol; yield: 11.4 g (80%); $^1$H-NMR (CDCl3): 7.1 (2H, d); 7.05 (4H, d); 6.85 (2H, d), 6.75 (2H, d); 5.4 (1H.s, OH); 4.25 (2H, q); 4.05 (2H, t); 2.95 (12H, s); 2.6 (2H, t); 2.25 (2H, m), 1.35 (3H, t)

Methylium, bis[4-(dimethylamino)phenyl](4-(3-carboethoxypropyl)phenyl)-chloride 13

[4-(1-Oxa-3-carboethoxypropyl)phenyl]bis[4-(dimethylamino)phenyl-methane 12 (460 mg, 1 mmol) was dissolved in 25 mL ethyl acetate. Tetrachloro-p-benzochinone (490 mg/2 mmol) was added and the reaction mixture was refluxed for 1 hr. The reaction mixture was cooled to room temperature. Ethyl acetate (75 mL) was added and the product was extracted with water (5×50 mL). The combined aqueous phase was washed with ethyl acetate (2×50 mL) and concentrated to give 200 mg (40%) of product. MW $C_{29}H_{35}ClN_2O_4$ 511.1 g/mol $^1$H-NMR (CD3CN): 7.33 (4H, d); 7.08 (2H, d); 6.92 (4H, d); 4.15 (2H, t); 4.10 (2H, q); 3.23 (12H, s); 2.48 (2H, t); 2.08 (2H, m); 1.21 (3H, t)

[4-(1-Oxa-3-carboxypropyl)phenyl]bis[4-(dimethylamino)phenyl-methane 14

[4-(1-Oxa-3-carboxypropyl)phenyl]bis[4-(dimethylamino)phenyl-methane 12 (5 g, 10.5 mmol) was dissolved in acetone (30 mL). Sodium hydroxide (10 mL of a 2N aqueous solution) was added. The reaction mixture was stirred at room temperature until the ester was cleaved (TLC control). The acetone was removed and the aqueous solution adjusted to pH 3-4 with 1 N HCl. The aqueous phase was extracted with ethyl acetate (3×50 mL). The combined organic phase was washed with water and brine and dried over sodium sulfate. The solvent was removed to give 4 g of a light green resin (Yield: 90%). The compound was used without further purification. MW:$C_{27}H_{32}N_2O_4$ 448.6 g/mol. $^1$H-NMR (CDCl3): 6.96 (2H, d); 6.88 (4H, d); 6.81 (2H, d); 5.24 (1H, s); 3.92 (2H, t); 2.83 (12H, s); 2.34 (2H, t); 1.91 (2H, m)

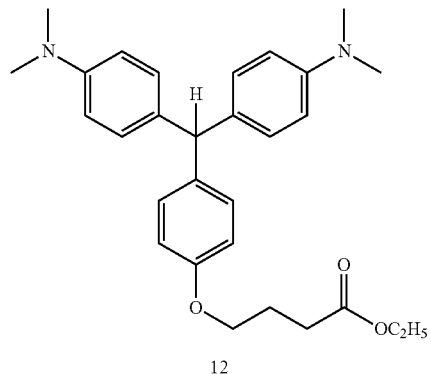

12

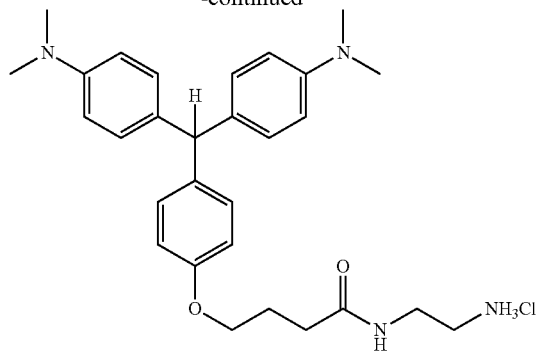

16 a) 2N NaOH:14
b) CH3COOEt/NEt3;
c) H2N—CH4—NHBoc 15;
d) HCL/EtOH

[4-(Boc-9-amino-6-aza-1-oxa-5-oxo-nonyl)phenyl]bis[4-(dimethylamino)phenylmethane 15

[4-(1-Oxa-3-carboxypropyl)phenyl]bis[4-(dimethylamino)phenyl-methane 14 (4.1 g, 9.14 mmol) was dissolved in a mixture of dry THF/$CH_2Cl_2$. Triethylamine (1.4 mL, 10 mmol) was added. The reaction mixture was cooled to 0° C. Ethyl chloroformate (0.95 mL, 10 mmol) was added and the reaction mixture was stirred for 30 min (TLC) control. NBOC-ethylenediamine (1.6 g, 10 mmol) was added. The reaction mixture was stirred for 30 min at room temperature (TLC control silica gel, ethyl acetate). The solvent was removed and the residue was taken up in ethyl acetate. The organic phase was washed with diluted sodium bicarbonate, water and brine and dried over sodium sulfate. The solvent was removed under vacuum and the residue purified by column chromatography on silicagel; eluent: ethyl acetate (RF 0.2). Light blue crystals were obtained. MW $C_{34}H_{46}N_4O_4$ 574.8 g/mol. Yield: 4.2 g (80%). $^1$H-NMR (CD3CN): 7.01 (2H, d); 6.94 (4H, d); 6.82 (2H, d); 6.69 (4H, d); 6.59 (1H, s, CONH); 5.59 (1H, s, CONH); 5.28 (1H, s, OH); 3.95 (2H, t); 3.21 (2H, m); 3.11 (2H, m); 2.88 (12H, s); 2.28 (2H, t); 1.99 (2H, m); 1.4 (9H, s, BOC)

[4-(9-amino-6-aza-1-oxa-5-oxo-nonyl)phenyl]bis[4-(dimethylamino)phenyl-methane 16

[4-(Boc-9-amino-6-aza-1-oxa-5-oxo-nonyl)phenyl]bis[4-(dimethylamino)phenylmethane (118 mg, 0.2 mmol) was dissolved in HCl/ethanol (2 mL of a 5% solution). The reaction mixture was kept overnight at room temperature. The solvent was removed and the residue dried. The product was used as such in the next reaction step.

16 $\xrightarrow{a, b, c}$

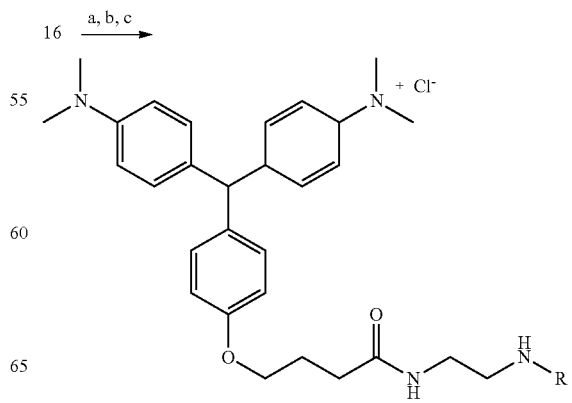

-continued

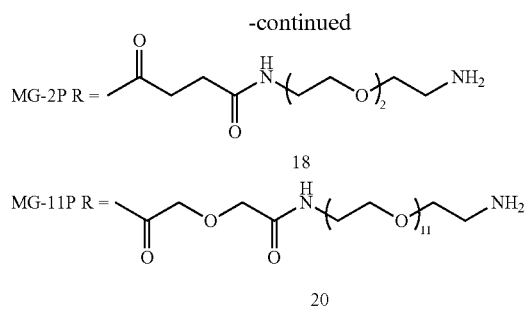

MG 2P: a) BOC-NH-PEG2-5ucc-O5U 14;
b) TCB;
c) 1N HCl/EtOH
MG 11: a) BOC-NH-PEG11-Glycol-O-5U 17;
b) TCB;
c) 1N HCl/EtOH

[4-(Boc-9-Aminoethyl-PEG2)-6,9,15-triaza-1,12-dioxa-5,10,14-trioxopentaundecanyl)phenyl]bis[4-(dimethylamino)phenyl-methane Leuko-MG-2P 17

[4-(9-Amino-6-aza-1-oxa-5-oxo-nonyl)phenyl]bis[4-(dimethylamino)phenyl-methane (118 mg, 0.2 mmol) 16 was reacted with the NHS-ester of boc-[4-amino-5-aza-8,11 dioxa-4-oxo-tetradecanoic acid 5 in 1 DMF (1 mL)/1N NaHCO$_3$ (1 mL). The reaction mixture was concentrated and purified by chromatography on silicagel (eluent: ethyl acetate/10-30% methanol). MW: $C_{34}H_{46}N_4O_4$ 574.8 g/mol

[4-(9-Aminoethyl-PEG2)-6,9,15-triaza-1,12-dioxa-5,10,14-trioxo-pentaundecanyl)MG-2P 18

Leuko-MG2 17 (161 mg/0.28 mmol) was dissolved in 25 mL of ethyl acetate. Tetrachloro-p-benzochinone (100 mg/0.4 mmol) was added and the reaction mixture was refluxed for 1 hr. The reaction mixture was concentrated to 2 mL. Hydrochlorid acid (2 mL of a 1N solution) was added and the reaction mixture was stirred at room temperature for 1 hr. The reaction mixture was partitioned between 100 mL ethyl acetate and 150 mL of water. The water phase was separated and washed with ethyl acetate (2×100 mL). The aqueous phase was concentrated. The residue was dried at 60° C. under high vacuum to give 130 mg of dye (yield: 88%). MW: $C_{29}H_{37}N_4O_2Cl$ 509.1 g/mol $^1$H-NMR (MeOD): 7.42 (4H, d); 7.36 (2H, d); 7.17 (2H, d); 7.04 (4H, d); 4.25 (2H, t); 3.71 (2H, m); 3.65 (4H, m); 3.55 (2H, t); 3.36 (2H, t); 3.31 (12H, s); 3.30 (2H, m); 3.07 (2H, m); 2.49 (4H; m); 2.44 (2H, t); 2.15 (2H, q).

[4-(Boc-Aminoethyl-PEG 11)-6,9,15-triaza-1,12-dioxa-5,10,14-trioxopentaundecanyl)Leuko-MG-NHBOC 19

O-[2-Boc-amino)-ethyl]-O'[2-(diglycolyl-amino)ethyl] decaethylene glycol P11 (152 mg, 0.2 mmol) were dissolved in dry DMF (0.5 mL). TSTU (66 mg, 2.2 mmol) and DEA (39 μL, 2.2 mmol) were added. The reaction mixture was kept overnight at room temperature. [4-(9-Amino6-aza-1-oxa-5-oxo-nonyl)phenyl]bis[4-(dimethylamino)phenyl-methane (100 mg, 0.2 mmol) 16 was dissolved in dry DMF (0.2 mL) and added to the active ester of P11. The reaction mixture was kept at room temperature for 3 hrs. The solvent was removed under vacuum and the residue purified on silicagel (eluent: ethyl acetate/10-30% methanol). MW: $C_{62}H_{91}N_6O_{18}$ 1208.5 g/mol. Yield: 150 mg (62%). (MG(H)—O—(CH$_2$) 3-CONH—C$_2$H$_4$—NHCO—CH$_2$—O—CH$_2$—CONH—(C$_2$H$_4$O)$_{11}$—C$_2$H$_2$—NH$_2$NHBOC; $^1$H-NMR (CD3CN): 7.28 (1H, d), 7.17 (2H, d), 7.11 (1H, d), 7.02 (2H, d), 6.80 (2H, dd), 6.67 (2H, dd), 5.4 (1H, s), 3.95 (2H, m), 3.91 (2H, d), 3.88 (2H, s), 3.54 (42H, m), 3.45 (2H, t), 3.39 (2H, m), 3.29 (2H, m), 3.27 (2H, m), 2.89 (12H, s), 2.30 (2H, m), 2.00 (2H, m), 1.40 (9H, s).

MG-11P 20

Leuko-MG-11P-NHBoc 19 (150 mg, 0.124 mmol) was dissolved in 25 mL acetonitrile. The reaction mixture was heated to 50 C. Tetrachloroquinone (100 mg, 0.4 mmol) was dissolved in 30 mL boiling acetonitrile and dropwise added under stirring to the leukobase. The dark green dye formation was followed by $^1$H-NMR control. After several hours the reaction mixture was cooled to room temperature. The acetonitrile was removed and the reaction mixture was partitioned between water (150 mL) and ethyl acetate (50 mL). The water phase was separated and washed several times with ethyl acetate. The water phase was concentrated to give a green residue. Hydrochloric acid in ethanol (2 mL of a 20% solution) was added and the reaction mixture was stirred for 1 hr. The reaction mixture was concentrated to dryness to give 60 mg of a green powder. Yield: 53% MG-O—(CH$_2$)$_3$—CONH—C$_2$H$_4$—NHCO—CH$_2$—O—CH$_2$—CONH—(C$_2$H$_4$O)$_{11}$—C$_2$H$_2$—NH$_2$ $^1$H-NMR (MeOD): 7.43 (4H, d); 7.36 (2H, d), 7.17 (2H, d), 7.05 (4H, d), 4.20 (2H, t), 4.06 (2H, d); 4.05 (2H, d), 3.77 (2H, t), 3.78-3.58 (44H, m), 3.45 (2H, t), 3.32 (12H, s), 3.18 (2H, t), 2.45 (2H, t), 2.15 (2H, m). $C_{57}H_{91}N_6O_{16}$+MS/M+=1116.53

MG-11P-Biotin

MG-11p 20 (11 mg; 0.01 mmol) was dissolved in 0.2 mL DMSO. A solution of BiotinNHS ester (6.5 mg; 0.02 mmol) in 0.1 mL DMSO was added followed by 0.02 ml of DEA (1 mMol in DMSO). The reaction mixture was stirred for 2 hrs at room temperature, then passed through a short column of neutral aluminum oxide. DMSO and DEA were eluted with chloroform. The product was eluted with chloroform/10-20% methanol to give 8 mg of a green solid. Yield: 58%.

MG-O—(CH$_2$)$_3$—CONH—C$_2$H$_4$—NHCO—CH$_2$—O—CH$_2$—CONH—(C$_2$H$_4$O)$_{11}$—C$_2$H$_4$—NH-Biotin $^1$H-NMR (MeOD): 7.43 (4H, d), 7.37 (2H, d), 7.18 (2H, d), 7.06 (4H, d), 4.51 (1H, m), 4.32 (1H, m), 4.21 (2H, m), 4.06 (2H, s), 4.05 (2H, s), 3.65 (44H, m), 3.55 (2H, m), 3.47 (2H, m), 3.38 (6H, m), 3.32 (12H, s), 3.25 (4H, m), 3.06 (1H, m), 2.93 (3H, m), 2.45 (2H, m), 2.22 (2H, m), 2.16 (2H, qui). $C_{67}H_{105}Cl N_8O_{18}S$+; MS/M+=1342.60

Biotin-PEG5000-MG

MG-2P 18 (5 mg; 0.01 mmol) and Biotin-PEG5000-NHS ester 8 (Nektar Therapeutics) (50 mg; 0.01 mmol) were dissolved in 0.2 mL of DMF and 0.01 mL of DEA (1 mMol in DMF) was added. The reaction mixture was stirred for 1 hr. The reaction mixture was passed through a short column of neutral aluminum oxide. DMF and DEA were eluted with chloroform. The product was eluted with chloroform/10-20% methanol. Mn=5747.8.

N-[4-[(4-Carboxyphenyl)[4-(dimethylamino)phenyl]
methylene]-2,5-cyclohexadienlylidene]-N-methyl-
methanaminium chloride 21

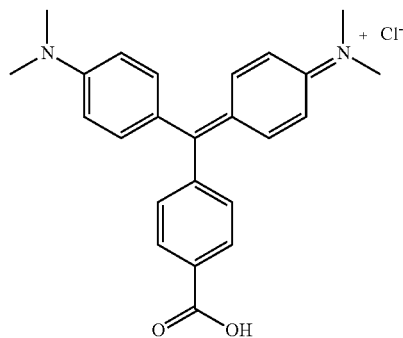

All publications and patents mentioned herein, included those listed below, are hereby incorporated by reference in their entirety as if each individual publication or patent was specifically and individually incorporated by reference. In case of conflict, the present application, including any definitions herein, will control.

Also incorporated by reference are the following: U.S. Pat. Nos. 5,334,537; 5,998,142; 6,287,765; 6,297,059; 6,331,394; 6,358,710; WO 02/23188; WO 02/18952; Bark and Hahn, Methods 20:429-435 (2000); Barker et al., Anal. Chem. 71: 1767-1172 (1999); Barker et al., Anal. Chem. 71: 2071-2075 (1999); Bradbury, Nature Biotechnology 19: 528-529 (2001); Benhar, Biotechnology Advances 19: 1-33 (2001); Carrero and Voss, J. Biol. Chem. 271: 53325337 (1996); Chamberlain and Hahn, Traffic 1: 755-762 (2000); Chen et al., Nature Biotechnology 19: 537-542 (2001); Hahn et al., J. Biol. Chem. 265: 20335-20345 (1990); Marks et al., J. Mol. Biol. 222: 581-597 (1991); Post et al., J. Biol. Chem. 269: 12880-12887 (1994); Post et al., Mol. Biol. Cell 6: 1755-1768 (1995); Ramjiawan et al., Cancer 89: 1134-44 (2000); Skerra, J. Mol. Recognition. 13: 167-187 (2000); and Sumner et al., Analyst 127: 11-16 (2002)

B. N. Giepmans, S. R. Adams, M. H. Ellisman, R. Y. Tsien, Science 312, 217 (Apr. 14, 2006); J. Yao, K. M. Munson, W. W. Webb, J. T. Lis, Nature 442, 1050 (Aug. 31, 2006); P. W. Wiseman et al., J. Cell Sci. 117, 5521 (Nov. 1, 2004); O. Pertz, K. M. Hahn, J. Cell Sci. 117, 1313 (Mar. 15, 2004); O. Pertz, L. Hodgson, R. L. Klemke, K. M. Hahn, Nature 440, 1069 (Apr. 20, 2006); M. T. Kunkel, Q. Ni, R. Y. Tsien, J. Zhang, A. C. Newton, J. Biol. Chem. 280, 5581 (Feb. 18, 2005); G. Miesenbock, D. A. De Angelis, J. E. Rothman, Nature 394, 192 (Jul. 9, 1998); S. T. Hess, A. A. Heikal, W. W. Webb, J. Phys. Chem. B 108, 10138 (2004); C. T. Dooley et al., J. Biol. Chem. 279, 22284 (May 21, 2004); L. W. Miller, V. W. Cornish, Curr. Opin. Chem. Biol. 9, 56 (February, 2005); A. Tirat, F. Freuler, T. Stettler, L. M. Mayr, L. Leder, Int. J. Biol. Macromol. 39, 66 (Aug. 15, 2006); B. R. Martin, B. N. Giepmans, S. R. Adams, R. Y. Tsien, Nat. Biotechnol. 23, 1308 (October, 2005:); S. R. Adams et al., J. Am. Chem. Soc. 124, 6063 (May 29, 2002); J. Nygren, N. Svanvik, M. Kubista, Biopolymers 46, 39 (July, 1998); J. R. Babendure, S. R. Adams, R. Y. Tsien, J. Am. Chem. Soc. 125, 14716 (Dec. 3, 2003); and T. Iwaki, C. Torigoe, M. Noji, M. Nakanishi, Biochemistry 32, 7589 (Jul. 27, 1993).

R. W. Siegel, J. R. Coleman, K. D. Miller, M. J. Feldhaus, J. Immunol. Methods 286, 141 (March, 2004); M. J. Feldhaus et al., Nat. Biotechnol. 21, 163 (February, 2003); D. W. Colby et al., Methods Enzymol. 388, 348 (2004); G. H. Patterson, S. M. Knobel, W. D. Sharif, S. R. Kain, D. W. Piston, Biophys. J. 73, 2782 (November, 1997); A. Simeonov et al., Science 290, 307 (Oct. 13, 2000); D. W. Colby et al., J. Mol. Biol. 342, 901 (Sep. 17, 2004); T. Tanaka, M. N. Lobato, T. H. Rabbitts, J. Mol. Biol. 331, 1109 (Aug. 29, 2003); K. M. Marks, M. Rosinov, G. P. Nolan, Chem Biol 11, 347 (March, 2004); R. Y. Tsien, FEBS Lett. 579, 927 (Feb. 7, 2005); O. Tacal, L. Ozer, J. Biochem. Mol. Toxicol. 18, 253 (2004); S. J. Culp et al., Chem. Biol. Interact. 122, 153 (Nov. 1, 1999); J. P. Jadhav, S. P. Govindwar, Yeast 23, 315 (March, 2006); Yeast Display scFv Antibody Library User's Manual (Pacific Northwest National Laboratory, Richland, W A 99352; -2003); G. Chao et al., Nat. Protocols 1, 755 (2006); V. Giudicelli et al., Nucleic Acids Res. 34, D781 (Jan. 1, 2006); H. Motulsky, The GraphPad Guide to Analyzing Radioligand Binding Data (GraphPad Software, Inc., 1996); Invitrogen, Theory of Binding Data Analysis, Fluorescence Polarization Technical Resource Guide, Fourth Edition (2006); R. B. Mujumdar, L. A. Ernst, S. R. Mujumdar, C. J. Lewis, A. S. Waggoner, Bioconjug. Chem. 4, 105 (March-April, 1993); P. J. Sims, A. S. Waggoner, C. H. Wang, J. F. Hoffman, Biochemistry 13, 3315 (Jul. 30, 1974); J. Lacowicz, Principles of Fluorescence Spectroscopy, 2nd edition (Kluwer Academic/Plenum, 1999); R. F. Kubin, A. N. Fletcher, J. Lumin. 27, 455 (1982); and W. H. Mueller, I. Hattesohl, H. J. Schuetz, G. Meyer, Nucleic Acids Res 9, 95 (1981).

Those skilled in the art will recognize, or be able to ascertain using no more than routine experimentation, many equivalents to the specific embodiments of the invention described herein. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations. Such equivalents are intended to be encompassed by the following claims.

We claim:

1. A ligand-dye complex, comprising a cognate ligand of a dye non covalently bound to the dye, wherein the cognate ligand comprises an scFv molecule consisting of a polypeptide sequence having at least 90% sequence identity to the polypeptide of SEQ ID NO: 3, wherein the dye comprises one of a thiazole orange or a thiazole orange analog that binds the scFv molecule, and wherein the bound dye and ligand exhibit an increase in detectable fluorescence signal at least ten times greater than the detectable fluorescence signal of the dye when not bound to the ligand.

2. The ligand-dye complex of claim 1, wherein the ligand-dye complex further comprises the scFv molecule bound to a protein.

3. The ligand-dye complex of claim 1, wherein the bound dye and ligand exhibit an extinction coefficient of greater than 30,000 and a maximum absorption at a wave length of greater than 350 nm.

4. The ligand-dye complex of claim 1, wherein the bound dye emits photons having a changed polarization upon binding the ligand.

5. The ligand-dye complex of claim 4 wherein the polarization change is greater than or equal to 20%.

6. The ligand-dye complex of claim 1, wherein the dye of the bound dye and ligand exhibits an increased emission wave length of at least 10 nm.

7. The ligand-dye complex of claim 1, wherein the ligand is fixed to a substrate.

8. The ligand-dye complex of claim 7, wherein the substrate comprises molecules of formula X(a)-R(b)-Y(c), wherein R is a spacer, X is a functional group that binds R to a surface, Y is a functional group for binding to the ligand, (a) is an integer from 0 to about 4, (b) is an integer from 0 or 1, and (c) is an integer not equal to 0.

9. The ligand-dye complex of claim 1, wherein the dye is thiazole orange analog TO1 comprising the following general structure:

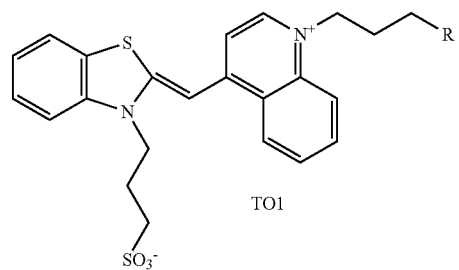

TO1 wherein R is selected from the group consisting of a fluorescent label optionally comprising a linker, a photoreactive group, and a reactive group.

10. The ligand-dye complex of claim 1, wherein the dye is thiazole orange analog TO1 comprising the following general structure:

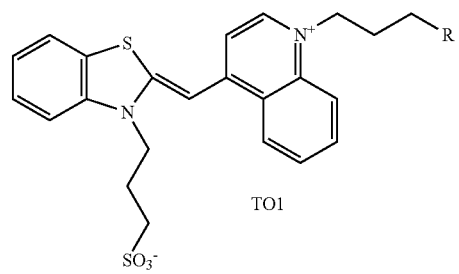

TO1 wherein R is a group that comprises biotin, a hapten, or a His-tag, optionally with a linker.

11. The ligand-dye complex of claim 9, wherein the thiazole orange analog TO1 has the following structure:

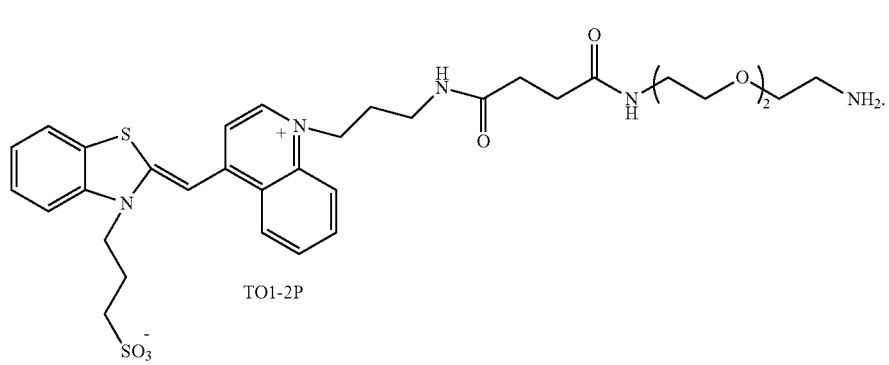

TO1-2P

12. The ligand-dye complex of claim 9, wherein the ligand-dye complex occupies a microenvironment and wherein the dye provides the increase in detectable fluorescence signal in response to pH, polarity, restriction, or mobility properties within the microenvironment.

13. The ligand-dye complex of claim 1, wherein the dye is thiazole orange analog TO1 comprising the following general structure:

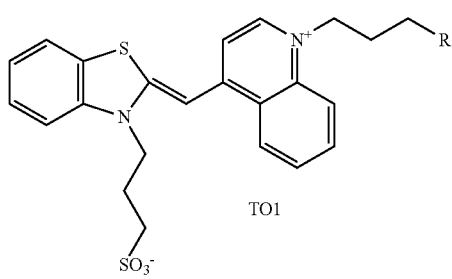

TO1 wherein R is a moiety that controls water solubility and non-specific binding.

14. The ligand-dye complex of claim 1, wherein the dye is thiazole orange analog TO1 comprising the following general structure:

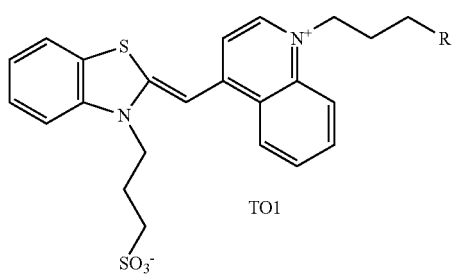

TO1 wherein R is a moiety that controls the ability of the dye to enter a cellular compartment.

15. The ligand-dye complex of claim 1, wherein the dye is thiazole orange analog TO1 comprising the following general structure:

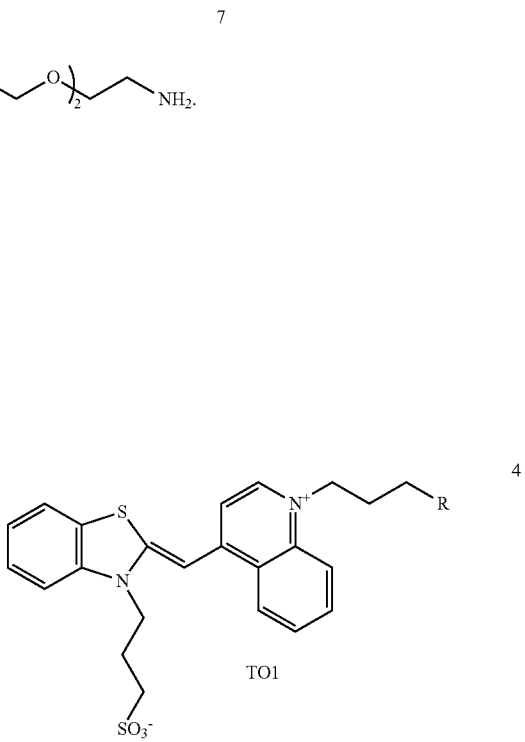

TO1 wherein R is a group that comprises a moiety to facilitate isolation of the ligand.

16. The ligand-dye complex of claim 1, wherein the scFv molecule has the polypeptide sequence of SEQ ID NO: 7.

17. The ligand-dye complex of claim 1, wherein the scFv molecule has the polypeptide sequence of SEQ ID NO: 9.

18. A ligand-dye complex comprising:
an scFv molecule having complementarity determining regions of SEQ ID NOs 76, 77 and 78 noncovalently bound to a dye comprising one of a thiazole orange or a thiazole orange analog that binds the scFv molecule;
wherein the bound dye and ligand exhibit an increase in detectable fluorescence signal at least ten times greater than the detectable fluorescence signal of the dye when not bound to the ligand.

19. The ligand-dye complex of claim 18 wherein the dye is thiazole orange analog TO1 comprising the following general structure:

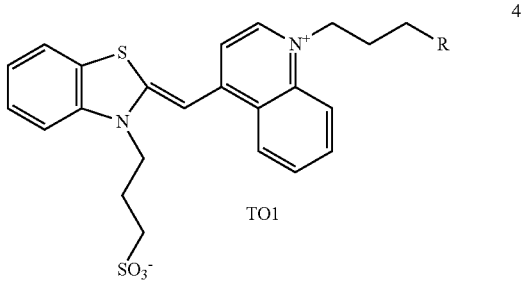

TO1 wherein R is selected from the group consisting of a fluorescent label optionally comprising a linker, a photoreactive group, and a reactive group.

20. The ligand-dye complex of claim 18 wherein the dye has the following structure:

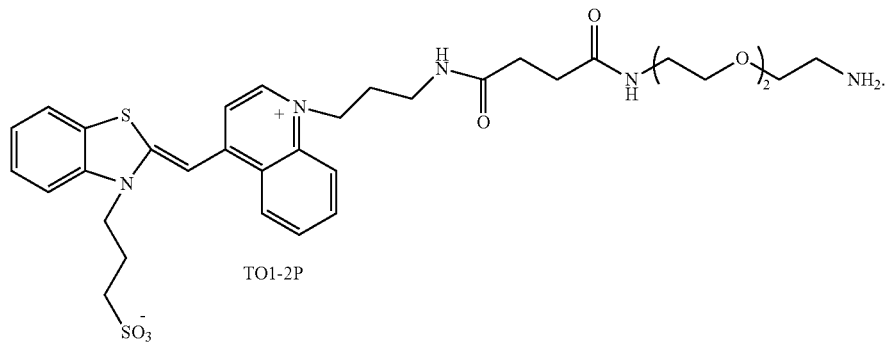

TO1-2P

21. A method of forming a ligand-dye complex for use in detecting expression of a gene in a cell, the method comprising:
adding a vector to a cell, wherein the vector comprises a nucleic acid gene encoding a scFv molecule consisting of a polypeptide sequence having at least 90% sequence identity to the polypeptide of SEQ ID NO: 3;
causing expression of the gene to produce a gene product comprising the scFv molecule;
adding dye to the cell to bind to the gene product, wherein the dye comprises one of thiazole orange or a thiazole orange analog comprising the following general structure:

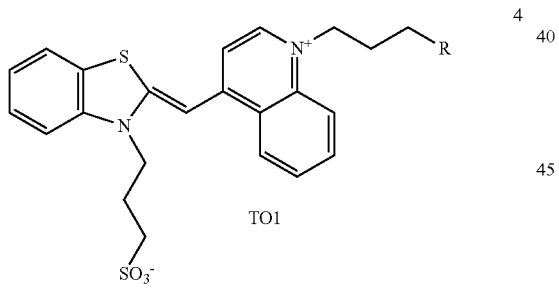

TO1 wherein R is selected from the group consisting of a moiety that controls water solubility and non-specific binding, a moiety that controls the ability of the dye to enter a cellular compartment, a group that comprises, optionally with a linker, biotin, a hapten, a His-tag, or a moiety to facilitate isolation of the ligand, a fluorescent label optionally comprising a linker, a photoreactive group, and a reactive group.

22. The method of claim 21, wherein the gene further encodes a second protein, and wherein the gene product comprises a fusion protein comprising the scFv molecule and the second protein.

23. The method of claim 22, wherein the dye is substantially excluded from an interior of the cell, and wherein fluorescence is detected only when a portion of the second protein that is fused to the scFv molecule is exposed at a surface of the cell.

24. The method of claim 21, wherein the dye is thiazole orange analog TO1-R, and wherein R is a moiety that controls the ability of the dye to enter a cellular compartment.

25. A method of forming and using a ligand-dye complex for detecting interaction of two proteins in a cell comprising:
adding a vector to a cell, wherein the vector comprises a nucleic acid gene encoding a first protein fused to a first portion of a scFv polypeptide sequence having at least 90% sequence identity to the polypeptide of SEQ ID NO: 3;
adding a vector to a cell, wherein the vector comprises a nucleic acid gene encoding a second protein fused to a second portion of the scFv polypeptide sequence;
causing expression of the genes to produce fusion proteins comprised of the first and second proteins fused to first and second portions, respectively, of the scFv polypeptide; and
adding dye to the cell, wherein the dye comprises one of thiazole orange or a thiazole orange analog comprising the following general structure:

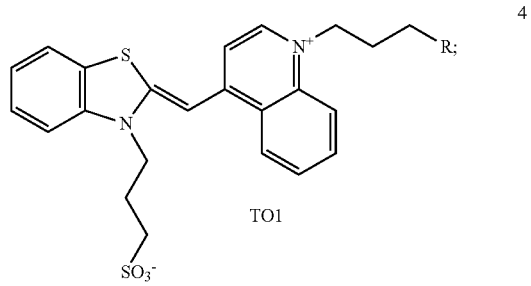

TO1 wherein R is selected from the group consisting of a moiety that controls water solubility and non-specific binding, a moiety that controls the ability of the dye to enter a cellular compartment, a group that comprises, optionally with a linker, biotin, a hapten, a His-tag, or a moiety to facilitate isolation of the ligand, a fluorescent label optionally comprising a linker, a photoreactive group, and a reactive group; and
detecting a fluorescence signal indicative of the dye binding to the fusion proteins, wherein the fluorescence signal is at least ten times greater than the detectable fluorescence signal of the dye when not bound to the fusion proteins.

26. The method of claim 25, wherein the first scFv polypeptide portion and the second scFv polypeptide portion interact to form a scFv molecule consisting of a polypeptide sequence having at least 90%-sequence identity to the polypeptide of SEQ ID NO 3, and wherein fluorescence is detectable when interaction between the first protein and the second protein brings the first scFv polypeptide portion into proximity of the second scFv polypeptide portion.

* * * * *

UNITED STATES PATENT AND TRADEMARK OFFICE
CERTIFICATE OF CORRECTION

PATENT NO. : 8,664,364 B2
APPLICATION NO. : 12/524328
DATED : March 4, 2014
INVENTOR(S) : Brigitte F. Schmidt et al.

It is certified that error appears in the above-identified patent and that said Letters Patent is hereby corrected as shown below:

In the Specification

Column 1, Lines 15-18, delete "The subject invention was made in part with support from the U.S. Government under Grant Number 1-U54-RR022241 awarded by the NIH. Accordingly, the U.S. Government has certain rights in this invention." and insert --This invention was made with United States government support under RR022241 awarded by the National Institutes of Health. The U.S. government has certain rights in the invention.--.

Signed and Sealed this
Nineteenth Day of April, 2022

Katherine Kelly Vidal
*Director of the United States Patent and Trademark Office*

SEQUENCE LISTING

<160> NUMBER OF SEQ ID NOS: 82

<210> SEQ ID NO 1
<211> LENGTH: 1222
<212> TYPE: DNA
<213> ORGANISM: Artificial Sequence
<220> FEATURE:
<223> OTHER INFORMATION: scFv sequence

```
<400> SEQUENCE: 1 catttcaat taagatgcag ttacttcgct gttttcaat attttctgtt attgcttcag      60
ttttagcaca ggaactgaca actatatgcg agcaaatccc ctcaccaact ttagaatcga    120
cgccgtactc tttgtcaacg actactattt tggccaacgg gaaggcaatg caaggagttt    180
ttgaatatta caaatcagta acgtttgtca gtaattgcgg ttctcacccc tcaaacaact    240
agcaaaggca gccccataaa cacacagtat gttttaagg acaatagctc gacgattgaa     300
ggtatatacc catacgacgt tccagactac gctctgcagg ctagtggtgg tggtggttct    360
ggtggtggtg gttctggtgg tggtggttct gctagccagg tgcagctggt ggaatctgag    420
gctgaggtga agaagcctgg gtcctcggtg aaggtctcct gcaaggcttc tggaggcacc    480
ttcagcagct atgctatcag ctgggtgcga caggcccctg acaagggct tgagtggatg     540
ggagggatca tccctatctt tggtacagca aactacgcac agaagttcca gggcagagtc    600
acgattaccg cggacgaatc cacgagcaca gcctacagtg agctgagcag cctgagatct    660
gaggacacgc gcgtgtatta ctgtgtcttg ttggatacaa ctatggttac gggatactac    720
tttgactact ggggccaggg aaccctggtc accgtctcct caggaattct aggatccggt    780
ggcggtggca gcggcggtgg tggttccgga ggcggcggtt ctaatttat gctgactcag     840
ccccctcag cgtctgggac ccctgggcag agcgtcacca tctcttgttc tggaagcggc     900
tcgaacatcg gaaacaataa agtaaactgg taccagcagc tcccaggaac ggcccccaaa    960
ctcctcatct atagtaataa tcagcggccc tcagggtcc ctgaccgatt ctctggctcc    1020
aagtctggca cctcagcctc cctggccatc agtgggctcc agtctgagga tgaggctgat   1080
tattactgtg cagcatggga tgacagcctg aatggttatg tcttcggaac tgggaccaag   1140
ctcaccgtcc tatccggaat tctagaacaa aagcttattt ctgaagaaga cttgtaatag   1200
ctcggcggcc gcatcgagat ct                                            1222

<210> SEQ ID NO 2
<211> LENGTH: 393
<212> TYPE: PRT
<213> ORGANISM: Artificial Sequence
<220> FEATURE:
<223> OTHER INFORMATION: scFv sequence

<400> SEQUENCE: 2

Met Gln Leu Leu Arg Cys Phe Ser Ile Phe Ser Val Ile Ala Ser Val
1               5                   10                  15

Leu Ala Gln Glu Leu Thr Thr Ile Cys Glu Gln Ile Pro Ser Pro Thr
            20                  25                  30

Leu Glu Ser Thr Pro Tyr Ser Leu Ser Thr Thr Thr Ile Leu Ala Asn
        35                  40                  45

Gly Lys Ala Met Gln Gly Val Phe Glu Tyr Tyr Lys Ser Val Thr Phe
    50                  55                  60

Val Ser Asn Cys Gly Ser His Pro Ser Thr Thr Ser Lys Gly Ser Pro
65                  70                  75                  80

Ile Asn Thr Gln Tyr Val Phe Lys Asp Asn Ser Ser Thr Ile Glu Gly
                85                  90                  95

Arg Tyr Pro Tyr Asp Val Pro Asp Tyr Ala Leu Gln Ala Ser Gly Gly
            100                 105                 110

Gly Gly Ser Gly Gly Gly Gly Ser Gly Gly Gly Gly Ser Ala Ser Gln
        115                 120                 125

Val Gln Leu Val Glu Ser Glu Ala Glu Val Lys Lys Pro Gly Ser Ser
    130                 135                 140
```

```
Val Lys Val Ser Cys Lys Ala Ser Gly Gly Thr Phe Ser Ser Tyr Ala
145                 150                 155                 160

Ile Ser Trp Val Arg Gln Ala Pro Gly Gln Gly Leu Glu Trp Met Gly
                165                 170                 175

Gly Ile Ile Pro Ile Phe Gly Thr Ala Asn Tyr Ala Gln Lys Phe Gln
            180                 185                 190

Gly Arg Val Thr Ile Thr Ala Asp Glu Ser Thr Ser Thr Ala Tyr Met
            195                 200                 205

Glu Leu Ser Ser Leu Arg Ser Glu Asp Thr Ala Val Tyr Tyr Cys Val
210                 215                 220

Leu Leu Asp Thr Thr Met Val Thr Gly Tyr Tyr Phe Asp Tyr Trp Gly
225                 230                 235                 240

Gln Gly Thr Leu Val Thr Val Ser Ser Gly Ile Leu Gly Ser Gly Gly
                245                 250                 255

Gly Gly Ser Gly Gly Gly Ser Gly Gly Gly Gly Ser Asn Phe Met
            260                 265                 270

Leu Thr Gln Pro Pro Ser Ala Ser Gly Thr Pro Gly Gln Ser Val Thr
            275                 280                 285

Ile Ser Cys Ser Gly Ser Gly Ser Asn Ile Gly Asn Asn Lys Val Asn
290                 295                 300

Trp Tyr Gln Gln Leu Pro Gly Thr Ala Pro Lys Leu Leu Ile Tyr Ser
305                 310                 315                 320

Asn Asn Gln Arg Pro Ser Gly Val Pro Asp Arg Phe Ser Gly Ser Lys
                325                 330                 335

Ser Gly Thr Ser Ala Ser Leu Ala Ile Ser Gly Leu Gln Ser Glu Asp
            340                 345                 350

Glu Ala Asp Tyr Tyr Cys Ala Ala Trp Asp Asp Ser Leu Asn Gly Tyr
            355                 360                 365

Val Phe Gly Thr Gly Thr Lys Leu Thr Val Leu Ser Gly Ile Leu Glu
370                 375                 380

Gln Lys Leu Ile Ser Glu Glu Asp Leu
385                 390

<210> SEQ ID NO 3
<211> LENGTH: 252
<212> TYPE: PRT
<213> ORGANISM: Artificial Sequence
<220> FEATURE:
<223> OTHER INFORMATION: scFv sequence

<400> SEQUENCE: 3

Gln Val Gln Leu Val Glu Ser Glu Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Val Leu Leu Asp Thr Thr Met Val Thr Gly Tyr Tyr Phe Asp Tyr Trp
            100                 105                 110
```

```
Gly Gln Gly Thr Leu Val Thr Val Ser Ser Gly Ile Leu Gly Ser Gly
        115                 120                 125
Gly Gly Gly Ser Gly Gly Gly Ser Gly Gly Gly Ser Asn Phe
        130                 135                 140
Met Leu Thr Gln Pro Pro Ser Ala Ser Gly Thr Pro Gly Gln Ser Val
145                 150                 155                 160
Thr Ile Ser Cys Ser Gly Ser Ser Asn Ile Gly Asn Asn Lys Val
                165                 170                 175
Asn Trp Tyr Gln Gln Leu Pro Gly Thr Ala Pro Lys Leu Leu Ile Tyr
            180                 185                 190
Ser Asn Asn Gln Arg Pro Ser Gly Val Pro Asp Arg Phe Ser Gly Ser
        195                 200                 205
Lys Ser Gly Thr Ser Ala Ser Leu Ala Ile Ser Gly Leu Gln Ser Glu
    210                 215                 220
Asp Glu Ala Asp Tyr Tyr Cys Ala Ala Trp Asp Ser Leu Asn Gly
225                 230                 235                 240
Tyr Val Phe Gly Thr Gly Thr Lys Leu Thr Val Leu
                245                 250

<210> SEQ ID NO 4
<211> LENGTH: 1221
<212> TYPE: DNA
<213> ORGANISM: Artificial Sequence
<220> FEATURE:
<223> OTHER INFORMATION: scFv sequence

<400> SEQUENCE: 4
cattttcaat taagatgcag ttacttcgct gttttcaat attttctgtt attgcttcag      60
ttttagcaca ggaactgaca actatatgcg agcaaatccc ctcaccaact ttagaatcga    120
cgccgtactc tttgtcaacg actactattt tggccaacgg aaggcaatg caaggagttt     180
ttgaatatta caaatcagta acgtttgtca gtaattgcgg ttctcacccc tcaacaacta    240
gcaaaggcag ccccataaac acacagtatg ttttaagga caatagctcg acgattgaag     300
gtagataccc atacgacgtt ccagactacg ctctgcaggc tagtggtggt ggtggttctg    360
gtggtggtgg ttctggtggt ggtggttctg ctagccaggt gcagctggtg aatctgagg     420
ctgaggtgaa gaagcctggg tcctcggtga aggtctcctg caaggcttct ggaggcacct    480
tcagcagcta tgctatcagc tgggtgcgac aggcccctgg acaagggctt gagtggatgg    540
gagggatcat ccctatcttt ggtacagcaa actacgcaca gaagttccag gcagagtca    600
cgattaccgc ggacgaatcc acgagcacag cctacatgga gctgagcagc ctgagatctg    660
aggacacggc cgtgtattac tgtgtcttgt tggatacaac tatggttacg gatactact     720
ttgactactg gggccaggga accctggtca ccgtctcctc aggaattcta ggatccggtg    780
gcggtggcag cggcggtggt ggttccgag gcggcggttc taattttatg ctgactcagc    840
cccctcagc gtctgggacc cccggcaga gcgtcaccat ctcttgttct ggaagcggct    900
cgaacatcgg aaacaataaa gtaaactggt accagcagct cccaggaacg gccccaaac    960
tcctcatcta tagtaataat cagcggccct caggggtccc tgaccgattc tctggctcca   1020
agtctggcac ctcagcctcc ctggccatca gtgggctcca gtctgaggat gaggctgatt   1080
attactgtgc agcatgggat gacagcctga atggttatgt cttcggaact gggaccaagc   1140
tcaccgtcct atccggaatt ctagaacaaa agcttatttc tgaagaagac ttgtaatagc   1200
tcggcggccg catcgagatc t                                             1221
```

```
<210> SEQ ID NO 5
<211> LENGTH: 250
<212> TYPE: PRT
<213> ORGANISM: Artificial Sequence
<220> FEATURE:
<223> OTHER INFORMATION: scFv sequence

<400> SEQUENCE: 5

Gln Val Gln Leu Gln Gln Gly Gly Ala Gly Leu Leu Lys Pro Ser Glu
1               5                   10                  15

Thr Leu Ser Leu Thr Cys Gly Val Tyr Gly Gly Ser Phe Ser Gly Tyr
            20                  25                  30

Tyr Trp Ser Trp Ile Arg Gln Ser Pro Gly Lys Gly Leu Glu Trp Ile
        35                  40                  45

Gly Glu Ile Asn His Ser Gly Ser Ala Asn Tyr Asn Pro Ser Val Lys
    50                  55                  60

Ser Arg Val Thr Ile Ser Val Asp Thr Ser Lys Asn Gln Phe Ser Leu
65                  70                  75                  80

Gln Leu Ser Ser Val Thr Ala Ala Asp Thr Ala Val Tyr Tyr Cys Ala
                85                  90                  95

Arg Asp Arg Ala Val Leu Thr Gly Glu Gly Trp Tyr Phe Asp Leu Trp
            100                 105                 110

Gly Arg Gly Thr Leu Val Thr Val Ser Ser Gly Ile Leu Gly Ser Gly
        115                 120                 125

Gly Gly Gly Ser Gly Gly Gly Ser Gly Gly Gly Ser Ser Tyr
    130                 135                 140

Glu Leu Thr Gln Pro Pro Ser Val Ser Val Ser Pro Gly Gln Thr Ala
145                 150                 155                 160

Ser Ile Thr Cys Ser Gly Asp Lys Leu Gly Asp Lys Tyr Thr Cys Trp
                165                 170                 175

Tyr Gln Gln Lys Pro Gly Gln Ser Pro Val Leu Val Leu Tyr Glu Asp
            180                 185                 190

Thr Lys Arg Pro Ser Gly Ile Pro Glu Arg Phe Ser Gly Ser Asn Ser
        195                 200                 205

Gly Asn Thr Ala Thr Leu Thr Ile Ser Arg Val Glu Ala Gly Asp Glu
    210                 215                 220

Ala Asp Tyr Tyr Cys Gln Leu Trp Asp Ser Ser Ser Asp His Tyr Val
225                 230                 235                 240

Phe Gly Ser Gly Thr Lys Leu Thr Val Leu
                245                 250

<210> SEQ ID NO 6
<211> LENGTH: 835
<212> TYPE: DNA
<213> ORGANISM: Artificial Sequence
<220> FEATURE:
<223> OTHER INFORMATION: scFv sequence

<400> SEQUENCE: 6
ctggtggtgg tggttctgct agccaggtgc agctacagca ggggggcgca ggactgttga    60
agccttcgga gaccctgtcc ctcacgtgcg gtgtctatgg tgggtctttc agtggttact   120
attggagctg gattcgccag tccccaggaa aggggctgga atggattggg gaaatcaatc   180
atagtggaag cgccaactac aacccgtccg tcaagagtcg tgtcaccata tcagtagaca   240
cgtccaagaa tcagttctcc ctgcagttga gctctgtgac cgctgcggac acggccgtgt   300
actactgtgc gagagatagg gcggtgttaa cgggggaggg ctggtacttc gatctctggg   360
gccgtggtac cctggtcacc gtctcctcag gaattctagg atccggtggc ggtggcagcg   420
```

```
gcggtggtgg ttccggaggc ggcggttctt cctatgagct gacacagcca ccctcagtgt    480
ccgtgtcccc aggacagaca gccagcatca cctgctctgg agataaattg ggggataaat    540
atacttgttg gtatcagcag aagccaggcc agtcccctgt actggtcctc tatgaagata    600
ccaagcggcc ctcagggatc cctgagcgat tctctggctc caactctggg aacacggcca    660
ccctgaccat cagcgggtc gaagccgggg atgaggccga ctattactgt cagctgtggg    720
atagtagtag tgatcattat gtcttcggaa gtgggaccaa gctgaccgtc ctatccggaa    780
ttctagaaca aaagcttatt tcagaagaag acttgtaata gctcggcggc cgcat         835
```

```
<210> SEQ ID NO 7
<211> LENGTH: 252
<212> TYPE: PRT
<213> ORGANISM: Artificial Sequence
<220> FEATURE:
<223> OTHER INFORMATION: scFv sequence

<400> SEQUENCE: 7
```

Gln Val Gln Leu Val Glu Ser Glu Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Thr Ile Pro Ile Phe Gly Thr Ala Asp Tyr Ala Gln Glu Phe
    50                  55                  60

Gln Gly Arg Val Thr Ile Thr Thr Asp Glu Ser Thr Ser Thr Ala Tyr
65                  70                  75                  80

Met Glu Leu Ser Gly Leu Arg Ser Glu Asp Thr Ala Val Tyr Tyr Cys
                85                  90                  95

Val Leu Leu Gly Thr Thr Met Val Thr Gly His Tyr Phe Asp Tyr Trp
            100                 105                 110

Gly Gln Gly Thr Leu Val Thr Val Ser Ser Gly Ile Leu Gly Ser Gly
        115                 120                 125

Gly Gly Gly Ser Gly Gly Gly Gly Ser Gly Gly Gly Gly Ser Asn Phe
    130                 135                 140

Met Leu Thr Gln Pro Pro Ser Ala Ser Gly Thr Pro Gly Gln Ser Val
145                 150                 155                 160

Thr Ile Ser Cys Ser Gly Ser Gly Ser Asn Ile Gly Asn Asn Lys Val
                165                 170                 175

Asn Trp Tyr Gln Gln Leu Pro Gly Thr Ala Pro Lys Leu Leu Ile Tyr
            180                 185                 190

Ser Asn Asn Gln Arg Pro Ser Gly Val Pro Asp Arg Phe Ser Gly Ser
        195                 200                 205

Lys Ser Gly Thr Ser Ala Ser Leu Ala Ile Ser Gly Leu Gln Ser Glu
    210                 215                 220

Asp Glu Ala Asp Tyr Tyr Cys Ala Ala Trp Asp Gly Leu Ser Gly
225                 230                 235                 240

Tyr Val Phe Gly Thr Gly Thr Lys Leu Thr Val Leu
                245                 250

```
<210> SEQ ID NO 8
<211> LENGTH: 845
<212> TYPE: DNA
<213> ORGANISM: Artificial Sequence
<220> FEATURE:
<223> OTHER INFORMATION: scFv sequence
```

<400> SEQUENCE: 8

```
ggttctggtg gtggtggttc tgctagccag gtgcagctgg tggaatctga ggctgaggtg      60
aagaagcctg gtcctcggt gaaggtctcc tgcaaggcct ctggaggcac cttcagcagc     120
tatgctatca gctgggtgcg gcaggcccct ggacaagggc ttgagtggat gggagggacc     180
atccctatct ttggtacagc agactacgca caggagttcc agggcagagt cacgattacc     240
acggacgaat ccacgagcac agcctacatg gagctgagcg gcctgagatc tgaggacacg     300
gccgtgtatt actgtgtttt gttgggtaca actatggtta cgggacacta ctttgactac     360
tggggccagg gaaccctggt caccgtctcc tcaggaattc taggatccgg tggcggtggc     420
agcggcggtg gtggttccgg aggcggcggt tctaatttta tgctgactca gccccctca     480
gcgtctggga cccccgggca gagcgtcacc atctcttgtt ctggaagcgg ctcgaacatc     540
ggaaacaata agtaaactg gtaccagcag ctcccaggaa cggcccccaa actcctcatc     600
tatagtaata atcagcggcc ctcagggtc cctgaccgat tctctggctc caagtctggc     660
acctcagcct ccctggccat cagtgggctc cagtctgagg atgaggctga ttattactgt     720
gcagcatggg atgacggtct gagtggttat gtcttcggaa ctgggaccaa gcttaccgtc     780
ctgtccggat ccgaacaaaa gcttatttct gaagaggact tgtaatagct cggcggccgc     840
atcga                                                                 845
```

<210> SEQ ID NO 9
<211> LENGTH: 252
<212> TYPE: PRT
<213> ORGANISM: Artificial Sequence
<220> FEATURE:
<223> OTHER INFORMATION: scFv sequence

<400> SEQUENCE: 9

```
Gln Val Gln Leu Val Glu Ser Glu Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Thr Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Val Leu Leu Gly Thr Thr Met Val Thr Gly Tyr Tyr Phe Asp Tyr Trp
            100                 105                 110

Gly Gln Gly Thr Leu Val Thr Val Ser Ser Gly Ile Leu Gly Ser Gly
        115                 120                 125

Gly Gly Gly Ser Gly Gly Gly Gly Ser Gly Gly Gly Ser Asn Phe
    130                 135                 140

Thr Leu Thr Gln Pro Pro Ser Ala Ser Gly Thr Pro Gly Gln Ser Val
145                 150                 155                 160

Thr Ile Ser Cys Ser Gly Ser Gly Ser Asn Ile Gly Asn Asn Lys Val
                165                 170                 175

Asn Trp Tyr Gln Gln Leu Pro Gly Thr Ala Pro Lys Leu Leu Ile Tyr
            180                 185                 190

Ser Asn Asn Gln Arg Pro Ser Gly Val Pro Asp Arg Phe Ser Gly Ser
```

```
                   195                 200                 205
Lys Ser Gly Thr Ser Ala Ser Leu Ala Ile Ser Gly Leu Gln Ser Glu
            210                 215                 220

Asp Glu Ala Asp Tyr Tyr Cys Ala Ala Trp Asp Ser Leu Asn Gly
225                 230                 235                 240

Tyr Val Phe Gly Thr Gly Thr Lys Leu Thr Val Leu
                245                 250

<210> SEQ ID NO 10
<211> LENGTH: 864
<212> TYPE: DNA
<213> ORGANISM: Artificial Sequence
<220> FEATURE:
<223> OTHER INFORMATION: scFv sequence

<400> SEQUENCE: 10
gctctgcagg ctagtggtgg tggtggttct ggtggtggtg gttctggtgg tggtggttct      60
gctagccagg tgcagctggt ggaatctgag gctgaggtga agaagcctgg gtcctcggtg     120
aaggtctcct gcaaggcttc tggaggcacc ttcagcagct atgctatcag ctgggtgcga     180
caggcccctg gacaagggct cgagtggatg ggagggacca tccctatctt tggtacagca     240
aactacgcac agaagttcca gggcagagtc acgattaccg cggacgagtc cacgagcaca     300
gcctacatgg agctgagcag cctgagatct gaggacacgg ccgtgtatta ctgtgtcttg     360
ttgggtacaa ctatggttac gggatactac tttgactact ggggccaggg aaccctggtc     420
accgtctcct caggaattct aggatccggt ggcggtggca gcggcggtgg tggttccgga     480
ggcggcggtt ctaattttac gctgactcag ccccccctcag cgtctgggac ccccgggcag     540
agcgtcacca tctcttgttc tggaagcggc tcgaacatcg aaacaataa agtaaactgg     600 taccagcagc tcccaggaac ggcccccaaa ctcctcatct atagtaataa tcagcggccc     660 tcagggggtcc ctgaccgatt ctctggctcc aagtctggca cctcagcctc cctggccatc     720
agtgggctcc agtctgagga tgaggctgat tattactgtg cagcatggga tgacagcctg     780
aatggttatg tcttcggaac tgggaccaag ctcaccgtcc tatccggaat tctagaacaa     840
aagcttattt ctgaagaaga cttg                                            864

<210> SEQ ID NO 11
<211> LENGTH: 264
<212> TYPE: PRT
<213> ORGANISM: Artificial Sequence
<220> FEATURE:
<223> OTHER INFORMATION: scFv sequence, (GILEQKLISEEDL at end of
      sequence is derived from a vector)

<400> SEQUENCE: 11

Gln Val Gln Leu Val Glu Ser Glu Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Arg Ile Asp Gly Asp Gly Ser Ser Thr Asn Tyr Ala Asp Ser Val
    50                  55                  60

Lys Gly Arg Phe Thr Ile Ser Arg Asp Asn Ala Lys Ser Thr Leu Tyr
65                  70                  75                  80

Leu Gln Met Asn Ser Leu Arg Ala Glu Asp Thr Ala Val Tyr Tyr Cys
                85                  90                  95
```

```
Thr Arg Ala Arg Tyr Phe Gly Ser Val Ser Pro Tyr Gly Met Asp Val
            100                 105                 110
Trp Gly Gln Gly Thr Thr Val Thr Val Ser Ser Gly Ile Leu Gly Ser
        115                 120                 125
Gly Gly Gly Gly Ser Gly Gly Gly Ser Gly Gly Gly Gly Ser Asp
    130                 135                 140
Ile Arg Val Thr Gln Ser Pro Ser Ser Val Ser Ala Ser Val Gly Asp
145                 150                 155                 160
Arg Val Thr Ile Ser Cys Arg Ala Ser Gln Gly Ile Ala Thr Trp Leu
                165                 170                 175
Gly Trp Tyr Gln Gln Lys Pro Gly Lys Pro Gln Leu Leu Ile Tyr
        180                 185                 190
Ser Ala Ser Thr Leu Gln Thr Gly Val Pro Ser Arg Phe Ser Gly Ser
        195                 200                 205
Gly Ser Gly Thr Asp Phe Thr Leu Thr Ile Ser Ser Leu Gln Pro Glu
    210                 215                 220
Asp Val Ala Thr Tyr Tyr Cys Gln Glu Gly Ser Thr Phe Pro Leu Thr
225                 230                 235                 240
Phe Gly Gly Gly Thr Lys Val Asp Ile Lys Ser Gly Ile Leu Glu Gln
                245                 250                 255
Lys Leu Ile Ser Glu Glu Asp Leu
            260
```

```
<210> SEQ ID NO 12
<211> LENGTH: 881
<212> TYPE: DNA
<213> ORGANISM: Artificial Sequence
<220> FEATURE:
<223> OTHER INFORMATION: scFv sequence

<400> SEQUENCE: 12
ctctgcaggc tagtggtggt ggtggttctg gtggtggtgg ttctgctagc caggtgcagc    60
tggtggagtc tgagggaggc ttggtacagc ctggagggtc cctgagactc tcctgtgcag   120
cctctggatt caccttcagt agttatgaaa tgaactgggt ccgccaggct ccaggtaagg   180
ggctggagtg ggtctcacgt attgatggtg atgggagcag cacaaactac gcggactccg   240
tgaagggccg attcaccatc tccagagaca acgccaagag cacgctgtat ctgcaaatga   300
atagtctgag agccgaggac acggctgtgt attactgtac aagggccaga tactttggtt   360
cggtgagccc ctacggtatg gacgtctggg gccaagggac cacggtcacc gtctcctcag   420
gaattctagg atccggtggc ggtggcagcg gcggtggtgg ttccggaggc ggcggttctg   480
acatccgggt gacccagtct ccttcttccg tgtctgcatc tgtgggtgac agagtcacca   540
tcagttgtcg ggcgagtcag gggattgcca cctggttagg ctggtatcag cagaagccag   600
ggaaaccccc tcagctcctt atctattctg catccacttt gcaaactggg gtcccatcaa   660
ggttcagcgg cagtggatct gggacagatt tcactcttac catcagcagc ctgcagccgg   720
aggatgttgc aacttactat tgtcaagagg gtagcacttt ccctctcact ttcggcggag   780
ggaccaaagt ggatatcaaa tccggaattc tagaacaaaa gcttatttct gaagaagact   840
tgtaatagct cggcggccgc atcgagatct gataacaaca g                       881
```

```
<210> SEQ ID NO 13
<211> LENGTH: 163
<212> TYPE: PRT
<213> ORGANISM: Artificial Sequence
<220> FEATURE:
<223> OTHER INFORMATION: scFv sequence, (GILEQKLISEEDL at end of
```

-continued sequence is derived from a vector)

<400> SEQUENCE: 13

Ser Ala Ser Thr Gly Ser Phe Asp Ser Trp Gly Gln Gly Thr Leu Val
1               5                   10                  15

Thr Val Ser Ser Gly Ile Leu Gly Ser Gly Gly Gly Ser Gly Gly
            20                  25                  30

Gly Gly Ser Gly Gly Gly Ser Gln Ala Val Val Thr Gln Glu Pro
        35                  40                  45

Ser Val Thr Val Ser Pro Gly Gly Thr Val Ile Leu Thr Cys Gly Ser
    50                  55                  60

Ser Thr Gly Ala Val Thr Ser Gly His Tyr Ala Asn Trp Phe Gln Gln
65                  70                  75                  80

Lys Pro Gly Gln Ala Pro Arg Ala Leu Ile Phe Glu Thr Asp Lys Lys
                85                  90                  95

Tyr Ser Trp Thr Pro Gly Arg Phe Ser Gly Ser Leu Leu Gly Ala Lys
                100                 105                 110

Ala Ala Leu Thr Ile Ser Asp Ala Gln Pro Glu Asp Glu Ala Glu Tyr
            115                 120                 125

Tyr Cys Leu Leu Ser Asp Val Asp Gly Tyr Leu Phe Gly Gly Gly Thr
        130                 135                 140

Gln Leu Thr Val Leu Ser Gly Ile Leu Glu Gln Lys Leu Ile Ser Glu
145                 150                 155                 160

Glu Asp Leu

<210> SEQ ID NO 14
<211> LENGTH: 651
<212> TYPE: DNA
<213> ORGANISM: Artificial Sequence
<220> FEATURE:
<223> OTHER INFORMATION: scFv sequence

<400> SEQUENCE: 14
ggctagtggt ggtggtggtt ctggtggtgg tggttctgct agcactggca gctttgactc      60
ctggggccag ggaaccctgg tcaccgtctc ctcaggaatt ctaggatccg gtggcggtgg     120
cagcggcggt ggtggttccg gaggcggcgg ttctcaggct gtggtgactc aggagccgtc     180
agtgactgtg tccccaggag ggacagtcat tctcacttgt ggctccagca ctggagctgt     240
caccagtggt cattatgcca actggttcca gcagaagcct ggccaagccc cagggcact      300
tatatttgaa accgacaaga aatattcctg gaccctggc cgattctcag gctccctcct     360
tggggccaag gctgccctga ccatctcgga tgcgcagcct gaagatgagg ctgagtatta     420
ctgtttgctc tccgacgttg acggttatct gttcggagga ggcacccagc tgaccgtcct     480
ctccggaatt ctagaacaaa agcttatttc tgaagaagac ttgtaatagc tcggcggccg     540
catcgagatc tgataacaac agtgtagatg taacaaaatc gactttgttc ccactgtact     600
tttagctcgt acaaaataca atatactttt catttctccg taaacaacat g             651

<210> SEQ ID NO 15
<211> LENGTH: 155
<212> TYPE: PRT
<213> ORGANISM: Artificial Sequence
<220> FEATURE:
<223> OTHER INFORMATION: scFv sequence

<400> SEQUENCE: 15

Gln Val Gln Leu Gln Glu Ser Gly Pro Gly Leu Val Lys Pro Ser Glu
1               5                   10                  15

Thr Leu Ser Leu Thr Cys Thr Val Ser Gly Ala Ser Ile Ser Ser
            20                  25                  30

Ile Thr Tyr Tyr Trp Gly Trp Ile Arg Gln Pro Pro Gly Lys Gly Pro
        35                  40                  45

Glu Trp Ile Gly Ser Met Tyr Tyr Ser Gly Arg Thr Tyr Tyr Asn Pro
 50                  55                  60

Ala Leu Lys Ser Arg Val Thr Ile Ser Pro Asp Lys Ser Lys Asn Gln
 65                  70                  75                  80

Phe Phe Leu Lys Leu Thr Ser Val Thr Ala Ala Asp Thr Ala Val Tyr
                85                  90                  95

Tyr Cys Ala Arg Glu Gly Pro Thr His Tyr Tyr Asp Asn Ser Gly Pro
            100                 105                 110

Ile Pro Ser Asp Glu Tyr Phe Gln His Trp Gly Gln Gly Thr Leu Val
        115                 120                 125

Thr Val Ser Ser Gly Ile Leu Gly Ser Gly Gly Gly Ser Gly Gly
130                 135                 140

Gly Gly Ser Gly Gly Gly Gly Leu Gln Glu Phe
145                 150                 155

<210> SEQ ID NO 16
<211> LENGTH: 781
<212> TYPE: DNA
<213> ORGANISM: Artificial Sequence
<220> FEATURE:
<223> OTHER INFORMATION: scFv sequence

<400> SEQUENCE: 16
actagcaaag gcagccccat aaacacacag tatgttttta aggacaatag ctcgacgatt        60
gaaggtagat acccatacga cgttccagac tacgctctgc aggctagtgg tggtggtggt       120
tctggtggtg gtggttctgg tggtggtggt tctgctagcc aggtgcagct gcaggagtcg       180
ggcccaggac tggtgaagcc ttcggagacc ctgtccctca cctgcactgt ctctggtgcc       240
tccatcagca gtagtcatta ctactggggc tggatccgcc agcccccagg aaggggcct       300 gagtggattg ggagtatgta ttatagtggg agaacgtact acaacccggc cctcaagagt       360
cgagtcacca tatcaccaga caagtcgaag aaccagttct tcttgaagtt gacctctgta       420
accgccgcgg acacggccgt gtattactgt gcgaggagg gacccacaca ttactatgat       480
aatagtggtc caataccttc ggatgagtat ttccagcact ggggccaggg taccctggtc       540
actgtctcct caggaattct aggatccggt ggcggtggca gcggcggtgg tggttccgga       600
ggcggcgggc tgcaggaatt ctagaacaaa agcttatttc tgaagaagac ttgtaatagc       660
tcggcggccg catcgagatc tgataacaac agtgtagatg taacaaaatc gactttgttc       720
ccactgtact tttagctcgt acaaaataca atatactttt catttctccg taaacaacat       780
g                                                                       781

<210> SEQ ID NO 17
<211> LENGTH: 268
<212> TYPE: PRT
<213> ORGANISM: Artificial Sequence
<220> FEATURE:
<223> OTHER INFORMATION: scFv sequence, (GILEQKLISEEDL at end of
      sequence is derived from a vector)

<400> SEQUENCE: 17

Gln Val Gln Leu Gln Gln Trp Asp Ala Gly Leu Val Lys Pro Ser Gln
1               5                   10                  15

```
Thr Leu Ser Leu Thr Cys Ala Ile Ser Gly Asp Ser Val Ser Ser Asn
        20                  25                  30

Ser Ala Ala Trp Asn Trp Ile Arg Gln Ser Pro Ser Arg Gly Leu Glu
        35                  40                  45

Trp Pro Gly Arg Thr Tyr Tyr Arg Ser Lys Trp Gln Asn Asn Tyr Ala
50                  55                  60

Leu Ser Val Gln Gly Arg Ile Thr Ile Asn Pro Asp Thr Ser Asn Asn
65                  70                  75                  80

Gln Phe Ser Leu Gln Leu Asp Ser Met Thr Pro Glu Asp Thr Gly Val
                85                  90                  95

Tyr Tyr Cys Thr Arg Gly Gly Ser Leu Asp Tyr Trp Gly Gln Gly
            100                 105                 110

Thr Leu Val Thr Val Ser Ser Gly Ser Ala Ser Ala Pro Thr Gly Ile
        115                 120                 125

Leu Gly Ser Gly Gly Gly Ser Gly Gly Gly Ser Gly Gly Gly
        130                 135                 140

Gly Ser Ser Tyr Glu Leu Thr Gln Pro Pro Ser Val Ser Val Ser Pro
145                 150                 155                 160

Gly Gln Thr Ala Thr Ile Thr Cys Ser Gly Asp Glu Met Gly Asp Lys
            165                 170                 175

Tyr Ala Tyr Trp Tyr Gln Gln Lys Pro Gly Gln Ala Pro Val Leu Val
                180                 185                 190

Ile Tyr Lys Asp Ser Glu Arg Pro Ser Gly Ile Pro Glu Arg Phe Ser
        195                 200                 205

Gly Ser Ser Ser Gly Thr Thr Val Thr Leu Thr Ile Ser Gly Val Gln
210                 215                 220

Ala Glu Asp Glu Ala Asp Tyr Tyr Cys Gln Ser Ala Asp Ser Ser Gly
225                 230                 235                 240

Thr Ser Val Val Phe Gly Gly Gly Thr Lys Val Thr Val Leu Ser Gly
            245                 250                 255

Ile Leu Glu Gln Lys Leu Ile Ser Glu Glu Asp Leu
        260                 265
```

<210> SEQ ID NO 18
<211> LENGTH: 908
<212> TYPE: DNA
<213> ORGANISM: Artificial Sequence
<220> FEATURE:
<223> OTHER INFORMATION: scFv sequence

<400> SEQUENCE: 18

```
ctctgcaggc tagtggtggt ggtggttctg gtggtggtgg ttctggtggt ggtggttctg    60
ctagccaggt gcagctacag cagtgggacg caggactgga gaagccctcg cagaccctct   120
cactcacctg tgccatctcc ggggacagtg tctctagcaa cagtgctgct tggaactgga   180
tcaggcagtc cccatcgaga ggtcttgagt ggccgggaag acatactac aggtccaagt   240 ggcaaaacaa ttatgcactc tctgtgcaag gtcgaataac catcaaccca gacacatcca   300
acaaccaatt ctccctgcag ctggactcta tgactcccga ggacacgggt gtatattact   360
gtacaagggg cggcgggtcc ttagactact ggggccaggg aaccctggtc accgtctcct   420
cagggagtgc atccgcccca accggaattc taggatccgg tggcggtggc agcggcggtg   480
gtggttccgg aggcggcggt tcttcctatg agctgacaca gccaccctca gtgtccgtgt   540
ccccaggaca gacagccacc atcacctgct ctggagatga aatgggggat aaatatgctt   600
attggtacca gcagaagcca ggccaggccc ctgtgctggt gatatataaa gacagtgaga   660
```

```
ggccctcagg gatccctgag cgattctctg ctccagctc agggacaaca gtcaccttga      720
ccatcagtgg agtccaggca aagacgagg ctgactatta ctgtcaatca gcagacagca      780
gtggtacttc tgtggtattc ggcggaggga ccaaggtcac cgtcctatcc ggaattctag      840
aacaaaagct tatttctgaa gaagacttgt aatagctcgg cggccgcatc gagatctgat      900
aacaacag                                                              908
```

```
<210> SEQ ID NO 19
<211> LENGTH: 124
<212> TYPE: PRT
<213> ORGANISM: Artificial Sequence
<220> FEATURE:
<223> OTHER INFORMATION: scFv sequence, (EF at end of sequence is
      derived from a vector)

<400> SEQUENCE: 19

Gln Val Gln Leu Gln Gln Ser Gly Pro Gly Leu Val Arg Pro Ser Gln
1               5                   10                  15

Thr Leu Ser Leu Thr Cys Ala Ile Ser Gly Asp Ser Val Pro Lys Asn
            20                  25                  30

Gly Ala Ser Trp Asn Trp Ile Arg Leu Ser Pro Ser Arg Gly Leu Glu
        35                  40                  45

Trp Leu Gly Arg Thr His Tyr Ser Ser Arg Trp Tyr His Asp Tyr Ala
    50                  55                  60

Phe Phe Val Lys Ser Arg Ile Thr Ile Asn Val Asp Thr Ser Glu Thr
65                  70                  75                  80

Gln Val Ser Leu Gln Leu Asp Ser Val Thr Pro Asp Asp Thr Gly Val
                85                  90                  95

Tyr Tyr Cys Ala Arg Glu Ser Gln Arg Arg Gly Trp Phe Asp Leu Trp
            100                 105                 110

Gly Gln Gly Thr Leu Val Thr Val Ser Gln Glu Phe
        115                 120
```

```
<210> SEQ ID NO 20
<211> LENGTH: 853
<212> TYPE: DNA
<213> ORGANISM: Artificial Sequence
<220> FEATURE:
<223> OTHER INFORMATION: scFv sequence

<400> SEQUENCE: 20
ggtggtggtg gttctggtgg tggtggttct gctagccagg tacagctgca gcagtcaggt      60
ccaggactgg tgaggccctc gcagaccctc tcactcacct gtgccatctc cggggacagt     120
gtccctaaga cgtgcatc ttggaactgg atcaggctgt caccatcgcg aggccttgag     180
tggctgggaa ggactcacta cagttccagg tggtatcatg attatgcatt ctttgtgaag     240
agtcgaataa ccatcaacgt agatacatcc gagacccaag tcagtctgca gctggactct     300
gtgactcccg acgacacggg tgtttattac tgtgcaagag aatctcaacg taggggatgg     360
ttcgacctct ggggccaggg aaccctggtc accgtctccc aggaattcta ggatccggtg     420
gcggtggcag cggcggtggt ggttccggag gcggcggttc taattttatg ctgactcagc     480 ccactctgt gtcggagtct ccggggagga cggttacctt ctcctgcacc cgcagcagtg     540
gcggcattgc cagcaactat gtgcagtggt accaacagcg cccgggcagt acccccacca     600
ctgtgatcta tgggatagc caaagaccct ctggagtccc tgatcggttc tctggctcca     660
tcgacagctc ctccaattct gcctccctca ccatctcagg gctgaaggct gaggacgagg     720
ctgactacta ctgtcagtcc tctgatggta gctcttgggt gttcggcgga ggcacccagc     780
```

```
tgaccgtcct ctccggaatt ctagaacaaa agcttatttc tgaagaagac ttgtaatagc      840
tcggcggccg cat                                                         853
```

<210> SEQ ID NO 21
<211> LENGTH: 279
<212> TYPE: PRT
<213> ORGANISM: Artificial Sequence
<220> FEATURE:
<223> OTHER INFORMATION: scFv sequence, (GILEQKLISEEDL at end of
      sequence is derived from a vector)

<400> SEQUENCE: 21

Gln Val Gln Leu Gln Gln Ser Gly Pro Gly Arg Val Lys Pro Ser Gln
1               5                   10                  15

Thr Leu Ser Leu Thr Cys Asp Ile Ser Gly Asp Ser Val Ser Ser Asn
            20                  25                  30

Ser Val Ala Trp Asn Trp Ile Arg Gln Ser Pro Ser Arg Gly Leu Glu
        35                  40                  45

Trp Leu Gly Arg Thr Tyr Tyr Arg Ser Lys Trp Ile Asn Glu Tyr Gly
    50                  55                  60

Pro Phe Val Arg Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Thr Met Ala Asn Ser Gly Tyr Asp Arg Ser Ser Gly
            100                 105                 110

His Asn Tyr Gly Met Asp Val Trp Gly Gln Gly Thr Thr Val Thr Val
        115                 120                 125

Ser Ser Gly Ser Ala Ser Ala Pro Thr Gly Ile Leu Gly Ser Gly Gly
    130                 135                 140

Gly Gly Ser Gly Gly Gly Ser Gly Gly Gly Ser Ser Tyr Glu
145                 150                 155                 160

Leu Thr Gln Pro Pro Ser Val Ser Val Ser Pro Gly Gln Thr Ala Arg
                165                 170                 175

Ile Thr Cys Ser Gly Asp Ala Leu Pro Lys Gln Tyr Thr Tyr Trp Tyr
            180                 185                 190

Gln Gln Lys Ala Gly Gln Ala Pro Val Leu Val Ile Tyr Lys Asp Thr
        195                 200                 205

Glu Arg Pro Ser Gly Ile Pro Glu Arg Phe Ser Gly Thr Ser Ser Gly
    210                 215                 220

Thr Thr Val Thr Leu Thr Ile Ser Gly Val Gln Ala Glu Asp Glu Ala
225                 230                 235                 240

Asp Tyr Tyr Cys Gln Ser Ala Asp Ser Ser Gly Ser Tyr Val Phe Phe
                245                 250                 255

Gly Gly Gly Thr Lys Val Thr Val Leu Ser Gly Ile Leu Glu Gln Lys
            260                 265                 270

Leu Ile Ser Glu Glu Asp Leu
        275

<210> SEQ ID NO 22
<211> LENGTH: 935
<212> TYPE: DNA
<213> ORGANISM: Artificial Sequence
<220> FEATURE:
<223> OTHER INFORMATION: scFv sequence

<400> SEQUENCE: 22

```
cgctctgcag gctagtggtg gtggtggttc tggtggtggt ggttctggtg gtggtggttc      60
tgctagccag gtacagctgc agcagtcagg tccaggacgg gtgaagccct cgcagaccct     120
ctcactcacc tgtgacatct ccggggacag tgtctctagc aacagtgttg cttggaactg     180
gatcaggcag tccccatcga gaggcct tga gtggctggga aggacatact acaggtccaa     240
gtggattaat gaatatggac catttgtaag aagtcgaata accatcaacc cagacacatc     300
caagaatcag ttctccctgc agttgaactc tgtgactccc gaggacacgg ctgtctatta     360
ctgtgcaaca atggcgaata gtggctacga tcggtcctct ggtcacaact acggaatgga     420
cgtctggggc caagggacca cggtcaccgt ctcctcaggg agtgcatccg ccccaaccgg     480
aattctagga tccggtggcg gtggcagcgg cggtggtggt tccggaggcg gcggttcttc     540
ctatgagttg actcagccac cctcggtgtc agtgtcccca ggacagacgg ccaggatcac     600
ctgctctgga gatgcattgc caaagcaata tacttattgg taccagcaga aggcaggcca     660
ggcccctgtc ttggtgatat ataaagacac tgagaggccc tcagggatcc ctgagcgatt     720
ctctggtacc agttcaggga acacagtcac attgaccatc agtggagtcc aggcagaaga     780
cgaggctgac tattactgtc aatcagcaga cagcagtggt tcctatgttt tcttcggcgg     840
agggaccaag gtgaccgtcc tatccggaat tctagaacaa aagcttattt ctgaagaaga     900
cttgtaatag ctcggcggcc gcatcgagat ctgat                                935
```

<210> SEQ ID NO 23
<211> LENGTH: 27
<212> TYPE: DNA
<213> ORGANISM: Artificial Sequence
<220> FEATURE:
<223> OTHER INFORMATION: Primer

<400> SEQUENCE: 23

```
ggggctacca gtttgagggg acgacga                                          27
```

<210> SEQ ID NO 24
<211> LENGTH: 33
<212> TYPE: DNA
<213> ORGANISM: Artificial Sequence
<220> FEATURE:
<223> OTHER INFORMATION: Primer

<400> SEQUENCE: 24

```
ggcccctgcg gccgttagct cactcattag gca                                   33
```

<210> SEQ ID NO 25
<211> LENGTH: 40
<212> TYPE: DNA
<213> ORGANISM: Artificial Sequence
<220> FEATURE:
<223> OTHER INFORMATION: Primer

<400> SEQUENCE: 25

```
tatataggcc cagccggcct acccatacga cgttccagac                            40
```

<210> SEQ ID NO 26
<211> LENGTH: 40
<212> TYPE: DNA
<213> ORGANISM: Artificial Sequence
<220> FEATURE:
<223> OTHER INFORMATION: Primer

<400> SEQUENCE: 26

```
tatataggcc cctgcggcca attccggata ggacggtgag                            40
```

<210> SEQ ID NO 27
<211> LENGTH: 863
<212> TYPE: DNA
<213> ORGANISM: Artificial Sequence
<220> FEATURE:
<223> OTHER INFORMATION: scFv sequence

<400> SEQUENCE: 27

```
ctctgcaggc tagtggtggt ggtggttctg gtggtggtgg ttctggtggt ggtggctctg      60
ctagccaggt gcagctggtg aatctgaggc tgaggtgaa  gaagcctggg tcctcggtga     120
aggtctcctg caaggcttct ggaggcacct ccagcagcta tgctatcagc tgggtgcgac     180
aggcccctgg acaagggctt gagtggatgg gagggatcat ccctatcttt ggtacagcaa     240
actacgcaca gaagttccag gcagagtca  cgattaccgc ggacgaatcc acgagcacag     300
cctacatgga gctgagcagc tgagatctg  aggacacggc cgtgtattac tgtgtcttgt     360
tggatacaac tatggttacg ggatactact ttgactactg gggccaggga accctggtca     420
ccgtctcctc aggaattcta ggatccgtg  gcggtggcag cggcggtggt ggttccggag     480
gcggcggttc taattttatg ctgactcagc cccctcagc  gtctgggacc ccgggcaga      540
gcgtcaccat ctcttgttct ggaagcggct cgaacatcgg aaacaataaa gtaaactggt     600
accagcagct cccaggaacg gcccccaaac tcctcatcta tagtaataat cagcggccct     660
caggggtccc tgaccgattc tctggctcca agtctggcac ctcagcctcc ctggccatca     720
gtgggctcca gtctgaggat gaggctgatt attactgtgc agcatgggat gacagcctga     780
atggttatgt cttcggaact gggaccaagc tcaccgtcct atccggaatt ctagaacaaa     840
agcttatttc tgaagaagac ttg                                             863
```

<210> SEQ ID NO 28
<211> LENGTH: 864
<212> TYPE: DNA
<213> ORGANISM: Artificial Sequence
<220> FEATURE:
<223> OTHER INFORMATION: scFv sequence

<400> SEQUENCE: 28

```
gctctgcagg ctagtggtgg tggtggttct ggtggtggtg gttctggtgg tggtggttct      60
gctagccagg tgcagctggt ggaatctgag gctgaggtga agaagcctgg gtcctcggtg     120
aaggtctcct gcaaggcttc tggaggcacc ttcagcagct atgctatcag ctgggtgcga     180
caggcccctg acaagggct  cgagtggatg ggagggacca tccctatctt tggtacagca     240
aactacgcac agaagttcca gggcagagtc acgattaccg cggacgagtc cacgagcaca     300
gcctacatgg agctgagcag cctgagatct gaggacacgg ccgtgtatta ctgtgtcttg     360
ttgggtacaa ctatggttac gggatactac tttgactact ggggccaggg aaccctggtc     420
accgtctcct caggaattct aggatccggt ggcggtggca gcggcggtgg tggttccgga     480
ggcggcggtt ctaattttac gctgactcag ccccctcag  cgtctgggac cccgggcag      540
agcgtcacca tctcttgttc tggaagcggc tcgaacatcg gaaacaataa agtaaactgg     600
taccagcagc tcccaggaac ggcccccaaa ctcctcatct atagtaataa tcagcggccc     660
tcaggggtcc ctgaccgatt ctctggctcc aagtctggca cctcagcctc cctggccatc     720
agtgggctcc agtctgagga tgaggctgat tattactgtg cagcatggga tgacagcctg     780
aatggttatg tcttcggaac tgggaccaag ctcaccgtcc tatccggaat tctagaacaa     840
aagcttattt ctgaagaaga cttg                                            864
```

<210> SEQ ID NO 29
<211> LENGTH: 864
<212> TYPE: DNA
<213> ORGANISM: Artificial Sequence
<220> FEATURE:
<223> OTHER INFORMATION: scFv sequence

<400> SEQUENCE: 29

```
gctctgcagg ctagtggtgg tggtggttct ggtggtggtg gttctggtgg tggtggttct      60
gctagccagg tgcagctggt ggaatctggg gctgaggtga ggaagcctgg gtcctcggtg     120
aaggtctcct gcaaggcttc tggaggcacc ttcagcagtt atgctatcag ctgggtgcga     180
caggcccctg gacaagggct tgagtggatg ggagggatca tccctatctt tggtacagca     240
aactacgcgc agaagttcca gggcagagtc acgattaccg cggacgaatc cacgagcaca     300
gcctacatgg agctgagcag cctgagatct gaggacacgg ccgtgtatta ctgtgtcctg     360
ttgggtacaa ccatggttac gggatactac tttgactact ggggccaggg agccctggtc     420
accgtctcct caggaattct aggatccggt ggcggtggca gcggcggtgg tggttccgga     480
ggcggcggtt ctaattttat gctaactcag ccccccctcag cgtctggggc ccccgggcag     540
agcgtcacca tcccttgttc tggaagcggc tcgaacatcg aaacaataa agtaaactgg     600
taccagcagc tcccaggaac ggcccccaaa ctcctcatct atagtaataa tcagcggccc     660
tcaggggtcc ctgaccgatt ctctggctcc aagtctggca cctcagcctc cctggccatc     720
agtgggctcc agtctgagga tgaggctgat tattactgtg cagcatggga tgacagcctg     780
aatggttatg tcttcggaac tgggaccaag ctcaccgtcc tatccggaat tctagaacaa     840
gagcttattt ctgaagaaga cttg                                              864
```

<210> SEQ ID NO 30
<211> LENGTH: 864
<212> TYPE: DNA
<213> ORGANISM: Artificial Sequence
<220> FEATURE:
<223> OTHER INFORMATION: scFv sequence

<400> SEQUENCE: 30

```
gctctgcagg ctagtggtgg tggtggttct ggtggtggtg gttctggtgg tggtggttct      60
gctagccagg tgcagctggt ggaatctgag gctgaggtga agaagcctgg gtcctcggtg     120
aaggtctcct gcaaggcttc tggaggcacc tccagcagct atgctatcag ctgggtgcga     180
caggcccctg gacaagggct tgagtggatg ggagggatca tccctacctt tggtacagca     240
aactacgcac agaagttcca gggcagagtc acgattaccg cggacgaatc cacgagcaca     300
gcctacatgg agctgagcag cctgagatct gaggacacgg ccgtgtatta ctgtgtcttg     360
ttggatacaa ctatggttac gggatactac tttgactact ggggccaggg aaccctggtc     420
accgtctcct caggaattct aggatccggt ggcggtggca gcggcggtgg tggttccgga     480
ggcggcggtt ctaattttat gctgactcag ccccctcag cgtctgggac ccccgggcag     540
agcgtcacca tctcttgttc tggaagcggc tcgaacatcg aaacaataa agtaaactgg     600
taccagcagc tcccaggaac ggcccccaaa ctcctcatct atagtaataa tcagcggccc     660
tcaggggtcc ctgaccgatt ctctggctcc aagtctggca cctcagcctc cctggccatc     720
agtgggctcc agtctgagga tgaggctgat tattactgtg cagcatggga tgacagcctg     780
aatggttatg tcttcggaac tgggaccaag ctcaccgtcc tatccggaat tctagaacaa     840
aagcttattt ctgaagaaga ctcg                                              864
```

```
<210> SEQ ID NO 31
<211> LENGTH: 865
<212> TYPE: DNA
<213> ORGANISM: Artificial Sequence
<220> FEATURE:
<223> OTHER INFORMATION: scFv sequence

<400> SEQUENCE: 31
cgctctgcag gctagtggtg gtggtggttc tggtggtggt ggttctggtg gtggtggttc    60
tgctagccag gtgcagctgg tggaatctga ggctgaggtg aagaagcctg gtcctcggt    120 gaaggtctcc tgcaaggctt ctggaggcac cttcagcagc tatgctatca gctgggtgcg    180
acaggcccct ggacaagggc tcgagtggat gggagggatc atccctatct tggtacagc    240 aaactacgca cagaagttcc agggcagagt cacgtttacc gcggacgaat ccacgagcac    300
agcctacatg gagctgagca gcctgagatc tgaggacacg gccgtgtatt actgtgtctt    360
gttggataca actatggtta cgggatacta ctttgactac tggggccagg gaaccctggt    420
caccgtctcc tcaggaattc taggatccgg tggcggtggc agcggcggtg gtggttccgg    480
aggcggcggt tctaatttta tgctgactca gccccctca gcgtctggga ccccgggca    540 gagcgtcacc atctcttgct ctggaagcgg ctcgaacatc ggaaacaata agtaaactg    600 gtaccagcag ctcccaggaa tggcccccaa actcctcatc tatagtaata atcagcggcc    660
ctcaggggtc cctgaccgat tctctggctc caagtctggc acctcagcct ccctggccat    720
cagtgggctc cagtctgagg atgaggctgg ttattattgt gcagcatggg atggcagcct    780
gaatggttat gtcttcggaa ctgggaccaa gctcaccgtc ctatccggaa ttctagaaca    840
aaagcttatt tctgaagaag actcg                                          865

<210> SEQ ID NO 32
<211> LENGTH: 850
<212> TYPE: DNA
<213> ORGANISM: Artificial Sequence
<220> FEATURE:
<223> OTHER INFORMATION: scFv sequence

<400> SEQUENCE: 32
tggtggtggt ggctctggtg gtggtggttc tggtggtggt ggttctgcta gccaggtgca    60
gctggtggaa tctgaggctg aggtgaagaa gcctgggtcc gcggtgaagg tctcctgcaa    120
ggcttctgga ggcacctcca gcagctatgc tatcagctgg gtgcgacagg cccctggaca    180
agggcttgag tggatgggag ggatcatccc tatctttggt acagcaaact acgcacagaa    240
gttccagggc agagtcacga ttaccgcgga cgaatccacg agcacagcct acatggagct    300
gagcagcctg agatctgagg acacggccgt gtattactgt gtcttgttgg atacaaccgt    360
ggttacggga tactactttg actactgggg ccagggaacc ctggtcaccg tctcctcagg    420
aattctagga tccggtggcg gtggcagcgg cggtggtggt tccggaggcg gcggttctaa    480
ttttatgctg actcagcccc cctcagcgtc tgggaccccc gggcagagcg tcaccatctc    540
ttgttctgga agcggctcga gcatcggaag caataaagta aactggtacc agcagctccc    600
agggacggcc cccaaactcc tcatctatag taataatcag cggccctcag ggtccctgg    660 ccgattctct ggctccaagt ctggcacctc ggctccctg ccatcagtg gctccagtc    720 tgaggatgag gctgattatt actgtgcagc atgggatgac agcctgagtg gttatgtctt    780
cggaactggg accaagctca ccgccctatc cggaattcta ggacaagagc ttatttctga    840
agaagacttg                                                           850
```

<210> SEQ ID NO 33
<211> LENGTH: 863
<212> TYPE: DNA
<213> ORGANISM: Artificial Sequence
<220> FEATURE:
<223> OTHER INFORMATION: scFv sequence

<400> SEQUENCE: 33

| | | | | | |
|---|---|---|---|---|---|
| ctctgcaggc | tagtggtggt | ggtggttctg | gtggtggtgg | ttctggtggt | ggtggttctg | 60 |
| ctagccaggt | gcagctggtg | gagtctgggg | ctgaggtgaa | gaagcctggg | tcctcggtga | 120 |
| aggtctcctg | caaggcttct | ggaggcacct | ccagcaacta | tgctatcagc | tgggtgcgac | 180 |
| aggcccctgg | acaggggctt | gagtggatgg | gagggatcat | ccctatcttt | ggtacagcaa | 240 |
| actacgcaca | gaagttccag | gcagagtca | cgattaccgc | ggacgaatcc | acgagcacag | 300 |
| cctacatgga | gctgagcagc | ctgagatctg | aggacacggc | cgtgtattac | tgtgtcttgt | 360 |
| tggatacaac | tatggttacg | ggatactact | ttgactactg | gggccaggga | accctggtca | 420 |
| ccgtctcctc | aggaattcta | ggatccggtg | gcggtggcag | cggcggcggt | ggttccggtg | 480 |
| gcggcggttc | taattttatg | ctgactcagc | cccctcagc | gtctgggacc | ccgggcaga | 540 |
| gcgtcaccat | ctcttgttct | ggaagcggct | cgaacatcgg | aaacaataaa | gtaaactggt | 600 |
| accagcagct | cccaggaacg | gcccccaaac | tcctcatcta | tagtaataat | cagcggccct | 660 |
| caggggtccc | cgaccgattc | tctagctcca | gtctggcac | ctcagcctcc | ctggccatca | 720 |
| gtgggctcca | gtctgaggat | gagactgatt | attactgtgc | agcgtgggat | gacagcctga | 780 |
| atggttatgt | cttcggaact | gggaccaagc | tcaccgtcct | atccggaatc | tagaacaaa | 840 |
| agcttattcc | tgaaggagac | ttg | | | | 863 |

<210> SEQ ID NO 34
<211> LENGTH: 867
<212> TYPE: DNA
<213> ORGANISM: Artificial Sequence
<220> FEATURE:
<223> OTHER INFORMATION: scFv sequence

<400> SEQUENCE: 34

| | | | | | |
|---|---|---|---|---|---|
| tacgctctgc | aggctagtgg | tggtggtggt | tctggtggtg | gtggttctgg | tggtggtggt | 60 |
| tctgctagcc | aggtgcagct | ggtggaatct | gaggctgagg | cgaagaagcc | tgggtcctcg | 120 |
| gtgaaggtct | cctgcaaggc | ttctggaggc | accttcagca | gctatgctat | cagctgggtg | 180 |
| cgacaggccc | ctgacaagg | gcttgagtgg | gtgggaggga | tcatccccat | ctttggtaca | 240 |
| gcaaactacg | cacagaagtt | ccagggcaga | gtcacgatta | ccgcggacga | atccacgagc | 300 |
| acagcctaca | tggagctgag | cagcctgaga | tctgaggaca | cggccgtgta | ttactgtgtc | 360 |
| ttgttgggta | caactatggt | tacgggatac | tactttgact | actggggcca | gggaaccctg | 420 |
| gtcaccgtct | cctcaggaat | tctaggatcc | ggtggcggtg | gcagcggcgg | tggtggttcc | 480 |
| ggaggcggcg | gttctaattt | tatgctgact | cagccccct | cagcgtctgg | gaccccgggg | 540 |
| cagagcgtca | ccatctcttg | ttctggaagc | ggctcgaaca | tcggaaacaa | taaagtaaac | 600 |
| tggtaccagc | agctcccagg | aacggccccc | aaactcctca | tctatggtaa | taatcagcgg | 660 |
| ccctcagggg | tccctgaccg | attctccggc | tccaagtctg | gcacctcagc | tccctggcc | 720 |
| atcggtgggc | tccagtctga | ggatgaggct | gattattact | gtgcagcatg | ggatgacagc | 780 |
| ctgaatggtt | atgtcttcgg | aactgggacc | aagctcaccg | tcctatccgg | aattctagaa | 840 |
| caaaagctta | tttctgaagg | agacttg | | | | 867 |

```
<210> SEQ ID NO 35
<211> LENGTH: 865
<212> TYPE: DNA
<213> ORGANISM: Artificial Sequence
<220> FEATURE:
<223> OTHER INFORMATION: scFv sequence

<400> SEQUENCE: 35
cgctctgcag gctagtggtg gtggtggttc tggtggtggt ggttctggtg gtggtggttc     60
tgctagccag gtgcagctgg tggaatctga ggctgaggtg gagaagcctg gtcctcggt    120 gaaggtctcc tgcaaggctt ctggaggcac cttcagcagc tatgctatca gctgggtgcg    180
acaggcccct ggacaagggc tcgagtgggt gggagggatc atccctatct tggtacagc    240 aaactacgca cagaagttcc agggcagagt cacgattacc gcggacgaat ccacgagcac    300
agcctacatg agctgagca gcctgagatc tgaggacacg ccgtgtatt actgtgtctt    360 gttgggtaca actatggcta cgggacacta ctttgactac tggggccagg gaccctggt    420 caccgtctcc tcaggaattc taggatccgg tggcggtggc agcggcggtg gtggttccgg    480
aggcggcggt tctaatttta tgctgactca gccccctca gcgtctggga ccccgggca    540 gggcgtcacc atctcttgtt ctggaagcgg ctcgaacatc ggaaacaata agtaaactg    600 gtaccagcag ctcccaggaa cggccccaa actcctcatc tatagtaata atcagcggcc    660
ctcaggggcc cctgaccgat tctctggctc aagtctggc acctcagcct ccctggccat    720
cagtgggctc cagtctgagg atgaggctga ttattactgt gcagcatggg atgacagcct    780
gaatggttat gtcttcggaa ctgggaccaa gctcaccgtc ctatccggaa ttctagaaca    840
gaagcctatt tctgaagaag acttg                                         865

<210> SEQ ID NO 36
<211> LENGTH: 863
<212> TYPE: DNA
<213> ORGANISM: Artificial Sequence
<220> FEATURE:
<223> OTHER INFORMATION: scFv sequence

<400> SEQUENCE: 36
ctctgcaggc tagtggtggt ggtggttctg gtggtggtgg ttctggtggt ggtggttctg     60
ctagccaggt gcagctggtg gaatctgagg ctgaggtgaa gaagcctggg tcctcggtga    120
aggtctcctg caaggcttct ggaggcacct tcagcagcta tgctatcagc tgggtgcgac    180
aggcccctgg acaagggctt gagtggatgg gagggatcat ccctatcttt ggtacagcag    240
actacgcaca gaagttccag gcagagtca cgattaccgc ggacgaatcc acgagcacag    300
cctacatgga gctgagcagc ctgagatctg aggacacggc cgtgtattac tgtgtcttgt    360
tgggtacaac tatggttacg gatactact ttgactactg gggcaggga accctggtca    420 ccgtctcctc aggaattcta ggatccggtg gcggtggcag cggcggtggt ggttccggag    480
gcggcggttc taatttatg ctgactcagc ccccctcagc gtctgggacc cccgggcaga    540
gcgtcaccat ctcttgttct ggaagcggct cgaacatcgg aaacaataaa gtaaactggt    600
accagcagct cccaggaacg gccccaaac tcctcatcta tagtaataat cagcggccct    660
caggggtccc tgaccgattc tctggctcca agtctggcac ctcagcctcc ctggccatca    720
gtgggctcca gtctgaggat gaggctgatt attactgtgc agcatgggat gacagcctga    780
atggttatgt cttcggaact gggaccaagc tcaccgtcct atccggaatt ctagaacaaa    840
agcttatttc tgaagaagac ttg                                           863
```

```
<210> SEQ ID NO 37
<211> LENGTH: 865
<212> TYPE: DNA
<213> ORGANISM: Artificial Sequence
<220> FEATURE:
<223> OTHER INFORMATION: scFv sequence

<400> SEQUENCE: 37
cgctctgcag gctagtggtg gtggtggttc tggtggtggt ggttctggtg gtggtggttc      60
tgctagccag gtgcagctgg tggaatctga ggctgaggtg aagaagcctg gtcctcggt     120 gaaggtctcc tgcaaggctt ctggaggcac ctccagcagc tatgctatca gctgggtgcg     180
acaggcccct ggacaagggc ttgagtggat gggagggatc atccctatct tggtacagc     240 aaactacgca cagaagttcc agggcagagt cacgattacc gcggacgaat ccacgagcac     300
agcctacatg gagctgagca gcctgagatc tgaggacacg gccgtgtatt actgtgtctt     360
gttggataca actatggtta cgggatacta ctttgactac tggggccagg gaaccctggt     420
caccgtctcc tcaggaattc taggatccgg tggcggtggc agcggcggtg gtggttccgg     480
aggcggcggt tctaatttta tgctgactca gcccccctca gcgtctggga ccccgggca     540 gagcgtcacc atctcttgtt ctggaagcgg ctcgaacatc ggaaacaata agtaaactg     600 gtaccagcag ctcccaggaa cggccccaa actcctcatc tatagtaata atcagcggcc     660
ctcaggggtc cctgaccgat tctctggctc caagtctggc acctcagcct ccctggccat     720
cagtgggctc cagtctgagg atgaggctga ttattactgt gcagcatggg atgacagcct     780
gaatggttat gtcttcggaa ctgggaccaa gctcaccgtc ctatccggaa ttctagaaca     840
aaagcttatt tctgaagaag acttg                                          865

<210> SEQ ID NO 38
<211> LENGTH: 844
<212> TYPE: DNA
<213> ORGANISM: Artificial Sequence
<220> FEATURE:
<223> OTHER INFORMATION: scFv sequence

<400> SEQUENCE: 38
ttctggtggt ggtggttctg ctaaccaggt gcagctggtg gaatctgagg ctgaggtgaa      60
gaagcctggg tcctcggtga aggtctcctg caaggcttct ggaggtacct tcggcagcta     120
tgctatcagc tgggtgcgac aggcccctgg acaagggctt gagtggatgg gagggtcat     180 ccctatcttt ggtacagcag actacgcaca gaagttccgg ggcagagtca cgattaccgc     240
ggacgaatcc acgagcacag cctacatgga gctgagcagc ctgagatctg aggacacggc     300
cgtgtattac tgtgtcctgt tgggtacaac tatggttacg gatactact ttgactactg     360 gggccaggga accctggtca ccgtctcctc aggaattcta ggatccggtg gcggtggcag     420
cggcggtggt ggttccggag gcggcggttc taattttatg ctgactcagc cccctcagc     480 gtctggacc ccgggcaga gcgtcaccat ctcttgttct ggaagcggct cgaacatcgg     540
aaacaataaa gtaaactggt accagcagct cccaggaacg gccccaaac tcctcatcta     600 tagtaataat cagcggccct caggggtccc tgaccgattc tctggctcca agtctggcac     660
ctcagcctcc ctggccatca gtgggctcca gtctgaggat gaggctgatt attactgtgc     720
agcatgggat gacagcctga atggttatgt cttcggaact gggaccaagc tcaccgtcct     780
atccggatcc gaacaaaagc ttatttctga gaggacttg taatagctcg atgcggccgc     840
atcg                                                                 844
```

<210> SEQ ID NO 39
<211> LENGTH: 848
<212> TYPE: DNA
<213> ORGANISM: Artificial Sequence
<220> FEATURE:
<223> OTHER INFORMATION: scFv sequence

<400> SEQUENCE: 39

| | | | | | |
|---|---|---|---|---|---|
| ggttctggtg | gtggtggttc | tgctaaccag | gtgcagctgg | tggagtctgg | ggctgaggtg | 60 |
| aagaagcctg | ggtcctcggt | gaaggtctcc | tgcaaggctt | ctggaggcac | ctccagcaac | 120 |
| tatgctatca | gctgggtgcg | acaggcccct | ggacagggc | ttgagtggat | gggagggatc | 180 |
| atccctatct | ttggtacagc | agactacgca | cagaagttcc | agggcagagt | cacgattacc | 240 |
| gcggacaaat | ccacgagcac | agcctacatg | gagctgagcg | gcctgagatc | tgaggacacg | 300 |
| gccgtgtatt | actgtgtctt | gttgggtaca | actatggtta | cggacacta | ctttgactac | 360 |
| tggggccagg | gaaccctggt | caccgtctcc | tcaggaattc | taggatccgg | tggcggtggc | 420 |
| agcggcggtg | gtggttccgg | aggcggcggt | tctaatttta | tgctgactca | gccccctca | 480 |
| gcgtctggga | cccccgggca | gagcgtcacc | atctcttgtt | ctggaagcga | ctcgaacatc | 540 |
| ggaaataata | agtaaactg | gtaccagcag | ctcccaggaa | cggcccccaa | actcctcgtc | 600 |
| tatagtaata | atcagcggcc | ctcaggggtc | cctgaccggt | tctctggctc | caagtctggc | 660 |
| acctcagcct | ccctggccat | cagtgggctc | cagtctgagg | atgaggctga | ttattactgt | 720 |
| gcagcatggg | atgacagcct | gaatggttat | gtcttcggaa | ctgggaccaa | gctcaccgtc | 780 |
| ctatccggga | tccgaacaaa | agcttatttc | tgaagaggac | ttgtaatagc | tcgatgcggc | 840 |
| cgcatcga | | | | | | 848 |

<210> SEQ ID NO 40
<211> LENGTH: 846
<212> TYPE: DNA
<213> ORGANISM: Artificial Sequence
<220> FEATURE:
<223> OTHER INFORMATION: scFv sequence

<400> SEQUENCE: 40

| | | | | | |
|---|---|---|---|---|---|
| ggttctggtg | gtggtggttc | tgctggccag | gtgcagctgg | tggaatctga | ggctgaggtg | 60 |
| aagaagcctg | ggtcctcggt | gaaggtctcc | tgcaaggctt | ctggaggcac | ttcagcagc | 120 |
| tatgctatca | gctgggtgcg | acaggcccct | ggacaagggc | tcgagtggat | gggagggacc | 180 |
| atccctatct | ttggtacagc | agactacgca | cagaagttcc | agggcagagt | cacgattacc | 240 |
| gcggacgagt | ccacgagcac | agcctacatg | gagctgagca | gcctgagatc | tgaggacacg | 300 |
| gccgtgtatt | actgtgtctt | gttgggtaca | actatggtta | cggatacta | ctttgactac | 360 |
| tggggccagg | gaaccctggt | caccgtctcc | tcaggaattc | taggatccgg | tggcggtggc | 420 |
| agcggcggtg | gtggttccgg | aggcggcggt | tctaatttta | cgctgactca | gccccctca | 480 |
| gcgtctgggg | cccccgggca | gagcgtcacc | atctcttgtt | ctggaagcgg | ctcgaacatc | 540 |
| ggaaacaata | agtaaactg | gtaccagcag | ctcccaggaa | cggcccccaa | actcctcatc | 600 |
| tatagtaata | aacagcggcc | ctcaggggtc | cctgaccgat | tctctggctc | caagtctggc | 660 |
| acctcagcct | ccctggccat | cagtgggctc | cagtctgagg | atgaggctga | ttattactgt | 720 |
| gcagcatggg | atgacagcct | gaatggttat | gtcttcggaa | ctgggaccaa | gctcaccgtc | 780 |
| ctatccggat | ccgaacaaaa | gcttatttct | gaagaggact | tgtaatagct | cgatgcggcc | 840 |
| gcatcg | | | | | | 846 |

<210> SEQ ID NO 41
<211> LENGTH: 856
<212> TYPE: DNA
<213> ORGANISM: Artificial Sequence
<220> FEATURE:
<223> OTHER INFORMATION: scFv sequence

<400> SEQUENCE: 41

```
tggtggtggt ggttccggtg gtggtggttc tgctaaccag gtgcagctgg tggaatctga     60
ggctgaggtg aagaagcctg gtcctcggt gaaggtctcc tgcaaggctt ctggaggtac    120
cttcggcagc tatgctatca gctgggtgcg acaggccccc ggacaagggc ttgagtggat    180
gggagggtc atccctatct ttggtacagc agactacgca cagaagttcc agggcagagt    240
cacgattacc gcggacgaat ccacgagcac agcctacatg agctgagca gcctgagatc    300
tgaggacacg gccgtgtatt actgtgtcct gttgggtaca actatggcta cgggacacta    360
ctttgactac tggggccagg gaccctggt caccgtctcc tcaggaattc taggatccgg    420
tggcggtggc agcggcggtg gtggttccgg aggcggcggt tctagttta tgctgactca    480
gccccctca gcgtctggga cccccggca gagcgtcacc atctcttgtt ctggaagcgg    540
ctcgaacatc ggaaacaata agtaaactg gtaccagcag ctcccaggaa cggcccccaa    600
actcctcatc tatagtaata atcagcggcc ctcaggggtc cctggccgat tctctggctc    660
caagtctggc acctcagcct ccctggccat cagtgggctc cagtctgagg atgaggctga    720
ttattactgt gcagcatggg atgacagcct gaatgattat gtcttcggaa ctgggaccaa    780
gctcaccgtc ctatccggat ccgaacaaaa gcttatttct gaagaggact tgtaatagct    840
cgatgcggcc gcatcg                                                    856
```

<210> SEQ ID NO 42
<211> LENGTH: 845
<212> TYPE: DNA
<213> ORGANISM: Artificial Sequence
<220> FEATURE:
<223> OTHER INFORMATION: scFv sequence

<400> SEQUENCE: 42

```
ggttctggtg gtggtggttc tgctagccag gtgcagctgg tggaatctga ggctgaggtg     60
aagaagcctg gtcctcggt gaaggtctcc tgcaaggcct ctggaggcac cttcagcagc    120
tatgctatca gctgggtgcg gcaggcccct ggacaagggc ttgagtggat gggagggacc    180
atccctatct ttggtacagc agactacgca caggagttcc agggcagagt cacgattacc    240
acggacgaat ccacgagcac agcctacatg agctgagcg gcctgagatc tgaggacacg    300
gccgtgtatt actgtgtttt gttgggtaca actatggtta cgggacacta ctttgactac    360
tggggccagg gaaccctggt caccgtctcc tcaggaattc taggatccgg tggcggtggc    420
agcggcggtg gtggttccgg aggcggcggt tctaatttta tgctgactca gccccctca    480
gcgtctggga cccccggca gagcgtcacc atctcttgtt ctggaagcgg ctcgaacatc    540
ggaaacaata agtaaactg gtaccagcag ctcccaggaa cggcccccaa actcctcatc    600
tatagtaata atcagcggcc ctcaggggtc cctgaccgat tctctggctc caagtctggc    660
acctcagcct ccctggccat cagtgggctc cagtctgagg atgaggctga ttattactgt    720
gcagcatggg atgacggtct gagtggttat gtcttcggaa ctgggaccaa gcttaccgtc    780
ctgtccggat ccgaacaaaa gcttatttct gaagaggact tgtaatagct cggcggccgc    840
atcga                                                                845
```

<210> SEQ ID NO 43
<211> LENGTH: 857
<212> TYPE: DNA
<213> ORGANISM: Artificial Sequence
<220> FEATURE:
<223> OTHER INFORMATION: scFv sequence

<400> SEQUENCE: 43

| | | | | | |
|---|---|---|---|---|---|
| ggttctggtg | gtggtggttc | cgctaaccag | gtgcagctgg | tggaatctga | ggctgaggtg | 60 |
| aagaagcctg | ggtcctcggt | gaaggtctcc | tgcaaggctt | ctggaggtac | cttcggcagc | 120 |
| tatgctatca | gctgggtgcg | acaggcccct | ggacaagggc | ttgagtggat | gggagggggtc | 180 |
| atccctatct | ttggtacagc | agactacgca | cagaagttcc | agggcagagt | cacgattacc | 240 |
| gcggacgaat | ccacgagcac | agcctacatg | gagctgagca | gcctgagatc | tgaggacacg | 300 |
| gccgtgtatt | actgtgtctt | gttgggtaca | actatggtta | cgggacacta | ctttgactac | 360 |
| tggggccagg | gaaccctggt | caccgtctcc | tcaggaattc | taggatccgg | tggcggtggc | 420 |
| agcggcggtg | gtggttccgg | aggcggcggt | tctaatttta | tgctgactca | gccccctca | 480 |
| gcgtctggga | ccccgggca | gagcgtcacc | atctcttgtt | ctggaagcgg | ctcgaacgtc | 540 |
| ggaaataata | aggtaaactg | gtaccagcag | ctcccaggaa | cggcccccaa | actcctcgtc | 600 |
| tatagtaata | atcagcggcc | ctcaggggtc | cctgaccgat | tctctggctc | caagtctggc | 660 |
| acctcagcct | ccctggccat | cagtgggctc | cagtctgagg | atgaggctga | ttattactgt | 720 |
| gcagcatggg | acgacagcct | gaatggttat | gtcttcggaa | ctgggaccag | gctcaccgtc | 780 |
| ctatccggga | tccgaacaaa | agcttatttc | tgaagaggac | ttgtaatagc | tcgatgcggc | 840 |
| cgcatcgaga | tctgata | | | | | 857 |

<210> SEQ ID NO 44
<211> LENGTH: 859
<212> TYPE: DNA
<213> ORGANISM: Artificial Sequence
<220> FEATURE:
<223> OTHER INFORMATION: scFv sequence

<400> SEQUENCE: 44

| | | | | | |
|---|---|---|---|---|---|
| ctggtggtgg | tgattctggt | ggtggtggtt | ctgctaacca | ggtgcagctg | gtggaatctg | 60 |
| aggctgaggt | gaagaagcct | gggtcctcgg | tgaaggtctc | ctgcaaggct | tctggaggta | 120 |
| ccttcggcag | ctatgctatc | agctgggtgc | gacaggcccc | tggacaaggg | cttgagtgga | 180 |
| tgggaggggt | catccctatc | tttggtacag | cagactacgc | acagaagttc | cagggcagag | 240 |
| tcacgattac | cgcggacgaa | tccacgagca | cagcctacat | ggagctgagc | ggcctgagat | 300 |
| ctgaggacac | ggccgtgtat | tactgtgtct | tgttgggtac | aactatggtt | acgggacact | 360 |
| actttgacta | ctggggccag | ggaaccctgg | tcaccgtctc | ctcaggaatt | ctaggatccg | 420 |
| gtggcggtgg | cagcggcggt | ggtggttccg | gaggcggcgg | ttctaatttt | atgctgactc | 480 |
| agcccccctc | agcgtctggg | accccgggc | agagcgtcac | catctcttgt | tctggaagcg | 540 |
| gctcgagcat | cggaaataat | aaagtaaact | ggtaccagca | gctcccagga | acggccccca | 600 |
| aactcctcgt | ctatagtaat | aatcagcggc | cctcaggggt | ccctgaccga | ttctctggct | 660 |
| ccaagtctgg | cacctcagcc | tccctggcca | tcagtgggct | ccagtctgag | gatgaggctg | 720 |
| attattactg | tgcagcatgg | gatgacagcc | tgaatggtta | tgtcttcgga | actgggacca | 780 |
| agctcaccgt | cctatccggg | atccgaacaa | aagcttattt | ctgaagaaga | cttgtaatag | 840 |
| ctcgatgcgg | ccgcatcga | | | | | 859 |

<210> SEQ ID NO 45
<211> LENGTH: 857
<212> TYPE: DNA
<213> ORGANISM: Artificial Sequence
<220> FEATURE:
<223> OTHER INFORMATION: scFv sequence

<400> SEQUENCE: 45

| | | | | | |
|---|---|---|---|---|---|
| tggtggtggt | ggttctggtg | gtggtggttc | tgctaaccag | gtgcagctgg | tggaatctga | 60 |
| ggctgaggtg | aagaagcctg | ggtcctcggt | gaaggtctcc | tgcaaggctt | ctggaggtac | 120 |
| cttcggcagc | tatgctatca | gctgggtgcg | acaggcccct | ggacagggc | ttgagtggat | 180 |
| gggagggtc | atccctatct | ttggtacagc | agactacgca | cagaagttcc | agggcagagt | 240 |
| cacgattacc | gcggacaaat | ccacgagcac | agcctacatg | gagctgagca | gcctgggatc | 300 |
| tgaggacacg | gccgtgtatt | actgtgtctt | gttgggtaca | actatggtta | cgggagacta | 360 |
| ctttgactac | tggggccagg | gaaccctggt | caccgtctcc | tcaggaattc | taggatccgg | 420 |
| tggcggtggc | agcggcggtg | gtggttccgg | aggcggcggt | tctaaccttta | tgctgactca | 480 |
| gccccccctca | gcgtctggga | cccccggca | gagcgtcacc | atctcttgtt | ctggaagcgg | 540 |
| ctcgaacatc | ggaaacaata | agtaaactg | gtaccagcag | ctcccaggaa | cggcccccaa | 600 |
| actcctcatc | tatagtaata | atcagcggcc | ctcaggggtc | cctgaccgat | tctctggctc | 660 |
| caagtctggc | acctcagcct | ccctggccat | cagtgggctc | cagtctgagg | atgaggctga | 720 |
| ttattactgt | gcagcatggg | atgacagcct | gaatggttat | gtcttcggaa | ctgggaccaa | 780 |
| gctcaccgtc | ctatccggga | tccgaacaaa | agcttatttc | tgaagaggac | ttgtaatagc | 840 |
| tcgatgcggc | cgcatcg | | | | | 857 |

<210> SEQ ID NO 46
<211> LENGTH: 877
<212> TYPE: DNA
<213> ORGANISM: Artificial Sequence
<220> FEATURE:
<223> OTHER INFORMATION: scFv sequence

<400> SEQUENCE: 46

| | | | | | |
|---|---|---|---|---|---|
| gtggtggtgg | tggttctggt | ggtggtggtt | ctggtggtgg | tggttctgct | agccaggtgc | 60 |
| agctggtgga | atctgaggct | gaggtgaaga | agcctgggtc | ctcggtgaag | gtctcttgca | 120 |
| aggcttctgg | aggcaccttc | agcagctatg | ctatcagctg | ggtgcgacag | gcccctggac | 180 |
| aagggctcga | gtggatggga | gggaccatcc | ctatctttgg | tacagcaaac | tacgcacaga | 240 |
| agttccaggg | cagagtcacg | attaccgcgg | acgagtccac | gagcacagcc | tacatggagc | 300 |
| tgagcagcct | gagatctgag | gacacggccg | tgtattactg | tgtcttgttg | ggtacaacta | 360 |
| tggttacggg | atactacttt | gactactggg | gccagggaac | cctggtcacc | gtctcctcag | 420 |
| gaattctagg | atccggtggc | ggtggcagcg | gcggtggtgg | ttccggaggc | ggcggttcta | 480 |
| atttttacgct | gactcagccc | ccctcagcgt | ctgggacccc | cggcagagc | gtcaccatct | 540 |
| cttgttctgg | aagcggctcg | aacatcggaa | acaataaagt | aaactggtac | cagcagctcc | 600 |
| caggaacggc | ccccaaactc | ctcatctata | gtaataatca | gcggccctca | ggggtccctg | 660 |
| accgattctc | tggctccaag | tctggcacct | cagccaccct | ggccatcagt | gggctccagt | 720 |
| ctgaggatga | ggctgattat | tactgtgcag | catgggatga | cagcctgaat | ggttatgtct | 780 |
| tcggaactgg | gaccaagctc | accgtcctat | ccggatccga | acaaaagctt | atttctgaag | 840 |
| aggacttgta | atagctcgat | gcggccgcat | cgagatc | | | 877 |

```
<210> SEQ ID NO 47
<211> LENGTH: 847
<212> TYPE: DNA
<213> ORGANISM: Artificial Sequence
<220> FEATURE:
<223> OTHER INFORMATION: scFv sequence

<400> SEQUENCE: 47
gtggttctgg tggtggtggt tctgctagcc aggtgcagct ggtggagtct ggggctgagg      60
tgaagaagcc tgggtcctcg gtgaaggtct cctgcaaggc ttctggaggc acctccagca     120
actatgctat cagctgggtg cgacaggccc tggacaggg gcttgagtgg atgggaggga     180
tcatccctat ctttggtaca gcagactacg cacagaagtt ccagggcaga gtcacgatta     240
ccgcggacga atccacgagc acagcctaca tggagctgag cagcctgaga tctgaggaca     300
cggccgtgta ttactgtgtc ttgttggata caactatggt tacgggatac tactttgact     360
actggggcca gggaaccctg gtcaccgtct cctcaggagt ctaggatcc ggtggcggtg     420 gcagcggcgg cggtggttcc ggtggcggcg gttctaattt tatgctgact cagccccct     480 cagcgtctgg acccccggg cagagcgtca ccatctcttg ttctggaagc ggctcgaaca     540
tcggaaacaa taaagtaaac tggtaccagc agctcccagg aacggccccc aaactcctca     600
tctatagtaa taatcagcgg ccctcagggg tccctgaccg attctctggc tccaagtctg     660
gcacctcagc ctccctggcc atcagtgggc tccagtctga ggatgaggct gattattact     720
gtgcagcatg ggatgcagc ctgaatggtt atgtcttcgg aactgggacc aagctcaccg     780
tcctatccgg gatccgaaca aaagcttatt tctgaagagg acttgtaata gctcgatgcg     840
gccgcat                                                               847

<210> SEQ ID NO 48
<211> LENGTH: 828
<212> TYPE: DNA
<213> ORGANISM: Artificial Sequence
<220> FEATURE:
<223> OTHER INFORMATION: scFv sequence

<400> SEQUENCE: 48
tgccagccag gtgcagctgg tggagtctgg ggctgaggtg aagaagcctg gtcctcggt      60 gaaggtctcc tgcaaggctt ctggaggcac ctccagcagc tatgctatca gctgggtgcg     120
acaggcccct ggacaagggc ttgagtggat gggagggatc atccctatct tggtacagc     180 agactacgca cagaagttcc agggcagagt cacgattacc gcggacgaat ccacgagcac     240
agcctacatg gagctgagcg cctgagatc tgaggacacg gccgtgtatt actgtgtctt     300
gttgggtaca actatggtta cgggacacta ctttgactac tggggccagg gaaccctggt     360
caccgtctcc tcaggaattc taggatccga tggcggtggc agcggcggtg gtggttccgg     420
aggcggcggg tctaatttta tgctgactca gcccccctca gcgtctggga cccccgggca     480
gagcgtcacc atctcttgtt ctggaagcgg ctcgaacatc ggaaataata agtaaactg     540 gtaccagcag ctcccgggaa cggccccaa actcctcgtc tatagtaata atcagcggcc     600
ctcaggggtc cctgaccgat tctctggctc caagtctggc acctcagcct ccctggccat     660
cagtgggctc cagtctgagg atgaggctga ttattactgt gcagcatggg atgcagcct     720 gaatggttat gtcttcggaa ctgggaccaa gctcaccgtc ctatccggga tccgaacaaa     780
agcttatttc tgaagaggac ttgtaatagc tcgatgcggc cgcatcga                  828

<210> SEQ ID NO 49
```

<211> LENGTH: 844
<212> TYPE: DNA
<213> ORGANISM: Artificial Sequence
<220> FEATURE:
<223> OTHER INFORMATION: scFv sequence

<400> SEQUENCE: 49

```
ggttctggtg gtggtggttc tgctaaccag gtgcagctgg tggaatctga ggctgaggtg      60
aagaagcctg ggtcctcggt gaaggtctcc tgcaaggctt ctggaggtac cttcggcagc     120
tatgctatca gctgggtgcg acaggcccct ggacaagggc ttgagtggat gggagggggtc    180
atccctatct ttggtacagc agactacgca cagaagttcc agggcagagt cacgattacc     240
gcggacgaat ccacgagcac agcctacatg agctgagcg gcctgagatc tgaggacacg     300
gccgtgtatt actgtgtctt gttgggtaca actatggtta cggacacta ctttgactac     360
tggggccagg gaaccctggt caccgtctcc tcaggaattc taggatccgg tggcggtggc     420
agcggcggtg tggttccgg aggcggcggt tctaatttta tgctgactca gccccctca      480
gcgtctggga cccccgggca gagcgtcacc atctcttgtt ctggaagcgg ctcgaacatc     540
ggaaataata agtaaactg gtaccagcag ctcccaggaa cggcccccaa actcctcgtc     600
tatagtaata atcagcggcc ctcaggggtc cctgaccgat tctctggctc caagtctggc     660
acctcagcct ccctggccat cagtgggctc cagtctgagg atgaggctga ttattactgt     720
gcagcatggg atgacagcct gaatggttat gtcttcggaa ctgggaccaa gctcaccgtc     780
ctatccggat ccgaacaaaa gcttatttct gaagaagact gtaatagct cggcggccgc     840
atcg                                                                   844
```

<210> SEQ ID NO 50
<211> LENGTH: 872
<212> TYPE: DNA
<213> ORGANISM: Artificial Sequence
<220> FEATURE:
<223> OTHER INFORMATION: scFv sequence

<400> SEQUENCE: 50

```
tggtggtggt ggttctggtg gtggtggttc tggtggtggt ggttctgcta gccaggtgca      60
gctggtggaa tctgaggctg aggtgaagaa gcctgggtcc tcggtgaagg tctcctgcaa     120
ggcttctgga ggcaccttca gcagctatgc tatcagctgg gtgcgacagg cccctggaca     180
agggctcgag tggatgggag ggaccatccc tatctttggt acagcaaact acgcacagaa     240
gttccagggc agagtcacga ttaccgcgga cgagtccacg agcacagcct acatggagct     300
gagcagcctg agatctgagg acacggccgt gtattactgt gtcttgttgg gtacaactat     360
ggttacggga tactactttg actactgggg ccagggaacc ctggtcaccg tctcctcagg     420
aattctagga tccggtggcg gtggcagcgg cggtggtggt tccggaggcg gcggttctaa     480
ttttacgctg actcagcccc cctcagcgtc tgggaccccc gggcagagcg tcaccatctc     540
ttgttctgga agcggctcga acatcggaaa caataaagta aactggtacc agcagctccc     600
aggaacggcc cccaaactcc tcatctatag taataatcag cggccctcag ggtccctga      660
ccgattctct ggctccaagt ctggcacctc agcctccctg gccatcagtg gctccagtc     720
tgaggatgag gctgattatt actgtgcagc atgggatgac agcctgaatg gttatgtctt     780
cggaactggg accaagctca ccgtcctacc cggatccgaa caaaagctta tttctgaaga     840
ggacttgtaa tagctcgatg cggccgcatc ga                                   872
```

<210> SEQ ID NO 51

<211> LENGTH: 829
<212> TYPE: DNA
<213> ORGANISM: Artificial Sequence
<220> FEATURE:
<223> OTHER INFORMATION: scFv sequence

<400> SEQUENCE: 51

| | | | | | |
|---|---|---|---|---|---|
| ggttctgcta | accaggtgca | gctggtggaa | tctgaggctg | aggtgaagaa | gcctgggacc | 60 |
| tcggtgaagg | tctcctgcaa | ggcttctgga | ggcacctcca | gcaactatgc | tatcagctgg | 120 |
| gtgcgacagg | cccctggaca | ggggcttgag | tggatgggag | gggtcatccc | tatctttggt | 180 |
| acagcagact | acgcacagaa | gttccagggc | agagtcacga | ttaccgcgga | cgaatccacg | 240 |
| agcacagcct | acatggagct | gagcggcctg | agatctgagg | acacggccgt | gtattactgt | 300 |
| gtcttgttgg | gtacaactat | ggttacggga | cactactttg | actactgggg | ccagggaacc | 360 |
| ctggtcaccg | tctcctcagg | aattctagga | tccggtggcg | gtggcagcgg | cggtggtggt | 420 |
| tccggaggcg | gcggttctaa | ttttatgctg | actcagcccc | cctcagcgtc | tgggaccccc | 480 |
| gggcagagcg | tcaccatctc | ttgttctgga | agcggctcga | acatcggaaa | taataaagta | 540 |
| aactggtacc | agcagctccc | aggaacggcc | cccaaactcc | tcgtctatag | taataatcag | 600 |
| cggccctcag | gggtccctga | ccgattctct | ggctccaagt | ctggcacctc | agcctccctg | 660 |
| gccatcagtg | ggctccagtc | tgaggatgag | gctgattatt | actgtgcagc | atgggatgac | 720 |
| agcctgaatg | gttatgtctt | cggaactggg | accaagctca | ccgtcctatc | cggatccgaa | 780 |
| caaaagctta | tttctgaaga | agacttgtaa | tagctcggcg | ccgcatcg | | 829 |

<210> SEQ ID NO 52
<211> LENGTH: 845
<212> TYPE: DNA
<213> ORGANISM: Artificial Sequence
<220> FEATURE:
<223> OTHER INFORMATION: scFv sequence

<400> SEQUENCE: 52

| | | | | | |
|---|---|---|---|---|---|
| ggttctggtg | gtggtggttc | tgctaaccag | gtgcagctgg | tggaatctga | ggctgaggtg | 60 |
| aagaagcctg | gtcctcggt | gaaggtctcc | tgcaaggctt | ctggaggtac | cttcggcagc | 120 |
| tatgctatca | gctgggtgcg | acaggcccct | ggacaagggc | ttgagtggat | gggagggtc | 180 |
| atccctatct | ttggtacagc | agactacgca | cagaagttcc | agggcagagt | cacgattacc | 240 |
| gcggacgaat | ccacgagcac | agcctacatg | gagctgagcg | gcctgagatc | tgaggacacg | 300 |
| gccgtgtatt | actgtgtctt | gttgggtaca | actgtggtta | cgggacacta | ctttgactac | 360 |
| tggggccagg | gaaccctggt | caccgtctcc | tcaggaattc | taggatccgg | tggcggtggc | 420 |
| agcggcggtg | gtggttccgg | aggcggcggt | tctaatttta | tgctgactca | gccccctca | 480 |
| gcgtctggga | ccccgggca | gagcgtcacc | atctcttgtt | ctggaagcgg | ctcgaacatc | 540 |
| ggaaataata | aagtaaactg | gtaccagcag | ctcccaggaa | cggcccccaa | actcctcatc | 600 |
| tatggtaata | atcagcggcc | ctcaggggtc | cctgaccgat | tctctggctc | caagtctggc | 660 |
| acctcagcct | ccctggccat | cagtgggctc | cagtctgagg | atgaggctga | ttattactgt | 720 |
| gcagcatggg | atgacagcct | gaatggttat | gtcttcggaa | ctgggaccaa | gctcaccgtc | 780 |
| ctatccggat | ccgaacaaaa | gcttatttct | gaagaagact | tgtaatagct | cggcggccgc | 840 |
| atcga | | | | | | 845 |

<210> SEQ ID NO 53
<211> LENGTH: 870
<212> TYPE: DNA

<213> ORGANISM: Artificial Sequence
<220> FEATURE:
<223> OTHER INFORMATION: scFv sequence

<400> SEQUENCE: 53

```
tggtggtggt ggttctggtg gtggtggttc tggtggtggt ggttctgcta gccaggtgca      60
gctggtggag tctggggctg aggtgaagaa gcctgggtcc tcggtgaagg tctcctgcaa     120
ggcttctgga ggcacctcca gcaactatgc tatcagctgg gtgcgacagg cccctggaca     180
ggggcttgag tggatgggag ggatcatccc tatctttggt acagcaaact acgcacagaa     240
gttccagggc agagtcacga ttaccgcgga cgaatccacg agcacagcct acatggagct     300
gagcagcctg agatctgagg acacggccgt gtattactgt gtcttgttgg atacaactat     360
ggttacggga tactactttg actactgggg ccagggaacc ctggtcaccg tctcctcagg     420
aattctagga tccggtggcg gtggcagcgg cggcggtggt tccggtggcg gcggttctaa     480
tttttatgctg actcagcccc cctcagcgtc tgggaccccc gggcagagcg tcaccatctc     540
tgttctctgga gcggctcga acatcggaaa caataaagta aactggtacc agcagctccc     600
aggaacggcc cccaaactcc tcatctatag taataatcag cggccctcag gggtccccga     660
ccgattctct agctccaagt ctggcacctc agcctccctg gccatcagtg gctccagtc     720
tgaggatgag actgattatt actgtgcagc gtgggatgac agcctgaatg gttatgtctt     780
cggaactggg accaagctca ccgtcctatc cggatccgaa caaaagctta tttctgaaga     840
ggacttgtaa tagctcgatg cggccgcatc                                      870
```

<210> SEQ ID NO 54
<211> LENGTH: 844
<212> TYPE: DNA
<213> ORGANISM: Artificial Sequence
<220> FEATURE:
<223> OTHER INFORMATION: scFv sequence

<400> SEQUENCE: 54

```
ttctggtggt ggtggttctg ctagccaggt gcagctggtg gagtctgggg ctgaggtgaa      60
gaagcctggg tcctcggtga aggtctcctg caaggcttct ggaggcacct ccagcaacta     120
tgctatcagc tgggtgcgac aggcccctgg acaggggctt gagtggatgg gagggatcat     180
ccctatcttt ggtacagcaa actacgcaca gaagttccag gcagagtca cgattaccgc     240
ggacgaatcc acgagcacag cctacatgga gctgagcagc ctgagatctg aggacacggc     300
cgtgtattac tgtgtcttgt tggatacaac tatggttacg ggatactact ttgactactg     360
gggccaggga accctggtca ccgtctcctc aggaattcta ggatccggtg gcggtggcag     420
cggcggtggt ggttccggag gcggcggttc taatttttatg ctgactcagc cccctcagc     480
gtctgggacc cccgggcaga gcgtcaccat ctcttgttct ggaagcggct cgaacatcgg     540
aaacaataaa gtaaactggt accagcagct cccaggaacg ccccaaac tcctcatcta     600
tagtaataat cagcggccct caggggtccc tgaccgattc tctggctcca agtctggcac     660
ctcagcctcc ctggccatca gtgggctcca gtctgaggat gaggctgatt attactgtgc     720
agcatgggat gacagcctga atggttatgt cttcggaact gggaccaagc tcaccgtcct     780
atccggatcc gaacaaaagc ttatttctga agaggacttg taatagctcg atgcggccgc     840
atcg                                                                   844
```

<210> SEQ ID NO 55
<211> LENGTH: 976
<212> TYPE: DNA

<213> ORGANISM: Artificial Sequence
<220> FEATURE:
<223> OTHER INFORMATION: scFv sequence

<400> SEQUENCE: 55

| | |
|---|---|
| tacgctctgc aggctagtgg tggtggtggt tctggtggtg gtggttctgc tagccaggtg | 60 |
| cagctggtgg agtctgaggg aggcttggta cagcctggag ggtccctgag actctcctgt | 120 |
| gcagcctctg gattcacctt cagtagttat gaaatgaact gggtccgcca ggctccaggt | 180 |
| aaggggctgg agtggatctc acgtattgat ggtgatggga gcagcacaaa ctacgcggac | 240 |
| tccgtgaagg gccgattcac catctccaga gacaacgcca agagcacgct gtatctgcaa | 300 |
| atgaatagtc tgagagccga ggacacggct gtgtattact gtacaagggc cagatacttt | 360 |
| ggttcggtga gcccctacgg tatggacgtc tggggccaag gaccacggt caccgtctcc | 420 |
| tcaggaattc taggatccgg tagcggtggc agcggcggtg gtggttccgg aggcggcggt | 480 |
| tctgacatcc gggtgaccca gtctccttct ccgtgtctg catctgtggg tgacagagtc | 540 |
| accatcagtt gtcgggcgag tcaggggatt gccacctggt tgggctggta tcagcagaag | 600 |
| ccagggaaac cccctcagtt ccttatctat tctgcatcca ctttgcaaac tggggtccca | 660 |
| tcaaggttca gcggcagtgg atctgggaca gatttcactc ttaccatcag cagcctgcag | 720 |
| ccggaggatg ttgcaactta ctattgtcaa gagggtagca cttttcctct cacttttcggc | 780 |
| ggagggaccg aagtggatat caaatccgga attctagaac aaaagcttat ttctgaagag | 840 |
| gacttgtaat agctcgatgc ggccgcatcg agatctgata caacagtgt agatgtaaca | 900 |
| aaatcgactt tgttcccact gtacttttag ctcgtacaaa atacaatata ctttttcattt | 960 |
| ctccgtaaac aacatg | 976 |

<210> SEQ ID NO 56
<211> LENGTH: 994
<212> TYPE: DNA
<213> ORGANISM: Artificial Sequence
<220> FEATURE:
<223> OTHER INFORMATION: scFv sequence

<400> SEQUENCE: 56

| | |
|---|---|
| tacgctctgc aggctagtgg tggtggtggt tctggtggtg gtggttctgc tagccaggtg | 60 |
| cagctggtgg agtctgaggg aggcttggta cagcctggag ggtccctgag actctcctgt | 120 |
| gcagcctctg gattcacctt cagtagttat gaaatgaact gggtccgcca ggctccaggt | 180 |
| aaggggctgg agtgggtctc acgtattgat ggtgatggga gcagcacaaa ctacgcggac | 240 |
| tccgtgaagg gccgattcac catctccaga gacaacgcca agggcacgct gtatctgcaa | 300 |
| atgaatagtc tgagagccga ggacacggct gtgtattact gtacaagggc cagatacttt | 360 |
| ggttcggtga gcccctacgg tatggacgtc tggggccaag gaccacggt caccgtctcc | 420 |
| tcaggaattc taggatccgg tggcggtggc agcggcggtg gtggttccgg aggcggcggt | 480 |
| tctgacatcc gggtgaccca gtctccttct ccgtgtctg catctgtggg tgacagagtc | 540 |
| accatcagtt gtcgggcgag tcaggggatt gccacctggt taggctggta tcagcagaag | 600 |
| ccagggaaac cccctcagtt ccttatctat tctgcatcca ctttgcaaac tggggtccca | 660 |
| tcaaggttca gcggcagtgg atctgggaca gatttcactc ttaccatcag cagcctgcag | 720 |
| ccggaggatg ttgcaactta ctattgtcaa gagggtagca cttttcctct cacttttcggc | 780 |
| ggagggacca agtggatat caaatccgga attctagaac aaaagcttat ttctgaagag | 840 |
| gacttgtaat agctcgatgc ggccgcatcg agatctgata caacagtgt agatgtaaca | 900 |

| | |
|---|---|
| aaatcgactt tgttcccact gtacttttag ctcgtacaaa atacaatata cttttcattt | 960 |
| ctccgtaaac aacatgtttt cccatgtaat atcc | 994 |

<210> SEQ ID NO 57
<211> LENGTH: 1035
<212> TYPE: DNA
<213> ORGANISM: Artificial Sequence
<220> FEATURE:
<223> OTHER INFORMATION: scFv sequence

<400> SEQUENCE: 57

| | |
|---|---|
| tgcaggctag tggtggtggt ggttctggtg gtggtggttc tgctagccag gtgcagctgg | 60 |
| tggagtctga gggaggcttg gtacagcctg ggggtccct gagactctcc tgtgcagcct | 120 |
| ctggattcac cttcagtagt tatgaaatga actgggtccg ccaggctcca ggtaaggggc | 180 |
| tggagtgggt ctcacgtatt gatggtgatg ggagcagcac aaactacgcg gactccgtga | 240 |
| agggccgatt caccatctcc agagacaacg ccaagagcac gctgtatctg caaatgaata | 300 |
| gtctgagagc cgaggacacg gctgtgtatt actgtacaag ggccagatac tttggttcga | 360 |
| tgagccccta cggtatggac gtctggggcc aagggaccac ggtcaccgtc tcctcaggaa | 420 |
| ttctaggatc cggtggcggt ggcagcggcg gtggtggttc cggaggcggc ggttctgaca | 480 |
| tccgggtgac ccagtctcct tcttccgtgt ctgcatctgt gggtgacaga gtcaccatca | 540 |
| gttgtcgggc gagtcagggg attgccacct ggttaggctg gtatcagcag aagccaggga | 600 |
| aacccctca gctccttatc tatcctgcat ccactttgca aactgggtc ccatcaaggt | 660 |
| ttagcggcag tggatctggg acagatttca ctcttaccat cagcagcctg cagccggagg | 720 |
| atgttgcaac ttactattgt caagaggta gcactttccc tctcactttc ggcggaggga | 780 |
| ccaaagtgga tatcaaatcc ggaattctag aacaaaagct tatttctgaa gaagacttgt | 840 |
| aatagctcgg cggccgcatc gagatctgat aacaacagtg tagatgtaac aaaatcgact | 900 |
| tgttcccac tgtactttta gctcgtacaa aatacaatat acttttcatt tctccgtaaa | 960 |
| caacatgttt tcccatgtaa tatcccttttt ctattttcg ttccgttacc aactttacac | 1020 |
| atactttata tagct | 1035 |

<210> SEQ ID NO 58
<211> LENGTH: 1022
<212> TYPE: DNA
<213> ORGANISM: Artificial Sequence
<220> FEATURE:
<223> OTHER INFORMATION: scFv sequence

<400> SEQUENCE: 58

| | |
|---|---|
| tgcaggctag tggtggtggt ggttctggtg gtggtggttc tggtggtggt ggttctgcta | 60 |
| gccaggtgca gctggtggag tctgagggag gcttggtaca gcctggaggg tccctgagac | 120 |
| tctcctgtgc agcctctgga ttcaccttca gtagttatga aatgaactgg gtccgccagg | 180 |
| ctccaggtaa ggggctggag tgggtctcac gtattgatgg tgatgggagc agcacaaact | 240 |
| acgcggactc cgtgaagggc cgattcacca tctccagaga caacgccaag agcacgctgt | 300 |
| atctgcaaat gaatagtctg agagccgagg acacggctgt gtattactgt acaagggcca | 360 |
| gatactttgg ttcggtgagc cctacggta tggacgtctg gggccaaggg accacggtca | 420 |
| ccgtctcctc aggaattcta ggatccggtg gcggtggcag cggcggtggt ggttccggag | 480 |
| gcggcggttc tgacatcagg gtgacccaat ctccttcttc cgtgtctgca tctgtgggtg | 540 |
| acagagtcac catcagttgt cgggcgagtc aggggattgc cacctggtta ggctggtatc | 600 |

| | |
|---|---|
| agcagaagcc agggaaaccc cctcagttcc ttatctattc tgcatccact ttgcaaactg | 660 |
| gagtcccatc aaggttcagc ggcagtggat ctgggacaga tttcactctt accatcagca | 720 |
| gcctgcagcc ggaggatgtt gcaacttact attgtcaaga gggtagcact ttccctctca | 780 |
| cttcggcgg agggaccaaa gtggatatca atccggaat tctagaacaa aagcttattt | 840 |
| ctgaagaaga cttgtaatag ctcggcggcc gcatcgagat ctgataacaa cagtgtagat | 900 |
| gtaacaaaat cgactttgtt cccactgtac ttttagctcg tacaaaatac aatatacttt | 960 |
| tcatttctcc gtaaacaaca tgttttccca gtaatatcc ttttctattt ttcgttccgt | 1020 |
| ta | 1022 |

<210> SEQ ID NO 59
<211> LENGTH: 1106
<212> TYPE: DNA
<213> ORGANISM: Artificial Sequence
<220> FEATURE:
<223> OTHER INFORMATION: scFv sequence
<220> FEATURE:
<221> NAME/KEY: misc_feature
<222> LOCATION: (27)..(27)
<223> OTHER INFORMATION: n is a, c, g, or t

<400> SEQUENCE: 59

| | |
|---|---|
| agtaacgttt gtcagtaatt gcggttntca ccctcaaca actagcaaag gcagccccat | 60 |
| aaacacacag tatgttttta aggacaatag ctcgacgatt gaaggtagat acccatacga | 120 |
| cgttccagac tacgctctgc aggctagtgg tggtggtggt tctggtggtg gtggttctgc | 180 |
| tagccaggtg cagctggtgg agtctgaggg gggcttggta cagcccggag gtccctgag | 240 |
| actctcctgt gcagcctctg gattcacctt cagtagttat gaaatgaact gggtccgcca | 300 |
| ggctccaggt aaggggctgg agtgggtctc acgtattgat ggtgatggga gcagcacaaa | 360 |
| ctacgcggac tccgtgaagg gccgattcac catctccaga caacgcca agagcacgct | 420 |
| gtatctgcag atgaatagtc tgagagccga ggacacggct gtgtattact gtacaagggc | 480 |
| cagatacctt ggttcggtga ccccctacgg tatggacgtc tggggccaag gaccacggt | 540 |
| caccgtctcc tcaggaattc taggatccgg tggcggtggc agcggcggtg gtggttccgg | 600 |
| aggcggcggt tctgacatcc gggtgaccca gtctccttct tccgtgtctg catctgtggg | 660 |
| tgacagagtc accatcagtt gtcgggcgag tcagggggatt gccacctggt taggctggta | 720 |
| tcagcagaag ccagggaaac cccctcagct ccttatctat tctgcatcca ctttgcaaac | 780 |
| tggggtccca tcaaggttca gcggcagtgg atctgggaca gatttcactc ttaccatcag | 840 |
| cagcctgcag ccggaggatg ttgcaactta ctattgtcaa gagggtagca ctttccctct | 900 |
| cacttcggc ggagggacca agtggatat caaatccgga attctagaac aaaagcttat | 960 |
| ttctgaagag acttgtaat agctcgatgc ggccgcatcg agatctgata acaacagtgt | 1020 |
| agatgtaaca aaatcgactt tgttcccact gtactttag ctcgtacaaa atacaatata | 1080 |
| cttttcattt ctccgtaaac aacatg | 1106 |

<210> SEQ ID NO 60
<211> LENGTH: 1051
<212> TYPE: DNA
<213> ORGANISM: Artificial Sequence
<220> FEATURE:
<223> OTHER INFORMATION: scFv sequence
<220> FEATURE:
<221> NAME/KEY: misc_feature
<222> LOCATION: (1047)..(1047)
<223> OTHER INFORMATION: n is a, c, g, or t

```
<400> SEQUENCE: 60
tacgctctgc aggctagtgg tggtggtggt tctggtggtg gtggttctgc tagccaggtg        60
cagctggtgg agtctgaggg aggcttggta cagcctggag ggtccctgag actctcctgt       120
gcagcctctg gattcacctt cagtagttat gaaatgaact gggtccgcca ggctccaggt       180
aaggggctgg agtgggtctc acgtattgat ggtgatggga gcagcacaaa ctacgcggac       240
tccgtgaagg gccgattcac catctccaga gacaacgcca gagcacgct gtatctgcaa        300
atgaatagtc tgagagccga ggacacggct gtgtattact gtacaagggc cagatactta       360
ggttcggtga gccctacgg tatggacgtc tggggccaag gaccacggt caccgtctcc         420
tcaggaatcc taggatccgg tggcggtggc agcggcggtg gtggttccgg aggcggcggt       480
tctgacatcc gggtgaccca gtctccttct ccgtgtctg catctgtggg tgacagagtc        540
accatcagtt gtcgggcgag tcaggggatt gccacctggt taggctggta tcagcagaag       600
ccaggggaac cccctcagct ccttatctat tctgcatcca ctttgcaaac tggggtccca       660
tcaaggttta gcggcagtgg atctgggaca gatttcactc ttaccatcag cagcctgcag       720
ccggaggatg ttgcaactta ctattgtcaa gagggtagca ctttccctct cactttcggc       780
ggagggacca agtggatat caaatccgga attctagaac aaaagcttat ttctgaagag        840
gacttgtaat agctcgatgc ggccgcatcg agatctgata caacagtgt agatgtaaca        900
aaatcgactt tgttcccact gtactttag ctcgtacaaa atacaatata cttttcattt        960
ctccgtaaac aacatgtttt ccccatgtaa tatcctttc tattttcgt tccgttacca        1020
actttacaca tactttatat agctatncac t                                      1051

<210> SEQ ID NO 61
<211> LENGTH: 1018
<212> TYPE: DNA
<213> ORGANISM: Artificial Sequence
<220> FEATURE:
<223> OTHER INFORMATION: scFv sequence

<400> SEQUENCE: 61
tacgctctgc aggctagtgg tggtggtggt tctggtggtg gtggttctgc tagccaggtg        60
cagctggtgg agtctgaggg aggcttggta cagcctggag ggtccctgag actctcctgt       120
gcagcctctg gtttcacctt cagtagttat gaaatgaact gggtccgcca ggctccaggt       180
aaggggctgg agtgggtctc acgtattgat ggtgatggga gcagcacaaa ctacgcagac       240
tccgtgaagg gccgattcac catctccaga gacaacgcca gagcacgct gtatctgcaa        300
atgaatagtc tgagagccga ggacacggct gtgtattact gtacaagggc cagatacttt       360
ggttcggtga gccctacgg tatggacgtc tggggccaag gaccacggt caccgtctcc         420
tcaggaattc taggatccgg tggcggtggc agcggcggtg gtggttccgg aggcggcggt       480
tctgacaccc gggtgaccca gtctccttct ccgtgtctg catctgtggg tgacagagtc        540
accatcagtt gtcgggcgag tcaggggatt gccacctggt taggctggta tcagcagaag       600
ccaggggaaac cccctcagtt ccttatctat tctgcatcca ctttgcaaac tggggtccca      660
tcaaggttca gcggcagtgg atctgggaca gatttcactc ttaccatcag cagcctgcag       720
ccggaggatg ttgcaaccta ctattgtcaa gagggtagca ctttccctct cactttcggc       780
ggagggacca aggtggatat caaatccgga attctagaac aaaagcttat ttctgaagaa       840
gacttgtaat agctcggcgg ccgcatcgag atctgataac aacagtgtag atgtaacaaa       900
atcgactttg ttcccactgt actttagct cgtacaaaat acaatatact tttcatttct        960
```

```
ccgtaaacaa catgtttttc ccatgtaata tccttttcta tttttcgttc cgttacca         1018

<210> SEQ ID NO 62
<211> LENGTH: 1232
<212> TYPE: DNA
<213> ORGANISM: Artificial Sequence
<220> FEATURE:
<223> OTHER INFORMATION: scFv sequence
<220> FEATURE:
<221> NAME/KEY: misc_feature
<222> LOCATION: (1174)..(1174)
<223> OTHER INFORMATION: n is a, c, g, or t

<400> SEQUENCE: 62
gcaaggagtt tttgaattta caaatcagta acgtttgtca gtaattgcgg ttctcacccc         60
tcaacaacta gcaaaggcag cccccataaa cacacagtat gtttttaagg acaatagctc       120
gacgattgaa ggtagatacc catacgacgt tccagactac gctctgcagg ctagtggtgg       180
tggtggttct ggtggtggtg gttctgctag ccaggtgcag ctggtggagt ctgagggagg       240
cttggtacag cctggagggt ccctgagact ctcctgtgca gcctctggat tcaccttcag       300
tagttatgaa atgaactggg tccgccaggc tccaggtaag gggctggagt gggtctcacg       360
tattgatggt gatgggagca gcacaaacta cgcggactcc gtgaagggcc gattcaccat       420
ctccagagac aacgccaaga gcacgctgta tctgcaaatg aatagtctga gagccgagga       480
cacggctgtg tattactgta caagggccag atactttggt tcgatgagcc cctacggtat       540
ggacgtctgg ggccaaggga ccacggtcac cgtctcctca ggaattctag gatccggtgg       600
cggtggcagc ggcggtggtg gttccggagg cggcggttct gacacccggg tgacccagtc       660
tccttcttcc gtgtctgcat ctgtgggtga cagagtcacc atcagttgtc gggcgagtca       720
ggggattgcc acctggttag ctggtatca gcagaagcca gggaaacccc ctcagctcct       780
tatctattct gcatccactt tgcaaactgg ggtcccatca aggttcagcg gcagtggatc       840
tgggacagat ttcactctta ccatcagcag cctgcagccg gaggatgttg caacttacta       900
ttgtcaagag ggtagcactt tccctctcac tttcggcgga gggaccaaag tggatatcaa       960
atccggaatt ctagaacaaa agcttatttc tgaagaaact tgtaatagct cgatgcggcc      1020
gcatcgagat ctgataacaa cagtgtagat gtaacaaaat cgactttgtt cccactgtac      1080
ttttagctcg tacaaaatac aatatacttt tcatttctcc gtaaacaaca tgttttccca      1140
tgtaatatcc ttttctattt ttcgttccgt tacnacttta cacatacttt atatagctat      1200
tcacttctat acactaaaaa actaaaacat tt                                    1232

<210> SEQ ID NO 63
<211> LENGTH: 937
<212> TYPE: DNA
<213> ORGANISM: Artificial Sequence
<220> FEATURE:
<223> OTHER INFORMATION: scFv sequence

<400> SEQUENCE: 63
gtggtggttc tggtggtggt ggttctggtg gtggtggttc tggcggtggt ggttctgcta         60
gccaggtgca gctggtggag tctgagggag gcttggtaca gcctggaggg tccctgagac       120
tctcctgtgc agcctctgga ttcaccttca gtagttatga aatgaactgg gtccgccagg       180
ctccaggtaa ggggctggag tgggtctcac gtattgatgg tgatgggagc agcacaaact       240
acgcggactc cgtgaagggc cgattcacca tctccagaga caacgccaag agcacgctgt       300
atctgcaaat gaatagtctg agagccgagg acacggctgt gtattactgt acaagggcca       360
```

-continued

| | |
|---|---|
| gatactttgg ttcgatgagc ccctacggta tggacgtctg gggccaaggg accacggtca | 420 |
| ccgtctcctc aggaattcta ggatccgtg gcggtggcag cggcggtggt ggttccggag | 480 |
| gcggcggctc tgacatccgg gtgacccagt ctccttcttc cgtgtctgca tctgtgggtg | 540 |
| acagagtcac catcagttgt cgggcgagtc aggggattgc cacctggtta ggctggtatc | 600 |
| agcagaagcc agggaaaccc cctcagctcc ttatctattc tgcacccact ttgcaaactg | 660 |
| gggtcccatc aaggttcagc ggcagtggat ctgggacaga tttcactctt accatcagca | 720 |
| gcctgcagcc ggaggatgtt gcaacttact attgtcaaga gggtagcact ttccctctca | 780 |
| ctttcggcgg agggaccaaa gtggatatca atccggaat tctagaacaa agcttatttt | 840 |
| ctgaagaaga cttgtaatag ctcgatgcgg ccgcatcgag atctgataac aacagtgtaa | 900 |
| atgtaacaaa atcgactttg ttcccactgt acttta | 937 |

<210> SEQ ID NO 64
<211> LENGTH: 1351
<212> TYPE: DNA
<213> ORGANISM: Artificial Sequence
<220> FEATURE:
<223> OTHER INFORMATION: scFv sequence

<400> SEQUENCE: 64

| | |
|---|---|
| tacttcatac attttcaatt aagatgcagt tacttcgctg tttttcaata ttttctgtta | 60 |
| ttgcttcagt tttagcacag gaactgacaa ctatatgcga gcaaatcccc tcaccaactt | 120 |
| tagaatcgac gccgtactct tgtcaacga ctactatttt ggccaacggg aaggcaatgc | 180 |
| aaggagtttt tgaatattac aaatcagtaa cgtttgtcag taattgcggt tctcaccct | 240 |
| caacaactag caaaggcagc cccataaaca cacagtatgt ttttaaggac aatagctcga | 300 |
| cgattgaagg tagataccca tacgacgttc cagactacgc tctgcaggct agtggtggtg | 360 |
| gtggttctgg tggtggtggt tctggtggtg gtggttctgc tagcactggc agctttgact | 420 |
| cctggggcca gggaaccctg gtcaccgtct cctcagggat tctaggatcc ggtggcggtg | 480 |
| gcagcggcgg tggtggttcc ggaggcggcg gttctcaggc tgtggtgact caggagccgt | 540 |
| cagtgactgt gttcccagga gggacagtca ctctcacttg tggctccagc actggagctg | 600 |
| tcaccagtgg tcactatgcc aactggttcc agcagaagcc tggccaagcc ccgggggcac | 660 |
| ttatatttga caccgacaag aaatattcct ggacccctgg ccgattctca ggctccctcc | 720 |
| tcggggccaa ggctgccctg accatctcgg atgcgcagcc tgaagatgag gctgagtatt | 780 |
| actgttcgct ctccgacgtt gacggttacc tgttcggagg aggcacccag ctgaccgtcc | 840 |
| tctccggaat tctagaacaa agcttatttt ctgaagaaga cttgtaatag ctcggcggcc | 900 |
| gcatcgagat ctgataacaa cagtgtagat gtaacaaaat cgactttgtt cccactgtac | 960 |
| ttttagctcg tacaaaatac aatatacttt tcatttctcc gtaaacaaca tgttttccca | 1020 |
| tgtaatatcc ttttctattt ttcgttccgt taccaacttt acacatactt tatatagcta | 1080 |
| ttcacttcta tacactaaaa aactaagaca attttaattt tgctgcctgc catatttcaa | 1140 |
| tttgttataa attcctataa tttatcctat tagtagctaa aaaagatgaa atgtgaatcg | 1200 |
| aatcctaaga gaattgagct ccaattcgcc ctatagtgag tcgtattaca attcactggc | 1260 |
| cgtcgtttta caacgtcgtg actgggaaaa ccctggcgtt acccaactta atcgccttgc | 1320 |
| agcacatccc cctttcgcca gctggcgtaa t | 1351 |

<210> SEQ ID NO 65
<211> LENGTH: 1397
<212> TYPE: DNA

<213> ORGANISM: Artificial Sequence
<220> FEATURE:
<223> OTHER INFORMATION: scFv sequence

<400> SEQUENCE: 65

```
caaaaattgt taatatacct ctatacttaa acgtcaagga gaaaaacccc ggatcgaatt      60
ccctacttca tacattttca attaagatgc agttacttcg ctgttttca atattttctg     120
ttattgcttc agtttagca caggaactga caactatatg cgagcaaatc ccctcaccaa     180
ctttagaatc gacgccgtac tctttgtcaa cgactactat tttggccaac gggaaggcaa     240
tgcaaggagt ttttgaatat acaaatcag taacgtttgt cagtaattgc ggttctcacc     300
cctcaacaac tagcaaaggc agccccataa acacacagta tgttttaag dacaatagct     360
cgacgattga aggtagatac ccatacgacg ttccagacta cgctctgcag ctagtggtg     420
gtggtggttc tggtggtggt ggttctggtg gtggtggttc tgctagcact ggcagctttg     480
actcctgggg ccagggaacc ctggtcaccg tctcctcagg aattctagga tccggtggcg     540
gtggcagcgg cggtggtggt tccggaggcg gcggttctca ggctgtggtg actcaggagc     600
cgtcagtgac tgtgtcccca ggagggacag tcattctcac ttgtggctcc agcactggag     660
ctgtcaccag tggtcattat gccaactggt tccagcagaa gcctggccaa gcccccaggg     720
cacttatatt tgaaaccgac aagaaatatt cctggacccc tggccgattc tcaggctccc     780
tccttgggc caaggctgcc ctgaccatct cggatgcgca gcctgaagat gaggctgagt     840
attactgttc gctctccgac gttgacggtt atctgttcgg aggaggcacc cagctgaccg     900
tcctctccgg aattctagaa caaaagctta tttctgaaga agacttgtaa tagctcgatg     960
cggccgcatc gagatctgat aacaacagtg tagatgtaac aaaatcgact tgttcccac    1020
tgtactttta gctcgtacaa aatacaatat acttttcatt tctccgtaaa caacatgttt    1080
tcccatgtaa tatcctttc tattttcgt tccgttacca actttacaca tactttatat    1140
agctattcac ttctatacac taaaaaacta agacaatttt aattttgctg cctgccatat    1200
ttcaatttgt tataaattcc tataatttat cctattagta gctaaaaaaa gatgaatgtg    1260
aatcgaatcc taagagaatt gagctccaat tcgccctata gtgagtcgta ttacaattca    1320
ctggccgtcg ttttacaacg tcgtgactgg gaaaaccctg gcgttaccca acttaatcgc    1380
cttgcagcac atccccc                                                   1397
```

<210> SEQ ID NO 66
<211> LENGTH: 1338
<212> TYPE: DNA
<213> ORGANISM: Artificial Sequence
<220> FEATURE:
<223> OTHER INFORMATION: scFv sequence

<400> SEQUENCE: 66

```
tacttcatac attttcaatt aagatgcagt tacttcgctg ttttcaata ttttctgtta      60
ttgcttcagt tttagcacag gaactgacaa ctatatgcga gcaaatcccc tcaccaactt     120
tagaatcgac gccgtactct tgtcaacga ctactatttt ggccaacggg aaggcaatgc     180
aaggagtttt tgaatattac aaatcagtaa cgtttgtcag taattgcggt tctcaccct     240
caacaactag caaaggcagc ccataaaca cacagtatgt tttaaggac aatagctcga     300
cgattgaagg tagataccca tacgacgttc agactacgc tctgcaggct agtggtggtg     360
gtggttctgg tggtggtggt tctgctagca ctggcagctt tgactcctgg gccagggaa     420
ccctggtcac cgtctcctca ggaatttcag gatccggtgg cggtggcagc ggcggtggtg     480
```

| | |
|---|---|
| gttccggagg cggcggttct caggctgtgg tgactcagga gccgtcagtg actgtgtccc | 540 |
| caggagggac agtcattctc acttgtggct ccagcactgg agctgtcacc agtggtcatt | 600 |
| atgccaactg gttccagcag aaacctggcc aagcccccag ggcacttata tttgacaccg | 660 |
| acaagaaata tccctggacc cctggccgat tctcaggctc cctccttggg gtcaaggctg | 720 |
| ccctgaccat ctcggatgcg cagcctgaag atgaggctga gtattactgt ttgctctccg | 780 |
| acgttgacgg ttatctgttc ggaggaggca cccagctgac cgtcctctcc ggaattctag | 840 |
| aacaaaagct tatttctgaa gaagacttgt aatagctcgg cggccgcatc gagatctgat | 900 |
| aacaacagtg tagatgtaac aaaatcgact tgttcccac tgtactttta gctcgtacaa | 960 |
| aatacaatat actttcatt tctccgtaaa caacatgttt tcccatgtaa tatccttttc | 1020 |
| tatttttcgt tccgttacca actttacaca tactttatat agctattcac ttctatacac | 1080 |
| taaaaaacta agacaatttt aattttgctg cctgccatat ttcaatttgt tataaattcc | 1140 |
| tataatttat cctattagta gctaaaaaaa gatgaatgtg aatcgaatcc taagagaatt | 1200 |
| gagctccaat tcgccctata gtgagtcgta ttacaattca ctggccgtcg ttttacaacg | 1260 |
| tcgtgactgg gaaaaccctg gcgttacccc aacttaatcg ccttgcagca catccccctt | 1320 |
| ttcgccagct ggcgtaat | 1338 |

<210> SEQ ID NO 67
<211> LENGTH: 1329
<212> TYPE: DNA
<213> ORGANISM: Artificial Sequence
<220> FEATURE:
<223> OTHER INFORMATION: scFv sequence

<400> SEQUENCE: 67

| | |
|---|---|
| atcgaattcc ctacttcata cattttcaat taagatgcag ttacttcgct gttttcaat | 60 |
| attttctgtt attgcttcag ttttagcaca ggaactgaca actatatgcg agcaaatccc | 120 |
| ctcaccaact ttagaatcga cgccgtactc tttgtcaacg actactattt tggccaacgg | 180 |
| gaaggcaatg caaggagttt ttgaatatta caaatcagta acgtttgtca gtaattgcgg | 240 |
| ttctcacccc tcaacaacta gcaaaggcag ccccataaac acacagtatg ttttaagga | 300 |
| caatagctcg acgattgaag gtagataccc atacgacgtt ccagactacg ctctgcaggc | 360 |
| tagtggtggt ggtggttctg gtggtggtgg ttctgctagc actggcagct ttgactcctg | 420 |
| ggccaggga accctggtca ccgtctcctc aggaattcta ggatccggtg gcggcggcag | 480 |
| cggcggtggt ggttccggag gcggcggttc tcaggctgtg gtgactcagg agccgtcagt | 540 |
| gactgtgtcc ccaggaggga cagtcattct cacttgtggc tccggcactg gagctgtcac | 600 |
| cagtggtcat tatgccaact ggttccagca gaagcctggc caagccccca gggcacttat | 660 |
| atttgacacc gacaagaagt attcctggac ccctggccga ttctcaggct ccctccttgg | 720 |
| ggccaaggct gccctgacca tctcggatgc gcagcctgaa gatgaggctg agtattactg | 780 |
| ttcgctctcc gacgttgacg gttatctgtt cggaggaggc acccagctga ccgtcctctc | 840 |
| cggaattcta gaacaaaagc ttatttctga agaagacttg taatagctcg gcggccgcat | 900 |
| cgagatctga taacaacagt gtagatgtaa caaaatcgac tttgttccca ctgtactttt | 960 |
| agctcgtaca aaatacaata tactttcat ttctccgtaa caacatgtt tcccatgta | 1020 |
| atatccttt ctattttcg ttccgttacc aactttacac atactttata tagctattca | 1080 |
| cttctataca ctaaaaaact aagacaattt taatttgct gcctgccata ttcaatttg | 1140 |
| ttataaattc ctataattta cctattagt agctaaaaaa agatgaatgt gaatcgaatc | 1200 |

-continued

| | |
|---|---|
| ctaagagaat tgagctccaa ttcgccctat agtgagtcgt attacaattc actgggccgt | 1260 |
| cgttttacaa cgtcgtgact gggaaaaccc tggcgttacc caacttaatc gccttgcagc | 1320 |
| acatccccc | 1329 |

<210> SEQ ID NO 68
<211> LENGTH: 1166
<212> TYPE: DNA
<213> ORGANISM: Artificial Sequence
<220> FEATURE:
<223> OTHER INFORMATION: scFv sequence

<400> SEQUENCE: 68

| | |
|---|---|
| tcaccaactt tagaatcgac gccgtactct ttgtcaacga ctactatttt ggccaacggg | 60 |
| aaggcaatgc aaggagtttt tgaatattac aaatcagtaa cgtttgtcag taattgcggt | 120 |
| tctcacccct caacaactag caaaggcagc cccataaaca cacagtatgt ttttaaggac | 180 |
| aatagctcga cgattgaagg tagataccca tacgacgttc cagactacgc tctgcaggct | 240 |
| agtggtggtg gtggttctgg tggtggtggt tctgctagca ctggcagctt tgactcctgg | 300 |
| ggccagggaa ccctggtcac cgtctcctca ggagttctag gatccggtgg cggtggcagc | 360 |
| ggcggtggtg gttccggagg cggcggttct caggctgtgg tgactcagga gccgtcagtg | 420 |
| actgtgtccc caggagggac agtcattctc acttgtggct ccagcactgg agctgtcacc | 480 |
| agtggtcatt atgccaactg gttccaggag aagcctggcc aagccccag gcacttata | 540 |
| tttgaaaccg acaagaaata ttcctggacc cctggccgat ctcaggctc cctccttggg | 600 |
| gccaaggctg ccctgaccat ctcggatgcg cagcctgaag atgaggctga gtattactgt | 660 |
| tcgctctccg acgttgacgg ttatctgttc ggaggaggca cccagctgac cgtcctctcc | 720 |
| ggaattctag aacaaaagct tatttctgaa gaagacttgt aatagctcgg cggccgcatt | 780 |
| cgagatctga taacaacagt gtagatgtaa caaaatcgac tttgttccca ctgtactttt | 840 |
| agctcgtaca aaatacaata tacttttcat ttctccgtaa acaacatgtt ttcccatgta | 900 |
| atatccttt ctatttttcg ttccgttacc aactttacac atactttata tagctattca | 960 |
| cttctataca ctaaaaaact aagacaattt taattttgct gcctgccata tttcaatttg | 1020 |
| ttataaattc ctataatttta tcctattagt agctaaaaaa agatgaatgt gaatcgaatc | 1080 |
| ctaagagaat tgagctccaa ttcgccctat agtgagtcgt attacaattc actggccgtc | 1140 |
| gttttacaac gtcgtgactg ggaaaa | 1166 |

<210> SEQ ID NO 69
<211> LENGTH: 877
<212> TYPE: DNA
<213> ORGANISM: Artificial Sequence
<220> FEATURE:
<223> OTHER INFORMATION: scFv sequence

<400> SEQUENCE: 69

| | |
|---|---|
| caatattttc tgttattgct tcagttttag cacaggaact gacaactata tgcgagcaaa | 60 |
| tcccctcacc aacttagaa tcgacgccgt actctttgtc aacgactact attttggcca | 120 |
| acgggaaggc aatgcaagga gtttttgaat attacaaatc agtaacgttt gtcagtaatt | 180 |
| gcggttctca cccctcaaca actagcaaag gcagccccat aaacacacag tatgttttta | 240 |
| aggacaatag ctcgacgatt gaaggtagat acccatacga cgttccagac tacgctctgc | 300 |
| aggctagtgg tggtggtggt tctggtggtg gtggttctgg tggtggtggt tctgctagca | 360 |
| ctggcagctt tgactcctgg ggccagggaa ccctggtcac cgtctcctca ggaattccag | 420 |

```
gatccggtgg cggtggcagc ggcggtggtg gttccggagg cggcggttct caggctgtgg    480
tgactcagga gccgtcagtg actgtgtccc caggagggaca agtcattctc acttgtggct    540
ccaacactgg agctgtcacc agtggtcatt atgccaactg gttccagcag aagcctggcc    600
aagcccccag ggcacttata tttgaaaccg acaagaaata ttcctggacc cctggccgat    660
tctcaggctc cctccttggg gccaaggctg ccctgaccat ctcggatgcg cagcctgaag    720
atgaggctga gtattactgt tcgctcgccg acgttgacgg ttatctgttc ggaggaggca    780
cccagctgac cgtcctctcc ggaattctag aacaaaagct tatttctgaa gaggacttgt    840
aatagctcga tgcggccgca tcgagatctg ataacaa                              877

<210> SEQ ID NO 70
<211> LENGTH: 1349
<212> TYPE: DNA
<213> ORGANISM: Artificial Sequence
<220> FEATURE:
<223> OTHER INFORMATION: scFv sequence

<400> SEQUENCE: 70
cgaattccct acttcataca ttttcaatta agatgcagtt acttcgctgt ttttcaatat      60
tttctgttat tgcttcagtt ttagcacagg aactgacaac tatatgcgag caaatcccct    120
caccaacttt agaatcgacg ccgtactctt tgtcaacgac tactattttg gccaacggga    180
aggcaatgca aggagttttt gaatattaca atcagtaac gtttgtcagt aattgcggtt    240 ctcaccccctc aacaactagc aaaggcagcc cataaacac acagtatgtt tttaaggaca    300
atagctcgac gattgaaggt agatacccat acgacgttcc agactacgct ctgcaggcta    360
gtggtggtgg tggttctggt ggtggtggtt ctgctagcac tggcagcttt gactcctggg    420 gccagggggac cctggtcacc gtctcctcag gaattctagg atccggtggc ggtggcagcg    480
gcggtggtgg ttccggaggc ggcggttctc aggctgtggt gactcaggag ccgtcagtga    540
ctgtgtcccc aggagggaca gtcattctca cttgtggctc cagcactgga gctgtcacca    600
gcggtcatta tgccaactgg ttccagcaga agcctggcca agcccccagg gcacttatat    660
ttgaaaccga caagaaatat tcctggaccc ctggccgatt ctcaggctcc ctccttgggg    720
ccaaggctgc cctgaccatc tcggatgcgc agcctgaaga tgaggctgag tattactgtt    780
cgctctccga cgtagacggt tatctgttcg gaggaggcac ccagctgacc gtcctctccg    840
gaattctaga acaaaagctt atttctgaag aggacttgta atagctcgat gcggccgcat    900
cgagatctga taacaacagt gtagatgtaa caaaatcgac tttgttccca ctgtactttt    960
agctcgtaca aaatacaata tacttttcat ttctccgtaa acaacatgtt ttcccatgta   1020
atatcctttt ctattttttcg ttccgttacc aactttacac atactttata tagctattca   1080
cttctataca ctaaaaaact aagacaattt taattttgct gcctgccata tttcaatttg   1140
ttataaattc ctataattta tcctattagt agctaaaaaa agatgaatgt gaatcgaatc   1200
ctaagagaat tgagctccaa ttcgccctat agtgagtcgt attacaattc actggccgtc   1260
gttttacaac gtcgtgactg ggaaaaccct ggcgttaccc aacttaatcg ccttgcagca   1320
catccccctt ttcgccagct ggcgtaata                                     1349

<210> SEQ ID NO 71
<211> LENGTH: 884
<212> TYPE: DNA
<213> ORGANISM: Artificial Sequence
<220> FEATURE:
<223> OTHER INFORMATION: scFv sequence
```

<400> SEQUENCE: 71

```
atggctctgc aggctagtgg tggtggtggt tctggtggtg gtggttctgg tggtggtggt    60
tctgctagcg aggtgcagct gttggagact gggggaggtg tggtacggcc tggggggtcc   120
ctgagactct cctgtgcagc ctctggattc acctttgatg attatggcat gagctgggtc   180
cgccaagctc cagggaaggg gctggagtgg gtctctggta ttaattggaa tggcggtaac   240
acaggttatg cagactctgt gaagggccga ttcaccatct ccagagacaa cgccaagaac   300
tccctgtatc tgcaaatgaa cagtctgaaa gccgaggaca cggccttgta ttactgtgcg   360
agaaaaagcc acattggga gattatctcc tatgacttct ggggccaggg aaccctggtc   420
accgtctcct cagaattcta ggatccggtg gcggtggcag cggcggtggt ggttccggag   480
gcggcggttc tgaaacgaca ctcacgcagt ctccagcatt catgtcagcg actccaggag   540
acaaggtcaa catctcctgc aaagccagcc aagacattga tgatgatatg aactggtacc   600
aacagaaacc aggagaaggt gctattttca ttattcaaga agctactact ctcgttcctg   660
gaatcccacc tcgattcagt ggcagcgggt gtggaacaga ttttacccte acaattaata   720
acatagaatc tgaggatgct gcatataact tctgtctaca acaggataat ttccctctag   780
ggcgttcggc caagggacca agtggaaat caaatccgga attctagaac aaaagcttat   840
ttctgaagaa gacttgtaat agctcggcgg ccgcatcgag atct                    884
```

<210> SEQ ID NO 72
<211> LENGTH: 977
<212> TYPE: DNA
<213> ORGANISM: Artificial Sequence
<220> FEATURE:
<223> OTHER INFORMATION: scFv sequence

<400> SEQUENCE: 72

```
gtggtggtgg ttctggtggt ggtggttctg tggtggtgg ttctgctagc caggtgcagc    60
tggtggaatc tgaggctgag gtgaagaagc ctgggtcctc ggtgaaggtc tcctgcaagg   120
cttctggagg caccttcagc agctatgcta tcagctgggt gcgacaggcc cctggacaag   180
ggcttgagtg gatgggaggg atcatcccta tctttggtac agcaaactac gcacagaagt   240
tccagggcag agtcacgatt accgcggacg aatccacgag catagcctac atggagctga   300
gcagcctgag atctgaggac acggccgtgt attactgtgc cttgttggat acaactatgg   360
ttacgggata ctactttgac tactggggcc agggaaccct ggtcaccgtc tcctcaggaa   420
ttctaggatc cggtggcggt ggcagcgcg gtggtggttc cggaggcggc ggttctaatt   480
ttatgctgac tcagcccccc tcagcgtctg gaccccggg cagagcgtc accatctctt   540
gttctggaag cggctcgaac atcggaaaca ataaagtaaa ctggtaccag cagctcccag   600
gaacggcccc caaactcctc atctatagta ataatcagcg gccctcaggg gtccctgacc   660
gattctctgg ctccaagtct ggcacctcag cctccctggc catcagtggg ctccagtctg   720
aggatgaggc tgattattac tgtgcagcat gggatgacag cctgaatggt tatgtcttcg   780
gagctgggac caagctcacc gtcctatccg gaattctaga caaaagcttt atttctgaag   840
aagacttgta atagctcggc ggccgcatc gagatctgat aacaacagtg tagatgtaac   900
aaaatcgact tgttcccac tgtacttta gctcgtacaa aatacaatat acttttcatt   960
tctccgtaaa caacatg                                                 977
```

<210> SEQ ID NO 73
<211> LENGTH: 121
<212> TYPE: PRT

-continued

<213> ORGANISM: Artificial Sequence
<220> FEATURE:
<223> OTHER INFORMATION: Heavy chain fragment of scFv sequence

<400> SEQUENCE: 73

Gln Val Gln Leu Val Glu Ser Glu Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Val Leu Leu Asp Thr Thr Met Val Thr Gly Tyr Tyr Phe Asp Tyr Trp
            100                 105                 110

Gly Gln Gly Thr Leu Val Thr Val Ser
        115                 120

<210> SEQ ID NO 74
<211> LENGTH: 121
<212> TYPE: PRT
<213> ORGANISM: Artificial Sequence
<220> FEATURE:
<223> OTHER INFORMATION: Heavy chain fragment of scFv sequence

<400> SEQUENCE: 74

Gln Val Gln Leu Val Glu Ser Glu Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Thr Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Val Leu Leu Gly Thr Thr Met Val Thr Gly Tyr Tyr Phe Asp Tyr Trp
            100                 105                 110

Gly Gln Gly Thr Leu Val Thr Val Ser
        115                 120

<210> SEQ ID NO 75
<211> LENGTH: 121
<212> TYPE: PRT
<213> ORGANISM: Artificial Sequence
<220> FEATURE:
<223> OTHER INFORMATION: Heavy chain fragment of scFv sequence

<400> SEQUENCE: 75

Gln Val Gln Leu Val Glu Ser Glu Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

```
Ala Ile Ser Trp Val Arg Gln Ala Pro Gly Gln Gly Leu Glu Trp Met
        35                  40                  45

Gly Gly Thr Ile Pro Ile Phe Gly Thr Ala Asp Tyr Ala Gln Glu Phe
    50                  55                  60

Gln Gly Arg Val Thr Ile Thr Thr Asp Glu Ser Thr Ser Thr Ala Tyr
65                  70                  75                  80

Met Glu Leu Ser Gly Leu Arg Ser Glu Asp Thr Ala Val Tyr Tyr Cys
                85                  90                  95

Val Leu Leu Gly Thr Thr Met Val Thr Gly His Tyr Phe Asp Tyr Trp
            100                 105                 110

Gly Gln Gly Thr Leu Val Thr Val Ser
        115                 120
```

<210> SEQ ID NO 76
<211> LENGTH: 5
<212> TYPE: PRT
<213> ORGANISM: Artificial Sequence
<220> FEATURE:
<223> OTHER INFORMATION: Complementarity Determining Region (CDR)

<400> SEQUENCE: 76

```
Ser Tyr Ala Ile Ser
1               5
```

<210> SEQ ID NO 77
<211> LENGTH: 17
<212> TYPE: PRT
<213> ORGANISM: Artificial Sequence
<220> FEATURE:
<223> OTHER INFORMATION: Complementarity Determining Region (CDR)

<400> SEQUENCE: 77

```
Gly Ile Ile Pro Ile Phe Gly Thr Ala Asn Tyr Ala Gln Lys Phe Gln
1               5                   10                  15

Gly
```

<210> SEQ ID NO 78
<211> LENGTH: 15
<212> TYPE: PRT
<213> ORGANISM: Artificial Sequence
<220> FEATURE:
<223> OTHER INFORMATION: Complementarity Determining Region (CDR)

<400> SEQUENCE: 78

```
Val Leu Leu Asp Thr Thr Met Val Thr Gly Tyr Tyr Phe Asp Tyr
1               5                   10                  15
```

<210> SEQ ID NO 79
<211> LENGTH: 17
<212> TYPE: PRT
<213> ORGANISM: Artificial Sequence
<220> FEATURE:
<223> OTHER INFORMATION: Complementarity Determining Region (CDR)

<400> SEQUENCE: 79

```
Gly Thr Ile Pro Ile Phe Gly Thr Ala Asn Tyr Ala Gln Lys Phe Gln
1               5                   10                  15

Gly
```

<210> SEQ ID NO 80
<211> LENGTH: 15
<212> TYPE: PRT
<213> ORGANISM: Artificial Sequence
<220> FEATURE:

```
-continued

<223> OTHER INFORMATION: Complementarity Determining Region (CDR)

<400> SEQUENCE: 80

Val Leu Leu Gly Thr Thr Met Val Thr Gly Tyr Tyr Phe Asp Tyr
1               5                   10                  15

<210> SEQ ID NO 81
<211> LENGTH: 17
<212> TYPE: PRT
<213> ORGANISM: Artificial Sequence
<220> FEATURE:
<223> OTHER INFORMATION: Complementarity Determining Region (CDR)

<400> SEQUENCE: 81

Gly Thr Ile Pro Ile Phe Gly Thr Ala Asp Tyr Ala Gln Glu Phe Gln
1               5                   10                  15

Gly

<210> SEQ ID NO 82
<211> LENGTH: 15
<212> TYPE: PRT
<213> ORGANISM: Artificial Sequence
<220> FEATURE:
<223> OTHER INFORMATION: Complementarity Determining Region (CDR)

<400> SEQUENCE: 82

Val Leu Leu Gly Thr Thr Met Val Thr Gly His Tyr Phe Asp Tyr
1               5                   10                  15
```